US011229702B1

(12) United States Patent
Manning et al.

(10) Patent No.: US 11,229,702 B1
(45) Date of Patent: Jan. 25, 2022

(54) HIGH CONCENTRATION FORMULATIONS OF ADALIMUMAB

(71) Applicant: Coherus Biosciences, Inc., Redwood City, CA (US)

(72) Inventors: Mark Manning, Johnstown, CO (US); Ryan Erik Holcomb, Fort Collins, CO (US)

(73) Assignee: Coherus Biosciences, Inc., Redwood City, CA (US)

( * ) Notice: Subject to any disclaimer, the term of this patent is extended or adjusted under 35 U.S.C. 154(b) by 151 days.

(21) Appl. No.: 15/337,519

(22) Filed: Oct. 28, 2016

Related U.S. Application Data

(60) Provisional application No. 62/413,226, filed on Oct. 26, 2016, provisional application No. 62/247,348, filed on Oct. 28, 2015.

(51) Int. Cl.
 *A61K 39/395* (2006.01)
 *C07K 16/24* (2006.01)

(52) U.S. Cl.
 CPC ...... *A61K 39/39591* (2013.01); *C07K 16/241* (2013.01); *C07K 2317/21* (2013.01)

(58) Field of Classification Search
 None
 See application file for complete search history.

(56) References Cited

U.S. PATENT DOCUMENTS

| | | | |
|---|---|---|---|
| 4,597,966 A | 7/1986 | Zolton et al. | |
| 5,104,651 A | 4/1992 | Boone et al. | |
| 5,716,988 A | 2/1998 | Ibrahim | |
| 5,789,554 A | 8/1998 | Leung et al. | |
| 5,886,154 A | 3/1999 | Lebing et al. | |
| 5,945,098 A | 8/1999 | Samo et al. | |
| 6,090,382 A | 7/2000 | Salfed et al. | |
| 6,171,576 B1 | 1/2001 | Meltzer | |
| 6,171,586 B1 | 1/2001 | Lam et al. | |
| 6,238,664 B1 | 5/2001 | Hellerbrand et al. | |
| 6,252,055 B1 | 6/2001 | Relton | |
| 6,258,562 B1 | 7/2001 | Salfeld et al. | |
| 6,281,336 B1 | 8/2001 | Laursen et al. | |
| 6,509,015 B1 | 1/2003 | Salfeld | |
| 6,696,056 B1 | 2/2004 | Cheung et al. | |
| 7,188,644 B2 | 3/2007 | Kelly | |
| 7,250,165 B2 | 7/2007 | Heavner et al. | |
| 7,648,702 B2 | 1/2010 | Gombotz et al. | |
| 7,879,976 B2 | 2/2011 | Friess | |
| 8,216,583 B2 | 7/2012 | Krause | |
| 8,420,081 B2 | 4/2013 | Fraunhofer | |
| 8,563,697 B2 | 10/2013 | Clarke | |
| 8,632,778 B2 | 1/2014 | Kakuta et al. | |
| 8,664,945 B2 | 3/2014 | Laville | |
| 8,795,670 B2 | 8/2014 | Krause et al. | |
| 8,802,100 B2 | 8/2014 | Krause et al. | |
| 8,802,101 B2 | 8/2014 | Krause et al. | |
| 8,802,102 B2 | 8/2014 | Krause et al. | |
| 8,821,865 B2 | 9/2014 | Neu et al. | |
| 8,883,146 B2 | 11/2014 | Fraunhofer et al. | |
| 8,889,135 B2 | 11/2014 | Fischkoff et al. | |
| 8,916,157 B2 | 12/2014 | Krause | |
| 8,940,305 B2 | 1/2015 | Krause et al. | |
| 9,085,619 B2 | 7/2015 | Fraunhofer | |
| 9,114,166 B2 | 8/2015 | Krause | |
| 9,272,041 B2 | 3/2016 | Krause | |
| 9,340,611 B2 * | 5/2016 | Manning | A61K 47/12 |
| 9,340,612 B2 * | 5/2016 | Manning | A61K 47/12 |
| 9,346,880 B2 * | 5/2016 | Manning | A61K 47/12 |
| 9,382,317 B2 * | 7/2016 | Manning | A61K 47/12 |
| 9,682,145 B2 * | 6/2017 | Manning | A61K 47/12 |
| 9,707,293 B2 * | 7/2017 | Manning | A61K 47/12 |
| 9,724,414 B2 * | 8/2017 | Manning | A61K 47/12 |
| 9,724,415 B2 * | 8/2017 | Manning | A61K 47/12 |
| 9,731,008 B2 * | 8/2017 | Manning | A61K 47/12 |
| 9,731,009 B2 * | 8/2017 | Manning | A61K 47/12 |
| 9,737,600 B2 | 8/2017 | Manning et al. | |
| 9,738,714 B2 | 8/2017 | Krause | |
| 9,757,454 B2 * | 9/2017 | Manning | A61K 47/12 |
| 9,770,507 B2 * | 9/2017 | Manning | A61K 47/12 |
| 9,782,479 B2 * | 10/2017 | Manning | A61K 47/12 |
| 9,782,480 B2 * | 10/2017 | Manning | A61K 47/12 |
| 9,789,185 B2 * | 10/2017 | Manning | A61K 47/12 |
| 9,808,525 B2 * | 11/2017 | Manning | A61K 47/12 |
| 9,861,695 B2 * | 1/2018 | Manning | A61K 47/12 |

(Continued)

FOREIGN PATENT DOCUMENTS

| | | |
|---|---|---|
| CA | 2872088 | 2/2004 |
| CN | 102049045 | 5/2011 |

(Continued)

OTHER PUBLICATIONS

Humira product insert, Abbott, p. 1-34, 2002.*
U.S. Appl. No. 16/023,046, Fraunhofer et al.
U.S. Appl. No. 16/023,152, Fraunhofer et al.
U.S. Appl. No. 16/023,161, Fraunhofer et al.
U.S. Appl. No. 16/023,205, Fraunhofer et al.
U.S. Appl. No. 16/178,137, Manning et al.
U.S. Appl. No. 16/178,164, Manning et al.
U.S. Appl. No. 16/178,309, Manning et al.
U.S. Appl. No. 16/178,319, Manning et al.
U.S. Appl. No. 61/004,992, Fraunhofer et al.
"Annex A Humira Story," AbbVie Biotechnology Limited, submitted to European Patent Office by owner of EP1406656B on Dec. 22, 2014.

(Continued)

*Primary Examiner* — Yunsoo Kim
(74) *Attorney, Agent, or Firm* — Fish & Richardson P.C.

(57) ABSTRACT

The present invention relates to aqueous pharmaceutical compositions comprising a high concentration (i.e., greater than 50 milligrams per milliliter) of adalimumab (including antibody proteins considered or intended as "biosimilar" or "bio-better" variants of commercially available adalimumab) suitable for long-term storage, and methods of manufacture of the compositions; methods of their administration; and articles containing the same.

15 Claims, No Drawings

(56) References Cited

U.S. PATENT DOCUMENTS

| | | | |
|---|---|---|---|
| 10,155,039 B2* | 12/2018 | Manning | A61K 47/12 |
| 10,159,732 B2* | 12/2018 | Manning | A61K 47/12 |
| 10,159,733 B2* | 12/2018 | Manning | A61K 47/12 |
| 10,195,275 B2* | 2/2019 | Manning | A61K 47/12 |
| 10,207,000 B2* | 2/2019 | Manning | A61K 39/39591 |
| 10,716,852 B2 | 7/2020 | Manning et al. | |
| 10,716,853 B2 | 7/2020 | Manning et al. | |
| 10,716,854 B2 | 7/2020 | Manning et al. | |
| 10,722,579 B2 | 7/2020 | Manning et al. | |
| 11,071,782 B2 | 7/2021 | Ogez et al. | |
| 2002/0004478 A1 | 1/2002 | Danko et al. | |
| 2003/0138417 A1 | 7/2003 | Kaisheva et al. | |
| 2003/0180287 A1 | 9/2003 | Gombotz et al. | |
| 2003/0206898 A1 | 11/2003 | Fischkoff et al. | |
| 2004/0022792 A1 | 2/2004 | Klinke | |
| 2004/0033228 A1 | 2/2004 | Krause et al. | |
| 2004/0033535 A1 | 2/2004 | Boyle et al. | |
| 2004/0038878 A1 | 2/2004 | Tanikawa et al. | |
| 2004/0039366 A1 | 2/2004 | MacLeod | |
| 2004/0170623 A1 | 9/2004 | Arvinte et al. | |
| 2006/0149042 A1 | 7/2006 | Konstantinov et al. | |
| 2006/0165733 A1 | 7/2006 | Betz et al. | |
| 2007/0036779 A1 | 2/2007 | Bardat et al. | |
| 2007/0169435 A1 | 7/2007 | Kinney | |
| 2007/0184050 A1 | 8/2007 | Ishikawa | |
| 2008/0124326 A1 | 5/2008 | Rehder et al. | |
| 2008/0275220 A1 | 11/2008 | Friess | |
| 2008/0311078 A1 | 12/2008 | Gokam et al. | |
| 2009/0151807 A1 | 6/2009 | Davis | |
| 2009/0291062 A1 | 11/2009 | Fraunhofer | |
| 2010/0166774 A1 | 7/2010 | Dali | |
| 2010/0278822 A1 | 11/2010 | Fraunhofer | |
| 2011/0060290 A1 | 3/2011 | Bonk | |
| 2012/0028877 A1 | 2/2012 | Gokam et al. | |
| 2013/0195888 A1 | 8/2013 | Wang et al. | |
| 2013/0216522 A1 | 8/2013 | Huille et al. | |
| 2013/0216525 A1 | 8/2013 | Chen | |
| 2013/0243764 A1 | 9/2013 | Ellis et al. | |
| 2013/0273066 A1 | 10/2013 | Gokam et al. | |
| 2013/0273067 A1 | 10/2013 | Gokarn et al. | |
| 2013/0312868 A1 | 11/2013 | Ilan | |
| 2013/0336968 A1 | 12/2013 | Danek-Bulius et al. | |
| 2014/0141007 A1 | 5/2014 | Fraunhofer et al. | |
| 2014/0141008 A1 | 5/2014 | Fraunhofer et al. | |
| 2014/0186361 A1 | 7/2014 | Manning et al. | |
| 2015/0102042 A1 | 4/2015 | Matsch | |
| 2015/0150982 A1 | 6/2015 | Michael et al. | |
| 2015/0182525 A1 | 7/2015 | Shi | |
| 2015/0182626 A1 | 7/2015 | Matsch | |
| 2015/0190513 A1 | 7/2015 | Manning et al. | |
| 2015/0191538 A1 | 7/2015 | Manning et al. | |
| 2015/0290080 A1 | 10/2015 | Weikart | |
| 2015/0344557 A1 | 12/2015 | Malik | |
| 2016/0015895 A1 | 1/2016 | Blondino | |
| 2016/0031982 A1 | 2/2016 | Manning et al. | |
| 2016/0039926 A1 | 2/2016 | Manning et al. | |
| 2016/0256545 A1 | 9/2016 | Manning et al. | |
| 2016/0256547 A1 | 9/2016 | Manning et al. | |
| 2016/0263226 A1 | 9/2016 | Manning et al. | |
| 2016/0303233 A1 | 10/2016 | Manning et al. | |
| 2016/0303234 A1 | 10/2016 | Manning et al. | |
| 2016/0303235 A1 | 10/2016 | Manning | |
| 2016/0304599 A1 | 10/2016 | Manning et al. | |
| 2016/0304600 A1 | 10/2016 | Manning et al. | |
| 2016/0304601 A1 | 10/2016 | Manning et al. | |
| 2016/0319011 A1 | 11/2016 | Gokam et al. | |
| 2016/0339102 A1 | 11/2016 | Gokarn et al. | |
| 2016/0362484 A1 | 12/2016 | Gokarn et al. | |
| 2016/0362486 A1 | 12/2016 | Gokarn et al. | |
| 2017/0143828 A1 | 5/2017 | Fraunhofer et al. | |
| 2017/0312361 A1 | 11/2017 | Manning et al. | |
| 2018/0021433 A1 | 1/2018 | Manning et al. | |
| 2018/0028653 A1 | 2/2018 | Manning et al. | |
| 2018/0028654 A1 | 2/2018 | Manning et al. | |
| 2018/0028655 A1 | 2/2018 | Manning et al. | |
| 2018/0028656 A1 | 2/2018 | Manning et al. | |
| 2018/0028657 A1 | 2/2018 | Manning et al. | |
| 2018/0043018 A1 | 2/2018 | Manning et al. | |
| 2018/0043019 A1 | 2/2018 | Manning et al. | |
| 2018/0055929 A1 | 3/2018 | Manning et al. | |
| 2018/0055930 A1 | 3/2018 | Manning et al. | |
| 2018/0140701 A1 | 5/2018 | Manning et al. | |
| 2018/0200202 A1 | 7/2018 | Joguparthi | |
| 2018/0256717 A1 | 9/2018 | Klaveness | |
| 2018/0311349 A1 | 11/2018 | Manning et al. | |
| 2018/0311350 A1 | 11/2018 | Manning et al. | |
| 2018/0311351 A1 | 11/2018 | Manning et al. | |
| 2018/0311352 A1 | 11/2018 | Manning et al. | |
| 2019/0060455 A1 | 2/2019 | Manning et al. | |
| 2019/0070292 A1 | 3/2019 | Manning et al. | |
| 2019/0070293 A1 | 3/2019 | Manning et al. | |
| 2019/0070294 A1 | 3/2019 | Manning et al. | |

FOREIGN PATENT DOCUMENTS

| | | |
|---|---|---|
| CN | 102257006 | 11/2011 |
| CN | 102988984 | 5/2015 |
| EP | 1324776 | 9/2009 |
| EP | 1528933 | 5/2012 |
| JP | 2001-503781 | 3/2001 |
| JP | 2010-523493 | 7/2010 |
| JP | 2011-509972 | 3/2011 |
| JP | 2011-518110 | 6/2011 |
| JP | 2015-527402 | 9/2015 |
| WO | WO 1997/029131 | 8/1997 |
| WO | WO 1997/45140 | 12/1997 |
| WO | WO 1998/004281 | 2/1998 |
| WO | WO 1998/056418 | 12/1998 |
| WO | WO 1999/037329 | 7/1999 |
| WO | WO 2000/56772 | 9/2000 |
| WO | WO 2000/67789 | 11/2000 |
| WO | WO 2002/013860 | 2/2002 |
| WO | WO 2002/100330 | 12/2002 |
| WO | WO 2004/091656 | 10/2004 |
| WO | WO 2006/022599 | 3/2006 |
| WO | WO 2006/131013 | 12/2006 |
| WO | WO 2006/138181 | 12/2006 |
| WO | WO 2007/092772 | 8/2007 |
| WO | WO 2009/015345 | 1/2009 |
| WO | WO 2009/073569 | 6/2009 |
| WO | WO 2009/073805 | 6/2009 |
| WO | WO 2009/084659 | 7/2009 |
| WO | WO 2010/062896 | 6/2010 |
| WO | WO 2010/066634 | 6/2010 |
| WO | WO 2010/129469 | 11/2010 |
| WO | WO 2010/141039 | 12/2010 |
| WO | WO 2011/061712 | 5/2011 |
| WO | WO 2011/080209 | 7/2011 |
| WO | WO 2011/104381 | 9/2011 |
| WO | WO 2011/141926 | 11/2011 |
| WO | WO 2012/037534 | 3/2012 |
| WO | WO 2012/065072 | 5/2012 |
| WO | WO 2012/089778 | 7/2012 |
| WO | WO 2012/143418 | 10/2012 |
| WO | WO 2012/165917 | 12/2012 |
| WO | WO 2013/006454 | 1/2013 |
| WO | WO 2013/011076 | 1/2013 |
| WO | WO 2013/063510 | 5/2013 |
| WO | WO 2013/096835 | 6/2013 |
| WO | WO 2013/164837 | 11/2013 |
| WO | WO 2013/186230 | 12/2013 |
| WO | WO 2014/039903 | 3/2014 |
| WO | WO 2014/099636 | 6/2014 |
| WO | WO 2014/130064 | 8/2014 |

OTHER PUBLICATIONS

"Development Pharmaceutics for Biotechnological and Biological Products (Annex to Note for Guidance on Development Pharmaceutics)," by Committee for Proprietary Medicinal Products, The European Agency for the Evaluation of Medicinal Products (Oct. 21, 1999).

(56) References Cited

OTHER PUBLICATIONS

"Note for Guidance on Development Pharmaceutics," by the Committee for Proprietary Medicinal Products (CPMP), The European Agency for the Evaluation of Medicinal Products (Jan. 28, 1998).
Akers et al., "Formulation Development of Protein Dosage Forms," Ch. 2 in Development and Manufacture of Protein Pharmaceuticals, Kluwer Academic/Plenum Publishers: New York, 4 7-127 (Nail et al., eds., 2002).
Alon et al., "Lidocaine for the Alleviation of Pain Associated with Subcutaneous Erythropoietin Injection," *J. American Soc. Nephrol.* 5(4):1161-1162, 1994.
Ann L. Daugherty, et al., "Formulation and Delivery Issues for Monoclonal Antibody Therapeutics," *Adv. Drug Deliv. Rev.* 58:686, 2006.
Arakawa et al., "Protection of Bovine Seram Albumin from Aggregation by Tween 80," *J. Pharm. Sci.* 89(5):646-651, May 2000.
ATGAM® Label (Nov. 2005).
Aulton, Ed., "Pharmaceutics, The Science of Dosage Form Design," 2nd Ed., Churchill Livingstone: New York, pp. 317-318, pp. 544-553 (2002).
Australian Examination Report No. 1 in Australian Appln. No. 2013312300, dated Jul. 28, 2017, 4 pages.
AVASTIN® Label (Feb. 2004).
Bahrenburg et al., "Buffer-free therapeutic antibody preparations provided a viable alternative to conventionally buffered solutions: From protein buffer capacity prediction to bioprocess applications," *Bio. J.* 10:610-622, 2015.
Barn et al., "Tween Protects Recombinant Human Growth Hormone against Agitation-Induced Damage via Hydrophobic Interactions," *J. Pharm. Sci.* 87(12):1554-1559, Dec. 1998.
Bischoff et al., "Deamidation of Asparagine and Glutamine Residues in Proteins and Peptides: Structural Determinants and Analytical Methodology," *J. Chromatography B* 662:261-278, 1994.
Branden A. Salinas, et al., "Understanding and Modulating Opalescence and Viscosity in a Monoclonal Antibody Formulation," 99 *J. Pharm. Sci.* 82, 2010.
Brazeau et al., "Current perspectives on pain upon injection of drugs," *J. Pharm. Sci.* 87(6):667-677, 1998.
Butler & Hamilton, "Quantitation of Specific Antibodies: Methods of Express, Standards, Solid-Phase Considerations, and Specific Applications," Ch. 9 in Immunochemistry of Solid-Phase Immunoassay, CRC Press (John E, Butler ed. 1991).
Campath (Alemtuzumab), Genzyme Corporation, 2006.
Capasso et al., "First Evidence of Spontaneous Deamidation of Glutamine Residue via Cyclic Imide to a- and y-Glutamic Residue nnder Physiological Conditions," *J. Chem. Soc. Chem. Comm.* pp. 1667-1668 (1991).
Carpenter and Manning, eds., Rational Design of Stable Protein Formulations. Theory and Practice, Pharmaceutical Biotechnology, vol. 13, Kluwer Academic/Plenum Publishers: New York (2002).
Carpenter et al., "Overlooking Subvisible Particles in Therapeutic Protein Products: Gaps That May Compromise Product Quality," *J. Pharm Sci.* 98(4):1201-1205, Apr. 2009.
Chinese Office Action in Chinese Appln. No. 20130058126.8, dated Nov. 16, 2015, 14 pages (with machine translation).
Christensen, "Proteins as buffers," *Annals New York Acad. Sci.* 133:34-40, Apr. 1966.
Christine C. Lee, et al., "Toward aggregation-resistant antibodies by design," 31 *Trends in Biotech.* 612, 2013.
Cleland & Langer, "Formulation and Delivery of Proteins and Peptides: Design and Development Strategies," Ch. 1 in Formulation and Delivery of Proteins and Peptides, ACS Symposium Series 567, 1-19 (1994).
Cleland et al., "The Development of Stable protein Formulations: A Close Look at Protein Aggregation, Deamidation, and Oxidation," *Critical Reviews in Therapeutic Drug Carrier Systems* 10(4):307-377 (1993).
Dean, "Lange's Handbook of Chemistiy," McGraw-Hill, p. 8.49, 8.65 (9th ed. 1999).

Douglas D. Banks, et al., "Native-State Solubility and Transfer Free Energy as Predictive Tools for Selecting Excipients to Include in Protein Formulation Development Studies," 101 *J. Pharm. Sci.* 2720 (2012).
Edward C. Keystone et al., "Golimumab, a Human Antibody to Tumor Necrosis Factor-a Given by Monthly Subcutaneous Injections, in Active Rheumatoid Arthritis Despite Methotrexate: The GO-FORWARD Study," 68 Ann. Rheum. Dis. 789 (2009).
Emily Ha et al., "Peroxide Formation inPolysorbate 80 and Protein Stability," 91 *J. Pharm. Sci.* 2252 (2002).
ENBREL® Label (Nov. 1998).
ENBREL® Label (Sep. 2002).
ENBREL® Summary Basis of Approval (1998).
Eurasian Office Action in Eurasion Appln. No. 201590518, dated Mar. 10, 2016, 5 pages.
European Search Report (extended) in European Appl. No. 13835291, dated Mar. 15, 2016, 6 pages.
Eva Y. Chi, et al., "Physical Stability of Proteins in Aqueous Solution: Mechanism and Driving Forces in Normative Protein Aggregation," 20 Pharm, Res. 1325 (2003).
Flebogamma® Label (Jan. 2004).
Fransson & Espander-Jansson, "Local Tolerance of Subcutaneous Injections," *J. Pharm. Pharmacol.* 48:1012-1015, 1996.
Frenken et al., "Identification of the Component Part in an Epoetin Alfa Preparation that Causes Pain after Subcutaneous Injection," *American J. Kidney Dis.* 22(4):553-556, 1993.
GAMIMUNE® Label (Oct. 2005).
GAMMAGARD LIQUID Label (Apr. 2005).
GAMUNEX® Label (Nov. 2005).
Gilbert and Cothran, "SC versus IV delivery: Reducing costs while increasing patient satisfaction," Hemotology & Oncology News & Issues, Dec. 2005, 25-29.
Gloff et al., "Pharmacokinetics & Protein Therapeutics," Advanced Drug Delivery Reviews, 4 (1990) 359-386.
Gokam et al., "Excipients for Protein Drugs," Ch. 17 in Excipient Development for Pharmaceutical, Biotechnology, and Drug Delivery Systems (Ashok Katdare & Mahe sh V. Chaubal eds., 2006).
Gokarn et al., "Self-buffering antibody formulations," *J. Pharm. Sci.* 97(8):3051-3066, 2008.
Golimumab/SIMPONI® label (Revised Dec. 2011).
Goolcharran et al., "The Effects of a Histidine Residue on the C-Terminal Side of an Asparaginyl Residue on the Rate of Deamidation Using Model Pentapeptides," *J. Pharm. Sci.* 89(6):818-825 (2000).
Granolleras et al., "Experience of pain after subcutaneous administration of different preparations of recombinant human erythropoietin: a randomized, double-blind crossover study," vol. 36, No. 6:294-298, 1991.
Guidance for Industry, Clinical Development Programs for Drags, Devices and Biological Products for the Treatment of Rheumatoid Arthritis (1999).
Hanauer, *Gastroenterology* 130:323-333 (Feb. 2006).
Handbook of Pharmaceutical Excipients, Pharmaceutical Press (Raymond C. Rowe, Paul J. Sheskey, & Sian C. Owen eds., 5th ed. 2006).
Harris et al., "Commerical Manufacturing Scale Formulation and Analytical Characterization of Therapeutic Recombinant Antibodies," *Drug Devel. Res.* 61:137-154, 2004.
Hawe et al., "Taylor Dispersion Analysis Compared to Dynamic Light Scattering for the Size Analysis of Therapeutic Peptides and Proteins and Their Aggregates," *Pharm. Res.* 28:2302-2310, May 2011.
Humira, Product Information Sheet, p. 1-16, 2002, Abbott Lab.
Humira.com [online], "Injection Assistance," HUMIRA®, Mar. 2005, [retrieved on Jan. 12, 2017], Retrieved from the Internet URL: http://web.archive.org/web/20050317083331/http://www.humira.com/hu/hustore/cgibin/ProdSubEV_Cat_205043_SubCat_210170_NavRoot_205042_NavID_301.htm, 2 pages.
HUMIRA® Label (Feb. 2007).
HUMIRA® Label (Feb. 2008).
HUMIRA® Label (Jan. 2003).
HUMIRA® Label (Jan. 2008).
HUMIRA® Label (Nov. 2006).

(56) References Cited

OTHER PUBLICATIONS

HUMIRA® Label (Oct. 2005).
HUMIRA® Label (Oct. 2016).
Infliximab/REMICADE® label (Nov. 1999).
International Preliminary Report on Patentability in International Appl. No. PCT/US2013/58618, dated Mar. 10, 2015, 10 pages.
International Search Report in International Appl. No. PCT/US2013/58618, dated Apr. 28, 2014, 4 pages.
Israel Office Action in Israeli Appl. No. 2336545, dated Jan. 21, 2018, 5 pages (w/ English Translation).
Japanese Office Action in Japanese Appl. No. 2015-531261, dated Apr. 25, 2018, 6 pages (with machine translation).
Japanese Office Action in Japanese Appl. No. 2015-531261, dated Jun. 21, 2017, 15 pages (with machine translation).
Jefferis et al., "Recognition Sites on Human IgG for Fcy Receptors: The Role of Glycosylation," *Immunol. Lett.* 44:111-117, 1995.
Jenny M. Phillips, "Manufacture and Quality Control of CAMPATH-1 Antibodies for Clinical Trials," 3 *Cytotherapy* 233 (2001).
John F. Carpenter, et al., Chapter 7: Freezing- and Drying-Induced Perturbations of Protein Structure and Mechamsms of Protein Protection by Stabilizing Additives, in Freeze-Drying/Lyophilijza Tion of Pharmaceutical and Biological Products 167 (2d ed. 2004).
John F. Carpenter et al., "Inhibition of Stress-Induced Aggregation of Protein Therapeutics," 309 *Methods in Enzymology* 236 (1999).
John F. Carpenter et al., "Rational Design of Stable Lyophilized Protein Formulations: Some Practical Advice," *Pharm. Res.* 14(8):969, 1997.
Jorgensen et al., "Pain Assessment of Subcutaneous Injections," *Ann. Pharma.* 30(7/8):729-732 (Jul./Aug. 1996).
Jose Baselga et al., "Phase II Study of Weekly Intravenous Recombinant Humanized Anti-p185HER2 Monoclonal Antibody in Patients with HER2/neu-overexpressing Metastatic Breast Cancer," 14 *J. Clin. Oncol.* 738 (1996).
Joseph M. Perchiacca et al., "Engineering Aggregation-resistant Antibodies," 3 *Ann. Rev. Chem. Biomol. Eng.* 263 (2012).
Karow et al., "Buffer capacity of biologics-from buffer salts to buffering by antibodies," *Biotechnol. Prog.* 29(2):480-492, 2013.
Kavanaugh et al., "Treatment with Adalimumab (D2E7) does not Affect Normal Immune Responsiveness," *Arthritis & Rheumatism* 46(9):S132, Sep. 2002.
Kaymakcalan et al., "Development of a Fully Human Anti-TNF Monoclonal Antibody," *J. Interferon & Cytokine Research*, Abstract 6.16, 18(5):A-125, May 1998.
Kempeni, "Preliminary results of early clinical trials with the fully human anti-TNFa monoclonal antibody D2E7" *Ann. Rheum. Dis.* 58(Suppl I):170-172 (1999).
Keystone et al., "Adalmumab (D2E7), A Fully Human Anti-TNF-α Monoclonal Antibody, Inhibits the Progression of Structural Joint Damage in Patients with Active RA Despite Doncomitant Methotrexate Therapy," *Arthritis & Rheumatism* 46(9):S205, Sep. 2002.
Larry R. Helms, et al., "Destabilizing Loop Swaps in the CD Rs of an Immunoglobulin VL Domain," 4 *Protein Sci.* 2073 (1995).
Laursen et al., "Pain Perception after Subcutaneous Injections of Media Containing Different Buffers," *Basic Clin. Pharmacol. Toxicol.* 98:218-221, 2006.
Lene Jorgensen et al., "Recent Trends in Stabilising Peptides and Proteins in Pharmaceutical Formulation—Considerations in the Choice of Excipients," 6 *Expert. Opin. Drug Deliv.* 1219 (2009).
Lorenz, "Technology Evaluation: Adalimumab, Abbott Laboratories," *Curr. Opin. Mol. Ther.* 4(2):185-190, 2002.
Maggio, "Use of excipients to control aggregation in peptide and protein formulations," *J. Excipients Food Chem.* 1(2):40-49, Aug. 2010.
Marco van de Weert & Theodore W. Randolph, Chapter 6: Physical Instability of Peptides and Proteins, in Pharmaceutical Formulation Development of Peptides and Proteins 107 (2012).
Masako Ohnishi & Hiromichi Sagitani, "The Effect of Nonionic Surfactant Structure on Hemolysis," 70 *J. Am. Oil Chem. Soc.* 679 (1993).
McCue et al., "Three Generations of Immunoglobulin G Preparations for Clinical Use," *Reviews Infect. Dis.* 8(4):s374-s381, 1986.
Michael J. Treuheit et al., "Inverse Relationship of Protein Concentration and Aggregation," 19 *Pharm. Res.* 511 (2002).
Nabuchi et al., "The Stability and Degradation Pathway of Recombinant Human Parathyroid Hormone: Deamidation of Asparaginyl Residue and Peptide Bond Cleavage at Aspartyl and Asparaginyl Residues," *Pharm. Res.* 14(12):1685-1690, 1997.
Napke et al., "Excipients and additives: hidden hazards in drug products and in product substitution," *Can. Med. Assoc. J.* 131:1449-1452, 1984.
Nash et al., "Randomized Crossover Comparison of Injection Site Pain with 40mg/0.4 or 0.8mL Formulations of Adalimumab in Patients with Rheumatoid Arthritis," *Rheu. Ther.* 3:257-270, 2016.
Nema et al., "Excipients and Their Use in Injectable Products," *FPA J. Pharm. Sci. Tech.* 51(4):166-171 (Jul./Aug. 1997).
Nozaki & Tanford, "Examination of Titration Behavior," *Methods Enzymol.* 11:715-734, 1967.
OCTAGAM® Label (Mar. 2007).
OCTAGAM®Label (Mar. 2004).
Olthuis et al., "Characterization of Proteins by Means of their Buffer Capacity, Measured with an ISFET-based Coulometric Sensor-Actuator System," *Biosensors & Bioelectronics* 9:743-751, 1994.
Pabotji et al., "Chemical and Physical Stability of Chimeric L6, a Mouse-Human Monoclonal Antibody," *Pharm. Res.* 11(5):764-771, 1994.
Parslow, "Immunoglobulins & Immunoglobulin Genes," Ch. 7 in Medical Immunology, Appleton & Lange (Daniel P. Stites, Abba I. Terr, & Tristram G. Parslow eds., 9th Ed., 1997).
Patel et al., "Chemical Pathways of Peptide Degradation. II. Kinetics of Deamidation of an Asparaginyl Residue in a Model Hexapeptide," *Pharm. Res.* 7(7):703-711, 1990.
PRIVIGEN® Label (Jul. 2007).
U.S. Appl. No. 60/690,582, filed Jun. 14, 2005.
REMICADE® Label (Aug. 1998).
REMICADE® Summary Basis of Approval (1999).
Robert G. Hamilton, The Human IGG Subclasses (2001).
Robert Ritzel et al., "Pharmacokinetic, Insulinotropic, and Glucagonostatic Properties of GLP-1 [7-36 amide] after Subcutaneous Injection in Healthy Volunteers. Dose-response-relationships," 38 *Diabetologia* 720 (1995).
Sampathkumar Krishnan et al., Chapter 16: Development of Formulations for Therapeutic Monoclonal Antibodies and Fc Fusion Proteins, in Formulation and Process Development Strategies for Manufacturing Biopharmaceuticals 383 (2010).
Santora et al., "Characterization of Recombinant human Monoclonal Tissue Necrosis Factor-a Antibody Using Cation-Exchange HPLC and Capillary Isoelectric Focusing," *Anal. Biochem.* 275:98-108, 1999.
Scotchler et al., "Deamidation of Glutaminyl Residues: Dependence on pH, Temperature, and Ionic Strength," *Anal. Biochem.* 59:319-322, 1974.
Singh and Singh, "Effect of Polyols on the Conformational Stability and Biological Activity of a Model Protein Lysozyme," *AAPS PharmSciTech*, Article 42, Jul. 2003, 4(3): 9 pages.
Sorbera et al., "Adalimumab," *Drugs Fut.* 26(7):639-646 (Jul. 2001).
Stefan Ewert et al., "Biophysical Properties of Human Antibody Variable Domains," 325 *J. Mol. Biol.* 531 (2003).
Stoner et al., "Protein-Solute Interactions Affect the Outcome of Ultrafiltration/Diafiltration Operations," *J. Pharm. Sci.* 93:2332-2342 (2004).
SYNAGIS® Label (Jul. 2004).
Taiwanese Office Action in Taiwanese Appl. No. 102132360, dated Oct. 25, 2017, 8 pages (with English translation).
Theodore W. Randolph & John F. Carpenter, "Engineering Challenges of Protein Formulations," 53 *Am. Inst. Chem. Eng. J.* 1902 (2007).
Tim J. Kamerzell et al., "Increasing IgG Concentration Modulates the Conformational Heterogeneity and Bonding Network that Influence Solution Properties," 113 *J. Phys. Chem. B*, 6109 (2009).
Tindall et al., "Mobile Phase Buffers, Part II," LC, GC Europe, 2-4, 2003.

(56) References Cited

OTHER PUBLICATIONS

TYSABRI® Label (Nov. 2004).
Van Gestel et al., "Development and Validation of the European League Against Rheumatism Response Criteria for Rheumatoid Arthritis," *Arthritis & Rheumatism* 39(1):34-40, Jan. 1996.
Van Slyke, "On the Measurement of Buffer Values and on the Relationship of Buffer Value to the Dissociation Constant of the Buffer and the Concentration and Reaction of the Buffer Solution," *J. Biol. Chem.* 52:525-570, 1922.
Vectibix® Label (Sep. 2006).
Veys et al., "Pain at the injection site of subcutaneously administered erythropoietin: phosphate-buffered epoetin alpha compared to cirate-buffered epoetin alpha and epoetin beta," *Clin. Nephrol.* 49(1):41-44, 1998.
Vivaglobin® Label (Jan. 2006).
Wang et al. "Antibody structure, instability, and formulation," Minireview, accepted Jun. 4, 2006.
Wang, "Instability, stabilization, and formulation ofliquid protein pharmaceuticals," *Int. J. Pharm.* 185:129-188, 1999.
Warne, "Development of high concentration protein biopharmaceuticals: The use of platform approaches in formulation development," *Eur. J. Pharm. Biopharm.* 78(2):208-212, Mar. 2011.
Wright et al., "Nonenzymatic Deamidation of Asparaginyl and Glutaminyl Residues in Protein," *Crit. Rev. Biochem. Mol. Biol.* 26(1):1-52, 1991.
"Declaration of Brian Reisetter, RPh, MBA, Ph.D.", filed with Petition for Inter Partes Review of U.S. Pat. No. 9,114,166 filed May 9, 2019, 15 pages.
"Expert Opinion of Prof. Dr. G. Winter", Jan. 13, 2014, in opposition proceedings re EP1528933.
"Fraunhofer Substantive Motion 3", in *Fraunhofer v. Gokarn*, Patent Interference No. 106,057, filed on Oct. 12, 2016, 57 pages.
"Immune Globulin Intravenous (Human), 10% Caprylate/ Chromatography Purified," Talecris Biotherapeutics, Inc., dated Nov. 2005, 17 pages.
"Abbott Ramps Up Biotech Manufacturing to Meet Humira Demand," Pharmaceutical Technology, Mar. 2003, 4 pages.
"Clinical Pharmacology and Biopharmaceutics Review(s)," by Center for Drug Evaluation and Research and Center for Biologies Evaluation and Research Application No. 125057/0, in Approval Package for Humira®, 67 pages, Approved Dec. 31, 2002.
FDA Approves Amgen's AMJEVITATM (Adalimumab-Atto) for Treatment of Seven Inflammatory Diseases (Sep. 23, 2019), https://www.amgen.com/media/news-releases/2016/09/fda-approves-amgens-amjevita-adalimumabatto-for-treatment-of-seven-inflammatory-diseases/, 8 pages.
"Grounds of Appeal," Exhibit 1085 in Opposition of EP 1528933, filed Feb. 26, 2016, 27 pages.
Marketing Authorization No. EU/1/16/1164) European Medicines Agency, "Amgenvita" https://ec.europa.eu/health/documents/community-register/html/h1164.htm, 5 pages, 2019.
2015 Express Scripts Basic Formulary, Aug. 2014, 2 pages.
Abbott Laboratories 2003 Annual Report, 80 pages.
AbbVie Filing in Support of Opposition Against EP 1324776 B1, Filed Jun. 16, 2010.
AbbVie Filing in Support of Opposition Against EP 1324776 B1, filed Jun. 16, 2010 (Corrected), 24 pages.
Adalimumab Product Approval Information—Licensing Action, Humira, Dec. 31, 2002, 1 page.
Additional Experimental Results for EP 03 748 438 (sic 439) Abbott Biotechnology, Submitted May 15, 2009 in Prosecution of EP1528933.
Affidavit of Christopher Butler dated Feb. 21, 2017, attaching "Injection Tips," Humira.com, http://web.archive.org!web/20050317083331/http://www.humira.com/hu/hustore/cgi-bin/ProdSubEV_Cat_205043_SubCat_210170_NavRoot_205042_NavID_301 .htm (Archived Mar. 17, 2005) As Exhibit A, 2 pages.
Affidavit of Marlene S. Bobka dated Feb. 21, 2017, attaching "Clinical Pharmacology and Biopharmaceutics Review(s)," by Center for Drug Evaluation and Research and Center for Biologies Evaluation and Research, Application No. 125057/0, in Approval Package for Humira, Approved Dec. 31, 2002 as Exhibit A, 67 pages.
Affidavit of Michael Deas attaching English Translation of OCTAGAM entry (75 008) in Rote Liste 2005, Cantor Publishers 2005, as Exhibit A, and original German-language Rote Liste 2005 entry 75 008 as Exhibit B and C, 13 pages.
Akers et al., "Formulation Development of Protein Dosage Forms, ch. 2 in Development and Manufacture of Protein Pharmaceuticals", Kluwer Academic/Plenum Publishers: New York, 47-127, 2002.
Arakawa et al., "Protection of Bovine Serum Albumin from Aggregation by Tween 80", J. Pharm. Sci., 89(5), 646-651, May 2000.
Aulton, ed., "Pharmaceutics, The Science of Dosage Form Design", 2nd ed., Churchill Livingstone: New York, 317-318, 544-553, 2002.
Bam et al., "Tween Protects Recombinant Human Growth Hormone against Agitation-Induced Damage via Hydrophobic Interactions", J. Pharm, Sci., 87(12), 1554-1559, Dec. 1998.
Banks et al., "Native-State Solubility and Transfer Free Energy as Predictive Tools for Selecting Excipients to Include in Protein Formulation Development Studies", J. Pharm. Sci., 2012, 101: 2720-2732.
Barrera et al., "Effects of treatment with a fully human anti-tumour necrosis factor a monoclonal antibody on the local and systemic homeostasis of interleukin 1 and TNFa in patients with rheumatoid arthritis", Ann. Rheum. Dis., 60, 660-669, 2001.
Barsamian et al., Physcians' Desk Reference: ZEVALIN, Thomson PDR, 60 Edition, year 2006, 8 pages.
Baselga et al., "Phase II Study of Weekly Intravenous Recombinant Humanized Anti-p185HER2 Monoclonal Antibody in Patients with HER2/neu-Overexpressing Metastatic Breast Cancer", J. Clin, Oncology, 1996, 14(3): 737-744.
Bischoff et al., "Deamidation of Asparagine and Glutamine Residues in Proteins and Peptides: Structural Determinants and Analytical Methodology", J. of Chromatography B, 662, 261-278, 1994.
Breu et al., "Biotech company preparing several drugs for takeoff," Drug Topics, dated Mar. 5, 2001, 1 page.
Burton et al., "Aspects of the Molecular Structure of IgG Subclasses", Monogr., Allergy vol. 19, pp. 7-35, 1986.
Canadian Office Action in Application No. 2884182, dated Oct. 18, 2019, 4 pages.
Capasso et al., "Effect of the Three-Dimensional Structure on the Deamidation Reaction of Ribonuclease A", J. Peptide Res., 54, 377-382, 1999.
Capasso et al., "First Evidence of Spontaneous Deamidation of Glutamine Residue via Cyclic Imide to α- and γ-Glutamic Residue under Physiological Conditions", J. Chem. Soc. Chem. Commun., pp. 1667-1668, 1991.
Carnahan et al., "Epratuzumab, a Humanized Monoclonal Antibody Targeting CD22: Characterization of in Vitro Properties", vol. 9, 3982s-3990s, Sep. 1, 2003.
Carpenter and Manning, eds., "Rational Design of Stable Protein Formulations.", Theory and Practice, Pharmaceutical Biotechnology, vol. 13, Kluwer Academic/Plenum Publishers: New York, 222 pages, 2002.
Carpenter et al., "Freezing and Drying-Induced Perturbations of Protein Structure and Mechanisms of Protein Production by Stabilizing Additives", Freeze-Drying/Lyophilization of Pharmaceutical and Biological Products, 2004, 167-197.
Carpenter et al., "Inhibition of Stress-induced Aggregation of Protein Therapeutics", Methods in Enzymology, 1999, 309: 236-255.
Chen et al., "Aggregation Pathway of Recombinant Human Keratinocyte Growth Factor and Its Stabilization," Pharmaceutical Research, vol. II, No. II, dated Jun. 6, 1994, 7 pages.
Chi et al., "Physical Stability of Proteins in Aqueous Solution: Mechanism and Driving Forces in Nonnative Protein Aggregation," Pharm. Research, vol. 20, No. 9, dated Sep. 2003, 12 pages.
Chinese Office Action in Application No. 201380058126.8, dated Oct. 23, 2019, 12 pages.
CNJ-016, Vaccinia Immune Globulin Intravenous, Label Apr. 2005, 18 pages.
*Coherus Biosciences Inc.*, Petitioner v. *AbbVie Biotechnology Ltd.*, "Amgen Inc. 's Answer, Affirmative Defenses, and Counterclaims

(56) References Cited

OTHER PUBLICATIONS filed in the U.S. District Court for the District of Delaware," C.A. No. 19-139-RGA, Case IPR2016-01018, U.S. Pat. No. 9,114,166, dated Aug. 18, 2019.
*Coherus Biosciences Inc.*, Petitioner v. *AbbVie Biotechnology Ltd.*, "Decision Denying Institution of Inter Partes Review", Case IPR2017-01009, U.S. Pat. No. 9,085,619, dated Sep. 7, 2017, 22 pages.
*Coherus Biosciences Inc.*, Petitioner v. *AbbVie Biotechnology Ltd.*, "Decision Denying Institution of Inter Partes Review," Case IPR2016-01018, U.S. Pat. No. 9,114,166, dated Nov. 7, 2016.
*Coherus Biosciences Inc.*, Petitioner v. *AbbVie Biotechnology Ltd.*, "Decision Denying Petitioner's Request for Rehearing in Inter Partes Review," Case IPR2016-01018, U.S. Pat. No. 9,114,166, dated Feb. 2, 2017.
*Coherus Biosciences Inc.*, Petitioner v. *AbbVie Biotechnology Ltd.*, "Declaration of David D. Sherry, M.D.", Case IPR2017-00827, U.S. Pat. No. 9,085,619, dated Jan. 30, 2017, 43 pages.
*Coherus Biosciences Inc.*, Petitioner v. *AbbVie Biotechnology Ltd.*, "Declaration of David D. Sherry, M.D.", Case IPR2017-01008, U.S. Pat. No. 9,085,619, dated Feb. 26, 2017, 43 pages.
*Coherus Biosciences Inc.*, Petitioner v. *AbbVie Biotechnology Ltd.*, "Declaration of David D. Sherry, M.D.", Case IPR2017-01009, U.S. Pat. No. 9,085,619, dated Feb. 26, 2017, 43 pages.
*Coherus Biosciences Inc.*, Petitioner v. *AbbVie Biotechnology Ltd.*, "Declaration of David D. Sherry M.D..", Case IPR2017-00826, U.S. Pat. No. 9,085,619, dated Jan. 30, 2017, 43 pages.
*Coherus Biosciences Inc.*, Petitioner v. *AbbVie Biotechnology Ltd.*, "Declaration of Klaus-Peter Radtke, Ph.D.", Case IPR2017-00826, U.S. Pat. No. 9,085,619, dated Jan. 30, 2017, 96 pages.
*Coherus Biosciences Inc.*, Petitioner v. *AbbVie Biotechnology Ltd.*, "Declaration of Klaus-Peter Radtke, Ph.D.", Case IPR2017-00827, U.S. Pat. No. 9,085,619, dated Jan. 30, 2017, 121 pages.
*Coherus Biosciences Inc.*, Petitioner v. *AbbVie Biotechnology Ltd.*, "Declaration of Klaus-Peter Radtke, Ph.D.", Case IPR2017-01008. U.S. Pat. No. 9,085,619, dated Feb. 28, 2017, 127 pages.
*Coherus Biosciences Inc.*, Petitioner v. *AbbVie Biotechnology Ltd.*, "Declaration of Klaus-Peter Radtke, Ph.D.", Case IPR2017-01009. U.S. Pat. No. 9,085,619, dated Feb. 28, 2017, 104 pages.
*Coherus Biosciences Inc.*, Petitioner v. *AbbVie Biotechnology Ltd.*, "Notice of Accepting Corrected Petition," Case IPR2016-01018, U.S. Pat. No. 9,114,166, May 16, 2016, 2 pages.
*Coherus Biosciences Inc.*, Petitioner v. *AbbVie Biotechnology Ltd.*, "Notice of Corrected Exhibit," Case IPR2016-01018, U.S. Pat. No. 9,114,166, dated May 13, 2016, 3 pages.
*Coherus Biosciences Inc.*, Petitioner v. *AbbVie Biotechnology Ltd.*, "Notice of Corrected List of Exhibits," Case IPR2016-01018, U.S. Pat. No. 9,114,166, dated May 13, 2016, 10 pages.
*Coherus Biosciences Inc.*, Petitioner v. *AbbVie Biotechnology Ltd.*, "Notice of Filing Date Accorded to Petition and time for Filing Patent Owner Preliminary Response", Case IPR2017-00826, U.S. Pat. No. 9,085,619, dated Feb. 24, 2017, 5 pages.
*Coherus Biosciences Inc.*, Petitioner v. *AbbVie Biotechnology Ltd.*, "Notice of Filing Date Accorded to Petition and time for Filing Patent Owner Preliminary Response", Case IPR2017-01008, U.S. Pat. No. 9,085,619, dated Mar. 24, 2017, 5 pages.
*Coherus Biosciences Inc.*, Petitioner v. *AbbVie Biotechnology Ltd.*, "Notice of Filing Date Accorded to Petition and time for Filing Patent Owner Preliminary Response", Case IPR2017-01009, U.S. Pat. No. 9,085,619, dated Mar. 24, 2017, 5 pages.
*Coherus Biosciences Inc.*, Petitioner v. *AbbVie Biotechnology Ltd.*, "Notice of Filing Date Accorded to Petition," Case IPR2016-01018, U.S. Pat. No. 9,114,166, dated May 11, 2016, 5 pages.
*Coherus Biosciences Inc.*, Petitioner v. *AbbVie Biotechnology Ltd.*, "Notice of Refund", Case IPR2017-00826, U.S. Pat. No. 9,085,619, dated Jun. 5, 2017, 2 pages.
*Coherus Biosciences Inc.*, Petitioner v. *AbbVie Biotechnology Ltd.*, "Notice of Refund", Case IPR2017-00827, U.S. Pat. No. 9,085,619, dated Jun. 5, 2017, 2 pages.
*Coherus Biosciences Inc.*, Petitioner v. *AbbVie Biotechnology Ltd.*, "Notice of Refund", Case IPR2017-01008, U.S. Pat. No. 9,085,619, dated Dec. 1, 2017, 2 pages.
*Coherus Biosciences Inc.*, Petitioner v. *AbbVie Biotechnology Ltd.*, "Notice of Refund", Case IPR2017-01009, U.S. Pat. No. 9,085,619, dated Dec. 30, 2017, 2 pages.
*Coherus Biosciences Inc.*, Petitioner v. *AbbVie Biotechnology Ltd.*, "Order Conduct of the Proceeding", Case IPR2017-00826, U.S. Pat. No. 9,085,619, dated Apr. 7, 2017, 6 pages.
*Coherus Biosciences Inc.*, Petitioner v. *AbbVie Biotechnology Ltd.*, "Order Conduct of the Proceeding", Case IPR2017-00827, U.S. Pat. No. 9,085,619, dated Apr. 7, 2017 6 pages.
*Coherus Biosciences Inc.*, Petitioner v. *AbbVie Biotechnology Ltd.*, "Order Conduct of the Proceeding", Case IPR2017-01008, U.S. Pat. No. 9,085,619, dated Apr. 7, 2017 6 pages.
*Coherus Biosciences Inc.*, Petitioner v. *AbbVie Biotechnology Ltd.*, "Order Conduct of the Proceeding", Case IPR2017-01009, U.S. Pat. No. 9,085,619, dated Apr. 7, 2017 6 pages.
*Coherus Biosciences Inc.*, Petitioner v. *AbbVie Biotechnology Ltd.*, "Order Dismissing the Proceedings", Case IPR2017-00826, U.S. Pat. No. 9,085,619, dated Apr. 11, 2017, 4 pages.
*Coherus Biosciences Inc.*, Petitioner v. *AbbVie Biotechnology Ltd.*, "Order Dismissing the Proceedings", Case IPR2017-00827, U.S. Pat. No. 9,085,619, dated Apr. 11, 2017 4 pages.
*Coherus Biosciences Inc.*, Petitioner v. *AbbVie Biotechnology Ltd.*, "Patent Owner Preliminary Response in Inter Partes Review," Case IPR2016-01018, U.S. Pat. No. 9,114,166, dated Aug. 9, 2016.
*Coherus Biosciences Inc.*, Petitioner v. *AbbVie Biotechnology Ltd.*, "Patent Owner's Mandatory Notices," Case IPR2016-01018, U.S. Pat. No. 9,114,166, May 27, 2016, 5 pages.
*Coherus Biosciences Inc.*, Petitioner v. *AbbVie Biotechnology Ltd.*, "Patent Owner's Powers of Attorney," Case IPR2016-01018, U.S. Pat. No. 9,114,166, dated May 24, 2016,2 pages.
*Coherus Biosciences Inc.*, Petitioner v. *AbbVie Biotechnology Ltd.*, "Patent Owners Mandatory Notice", Case IPR2017-00827, U.S. Pat. No. 9,085,619, dated Feb. 21, 2017 6 pages.
*Coherus Biosciences Inc.*, Petitioner v. *AbbVie Biotechnology Ltd.*, "Patent Owners Mandatory Notices" Case IPR2017-00826, U.S. Pat. No. 9,085,619, dated Feb. 21, 2017, 6 pages.
*Coherus Biosciences Inc.*, Petitioner v. *AbbVie Biotechnology Ltd.*, "Patent Owners Mandatory Notices" Case IPR2017-01008, U.S. Pat. No. 9,085,619, dated Mar. 23, 2017, 6 pages.
*Coherus Biosciences Inc.*, Petitioner v. *AbbVie Biotechnology Ltd.*, "Patent Owners Mandatory Notices" Case IPR2017-01009, U.S. Pat. No. 9,085,619, dated Mar. 23, 2017, 6 pages.
*Coherus Biosciences Inc.*, Petitioner v. *AbbVie Biotechnology Ltd.*, "Patent Owners Power of Attorney" Case IPR2017-00826, U.S. Pat. No. 9,085,619, dated Feb. 21, 2017, 2 pages.
*Coherus Biosciences Inc.*, Petitioner v. *AbbVie Biotechnology Ltd.*, "Patent Owners Power of Attorney" Case IPR2017-01008, U.S. Pat. No. 9,085,619, dated Mar. 17, 2017, 2 pages.
*Coherus Biosciences Inc.*, Petitioner v. *AbbVie Biotechnology Ltd.*, "Patent Owners Power of Attorney" Case IPR2017-01009, U.S. Pat. No. 9,085,619, dated Mar. 17, 2017, 2 pages.
*Coherus Biosciences Inc.*, Petitioner v. *AbbVie Biotechnology Ltd.*, "Patent Owners Power of Attorney", Case IPR2017-00827, U.S. Pat. No. 9,085,619, dated Feb. 21, 2017 2 pages.
*Coherus Biosciences Inc.*, Petitioner v. *AbbVie Biotechnology Ltd.*, "Patent Owners Preliminary Response", Case IPR2016-01018, U.S. Pat. No. 9,114,166, dated Aug. 9, 2016, 77 pages.
*Coherus Biosciences Inc.*, Petitioner v. *AbbVie Biotechnology Ltd.*, "Patent Owners Preliminary Response", Case IPR2017-00827, U.S. Pat. No. 9,085,619, dated Aug. 9, 2016, 77 pages.
*Coherus Biosciences Inc.*, Petitioner v. *AbbVie Biotechnology Ltd.*, "Patent Owners Preliminary Response", Case IPR2017-01008, U.S. Pat. No. 9,085,619, dated Jun. 11, 2017, 81 pages.
*Coherus Biosciences Inc.*, Petitioner v. *AbbVie Biotechnology Ltd.*, "Patent Owners Preliminary Response", Case IPR2017-01009, U.S. Pat. No. 9,085,619, dated Jun. 11, 2017, 59 pages.
*Coherus Biosciences Inc.*, Petitioner v. *AbbVie Biotechnology Ltd.*, "Patent Owners Second Updated Mandatory Notice", Case IPR2017-00827, U.S. Pat. No. 9,085,619, dated Mar. 17, 2017 5 pages.

(56) References Cited

OTHER PUBLICATIONS

*Coherus Biosciences Inc.*, Petitioner v. *AbbVie Biotechnology Ltd.*, "Patent Owners Second Updated Mandatory Notices" Case IPR2017-00826, U.S. Pat. No. 9,085,619, dated Mar. 17, 2017, 5 pages.
*Coherus Biosciences Inc.*, Petitioner v. *AbbVie Biotechnology Ltd.*, "Patent Owners Updated Mandatory Notice", Case IPR2017-00827, U.S. Pat. No. 9,085,619, dated Feb. 27, 2017 4 pages.
*Coherus Biosciences Inc.*, Petitioner v. *AbbVie Biotechnology Ltd.*, "Patent Owners Updated Mandatory Notices" Case IPR2017-00826, U.S. Pat. No. 9,085,619, dated Feb. 27, 2017, 4 pages.
*Coherus Biosciences Inc.*, Petitioner v. *AbbVie Biotechnology Ltd.*, "Patent Owners Updated Mandatory Notices" Case IPR2017-01008, U.S. Pat. No. 9,085,619, dated Jun. 11, 2017, 4 pages.
*Coherus Biosciences Inc.*, Petitioner v. *AbbVie Biotechnology Ltd.*, "Patent Owners Updated Mandatory Notices" Case IPR2017-01009, U.S. Pat. No. 9,085,619, dated Jun. 11, 2017, 4 pages.
*Coherus Biosciences Inc.*, Petitioner v. *AbbVie Biotechnology Ltd.*, "Patent Owners Updated Power of Attorney" Case IPR2017-01008, U.S. Pat. No. 9,085,619, dated Jun. 7, 2017, 4 pages.
*Coherus Biosciences Inc.*, Petitioner v. *AbbVie Biotechnology Ltd.*, "Patent Owners Updated Power of Attorney" Case IPR2017-01009, U.S. Pat. No. 9,085,619, dated Jun. 7, 2017, 4 pages.
*Coherus Biosciences Inc.*, Petitioner v. *AbbVie Biotechnology Ltd.*, "Petioners Request for Refund of Post Institution Fees", Case IPR2017-00827, U.S. Pat. No. 9,085,619, dated May 25, 2017 4 pages.
*Coherus Biosciences Inc.*, Petitioner v. *AbbVie Biotechnology Ltd.*, "Petioners Request for Refund of Post Institution Fees", Case IPR2017-01008, U.S. Pat. No. 9,085,619, dated Nov. 29, 2017, 5 pages.
*Coherus Biosciences Inc.*, Petitioner v. *AbbVie Biotechnology Ltd.*, "Petioners Request for Refund of Post Institution Fees", Case IPR2017-01009, U.S. Pat. No. 9,085,619, dated Nov. 29, 2017, 5 pages.
*Coherus Biosciences Inc.*, Petitioner v. *AbbVie Biotechnology Ltd.*, "Petition for Inter Partes Review of U.S. Pat. No. 9,085,619 to U.S.C. §§ 311-319 and 37 C.F.R. § 42", Case IPR2017-01008, U.S. Pat. No. 9,085,619, dated Mar. 2, 2017 81 pages.
*Coherus Biosciences Inc.*, Petitioner v. *AbbVie Biotechnology Ltd.*, "Petition for Inter Partes Review of U.S. Pat. No. 9,085,619 to U.S.C. §§ 311-319 and 37 C.F.R. § 42", Case IPR2017-01009, U.S. Pat. No. 9,085,619, dated Mar. 2, 2017 67 pages.
*Coherus Biosciences Inc.*, Petitioner v. *AbbVie Biotechnology Ltd.*, "Petition for Inter Partes Review," Case IPR2016-01018, U.S. Pat. No. 9,114,166, dated May 9, 2016 (Paper 1).
*Coherus Biosciences Inc.*, Petitioner v. *AbbVie Biotechnology Ltd.*, "Petitioner's Power of Attorney in a Post Grant Proceeding Before the Patent Trial and Appeal Board," Case IPR2016-01018, U.S. Pat. No. 9,114,166, dated May 9, 2016, 2 pages.
*Coherus Biosciences Inc.*, Petitioner v. *AbbVie Biotechnology Ltd.*, "Petitioners for Inter Partes Review of U.S. Pat. No. 9,085,619", Case IPR2017-00827, U.S. Pat. No. 9,085,619, dated Jan. 31, 2017, 79 pages.
*Coherus Biosciences Inc.*, Petitioner v. *AbbVie Biotechnology Ltd.*, "Petitioners for Inter Partes Review of U.S. Pat. No. 9,085,619," Case IPR2017-00826, U.S. Pat. No. 9,085,619, dated Jan. 31, 2017, 63 pages.
*Coherus Biosciences Inc.*, Petitioner v. *AbbVie Biotechnology Ltd.*, "Petitioners Power of Attorney Pursuant to 37 CFR 42.10(b) for Petition for Inter Par Tes Review", Case IPR2017-00826, U.S. Pat. No. 9,085,619, dated Jan. 31, 2017, 2 pages.
*Coherus Biosciences Inc.*, Petitioner v. *AbbVie Biotechnology Ltd.*, "Petitioners Power of Attorney Pursuant to 37 CFR 42.10(b) for Petition for Inter Par Tes Review", Case IPR2017-00827, U.S. Pat. No. 9,085,619, dated Jan. 31, 2017, 2 pages.
*Coherus Biosciences Inc.*, Petitioner v. *AbbVie Biotechnology Ltd.*, "Petitioners Power of Attorney Pursuant to 37 CFR 42.10(b) for Petition for Inter Par Tes Review", Case IPR2017-01008, U.S. Pat. No. 9,085,619, dated Jan. 31, 2017, 2 pages.

*Coherus Biosciences Inc.*, Petitioner v. *AbbVie Biotechnology Ltd.*, "Petitioners Power of Attorney Pursuant to 37 CFR 42.10(b) for Petition for Inter Par Tes Review", Case IPR2017-01009, U.S. Pat. No. 9,085,619, dated Jan. 31, 2017, 2 pages.
*Coherus Biosciences Inc.*, Petitioner v. *AbbVie Biotechnology Ltd.*, "Petitioners Request for Refund of Post-Institution Fees," Case IPR2016-01018, U.S. Pat. No. 9,114,166, dated Mar. 2, 2017, 3 pages.
*Coherus Biosciences Inc.*, Petitioner v. *AbbVie Biotechnology Ltd.*, "Petitioners Request for Refund of Post-Institution Fees," Case IPR2017-00826, U.S. Pat. No. 9,085,619, dated May 25, 2017, 4 pages.
*Coherus Biosciences Inc.*, Petitioner v. *AbbVie Biotechnology Ltd.*, "Petitioners Unopposed Motion to Dismiss Petitions Without Prejudice" Case IPR2017-00826, U.S. Pat. No. 9,085,619, dated Apr. 7, 2017, 4 pages.
*Coherus Biosciences Inc.*, Petitioner v. *AbbVie Biotechnology Ltd.*, "Petitioners Unopposed Motion to Dismiss Petitions Without Prejudice" Case IPR2017-00827, U.S. Pat. No. 9,085,619, dated Apr. 7, 2017, 4 pages.
*Coherus Biosciences Inc.*, Petitioner v. *AbbVie Biotechnology Ltd.*, "Petitioners Updated Mandatory Notices" Case IPR2017-00826, U.S. Pat. No. 9,085,619, dated Mar. 23, 2017, 4 pages.
*Coherus Biosciences Inc.*, Petitioner v. *AbbVie Biotechnology Ltd.*, "Petitioners Updated Mandatory Notices" Case IPR2017-00827, U.S. Pat. No. 9,085,619, dated Mar. 23, 2017, 4 pages.
*Coherus Biosciences Inc.*, Petitioner v. *AbbVie Biotechnology Ltd.*, "Petitioners Updated Mandatory Notices" Case IPR2017-01008, U.S. Pat. No. 9,085,619, dated Mar. 23, 2017, 4 pages.
*Coherus Biosciences Inc.*, Petitioner v. *AbbVie Biotechnology Ltd.*, "Petitioners Updated Mandatory Notices" Case IPR2017-01009, U.S. Pat. No. 9,085,619, dated Mar. 23, 2017, 4 pages.
*Coherus Biosciences Inc.*, Petitioner v. *AbbVie Biotechnology Ltd.*, "Plaintiff Coherus Biosciences, Inc.'s Answer to Defendant Amgen Inc.'s Counterclaims in the U.S. District Court for the District of Delaware," C.A. No. 19-139-RGA, Case IPR2016-01018, U.S. Pat. No. 9,114,166, dated Jun. 24, 2019.
*Coherus Biosciences Inc.*, Petitioner v. *AbbVie Biotechnology Ltd.*, "Plaintiff Coherus Biosciences, Inc.'s First Amended Complaint in the U.S. District Court for the District of Delaware," C.A. No. 19-139-RGA, Case IPR2016-01018, U.S. Pat. No. 9,114,166, dated Mar. 5, 2019.
*Coherus Biosciences Inc.*, Petitioner v. *AbbVie Biotechnology Ltd.*, "Plaintiff Coherus Complaint filed in the U.S. District Court for the District of Delaware," C.A. No. 19-139-RGA, Case IPR2016-01018, U.S. Pat. No. 9,114,166, dated Jan. 24, 2019.
*Coherus Biosciences Inc.*, Petitioner v. *AbbVie Biotechnology Ltd.*, "Request for Rehearing in Inter Partes Review," Case IPR2016-01018, U.S. Pat. No. 9,114,166, dated Dec. 2, 2016 (Paper 11).
*Coherus Biosciences Inc.*, Petitioner v. *AbbVie Biotechnology Ltd.*, "Decision Denying Institution of Inter Partes Review," Case IPR2017-01008, U.S. Pat. No. 9,085,619, dated Sep. 7, 2017, 26 pages.
*Coherus Biosciences Inc.*, Petitioner v. *AbbVie Biotechnology Ltd.*, Patent Owner, "Decision Denying Institution of Inter Partes Review 37 C.F.R. § 42.108", filed Sep. 7, 2017, 25 pages. [Case IPR2017-00822, U.S. Pat. No. 9,085,619].
*Coherus Biosciences Inc.*, Petitioner v. *AbbVie Biotechnology Ltd.*, Patent Owner, "Decision Denying Institution of Inter Partes Review 37 C.F.R. § 42.108," filed Sep. 7, 2017, 16 pages. [Case IPR2017-00823, U.S. Pat. No. 9,085,619].
*Coherus Biosciences Inc.*, Petitioner v. *AbbVie Biotechnology Ltd.*, Patent Owner, "Declaration of Klaus-Peter Radtke, Ph.D.", dated Apr. 3, 2017, 95 pages. [Case IPR2017-00822, U.S. Pat. No. 9,085,619].
*Coherus Biosciences Inc.*, Petitioner v. *AbbVie Biotechnology Ltd.*, Patent Owner, "Declaration of Klaus-Peter Radtke, Ph.D.", dated Apr. 3, 2017, 99 pages. [Case IPR2017-00823, U.S. Pat. No. 9,085,619].
*Coherus Biosciences Inc.*, Petitioner v. *AbbVie Biotechnology Ltd.*, Patent Owner, "Declaration of Klaus-Peter Radtke, Ph.D.", dated Jan. 30, 2016, 95 pages. [Case IPR2017-00822, U.S. Pat. No. 9,085,619].

(56) References Cited

OTHER PUBLICATIONS

*Coherus Biosciences Inc.*, Petitioner v. *AbbVie Biotechnology Ltd.*, Patent Owner, "Declaration of Klaus-Peter Radtke, Ph.D.", dated Jan. 30, 2017, 99 pages. [Case IPR2017-00823, U.S. Pat. No. 9,085,619].
*Coherus Biosciences Inc.*, Petitioner v. *AbbVie Biotechnology Ltd.*, Patent Owner, "Declaration of Mark C. Manning, Ph.D.", dated May 6, 2016, 163 pages. [Case IPR2017-00822, U.S. Pat. No. 9,085,619].
*Coherus Biosciences Inc.*, Petitioner v. *AbbVie Biotechnology Ltd.*, Patent Owner, "Notice of Filing Date Accorded to Petition and Time for Filing Patent Owner Preliminary Response," Case IPR2017-00822, U.S. Pat. No. 9,085,619, dated Feb. 24, 2017, 5 pages.
*Coherus Biosciences Inc.*, Petitioner v. *AbbVie Biotechnology Ltd.*, Patent Owner, "Notice of Filing Date Accorded to Petition and Time for Filing Patent Owner Preliminary Response," Case IPR2017-00823, U.S. Pat. No. 9,085,619, dated Feb. 24, 2017, 5 pages.
*Coherus Biosciences Inc.*, Petitioner v. *AbbVie Biotechnology Ltd.*, Patent Owner, "Notice of Refund," Case IPR2017-00822, U.S. Pat. No. 9,085,619, dated Dec. 1, 2017, 2 pages.
*Coherus Biosciences Inc.*, Petitioner v. *AbbVie Biotechnology Ltd.*, Patent Owner, "Notice of Refund," Case IPR2017-00823, U.S. Pat. No. 9,085,619, dated Dec. 1, 2017, 2 pages.
*Coherus Biosciences Inc.*, Petitioner v. *AbbVie Biotechnology Ltd.*, Patent Owner, "Order Conduct of the Proceeding 37 C.F.R. § 42.5", filed Apr. 7, 2017, 6 pages. [Case IPR2017-00822, Case IPR2017-00823, Case IPR2017-00826, Case IPR2017-00827, Case IPR2017-01008, Case IPR2017-01009 U.S. Pat. No. 9,085,619].
*Coherus Biosciences Inc.*, Petitioner v. *AbbVie Biotechnology Ltd.*, Patent Owner, "Patent Owner's Preliminary Response", filed Jun. 11, 2017, 58 pages. [Case IPR2017-00822, U.S. Pat. No. 9,085,619].
*Coherus Biosciences Inc.*, Petitioner v. *AbbVie Biotechnology Ltd.*, Patent Owner, "Patent Owner's Preliminary Response," Case IPR2016-01018, U.S. Pat. No. 9,114,166, dated Aug. 9, 2016, 77 pages.
*Coherus Biosciences Inc.*, Petitioner v. *AbbVie Biotechnology Ltd.*, Patent Owner, "Patent Owner's Mandatory Notices," Case IPR2017-00822, U.S. Pat. No. 9,085,619, dated Feb. 21, 2017, 6 pages.
*Coherus Biosciences Inc.*, Petitioner v. *AbbVie Biotechnology Ltd.*, Patent Owner, "Patent Owner's Mandatory Notices," Case IPR2017-00823, U.S. Pat. No. 9,085,619, dated Feb. 21, 2017, 6 pages.
*Coherus Biosciences Inc.*, Petitioner v. *AbbVie Biotechnology Ltd.*, Patent Owner, "Patent Owner's Power of Attorney," Case IPR2017-00822, U.S. Pat. No. 9,085,619, dated Feb. 21, 2017, 2 pages.
*Coherus Biosciences Inc.*, Petitioner v. *AbbVie Biotechnology Ltd.*, Patent Owner, "Patent Owner's Power of Attorney," Case IPR2017-00823, U.S. Pat. No. 9,085,619, dated Feb. 21, 2017, 2 pages.
*Coherus Biosciences Inc.*, Petitioner v. *AbbVie Biotechnology Ltd.*, Patent Owner, "Patent Owner's Preliminary Response," filed Jun. 11, 2017, 48 pages. [Case IPR2017-00823, U.S. Pat. No. 9,085,619].
*Coherus Biosciences Inc.*, Petitioner v. *AbbVie Biotechnology Ltd.*, Patent Owner, "Patent Owner's Second Updated Mandatory Notices," Case IPR2017-00823, U.S. Pat. No. 9,085,619, dated Mar. 17, 2017, 5 pages.
*Coherus Biosciences Inc.*, Petitioner v. *AbbVie Biotechnology Ltd.*, Patent Owner, "Patent Owner's Updated Mandatory Notices," Case IPR2017-00822, U.S. Pat. No. 9,085,619, dated Mar. 23, 2017, 4 pages.
*Coherus Biosciences Inc.*, Petitioner v. *AbbVie Biotechnology Ltd.*, Patent Owner, "Patent Owner's Updated Mandatory Notices," Case IPR2017-00823, U.S. Pat. No. 9,085,619, dated Feb. 27, 2017, 4 pages.
*Coherus Biosciences Inc.*, Petitioner v. *AbbVie Biotechnology Ltd.*, Patent Owner, Petition for Inter Partes Review of U.S. Pat. No. 9,085,619 Pursuant to 35 U.S.C. §§ 311-319 and 37 C.F.R. § 42, Jan. 31, 2017, 57 pages. [Case IPR2017-00822, U.S. Pat. No. 9,085,619].
*Coherus Biosciences Inc.*, Petitioner v. *AbbVie Biotechnology Ltd.*, Patent Owner, "Petition for Inter Partes Review of U.S. Pat. No. 9,085,619 Pursuant to 35 U.S.C. §§ 311-319 and 37 C.F.R. § 42," Jan. 31, 2017, 64 pages. [Case IPR2017-00823, U.S. Pat. No. 9,085,619].

*Coherus Biosciences Inc.*, Petitioner v. *AbbVie Biotechnology Ltd.*, Patent Owner, "Petitioner's Power of Attorney Pursuant to CFR 42.10(b) for Petition for Inter Partes Review," Case IPR2017-00822, U.S. Pat. No. 9,085,619, dated Jan. 31, 2017, 2 Pages.
*Coherus Biosciences Inc.*, Petitioner v. *AbbVie Biotechnology Ltd.*, Patent Owner, "Petitioner's Power of Attorney Pursuant to CFR 42.10(b) for Petition for Inter Partes Review," Case IPR2017-00823, U.S. Pat. No. 9,085,619, dated Jan. 31, 2017, 2 Pages.
*Coherus Biosciences Inc.*, Petitioner v. *AbbVie Biotechnology Ltd.*, Patent Owner, "Petitioner's Request for Refund of Post-Institution Fee No. 2," Case IPR2017-00822, U.S. Pat. No. 9,085,619, dated Nov. 29, 2017, 5 pages.
*Coherus Biosciences Inc.*, Petitioner v. *AbbVie Biotechnology Ltd.*, Patent Owner, "Petitioner's Request for Refund of Post-Institution Fee," Case IPR2017-00822, U.S. Pat. No. 9,085,619, dated Nov. 29, 2017, 5 pages.
*Coherus Biosciences Inc.*, Petitioner v. *AbbVie Biotechnology Ltd.*, Patent Owner, "Petitioner's Request for Refund of Post-Institution Fee," Case IPR2017-00823, U.S. Pat. No. 9,085,619, dated Nov. 29, 2017, 5 pages.
*Coherus Biosciences Inc.*, Petitioner v. *AbbVie Biotechnology Ltd.*, Patent Owner, "Petitioner's Updated Mandatory Notices," Case IPR2017-00823, U.S. Pat. No. 9,085,619, dated Mar. 23, 2017, 4 pages.
*Coherus Biosciences Inc.*, Petitioner v. *AbbVie Biotechnology Ltd.*, Patent Owner, "Replacement Petition for Inter Partes Review of U.S. Pat. No. 9,085,619 Pursuant to 35 U.S.C. §§ 311-319 and 37 C.F.R. § 42", filed Apr. 10, 2017, 58 pages. [Case IPR2017-00822, U.S. Pat. No. 9,085,619].
*Coherus Biosciences Inc.*, Petitioner v. *AbbVie Biotechnology Ltd.*, Patent Owner, "Replacement Petition for Inter Partes Review of U.S. Pat. No. 9,085,619 Pursuant to 35 U.S.C. §§ 311-319 and 37 C.F.R. § 42," Apr. 10, 2017, 65 pages. [Case IPR2017-00823, U.S. Pat. No. 9,085,619].
*Coherus Biosciences Inc.*, Petitioner v. *AbbVie Biotechnology Ltd.*, Patent Owner, "Declaration of Mark C. Manning, Ph.D.," Exhibit 1002 filed with Petition for Inter Partes Review of U.S. Pat. No. 9,114,166, filed May 6, 2016, 163 pages.
*Coherus Biosciences Inc.*, Petitioner v. *AbbVie Biotechnology Ltd.*, Patent Owner. "Patent Owner's Second Updated Mandatory Notices," Case IPR2017-00822, U.S. Pat. No. 9,085,619, dated Mar. 17, 2017, 5 pages.
*Coherus Biosciences Inc.*, Petitioner v. *AbbVie Biotechnology Ltd.*, Patent Owner. "Patent Owner's Updated Mandatory Notices," Case IPR2017-00822, U.S. Pat. No. 9,085,619, dated Feb. 27, 2017, 4 pages.
*Coherus Biosciences Inc.*, Petitioner v. *AbbVie Biotechnology Ltd.*, Patent Owner. "Patent Owner's Updated Mandatory Notices," Case IPR2017-00822, U.S. Pat. No. 9,085,619, dated Jun. 11, 2017, 4 pages.
*Coherus Biosciences Inc.*, Petitioner v. *AbbVie Biotechnology Ltd.*, Patent Owner. "Patent Owner's Updated Power of Attorney," Case IPR2017-00822, U.S. Pat. No. 9,085,619, dated Jun. 7, 2017, 4 pages.
Coherus Biosciences, Inc., Third Amended and Restated Investor Rights Agreement, May 9, 2014, 68 pages.
Communication from Elkington and Fife LLP regarding European Patent Application No. 12481765.6, 2015, 3 pages.
CVS/Caremark™ Performance Drug List, Oct. 2015, 10 pages.
D82 from Opposition of EP 1528933, Filed by AbbVie on Feb. 26, 2016 (CAS Registry for Adalimumab), 6 pages.
Daughertry and Mrsny, Formulation and Delivery Issues for Monoclonal Antibody Therapeutics, Advanced Drug Delivery Reviews, 2006, 58: 686-706.
Decision in Opposition Proceedings Revoking EP 1528933 B1, Sep. 9, 2015.
Dobrow, "DTC Report—DTC Gets Smart", Medical Marketing & Media, URL <http://www.mmm-online.com/dtc-report-dtc-gets-smart/printarticle/339357/>, retrieved on Apr. 1, 2014, 5 pages.
Dobrow, "MM&M 2014 Large Pharma Marketing Team of the Year: HUMIRA", Medical Marketing & Media, URL <http://www.mmm-online.com/mmm-2014-large-pharma-marketing-team-of-the-year-humira.htm>, retrieved on Jan. 1, 2014, 2 pages.

(56) References Cited

OTHER PUBLICATIONS

Dominican Office Action in Application No. P2015-0051, dated Dec. 4, 2019, 9 pages.
DrugBank: Adalimumab. www.drugbank.ca/drugs/DB00051, Last Visited May 5, 2016, 15 pages.
Employee Profiles, Legacy BioDesign LLC Webpage, 2 pages, 2019.
Enbrel (etanercept), "FDA Arthritis Advisory Committee", Aug. 17, 2001, Immunex Corporation and Wyeth-Ayerst Laboratories, 55 pages.
Esbenshade et al., "Pharmacological and behavioral properties of A-349821, a selective and potent human histamine H3 receptor antagonist", Biochemical Pharmacology. 68 (5): 933-945, 2004.
Ewert et al., "Biophysical Properties of Human Antibody Variable Domains", J. Mo. Biol., 2003, 325: 521-553.
Exhibit D filed with Coherus Complaint filed in the U.S. District Court for the District of Delaware, C.A. No. 19-139 (RGA) dated Jan. 24, 2019, 13 pages.
Exhibit D filed with Plaintiff Coherus Biosciences, Inc.'s First Amended Complaint in the U.S. District Court for the District of Delaware, C.A. No. 19-139 (RGA) dated Mar. 5, 2019, 78 pages.
Exhibit E filed with Coherus Complaint filed in the U.S. District Court for the District of Delaware, C.A. No. 19-139 (RGA) dated Jan. 24, 2019, 121 pages.
Exhibit E filed with Plaintiff Coherus Biosciences, Inc.'s First Amended Complaint in the U.S. District Court for the District of Delaware, C.A. No. 19-139 (RGA) dated Mar. 5, 2019, 13 pages.
Exhibit F filed with Plaintiff Coherus Biosciences, Inc.'s First Amended Complaint in the U.S. District Court for the District of Delaware, C.A. No. 19-139 (RGA) dated Mar. 5, 2019, 121 pages.
Exhibit G filed with Plaintiff Coherus Biosciences, Inc.'s First Amended Complaint in the U.S. District Court for the District of Delaware, C.A. No. 19-139 (RGA) dated Mar. 5, 2019, 112 pages.
Falconer et al., "Stabilization of a monoclonal antibody during purification and formulation by addition of basic amino acid excipients", J Chem Technol. Biotechnol., 86, 942-948, 2011.
Fayos et al., "On the Origin of the Thermostabilization of Proteins Induced by Sodium Phosphate," JACS Communications dated Mar. 3, 2005, 2 pages.
FDA, What are "Biologics" Questions and Answers (Feb. 6, 2018, https://www.fda.gov/about-fda/center-biologics-evaluation-and-research-cber/what-are-biologics-questions-and-answers, 1 page.
fda.gov [online], "Privigen®, Immune Globulin Intravenous (Human), 10% Liquid Initial," U.S. Approval: 2007, Retrieved from: https://www.fda.gov/files/vaccines%2C%20blood%20%26%20biologics/published/Package-Insert---Privigen.pdf, 7 pages.
Frokjaer et al., eds., Pharmaceutical Formulation Development of Peptides and Proteins, Taylor & Francis: London, 2000.
Gatlin et al., "Formulation and Administration Techniques to Minimize Injection Pain and Tissue Damage Associated with Parenteral Products", Injectable Drug Development: Techniques to Reduce Pain and Irritation, pp. 401-425, 1999.
Gebhart, "Biotech company preparing several drugs for takeoff", Drug Topics, vol. 145, No. 5, p. 50, 2001.
Gelfand, "Differences between IGIV products: Impact on clinical outcome", International Immunopharmacology 6, 592-599, 2006.
Gennaro, ed., Remington: The Science and Practice of Pharmacy, 20th ed., Solutes, 785-786, 2000.
Goolcharran et al., "The Effects of a Histidine Residue on the C-Terminal Side of an Asparaginyl Residue on the Rate of Deamidation Using Model Pentapeptides", J. of Pharmaceutical Sciences, vol. 89, Issue 6, 818-825, 2000.
Gottlieb et al., "Efficacy and Safety of Anti-TNF-Agents in Psoriasis", Anti-TNF-Therapies in the Treatment of Dermatologic Diseases, Skin & Allergy News, 11 pages, 2005.
Gura, "The Art of Entrepreneurship", Science Translational Medicine, vol. 346 Issue 6213, p. 1146, Nov. 27, 2014.
Ha et al., "Peroxide Formation in Polysorbate 80 and Protein Stability", J. Pharm. Sci., 2002, 91: 2252-2264.

Hanna, K., "Tolerability of a New Intravenous Immunoglobulin Preparation (IGIV) in Pediatric and Adult Patients", Presented at the 60th Anniversary Meeting of the American Academy of Allergy, Asthma & Immunology, Mar. 10, 2003, J. Allergy Clinical Immunology, vol. III, No. 2, Part 2, a631, 2 pages.
Helms et al., "Destabilizing loop swaps in the CDRs of an immunoglobulin VL domain," Protein Science, dated Aug. 3, 1995, 9 pages.
Hendrickson, Birth of a Blockbuster: Abbott Mounts Humira's Marketing Campaign, Boston Business Journal Article (Oct. 20, 2003), Last Accessed Mar. 25, 2016.
HepaGam B™, Summar Basis for Approval, Jan. 2006, 12 pages.
HUMIRA® Label, Nov. 2015.
HumiraTM (adalimumab) pamphlet, Dec. 20, 2002.
Humphreys, Top 200 Medicines—Special Report, pharmalive.com, URL <http://www.pharmalive.com/special-report-top-200-medicines/> 5 pages, 2015.
Indian Office Action in Application No. 806/KOLNP/2015, dated Nov. 15, 2019, 6 pages.
International Search Report and Written Opinion for corresponding PCT Application No. PCT/US2017/028663, dated Sep. 5, 2017, 11 pages.
Japanese Office Action in Application No. 2018-244382, dated Jan. 14, 2020, English Translation, 5 pages.
Jones, "Analysis of polypeptides and proteins", Adv. Drug Delivery Rev. 10: 29-90, 1993.
Jorgensen et al., "Pain Assessment of Subcutaneous Injections", Ann. Pharma., 30(7/8), 729-732, 1996.
Kamerzell et al., Increasing IgG Concentration Modulates the Conformational Heterogeneity and Bonding Network that Influence Solution Properties, J. Phys. Chem. B, 113, dated Mar. 6, 2009, 10 pages.
Katdare et al., "Excipient Development for Pharmaceutical, Biotechnology, and Drug Delivery Systems," Taylor & Francis Group, LLC, year 2006, 43 pages.
Kempeni, "Preliminary results of early clinical trials with the fully human anti-TNFa monoclonal antibody D2E7", Ann Rheum Dis, 58:(Suppl I), I70-I72, 1999.
Keystone et al., "Golimumab, a human antibody to tumour necrosis factor a given by monthly subcutaneous injections, in active rheumatoid arthritis despite methotrexate therapy: the GO-FORWARD Study", Ann, Rheum, Dis., 2009, 68: 789-796.
Keystone et al., "The Fully Human Anti-TNF Monoclonal Antibody, Adalimumab (D2E7), Dose Ranging Study: The 24-Week Clinical Results in Patients with Active RA on Methotrexate Therapy (The Armada Trial)", Annu. Eur. Congr. Rheumatol., Abstract OP0086, Jun. 13-16, 2001.
King, "The Best Selling Drugs of All Time, Humira Joins the Elite", Forbes, Jan. 28, 2013, 4 pages.
Krishnamurthy et al., "The Stability Factor: Importance in Formulation Development", Curr. Pharm. Biotech, 3, 361-371, 2002.
Krishnan et al., "Development of Formulations for Therapeutic Monoclonal Antibodies and Fc Fusion Proteins", Formulation and Process Development Strategies for Manufacturing Biopharmaceuticals, 2010, 383-427.
Levine et al., "The Use of Surface Tension Measurements in the Design of Antibody-Based Product Formulations", J. Parenteral Sci. & Tech., 45(3), 160-165, May/Jun. 1991.
Liu et al., "Reversible Self-Association Increases the Vicosity of a Concentrated Monoclonal Antibody in Aqueous Solution," published online in Wiley InterScience, dated Feb. 2005, 13 pages.
Lorenz, "Technology evaluation: Adalimumab, Abbott Laboratories", Current Opinion in Molecular Therapeutics, 4(2), 185-190, 2002.
Manning et al., "Stability of Protein Pharmaceuticals", PharmRes., 6(11), 903-918, 1989.
Matteson et al., "Treatment of active refractory rheumatoid arthritis with humanized monoclonal antibody CAMPATH-1H administered by daily subcutaneous injection, Arthritis & Rheumatism", 1995, 38(9): 1187-1193.
McDonnell, "Production of Antibodies in Hybridoma and Non-hybridoma Cell Lines", ch. 3 in Animal Cell Culture, Cell Engineering 9, 65-88, (ed. M. Al-Rubeai, 2015).

(56) References Cited

OTHER PUBLICATIONS

Meadows and Hollowell, "Off-label' drug use: an FDA regulatory term, not a negative implication of its medical use", Intnl. J. Inpotence Research, 20: 135-144, 2008.

Mezzasalma et al., "Enhancing Recombinant Protein Quality and Yield by Protein Stability Profiling," Journal of Biomolecular Screening 12(3); year 2007, 11 pages.

Nabuchi et al., "The Stability and Degradation Pathway of Recombinant Human Parathyroid Hormone: Deamidation of Asparaginyl Residue and Peptide Bond Cleavage at Aspartyl and Asparaginyl Residues", Pharmaceutical Research, vol. 14 Issue 12, 1685-1690, 1997.

Nail et al., "Development and Manufacture of Protein Pharmaceuticals," Kluwer Academic I Plenum Publishers, year 2002, 82 pages.

Nema et al., "Excipients and Their Use in Injectable Products", FDA J. Pharm. Sci. & Tech, 51(4), 166-171, Jul./Aug. 1997.

Olthuis et al., "Characterization of Proteins by Means of their Buffer Capacity, Measured With and ISFET-Based Coulometric Sensor-Actuator System," Biosensors & Bioelectronics, Year 1994, 9 pages.

Patel et al., "Chemical Pathways of Peptide Degradation. II. Kinetics of Deamidation of an Asparaginyl Residue in a Model Hexapeptide", Pharmaceutical Research, vol. 7, Issue 7, 703-711, 1990.

Patent Term Extension Application Salfeld '382 Patent filed with Petition for Inter Partes Review of U.S. Pat. No. 9,114,166, filed May 9, 2019, 2 pages.

Perkins et al., "Determination of the Origin of Charge Heterogeneity in a Murine Monoclonal Antibody", Pharmaceutical Research, vol. 17, Issue 9, 1110-1117, 2000.

Phillips et al., "Manufacture and quality control of CAMPATH-1 antibodies for clinical trials", Cytotherapy, 2001, 3(3): 233-242.

Physicians' Desk Reference entry for GAMIMUNE N, 5%, pp. 925-928, 56th edition, 2002, 6 pages.

Physicians' Desk Reference entry for GAMUNEX, pp. 872-876, 59th edition, 2005.

Physicians' Desk Reference, 56th ed., pp. 558-559, 914-931, 805-807, 2026-2028, 2295-2297, 2524-2525, 33 pages, 2002.

Physicians' Desk Reference, 58th edition, pp. 470-474, Humira Label 2003, 2004.

Physicians' Desk Reference, 56th ed., 2002, pp. 1178-1182.
Physicians' Desk Reference, 56th ed., 2002, pp. 1414-1417.
Physicians' Desk Reference, 56th ed., 2002, pp. 1428-1430, 1750-1752.
Physicians' Desk Reference, 56th ed., 2002, pp. 1958-1962.
Physicians' Desk Reference, 56th ed., 2002, pp. 2028-2029.
Physicians' Desk Reference, 56th ed., 2002, pp. 2297-2299.
Physicians' Desk Reference, 56th ed., 2002, pp. 2399-2401.
Physicians' Desk Reference, 56th ed., 2002, pp. 2498-2502.
Physicians' Desk Reference, 56th ed., 2002, pp. 3046-3047.
Physicians' Desk Reference, 56th ed., 2002, pp. 992-995.
Physicians' Desk Reference, 56th ed., pp. 582-592, 988-991, 1434-1437, 1752-1760, 1772-1774, 1930-1934, 2502-2507, 3140-3142, (2002).

Physicians' Desk Reference, 56th ed., pp. 914-915, 917-919, 925-931, 992-995, 1178-1182, 1414-1417, 1428-1430, 1752-1755, 1958-1962, 2028-2029, 2295-2297, 2498-2052, 3046-3047 (2002).

Physicians' Desk Reference, 56th ed., pp. 925-928, 2002.
Physicians' Desk Reference, 56th ed., Suppl. A, pp. A4-A9, (2002).
Physicians' Desk Reference, 57th ed., Suppl. A, pp. A64-A67, A84-A88, (2003).

Preliminary Ruling in Opposition Proceedings Revoking EP 1528933 B1, Oct. 22, 2014.

Press Release, "Amgen and Immunomedics Announce Emphasis on Development of AMG 412 (Epratuzumab) as Combination Therapy While Closing Single Agent Trial", PRNewswire-FirstCall, Jan. 2003, 2 pages.

PRIVIGEN® Label, Oct. 2016, 7 pages.

Prosecution History of U.S. Appl. No. 15/799,851 Reply to Final Office Action, filed Sep. 18, 2018, 102 pages.

Prosecution History of U.S. Appl. No. 15/799,851, Notice of Allowance, dated Oct. 18, 2018, 7 pages.

Q1 2016 Coherus Biosciences Earnings Call, May 9, 2016, 13 pages.

Raibekas et al., "Anion Binding and Controlled Aggregation of Human Interleukin-1 Receptor Antagonist," Biochemistry, 44, dated May 15, 2005, 9 pages.

Rau et al. in Annals of Rheumatic Diseases, XIV European League Against Rheumatism Congress, 1999, Abstract 907, "Effective Combination of the Fully Human Anti-TNF Antibody D2E7 and Methotrexate in Active Rheumatoid Arthritis," p. 217.

Rau et al., "Long-Term Efficacy and Tolerability of Multiple I.V. Doses of the Fully Human Anti-TNF-Antibody D2E7 in Patients with Rheumatoid Arthritis", Arthritis Rheum., 41(9), S55, Sep. 1998.

Richard Gonzalez, PowerPoint by AbbVie CEO, "AbbVie Long-Term Strategy," Oct. 30, 2015, 33 pages.

Ritzel et al., "Pharmacokinetic, insulinotropic, and glucagonostatic properties of GLP-1 [7-36 amide] after subcutaneous injection in healthy volunteers. Dose-response relationships", Diabetologia, 1995, 38: 720-725.

Rouet et al., "Stability engineering of the human antibody repertoire," FEBS Letters 588, dated Nov. 28, 2013, 9 pages.

Ruiz et al., "Aggregation of Recombinant Human Interferon Alpha 2b in Solution: Technical Note," AAPS PharmSciTech; 7 (4) Article 99, dated Dec. 22, 2006, 5 pages.

Santora et al, "Characterization of Recombinant human Monoclonal Tissue Necrosis Factor-a Antibody Using Cation-Exchange HPLC and Capillary Isoelectric Focusing", Analytic Biochem, 275, 98-108, 1999.

Schattenkirchner et al., "Efficacy and Tolerability of Weekly Subcutaneous Injections of the Fully Human Anti-TNF Antibody D2E7 in Patients with Rheumatoid Arthritis—Results of a Phase I Study", Arthritis Rheum., 41(9), S57, Sep. 1998.

Schein, "Solubility as a Function of Protein Structure and Solvent Components", BioTechnology 8, 308-317, Apr. 1990.

Schwartz, "Diafiltration for Desalting or Buffer Exchange", BioPress, 6 pages, 2003.

Schwartzman et al., "Does route of administration affect the outcome of TNF antagonist therapy?", Arthritis Research and Therapy, 6(Suppl. 2): S19-S23, 2004.

Scotchler et al., "Deamidation of Glutaminyl Residues: Dependence on pH, Temperature, and Ionic Strength, Analytical Biochemistry", 59, 319-322, 1974.

Seeking Alpha, "Coherus Biosciences: The Biosimilar Market is Enormous and This Company is Well Positioned," Dec. 29, 2014, 7 pages.

Serebrov M., "Wait Continues as New Market Teeters on Bring of Explosion," BioWorld: Thomson Reuters, dated May 3, 2016, 21 pages.

Shire, S. J., "Monoclonal Antibodies," Woodhead Publishing Series in Biomedicine: No. 77, year 2015, 219 pages.

Sorbera et al., "Adalimumab", Drugs Fut., 26(7), 639-646, 2001.

Stites et al., "Immunoglobulins & Immunoglobulin Genes," Medical Immunology: 9th Edition, year 1997, 22 pages.

Supplemental Amendment and Response, filed Feb. 13, 2012 in U.S. Prosecution History of U.S. Appl. No. 10/525,292 (U.S. Pat. No. 8,216,583), 13 pages.

Timmerman, "Abbot's Humira the 3rd-in-Class Drug that toppled Lipitor as No. 1", Xconomy, Apr. 16, 2012, 6 pages.

Treuheit et al., "Inverse Relationship of Protein Concentration and Aggregation", Pharm. Res., 2002, 19(4): 511-516.

Tsourounis, "Biologic therapies for the treatment of chronic plaque psoriasis", Formulary, 40: 184-199, 2005.

U.S. Prosecution History of U.S. Appl. No. 12/325,049, (U.S. Pat. No. 8,420,081), 2482 pages, filed Nov. 28, 2008.

U.S. Prosecution History of U.S. Appl. No. 13/774,735 (U.S. Pat. No. 8,883,146), 1215 pages, filed Feb. 22, 2013.

U.S. Prosecution History of U.S. Appl. No. 14/506,576 (U.S. Pat. No. 9,085,619), 489 pages, filed Oct. 3, 2014.

U.S. Prosecution History of U.S. Appl. No. 14/558,182 (U.S. Pat. No. 9,114,166), filed Dec. 2, 2014, 721 pages.

(56) References Cited

OTHER PUBLICATIONS

U.S. Prosecution History of U.S. Appl. No. 61/004,992, 237 pages, filed Nov. 30, 2007.
U.S. Prosecution History of U.S. Appl. No. 10/222,140, 109 pages, filed Aug. 19, 2002.
U.S. Prosecution History of U.S. Appl. No. 13/654,795, 6 pages 2015.
U.S. Prosecution History of U.S. Appl. No. 13/654,950 (U.S. Pat. No. 9,302,002), 7 pages, 2014.
U.S. Prosecution History of U.S. Appl. No. 14/020,733, 10 pages, 2015.
U.S. Prosecution History of U.S. Appl. No. 14/643,844 (U.S. Pat. No. 9,340,611), 7 pages, 2015.
United Healthcare 2015 Four-Tier Prescription Drug List, Jul. 2015, 35 pages.
United States Pharmacopeia and National Formulary (USP 24-NF 19). vol 2. Rockville, MD: United States Pharmacopeia Convention; 1999: 1971-1977, 2011-2021, 2404-2406.
USPTO Certified Priority Document PCT/US2006/022599 for U.S. Appl. No. 60/690,582, filed Jun. 14, 2005, 18 pages.
Van de Putte et al., "A Single Dose Placebo Controlled Phase I Study of the Fully Human Anti-TNF Antibody D2E7 in Patients with Rheumatoid Arthritis", Arthritis Rheum., 41(9), S57, Sep. 1998.
Van de Putte et al., "Efficacy of the Fully Human Anti-TNF Antibody D2E7 in Rheumatoid Arthritis. I.", Arthritis Rheum., 42(9), S400, Sep. 1999.
Van de Putte et al., "Six Month Efficacy of the Fully Human Anti-TNF Antibody D2E7 in Rheumatoid Arthritis", Annals of the Rheumatic Diseases, 59:(Suppl 1), Op.056, 2000.
Vincent Lee, "Peptide and Protein Drug Deliveiy", 247-301, Marcel Dekker, New York, N.Y., 1991.
Wang, "Instability, stabilization, and formulation of liquid protein pharmaceuticals", Int. J. Pharma., 185, 129-188, 1999.
Weaver, "Abbott Drug Unit Embarks on New Life Without Parent", The Wall Street Journal, Jan. 2, 2013.
Wright et al., "Nonenzymatic Deamidation of Asparaginyl and Glutaminyl Residues in Protein", Critical Reviews in Biochemistry and Molecular Biology, 26:1, 1-52, 1991.
Yim, "Summary Review for Regulatory Action," Division of Pulmonary, Allergy, and Rheumatology Products (DPARP), of Humira, 2015, 13 pages.
Zhang et al., "Comparative Study on Kinetics of Nonenzymatic Deamidation of Soy Protein and Egg White Lysozyme," J. Agric. Food Chem., 41, 2286-2290, 1993.
Zymewire Blog, Coherus Biosciences' Outsourcing Strategy, Sep. 28, 2014, 3 pages.
Bender et al., "Alternative buffers for pharmaceutical anti-TNF alpha monoclonal antibody formulations [Elektronische Ressource], PAPDEOTTOO, Feb. 6, 2013 (Feb. 6, 2013), Opp, XP009188701, 10 Pages.
Amgen Inc Translation of Statement of Opposition Against IL 237583, 17 pages, filed Apr. 28, 2021.
Andrick et al., "Predicting Hemagglutinin MHC-II Ligand Analogues in Anti-TNFα Biologies: Implications for Immunogenicity of Pharmaceutical Proteins" PLoS One, 10(8): e0135451, Aug. 13, 2015.
Baker et al., "Immunogenicity of protein therapeutics: The key causes, consequences and challenges" Self Nonself, 1(4):314-322, Oct. 1, 2010.
Bender et al., "Immunogenicity, efficacy and adverse events of adalimumab in RA patients" Rheumatology international, 27(3):269-274, Jan. 1, 2007.
Bessa et al., "The immunogenicity of antibody aggregates in a novel transgenic mouse model" Pharmaceutical Research, 32(7):2344-2359, Jul. 1, 2015.
Bi et al., "Development of a human antibody tolerant mouse model to assess the immunogenicity risk due to aggregated biotherapeutics" Journal of pharmaceutical sciences, Oct. 1, 2013, 102(10):3545-3555.

Brinks et al., "Immunogenicity of Therapeutic Proteins: The Use of Animal Models" Pharmaceutical research, 28(10): 2379-2385, Oct. 1, 2011.
Brinks et al., "Preclinical models used for immunogenicity prediction of therapeutic proteins" Pharmaceutical research, 30(7):1719-1728, Jul. 1, 2013.
Europeanpharmaceuticalreview.com, [online] "Breaking Old Habits: Moving Away From Commonly Used Buffers in Pharmaceuticals" retrieved on Jun. 4, 2021, retrieved from URL<https://www.europeanpharmaceuticalreview.com/article/13699/breaking-old-habits-moving-away-from-commonly-used-buffers-in-pharmaceuticals/>, 6 pages, Jul. 10, 2012.
Excipient development for pharmaceutical, biotechnology, and drug delivery systems, Chapter 17, 41 pages, Jan. 1, 2006.
Frederiksen et al., "Antibodies Against Infliximab Are Associated with De Novo Development of Antibodies to Adalimumab and Therapeutic Failure in Infliximab-to-Adalimumab Switchers with IBP" Inflammatory bowel diseases, 20(10):1714-1721, Oct. 1, 2014.
Frenken et al., "Identification of the component part in an epoetin alfa preparation that causes pain after subcutaneous injection" American journal of kidney diseases, 22(4):553-556 Oct. 1, 1993.
Garces et al., "The immunogenicity of anti-TNF therapy in immune-mediated inflammatory diseases: a systematic review of the literature with a meta-analysis" Annals of the rheumatic diseases, 72(12):1947-1955, Dec. 1, 2013.
Homann et al., "B cell epitopes on infliximab identified by oligopeptide microarray with unprocessed patient sera" Journal of translational medicine, 13(1):1-10, Dec. 2015.
HUMIRA, Medication package insert of Dec. 2011.
Jaber et al., "Assessment of the immunogenicity of different interferon beta-1a formulations using ex vivo T-cell assays" Journal of pharmaceutical and biomedical analysis, 43(4):1256-1261, Mar. 12, 2007.
Jawa et al., "T-cell dependent immunogenicity of protein therapeutics: Preclinical assessment and mitigation" Clinical immunology, Dec. 1, 2013, 149(3):534-555.
Jiskoot et al., "Mouse Models for Assessing Protein Immunogenicity: Lessons and Challenges" J Pharm Sci., 105(5):19 Pages, May 1, 2016.
Johnson et al., "Models for evaluation of relative immunogenic potential of protein particles in biopharmaceutical protein formulations" Journal of pharmaceutical sciences, 101(10): 7 Pages, Oct. 1, 2012.
Joubert et al., "Highly aggregated antibody therapeutics can enhance the in vitro innate and late-stage T-cell immune responses" Journal of Biological Chemistry, 287(30): 15 Pages, Jul. 20, 2012.
Kuriakose et al., "Immunogenicity of Biotherapeutics: Causes and Association with Posttranslational Modifications." Journal of Immunology Research., 1298473, 18 pages, Oct. 2016.
Radstake et al., "Formation of antibodies against infliximab and adalimumab strongly correlates with functional drug levels and clinical responses in rheumatoid arthritis" Annals of the rheumatic diseases, 68(11):1739-1745, Nov. 1, 2009.
Schultz et al., "Quantitative analysis of the CD4+ T cell response to therapeutic antibodies in healthy donors using a novel T cell:PBMC assay" PLoS One, 12(5):e0178544, May 31, 2017.
Van Mierlo et al., "The minipig as an alternative non-rodent model for immunogenicity testing using the TNFα blockers adalimumab and infliximab" Journal of immunotoxicology, 11(1): 11 Pages, Jan. 1, 2014.
Van Schouwenburg et al., "Immunogenicity of anti-TNF biologic therapies for rheumatoid arthritis" Nature Reviews Rheumatology, 9(3): 9 Pages, Mar. 2013.
Wang et al., "Monitoring of adalimumab and antibodies-to-adalimumab levels in patient semm by the homogeneous mobility shift assay" Journal of Pharmaceutical and Biomedical Analysis, 78:39-44, May 5, 2013.
West et al., "Immunogenicity negatively influences the outcome of adalimumab treatment in Crohn's disease" Alimentary pharmacology & therapeutics, 28(9):1122-1126, Nov. 2008.

(56) References Cited

OTHER PUBLICATIONS

Wullner et al., "Considerations for optimization and validation of an in vitro PBMC derived T cell assay for immunogenicity pre-diction of biotherapeutics." Clinical immunology, 137(1): 12 Pages, Oct. 1, 2010.

* cited by examiner

HIGH CONCENTRATION FORMULATIONS OF ADALIMUMAB

CROSS-REFERENCE TO RELATED APPLICATIONS

This application claims priority to U.S. Patent Application Ser. No. 62/413,226 filed Oct. 26, 2016 and U.S. Patent Application Ser. No. 62/247,348 filed Oct. 28, 2015, each of which is herein incorporated by reference in its entirety.

TECHNICAL FIELD

The present invention relates to aqueous pharmaceutical compositions comprising a high concentration (i.e., greater than 50 milligrams per milliliter ("mg/mL")) of adalimumab (including antibody proteins considered or intended as "bio-similar" or "bio-better" variants of commercially available adalimumab) suitable for long-term storage, and methods of manufacture of the compositions; methods of their administration; and articles containing the same.

BACKGROUND

Auto-immune diseases affect nearly 24 million people in the United States (roughly 8% of the population) alone making it one of the most prevalent diseases. Many auto-immune diseases are correlated with elevated levels of a naturally occurring protein in the body known as tumor necrosis factor ("TNFα"). TNFα is a cytokine capable of inducing fever, cell death, and inflammation among other illnesses. TNFα works by binding to and activating cell surface receptors which lead to the activation of genes involved in inflammation.

Adalimumab is an anti-inflammatory drug targeted to inhibiting TNFα from binding to these cell surface receptors. Adalimumab is the first fully human monoclonal antibody approved by the United States Food and Drug Administration (FDA) and is sold under the trademark Humira®. Humira® has been approved by the FDA for several auto-immune diseases including rheumatoid arthritis, psoriasis and, Crohn's disease.

A commercial formulation of Humira® contains a citrate/phosphate buffer which is known to cause significant patient discomfort (stinging) upon injection. Discomfort resulting from the citrate buffer used in Humira® is compounded by the amount of time required to complete the injection. According to its current approved FDA label, this Humira® product is stated to deliver a dosage of 40 mg to the patient in a formulation containing a concentration of 50 mg/mL.

Patient discomfort resulting from the composition of this Humira® formulation could be alleviated by (a) modifying the formulation to eliminate the cause of the uncomfortable stinging sensation and/or (b) increasing the concentration of the adalimumab in the dosage in order to reduce the volume of the administered dose, and hence the time required to administer it. A desire to achieve both these objectives has created need for adalimumab formulations that not only reduce pain by eliminating painful formulation ingredients, but also for formulations containing higher concentrations of adalimumab capable of delivering a desired amount of the drug in a smaller injection volume over a shorter time of injection.

There are a number of challenges in developing safe and effective high concentration adalimumab formulations. It is generally understood in the art that increasing the concentration of antibody in a given formulation can cause a decrease in stability marked by aggregation, misfolding, and fragmentation of the antibody, all of which can reduce the therapeutic potency of an antibody formulation. Moreover, aggregated, misfolded, and fragmented antibodies can result in formation of subvisible particles in an antibody formulation that could trigger an immune response in the patient causing pain, swelling, and even the need to stop taking the therapeutic antibody. Developing a high concentration formulation of adalimumab that does not exhibit these problems is highly desirable.

It is also generally understood in the art that increasing the concentration of protein in a therapeutic formulation can cause an unacceptable increase in product viscosity. Highly viscous formulations may be difficult to manufacture, which can increase the cost of production. Moreover, formulations having increased viscosity may have to compensate for the higher viscosity by requiring administration with larger bore needles, longer injection times or higher injection pressures, all of which can cause significant patient discomfort. Hence, it is highly desired to increase the concentration of an adalimumab formulation, without causing an unacceptable increase in viscosity, such as would require a larger and more painful needle bore.

While it is desired to achieve higher concentration adalimumab formulations capable of achieving stability and viscosity comparable to or better than an existing Humira® formulation containing 50 mg/mL, it is also desired to formulate such a high concentration composition with ingredients that do not cause a painful, stinging sensation upon administration to a patient. Achieving these objectives can result in an adalimumab formulation capable of being administered to patients more quickly and less painfully. Moreover, the ability of higher concentration adalimumab formulations to deliver the same amount of adalimumab in a small injection volume could afford not only shorter injection times and less discomfort for current single-injection doses (e.g. 10 mg, 20 mg, and 40 mg), but also the potential to convert an administration of the drug requiring multiple injections, to an administration of a single dose.

Recently, attempts have been made to create a high concentration adalimumab formuations while maintaining a low viscosity. U.S. Pat. No. 8,420,081, assigned to AbbVie, the maker of Humira®, discloses that ionic excipinets are detrimental to high concentration adalimumab formulations. This patent states that the hydrodynamic diameter (Dh) of adalimumab is not impacted by non-ionic excipinets (e.g. the polyol sorbitol) but is crucially impacted—increased dramatically—by the presence of ionizable excipients (e.g. buffers and salts). The '081 patent reports that this is important for high concentration adalimumab formulations because the proteins with lower Dh occupy lower spatial volumes and that protein formulations without ionic excipients will have substantially lower viscosities than formulations containing ionizable excipients (e.g. buffers). The '081 patent reports viscosities of 200 mg/mL adalimumab solutions in water for injection-no ionic excipients-were found to be well below 50 mPas, independent of pH. Thus, the art teaches that a high concentration adalimumab formulation should exclude ionic excipients (characterized, for example by low Dh or low conductivity) in order to have suitable viscosity.

Indeed, a commercial formulation of Humira® containing 100 mg/mL adalimumab, mannitol, and polysorbate 80 has been introduced by AbbVie. According to the current approved FDA label, Humira® products with this formulation are stated to deliver a dosage of 40 mg (in 0.4 mL) or 80 mg (in 0.8 mL) of adalimumab to the patient. Both mannitol and polysorbate 80 are non-ionic excipients. Thus, these Humira® products conform to the '081 patent disclosure and do not contain ionic excipients.

For these reasons, there is need for high concentration formulations of adalimumab that can exhibit stability and viscosity at least comparable to, or better than the currently approved formulation of Humira® supplied by AbbVie at a concentration of 50 mg/mL, and further, using formulation ingredients that have less tendency to produce a stinging sensation upon injection. High concentration formulations that achieve these objectives can reduce injection discomfort to patients by reducing the amount of time required for an injection to be administered, or by reducing the number of injections needed for a given dose. An added comfort benefit can result from formulating such high concentration formulations with buffers or other excipients that do not have the tendency to cause a painful stinging sensation upon injection.

SUMMARY OF THE INVENTION

In a first embodiment, disclosed is an aqueous pharmaceutical composition comprising a stable high concentration of adalimumab, wherein: (a) the composition has a concentration of adalimumab greater than 50 mg/mL; (b) the composition has long term stability comparable to or better than a commercially sold adalimumab formulation having a concentration of adalimumab selected from: (i) not greater than about 50 mg/mL; or (ii) not greater than about 100 mg/mL; and (c) the composition has viscosity approximately equal to, or less than, that of a commercially sold adalimumab formulation having a concentration of adalimumab selected from: (i) not greater than about 50 mg/mL; or (ii) not greater than about 100 mg/mL.

In a further embodiment, disclosed is an aqueous pharmaceutical composition comprising a stable high concentration of adalimumab, wherein: (A) the composition has a concentration of adalimumab greater than about 50 mg/mL; (B) the composition has long term stability comparable to or better than a commercially sold adalimumab formulation having a concentration of adalimumab selected from: (I) not greater than about 50 mg/mL; or (ii) not greater than about 100 mg/mL; (C) the composition has viscosity approximately equal to, or less than, that of a commercially sold adalimumab formulation having a concentration of adalimumab selected from (i) not greater than about 50 mg/mL; or (ii) not greater than about 100 mg/mL and (D) wherein the composition comprises: (i) adalimumab; (ii) a buffer selected from one, or a combination of phosphate buffer, histidine buffer, gluconate buffer, succinate buffer, acetate buffer, adipate buffer, glutamate buffer, maleate buffer and tartrate buffer, and combinations thereof; (iii) a stabilizer, or combination of stabilizers, selected from one or a combination of (a) polyols; (b) amino acids; and (c) salts; (iii) optionally, a surfactant, or combination of surfactants, selected from the group consisting of: (a) polysorbate surfactants; and (b) polaxamer surfactants; and wherein the composition is free of citrate buffer and has a pH between 3 to 8, 4 to 8 and 5 to 6.

In a further embodiment, disclosed is an aqueous pharmaceutical composition comprising a stable high concentration of adalimumab, wherein: (A) the composition has a concentration of adalimumab greater than about 50 mg/mL; (B) the composition has long term stability comparable to or better than a commercially sold adalimumab formulation having a concentration of adalimumab selected from: (I) not greater than about 50 mg/mL; or (ii) not greater than about 100 mg/mL; and (C) the composition has viscosity approximately equal to, or less than, that of a commercially sold adalimumab formulation having a concentration of adalimumab selected from: (i) not greater than about 50 mg/mL; or (ii) not greater than about 100 mg/mL; (D) the composition: (i) comprises a polyol, and is free or substantially free of surfactant; or (ii) comprises a surfactant, and is free or substantially free of polyol; or (iii) is free or substantially free of both surfactant and polyol; and (E) the composition has pH 3 to 8; 4 to 8; or 5 to 6, and optionally comprises a buffer.

In a further embodiment, disclosed is an aqueous pharmaceutical composition comprising a stable high concentration of adalimumab, wherein: (a) the composition has a concentration of adalimumab greater than about 50 mg/mL; (b) the composition has long term stability comparable to or better than a commercially sold adalimumab formulation having a concentration of adalimumab selected from: (i) not greater than about 50 mg/mL; or (ii) not greater than about 100 mg/mL; and (c) the composition has viscosity approximately equal to, or less than, that of a commercially sold adalimumab composition having a concentration of adalimumab selected from: (i) not greater than about 50 mg/mL; or (ii) not greater than about 100 mg/mL. (d) the composition comprises a buffer; (e) the composition comprises a polyol that is one, or a combination of mannitol, sorbitol, and trehalose; and (f) the composition comprises a surfactant.

In a further embodiment, disclosed is an aqueous pharmaceutical composition comprising a stable high concentration of adalimumab, wherein: (a) the composition has a concentration of adalimumab greater than about 50 mg/mL; (b) the composition has long term stability comparable to or better than a commercially sold adalimumab pharmaceutical composition having a concentration of adalimumab selected from: (i) not greater than about 50 mg/ml; or (ii) not greater than about 100 mg/mL; and (c) the composition has viscosity approximately equal to, or less than, that of a commercially sold adalimumab pharmaceutical composition having a concentration of adalimumab selected from: (i) not greater than about 50 mg/mL; or (ii) not greater than about 100 mg/ml (d) the composition comprises an acetate buffer; (e) the composition comprises a polyol that is one, or a combination of mannitol, sorbitol, and trehalose; and (f) the composition comprises a surfactant.

In a further embodiment, disclosed is a stable, aqueous pharmaceutical composition comprising adalimumab at a concentration of about 100 to 250 mg/mL wherein: (a) the composition has (i) long term stability comparable to or better than; (ii) viscosity approximately equal to or less than; and (iii) discomfort upon administration lesser than; a commercially sold adalimumb formulation having a concentration of adalimumab not greater than about 50 mg/ml that comprises a combination of citrate and phosphate buffers; mannitol; sodium chloride and polysorbate 80 ("PS 80"); and (b) the high concentration composition has reduced excipients as compared to the commercially sold adalimumab formulation, said reduction in excipients meeting at least one of the following criteria: (i) the composition replaces the phosphate and citrate with a different buffer system that does not comprise citrate; and/or (ii) the composition is free of surfactant; and/or (iii) the composition is free of polyol.

In a further embodiment, disclosed is a method for preparation of a high concentration formulation having a concentration of adalimumab greater than about 50 mg/ml and less than or equal to about 200-250 mg/mL, and a preferably a pH of 5 to 6, comprising the step of: preparing an adalimumab formulation that is modified over a known adalimumab formulation, where the known formulation has a pH of 5 to 6 and comprises no more than about 50 mg/mL, and such that the modification consists solely of increasing the adalimumab concentration of the known formulation to a concentration selected from (i) greater than 50 mg/mL and less than or equal to 200-250 mg/mL; and (ii) about 100 to 2250 mg/mL, without modifying the identity or concentration of any excipients present in the known formulation, whereby the resulting modified composition has stability and viscosity at least comparable to the known formulation.

The present invention is based in part on the surprising discovery that a given, pre-existing formulation of adalimumab, having a concentration of not more than about 50 mg/mL; and having both long term stability and a pharmaceutically acceptable viscosity, can be modified to a high concentration formulation containing more than 50 mg/mL and up to about 200-250 mg/mL adalimumab, without changing the identity or concentration of the existing formulation's other components, and without losing the stability or the acceptable viscosity characteristics of the pre-existing formulation. The present invention also affords the ability to prepare such a high concentration adalimumab composition with excipients that do not cause a painful stinging sensation upon injection to a patient.

The present invention is further based on the corresponding discovery that for a given formulation of adalimumab having acceptable stability and viscosity at a concentration of no more than 50 mg/mL of adalimumab, such formulation cannot be modified to a concentration above about 200-250 mg/mL, unless it is supplemented with (i) one or more stabilizing or viscosity reducing enhancing agents not present in the given formulation; or (ii) increased amounts of viscosity reducing agents or stabilizing agents already present therein.

A further discovery supporting this invention is our finding, which it is believed was heretofore unknown and unappreciated, that adalimumab remains relatively stable over a wide range of concentrations, provided its pH is maintained preferably in a range of 5 to 6. Hence in preferred embodiments of this invention, the high concentration formulations are within pH 5 to 6.

Whether formulated in a concentration range of more than 50 and up to about 200-250 mg/mL adalimumab; or at concentrations exceeding about 200-250 mg/mL, the present invention further affords the ability to prepare such high concentration adalimumab compositions, with excipients that do not cause a painful stinging sensation upon injection to a patient.

In further embodiments, for adalimumab formulations having concentrations greater than 50 mg/mL and up to about 200-250 mg/mL disclosed is a high concentration adalimumab composition wherein: (a) adalimumab is present at a concentration greater than 50 mg/mL and less than or equal to about 200 mg/mL; and (b) said high concentration composition, and a comparator adalimumab composition comprising adalimumab at a concentration of no more than about 50 mg/mL, are the same or essentially the same with respect to the identity and concentration of excipients contained therein; and both the high concentration formulation and the comparator have stability comparable to or better than, and viscosity comparable to or lower than, a commercially sold Humira® formulation having no greater than about 50 mg/mL or no greater than about 100 mg/mL.

In further embodiments, for adalimumab formulations having concentrations greater than 50 mg/mL and up to about 200-250 mg/mL, disclosed is a high concentration adalimumab composition wherein: (a) adalimumab is present at a concentration greater than 50 mg/mL and less than or equal to about 200 mg/ml; and (b) said high concentration composition, and a comparator adalimumab composition comprising adalimumab at a concentration of no more than about 50 mg/mL, are the same or essentially the same with respect to the identity and concentration of excipients contained therein; and both the high concentration formulation and the comparator have (i) stability comparable to or better than a commercially sold Humira® formulation having no greater than about 50 mg/mL or no greater than about 100 mg/mL, and (ii) viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP.

In further embodiments, for adalimumab formulations having concentrations greater than 50 mg/mL and up to about 200-250 mg/mL, disclosed is a high concentration adalimumab composition (a) having a concentration of adalimumab greater than 50 mg/ml and less than or equal to about 200 mg/mL; and wherein (b) the high concentration composition is able to exhibit stability and viscosity at least comparable to or better than a commercially sold Humira® composition containing no greater than about 50 mg/mL, or no greater than about 100 mg/mL, without need to incorporate in such high concentration composition either (i) any viscosity reducing agents or stabilizing agents not found in a comparator adalimumab composition comprising adalimumab at a concentration of no more than about 50 mg/mL; or (ii) amounts of viscosity modifying agents or stabilizing agents different from that found in the comparator composition.

In further embodiments, for adalimumab formulations having concentrations greater than 50 mg/mL and up to about 200-250 mg/mL, disclosed is a high concentration adalimumab composition, wherein: (a) adalimumab is present at a concentration greater than 50 mg/mL and less than or equal to about 200 mg/mL; and (b) the high concentration composition is able to exhibit stability at least comparable to or better than a commercially sold Humira® composition containing no greater than about 50 mg/mL, or no greater than about 100 mg/mL and viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP, without need to incorporate in such high concentration composition either (i) any viscosity reducing agents or stabilizing agents not found in a comparator adalimumab composition comprising adalimumab at a concentration of no more than about 50 mg/mL; or (ii) amounts of viscosity modifying agents or stabilizing agents different from that found in the comparator composition.

In further embodiments, for adalimumab formulations having concentrations greater about 200-250 mg/mL, disclosed is a high concentration adalimumab composition, wherein: (a) adalimumab is present at a concentration greater than or equal to about 200 to 250 mg/mL; (b) the high concentration composition, and a comparator adalimumab composition comprising adalimumab at a concentration of not more than about 50 mg/mL, compare to one another in the following respects: (i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein the high concentration composition has viscosity less than or approximately equal to that of commercially sold Humira® containing adalimumab at a concentration not greater than about 50 mg/mL or not greater than about 100 mg/mL; and/or (ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein the high concentration composition has stability equal to or better than a commercially sold Humira® formulation comprising adalimumab at a concentration not greater than about 50 mg/mL or not greater than about 100 mg/mL; and (c) the high concentration composition is not able to exhibit stability and viscosity at least comparable to or better than a commercially sold Humira® composition containing no greater than about 50 mg/mL, or no greater than about 100 mg/mL, unless the high concentration composition comprises (i) said viscosity reducing agent or stabilizing agent not found in the comparator composition; or (ii) said increased amount of viscosity modifying agent or stabilizing agent.

In further embodiments, for adalimumab formulations having concentrations greater than about 200-250 mg/mL, disclosed is a high concentration adalimumab composition, wherein: (a) adalimumab is present at a concentration greater than or equal to about 200 to 250 mg/mL; (b) the high concentration composition, and a comparator adalimumab composition comprising adalimumab at a concentration of not more than about 50 mg/mL, compare to one another in the following respects: (i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein the high concentration composition has viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP; and/or (ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein the high concentration composition has stability equal to or better than a commercially sold Humira® formulation comprising adalimumab at a concentration not greater than about 50 mg/mL or not greater than about 100 mg/mL; and (c) the high concentration composition is not able to exhibit stability at least comparable to or better than a commercially sold Humira® composition containing no greater than about 50 mg/mL or no greater than about 100 mg/mL, and viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP, unless the high concentration composition comprises (i) said viscosity reducing agent or stabilizing agent not found in the comparator composition; or (ii) said increased amount of viscosity modifying agent or stabilizing agent.

In further embodiments, for adalimumab formulations having concentrations greater than about 200-250 mg/mL, disclosed is a high concentration adalimumab composition, wherein: (a) adalimumab is present at a concentration greater than or equal to about 200 to 250 mg/mL; (b) the high concentration composition, and a comparator adalimumab composition comprising adalimumab at a concentration of not more than about 50 mg/mL, compare to one another in the following respects: (i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein both the high concentration composition, and the comparator, have viscosity less than or approximately equal to that of commercially sold Humira® containing adalimumab at a concentration not greater than about 50 mg/mL or not greater than about 100 mg/mL; and/or (ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein both the high concentration composition, and the comparator, have stability equal to or better than a commercially sold Humira® formulation comprising adalimumab at a concentration not greater than about 50 mg/mL or not greater than about 100 mg/mL; and (c) the high concentration composition is not able to exhibit stability and viscosity at least comparable to or better than a commercially sold Humira® composition containing no greater than about 50 mg/mL, or no greater than about 100 mg/mL, unless the high concentration composition comprises (i) said viscosity reducing agent or stabilizing agent not found in the comparator composition; or (ii) said increased amount of viscosity modifying agent or stabilizing agent.

In further embodiments, for adalimumab formulations having concentrations greater than about 200-250 mg/mL, disclosed is a high concentration adalimumab composition, wherein: (a) adalimumab is present at a concentration greater than or equal to about 200 to 250 mg/mL; (b) the high concentration composition, and a comparator adalimumab composition comprising adalimumab at a concentration of not more than about 50 mg/mL, compare to one another in the following respects: (i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein both the high concentration composition, and the comparator, have viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP; and/or (ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein both the high concentration composition, and the comparator, have stability equal to or better than a commercially sold Humira® formulation comprising adalimumab at a concentration not greater than about 50 mg/mL or not greater than about 100 mg/mL; and (c) the high concentration composition is not able to exhibit stability at least comparable to or better than a commercially sold Humira® composition containing no greater than about 50 mg/mL or no greater than about 100 mg/mL, and viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP, unless the high concentration composition comprises (i) said viscosity reducing agent or stabilizing agent not found in the comparator composition; or (ii) said increased amount of viscosity modifying agent or stabilizing agent.

The invention provides an aqueous pharmaceutical composition comprising a high concentration of adalimumab, wherein the composition exhibits long term stability and viscosity that is acceptable for injection, in the sense that the viscosity of the formulations are low enough that they will not require injection needles having bore sizes larger than those currently used for commercial Humira®, as presently supplied by AbbVie at a concentration of about 50 mg/mL. Preferably, the formulation will avoid citrate as a buffer, in favor of buffers and/or other excipients that will have less tendency to cause painful stinging upon injection. The high concentration compositions disclosed herein also require smaller injections volumes, resulting in shorter injection times and a further basis for improved patient experience. In certain embodiments, the high concentration formulations also obviate need for surfactants and polyols.

In a further aspect, the invention provides adalimumab present in the composition at a concentration selected from: greater than 50 mg/mL and less than 100 g/mL; at least 100 mg/mL; 100 to 300 mg/mL; 100 to 200 mg/mL; 100 to 150 mg/mL; 100 to 125 mg/mL; 75 mg/mL; 100 mg/mL; 125 mg/mL, 150 mg/mL; 175 mg/mL; 200 mg/mL; 225 mg/mL; 250 mg/mL; 275 mg/mL; and 300 mg/mL.

In another aspect, the invention provides an aqueous pharmaceutical composition comprising a high concentration of adalimumab, wherein the composition exhibits long term stability and is free, or substantially free, of a citrate buffer, a phosphate buffer, or both a citrate buffer and a phosphate buffer.

In one aspect, the invention provides an aqueous pharmaceutical composition comprising a high concentration of adalimumab, wherein the composition exhibits long term stability and is free, or substantially free, of a polyol, a surfactant, or both a polyol and a surfactant.

In one aspect, the invention provides an aqueous pharmaceutical composition comprising a high concentration of adalimumab and a surfactant, wherein the composition exhibits long term stability.

In another aspect, the invention provides an aqueous pharmaceutical composition comprising a high concentration of adalimumab, a surfactant, a buffer, and a tonicity agent, wherein the composition exhibits long term stability.

In one aspect, the invention provides an aqueous pharmaceutical composition comprising a high concentration of adalimumab, a buffer comprising a mono- or dicarboxylic acid and salts thereof, a stabilizer, a tonicity agent, a surfactant, and optionally, a chelating agent, wherein the composition exhibits long term stability.

In another aspect, the invention provides an aqueous pharmaceutical composition comprising a high concentration of adalimumab, a succinate buffer, a tonicity agent, a surfactant, and a stabilizer selected from amino acids, cyclodextrins, and polyols, wherein the composition exhibits long term stability.

In a further aspect, the invention provides an aqueous pharmaceutical composition comprising a high concentration of adalimumab, acetate, a polyol, an amino acid, and optionally a surfactant, wherein the composition exhibits long term stability.

In another aspect, the invention provides an aqueous pharmaceutical composition comprising a high concentration of adalimumab, succinate, a polyol, and optionally a surfactant, wherein the composition exhibits long term stability.

In another aspect, the invention provides an aqueous pharmaceutical composition comprising a high concentration of adalimumab, an amino acid, a polyol, and optionally a surfactant, wherein the composition exhibits long term stability.

In a further aspect, the invention provides an aqueous pharmaceutical composition comprising a high concentration of adalimumab, a polyol, and a surfactant, wherein the composition exhibits long term stability.

In another aspect, the invention provides an aqueous pharmaceutical composition comprising a high concentration of adalimumab, a phosphate buffer, a stabilizer, a surfactant, and optionally a salt, wherein the composition exhibits long term stability.

In further aspect, the invention provides an aqueous pharmaceutical composition comprising a high concentration of adalimumab and a surfactant, wherein the composition exhibits long term stability.

In a further aspect, the invention provides an aqueous pharmaceutical composition comprising a high concentration of adalimumab and pyrophosphate, wherein the composition exhibits long term stability.

In another aspect, the invention provides an aqueous pharmaceutical composition comprising a high concentration of adalimumab, an acetate buffer, a polyol, optionally a salt, and optionally a surfactant, wherein the composition exhibits long term stability.

In another aspect, the invention provides an aqueous pharmaceutical composition comprising a high concentration of adalimumab, an acetate buffer, optionally a tonicity agent, and optionally a surfactant, wherein the composition exhibits long term stability.

In a further aspect, the invention provides an aqueous pharmaceutical composition comprising a high concentration of adalimumab, a tonicity agent and optionally a surfactant, wherein the composition is free, or substantially free, of acetate, and exhibits long term stability.

In a further aspect, the invention provides an aqueous pharmaceutical composition comprising a comprising a high concentration of adalimumab that exhibits long term stability and is suitable for subcutaneous injection.

In another aspect, the invention provides an article of manufacture comprising a vessel containing an aqueous pharmaceutical composition comprising a comprising a high concentration of adalimumab that exhibits long term stability.

In a further aspect, the invention provides a device for administering adalimumab to a subject comprising, a needle and a vessel containing an aqueous pharmaceutical composition comprising a comprising a high concentration of adalimumab that exhibits long term stability.

In a further aspect, the invention embodied above wherein the compositions comprise one or more ionic excipients, wherein said excipients contribute to the composition having conductivity greater than 2.5, 3, 4, 5, 6, 7 or 8; osmolarity of 140 to about 400; and a hydrodynamic diameter of the adalimumab of greater than 4, 5, 6, 7, 8, 9, 10 or 11; and wherein the composition, upon administration to a subject, results in a degree of pain or discomfort no worse than, or better than, that of an AbbVie-supplied Humira® composition, having a concentration of adalimumab greater than or equal to about 50 mg/mL.

These and other aspects will become apparent from the following description of the various embodiments, although variations and modifications therein may be affected without departing from the spirit and scope of the novel concepts of the disclosure.

It is to be understood that both the foregoing general description and the following detailed description are exemplary and explanatory only and are not restrictive of the invention, as claimed.

Other objects, features and advantages of the present invention will become apparent from the following detailed description. It should be understood, however, that the detailed description and specific examples, while indicating suitable embodiments of the invention, are given by way of illustration only, since various changes and modifications within the scope and spirit of the invention will become apparent to one skilled in the art from this detailed description.

DETAILED DESCRIPTION

The invention will now be described in detail, by way of reference only, using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. In the case of conflict, the present document, including definitions will control.

Singleton, et al., Dictionary of Microbiology And Molecular Biology, 2d Ed., John Wiley and Sons, New York (1994), and Hale & Marham, The Harper Collins Dictionary of Biology, Harper Perennial, NY (1991) provide one of skill with a general dictionary of many of the terms used in this invention. Any methods and materials similar or equivalent to those described herein can be used in the practice or testing of the present invention. It is to be understood that this invention is not limited to the particular methodology, protocols, and reagents described, as these may vary.

Unless otherwise indicated, amino acid sequences are written left to right in amino to carboxyl orientation, respectively.

Various embodiments of the invention are now described in detail. As used in the description and throughout the claims, the meaning of "a", "an", and "the" includes plural reference unless the context clearly dictates otherwise. Also, as used in the description and throughout the claims, the meaning of "in" includes "in" and "on" unless the context clearly dictates otherwise.

Even if not explicitly stated, numeric values can be read to mean "about," "around," or "approximately" the value stated. In one embodiment, "about," "around," and "approximately" means values within 10%. In another embodiment, "about," "around," and "approximately" means values within 5%. In one embodiment, "about," "around," and "approximately" means values within 3%. In one embodiment, "about," "around," and "approximately" means values within 2%. In one embodiment, "about," "around," and "approximately" means values within 1%.

A. Definitions

As used herein the term "optionally" refers to distinct methods or compositions one of which contains the subsequent step(s) or composition(s) and one of which does not.

The term "adalimumab" is synonymous with the active pharmaceutical ingredient in Humira® as well as protein considered or intended as biosimilar or bio-better variants thereof. Adalimumab is a recombinant human IgG1 monoclonal antibody specific for human TNF. Adalimumab is also known as D2E7. Adalimumab has two light chains, each with a molecular weight of approximately 24 kilodaltons (kDa) and two IgG1 heavy chains each with a molecular weight of approximately 49 kDa. Each light chain consists of 214 amino acid residues and each heavy chain consists of 451 amino acid residues. Thus, adalimumab consists of 1330 amino acids and has a total molecular weight of approximately 148 kDa. The term adalimumab is also intended to encompass so-called bio-similar or bio-better variants of the adalimumab protein used in commercially available Humira®. For example, a variant of commercial Humira® may be acceptable to the FDA when it has essentially the same pharmacological effects as commercially available Humira®, even though it may exhibit certain physical properties, such as glycosylation profile, that may be similar if not identical to Humira®.

For the purposes of the present application, the term "adalimumab" also encompasses adalimumab with minor modifications in the amino acid structure (including deletions, additions, and/or substitutions of amino acids) or in the glycosylation properties, which do not significantly affect the function of the polypeptide. The term "adalimumab" encompasses all forms and formulations of Humira® and Amjevita™, including but not limited to concentrated formulations, injectable ready-to-use formulations; formulations reconstituted with water, alcohol, and/or other ingredients, and others.

Known formulations of adalimumab include those of Humira®, Amjevita™, and formulations disclosed in the literature. For example, the Amjevita™ package insert discloses that 40 mg/0.8 mL prefilled syringe or prefilled autoinjector delivers 0.8 mL (40 mg) of drug product and that each 0.8 mL of Amjevita™ is formulated with glacial acetic acid (0.48 mg), polysorbate 80 (0.8 mg), sodium hydroxide for pH adjustment, sucrose (72 mg), and Water for Injection, USP, pH 5.2. The Amjevita™ package insert also states that each 20 mg/0.4 mL prefilled syringe delivers 0.4 ml (20 mg) of drug product and each 0.4 mL of Amjevita™ is formulated with glacial acetic acid (0.24 mg), polysorbate 80 (0.4 mg), sodium hydroxide for pH adjustment, sucrose (36 mg), and Water for Injection, USP, pH 5.2.

The term "human TNFα" (which may be abbreviated as hTNFα, or simply hTNF), as used herein, is intended to refer to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) Nature 312:724-729; Davis, J. M., et al. (1987) Biochemistry 26:1322-1326; and Jones, E. Y., et al. (1989) Nature 338:225-228. The term human TNFα is intended to include recombinant human TNFα (rhTNFα), which can be prepared by standard recombinant expression methods or purchased commercially (R & D Systems, Catalog No. 210-TA, Minneapolis, Minn.)

The term "antibody," or "antibodies," as used herein, refers to immunoglobulin molecules comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Antibodies of the present invention include but are not limited to recombinant human antibodies including human monoclonal antibodies and 'fully' human monoclonal antibodies. Examples of antibodies of the invention include tumor necrosis factor (TNF)-α antibodies (also referred to as anti-TNFα antibodies). TNFα antibodies which may be formulated using the invention include adalimumab (adalimumab is sold under the trademark Humira® and is described in further detail in U.S. Pat. Nos. 6,090,382; 6,258,562; 6,509,015; and 8,664,945, each of which is incorporated herein by reference in its entirety), and an antibody with CDR1, CDR2, and CDR3 sequences like those described in U.S. Pat. Nos. 6,090,382; 6,258,562, and 8,216,583, and biosimilars thereof.

An antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

The term "antibody fragment," as used herein, refers to one or more fragments of an antibody that retain the ability to specifically bind to an antigen ("antigen-binding portion"; e.g., hTNFα). Examples of antigen binding portions which may be produced by the methods of the invention are described in further detail in U.S. Pat. Nos. 6,090,382; 6,258,562; 6,509,015 and 8,664,945 each of which is incorporated herein by reference in its entirety. Production of antibody fragments or portions using the methods and compositions of the invention are also included within scope of the invention.

The term "isolated antibody," as used herein, refers to an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may, however, have cross-reactivity to other antigens, such as TNFα molecules from other species. Moreover, an isolated antibody may be substantially free of other cellular material and/or chemicals.

The term "biosimilar" or "biosimilars," as used herein, refers to a biological product designed to have active properties similar to an FDA-licensed biological product.

The term "meglumine" refers to a compound with chemical formula $H_3NHCH_2(CHOH)_4CH_2OH$, also known as 1-Deoxy-1-methylaminosorbitol; N-Methyl-d-glucamine; and 1-Deoxy-1-methylamino-D-glucitol.

The terms "mannosylglycerate," "mannosyllactate," "mannosylglycolate", and "diglyceroiphosphate" are well known in the art and have their commonly accepted meanings. The following references describe these compounds in some detail: Faria et al., *Carbohydrate Res.* 2008, 343: 3025-3033; Borges et al., *Extremophiles* 2002, 6: 209-216; Faria et al., *ChemBioChem* 2003, 4: 734-741; Sawangwan et al., *Biotechnol. J.* 2010, 5: 187-191; and Pais et al., *J. Mol. Biol.* 2009, 394: 237-250. The application incorporates by reference the description of these compounds contained in these references.

The term "serine" refers to an amino acid whose codons are UCU, UCC, UCA, UCG, AGU, and AGC.

The term "proline" refers to an α-amino acid whose codons are CCU, CCC, CCA, and CCG.

The term "glycine" refers to an amino acid whose codons are GGT, GGC, GGA, and GGG.

The term "arginine" refers to an α-amino acid whose codons are CCU, CCC, CCA, and CCG.

The term "alanine" refers to an amino acid whose codons are GCT, GCC, GCA, and GCG.

The term "methionine" refers to an amino acid whose codon is ATG.

The term "glutamate" refers to a carboxylate anion or salt of glutamic acid (Glu), an amino acid whose codons are GAA and GAG. For the purposes of this application, the term "glutamate" also encompasses glutamic acid itself.

The term "sugar" refers to monosaccharides, disaccharides, and polysaccharides. Examples of sugars include, but are not limited to, sucrose, glucose, dextrose, and others.

The term "polyol" refers to an alcohol containing multiple hydroxyl groups. Examples of polyols include, but are not limited to, mannitol, sorbitol, and others.

The term "metal ion" refers to a metal atom with a net positive or negative electric charge. For the purposes of the present application, the term "metal ion" also includes sources of metal ions, including but not limited to metal salts.

The term "long-term storage" is understood to mean that the pharmaceutical composition can be stored for three months or more, for six months or more, or for one year or more. Generally speaking, the terms "long term storage" and "long term stability" further include stable storage durations that are at least comparable to or better than the stability required for currently available commercial formulations of adalimumab, without losses in stability that would render the formulation unsuitable for its intended pharmaceutical application. Long term storage is also understood to mean that the pharmaceutical composition is stored either as a liquid at 2-8° C., or is frozen, e.g., at −20° C., or colder for storage periods as generally described above. It is also contemplated that the composition can be frozen and thawed more than once. Long term storage stability is also intended to denote the ability of the pharmaceutical adalimumab compositions disclosed herein to resist particulates formation such that the compositions, under long term storage conditions typical of protein therapeutics, exhibits levels and types of particulates that are at least comparable to, or better than commercially available adalimumab formulations. A reduced tendency to form particulates in formulations disclosed herein results in adalimumab formulations having reduced immunogenicity, and therefore reduced potential to cause harm to patients resulting from such immunogenicity.

The term "stable" Is understood to mean adalimumab is physically stable, chemically stable, or both. With respect to storage, and long-term storage, is understood to mean that adalimumab contained in the pharmaceutical compositions does not lose more than 20%, 15%, 10%, or 5% of its activity relative to activity of the composition at the beginning of storage. The term also should be understood to mean that the adalimumab compositions are at least comparable to, and alternatively better than commercially available adalimumab compositions, in terms of their ability to resist formation of particulates, adalimumab aggregates, and/or adalimumab fragments during long term storage.

Stability of a protein in an aqueous formulation may also be defined as the percentage of monomer, aggregate, or fragment, or combinations thereof, of the protein in the formulation. A protein "retains its physical stability" in a formulation if it shows substantially no signs of aggregation, precipitation and/or denaturation upon visual examination of color and/or clarity, or as measured by UV light scattering or by size exclusion chromatography. In one aspect of the invention, a stable aqueous formulation is a formulation having less than about 10%, or less than about 5% of the protein being present as aggregate in the formulation.

In one aspect of the invention, the composition comprising a high concentration of adalimumab is stable under conditions (a period of time at a temperature) including, but not limited to: at least 1 week at 40° C., at least 6-10 days at 25-30° C., at least 1-2 weeks at 25-40° C., at least 4 weeks at 25° C., at least 9 weeks at 25° C., at least 13 weeks at 25° C., at least 13 weeks at 5° C., at least 26 weeks at 5° C., at least 52 weeks at 0-8° C., at least 96 weeks at 0-8° C., and least 104 weeks at 0-8° C.

Various analytical techniques for measuring protein stability, including techniques for measuring the type and degree of particulates that may be present in protein formulations, are available in the art and are reviewed in Peptide and Protein Drug Delivery, 247-301 (Vincent Lee ed., Marcel Dekker, New York, N.Y., 1991) and Jones, 1993 *Adv. Drug Delivery Rev.* 10: 29-90, for examples. Stability can be measured at a selected temperature for a selected time period as exemplified by the provided examples.

The term "mammal" includes, but is not limited to, a human.

The term "pharmaceutically acceptable carrier" refers to a non-toxic solid, semisolid or liquid filler, diluent, encapsulating material, formulation auxiliary, or excipient of any conventional type. A pharmaceutically acceptable carrier is non-toxic to recipients at the dosages and concentrations employed and is compatible with other ingredients of the formulation.

The term "composition" refers to a mixture that usually contains a carrier, such as a pharmaceutically acceptable carrier or excipient that is conventional in the art and which is suitable for administration into a subject for therapeutic, diagnostic, or prophylactic purposes. It may include a cell culture in which the polypeptide or polynucleotide is present in the cells or in the culture medium. For example, compositions for oral administration can form solutions, suspensions, tablets, pills, capsules, sustained release formulations, oral rinses or powders.

The terms "pharmaceutical composition" and "formulation" are used interchangeably.

The term "treatment" refers to any administration or application of remedies for disease in a mammal and includes inhibiting the disease, arresting its development, relieving the disease, for example, by causing regression, or restoring or repairing a lost, missing, or defective function; or stimulating an inefficient process. The term includes obtaining a desired pharmacologic and/or physiologic effect, covering any treatment of a pathological condition or disorder in a mammal. The effect may be prophylactic in terms of completely or partially preventing a disorder or symptom thereof and/or may be therapeutic in terms of a partial or complete cure for a disorder and/or adverse effect attributable to the disorder. It includes (1) preventing the disorder from occurring or recurring in a subject who may be predisposed to the disorder but is not yet symptomatic, (2) inhibiting the disorder, such as arresting its development, (3) stopping or terminating the disorder or at least its associated symptoms, so that the host no longer suffers from the disorder or its symptoms, such as causing regression of the disorder or its symptoms, for example, by restoring or repairing a lost, missing or defective function, or stimulating an inefficient process, or (4) relieving, alleviating or ameliorating the disorder, or symptoms associated therewith, where ameliorating is used in a broad sense to refer to at least a reduction in the magnitude of a parameter, such as inflammation, pain and/or tumor size.

The term "disease" refers to any condition, infection, disorder or syndrome that requires medical intervention or for which medical intervention is desirable. Such medical intervention can include treatment, diagnosis and/or prevention.

The term "therapeutically effective amount" refers to an amount which, when administered to a living subject, achieves a desired effect on the living subject. For example, an effective amount of the polypeptide of the invention for administration to the living subject is an amount that prevents and/or treats an hTNFα-mediated disease. The exact amount will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art.

The term "substantially free" means that either no substance is present or only minimal, trace amounts of the substance are present which do not have any substantial impact on the properties of the composition. In a particular embodiment, a composition is substantially free of a substance if at least 95%, 96%, 97%, 98%, 99%, 99.5%, or 99.8% of the substance has been removed. In another embodiment, substantially free means the substance is not present in amount sufficient to perform a function in composition for which a skilled artisan would use the substance. If reference is made to no amount of a substance, it should be understood as "no detectable amount."

By "isotonic" is meant that the formulation of interest has essentially the same osmotic pressure as human blood. Isotonic formulations will generally have an osmotic pressure from about 250 to 350 milliosmolar ("mOsM"), although tonicities as high as 1000 mOsM may be tolerated for direct injection into mammals. Isotonicity can be measured using a vapor pressure or ice-freezing type osmometer, for example.

As used herein, "buffer" refers to a buffered solution that resists changes in pH by the action of its acid-base conjugate components. The buffer of this invention has a pH in the range from about 4.0 to about 9.0; from about pH 5.0 to about 8.0; or from about pH 5.5 to about 7.5. A pH of any point in between the above ranges is also contemplated.

The term "high concentration" refers to the amount of a protein, such as an antibody, including adalimumab, in a composition at a concentration which is greater than about 50 mg/mL and/or at least about 100 mg/mL. The term "high concentration" encompasses, but is not limited to, protein, antibody, and/or adalimumab concentrations between about 100 to 300 mg/mL, between about 100 to 200 mg/mL, and between about 100 to 150 mg/mL; and adalimumab concentrations of about 100 mg/mL, 125 mg/mL, 150 mg/mL, 175 mg/mL, 200 mg/mL, 214 mg/mL, 225 mg/mL, 250 mg/mL, 275 mg/mL, and 300 mg/mL.

The term "viscosity" as used herein, may be "kinematic viscosity" or "absolute viscosity." "Kinematic viscosity" is a measure of the resistive flow of a fluid under the influence of gravity. When two fluids of equal volume are placed in identical capillary viscometers and allowed to flow by gravity, a viscous fluid takes longer than a less viscous fluid to flow through the capillary. If one fluid takes 100 seconds to complete its flow and another fluid takes 200 seconds, the second fluid is twice as viscous as the first on a kinematic viscosity scale. "Absolute viscosity," sometimes called "dynamic" or "simple viscosity," is the product of kinematic viscosity and fluid density. The dimension of kinematic viscosity is L2/T where L is a length and T is a time. Commonly, kinematic viscosity is expressed in centistokes (cSt). The SI unit of kinematic viscosity is mm2/s, which is 1 cSt. Absolute viscosity is expressed in units of centipoise (cP). The SI unit of absolute viscosity is the milliPascal-second (mPa·s), where 1 cP=1 mPa·s.

A high concentration adalimumab composition with "low viscosity" means (i) a high concentration adalimumab composition with a viscosity the same as, about the same as, or lower than the viscosity of Humira® with 50 mg/mL of adalimumab or another non-high concentration adalimumab composition (e.g. no greater than 50 mg/mL), (ii) a high concentration adalimumab composition with a viscosity the same as, about the same as, or lower than the viscosity of Humira® with 100 mg/mL of adalimumab or another adalimumab composition with about 100 mg/mL of adalimumab, (iii) a composition comprising at least one viscosity lowering excipient that has a lower viscosity than a composition without at least one such excipient, (iv) a high concentration adalimumab composition with a viscosity that is within 3%, 5%, 10%, 20%, 25%, 30%, 40%, or 50% of the viscosity of (a) Humira® with 50 mg/mL of adalimumab or another non-high concentration adalimumab composition (e.g. no greater than 50 mg/mL) or (b) Humira® with 100 mg/mL of adalimumab or another adalimumab composition with about 100 mg/mL of adalimumab, or (v) a high concentration adalimumab composition with a viscosity (a) about 30 cP or less, 25 cP or less, 20 cP or less, 15 cP or less, 14 cP or less, 13 cP or less, 12 cP or less, 11 cP or less, 10 cP or less, 9 cP or less, 8 cP or less, 7 cP or less, 6 cP or less, 5 cP or less, 4 cP or less, 3 cP or less, 2 cP or less, or 1 cP or less, (b) no more than about 30, 25, 20, 15, 14, 13, 12, 11, 10, 9, 8, 7, 6, 5, 4, 3, 2, or 1 cP, (c) about 30 to about 1 cP, about 20 to about 1 cP, about 10 to about 1 cP, or about 5 to about 1 cP or (d) about 30, 25, 20, 15, 14, 13, 12, 11, 10, 9, 8, 7, 6, 5, 4, 3, 2, or 1 cP.

As used herein, "purified" means that a molecule is present in a sample at a concentration of at least 95% by weight, or at least 98% by weight of the sample in which it is contained.

An "isolated" molecule is a nucleic acid molecule that is separated from at least one other molecule with which it is ordinarily associated, for example, in its natural environment. An isolated nucleic acid molecule includes a nucleic acid molecule contained in cells that ordinarily express the nucleic acid molecule, but the nucleic acid molecule is present extrachromosomally or at a chromosomal location that is different from its natural chromosomal location.

When pharmaceutical compositions containing adalimumab, including aqueous and lyophilized formulations of adalimumab, are stored on a long-term basis, the activity of adalimumab can be lost or decreased due to aggregation and/or degradation. Thus, the present invention provides aqueous formulations of adalimumab that allow stable long-term storage of adalimumab, so that adalimumab is stable over the course of storage either in liquid or frozen states. The provided formulations do not require any extra steps such as rehydrating.

Numerous embodiments of the present invention are explained in a greater detail below.

B. Adalimumab

All of the compositions of the present invention comprise adalimumab. As explained in the Background section of this application, adalimumab is a recombinant human IgG1 monoclonal antibody specific for human tumor necrosis factor (TNF).

Adalimumab suitable for storage in the present pharmaceutical composition can be produced by standard methods known in the art. For example, U.S. Pat. Nos. 6,090,382 and 8,216,583 describe various methods that a skilled artisan could use to prepare adalimumab protein for use in the formulations of the present invention. These methods are incorporated by reference herein. For example, adalimumab can be prepared by recombinant expression of immunoglobulin light and heavy chain genes in a host cell.

Purification of the expressed adalimumab can be performed by any standard method. When adalimumab is produced intracellularly, the particulate debris is removed, for example, by centrifugation or ultrafiltration. When adalimumab is secreted into the medium, supernatants from such expression systems can be first concentrated using standard polypeptide concentration filters. Protease inhibitors can also be added to inhibit proteolysis and antibiotics can be included to prevent the growth of microorganisms.

Adalimumab can be purified using, for example, hydroxyapatite chromatography, gel electrophoresis, dialysis, and affinity chromatography, and any combination of known or yet to be discovered purification techniques, including but not limited to Protein A chromatography, fractionation on an ion-exchange column, ethanol precipitation, reverse phase HPLC, chromatography on silica, chromatography on heparin SEPHAROSET®, an anion or cation exchange resin chromatography (such as a polyaspartic acid column), chromatofocusing, SDS-PAGE, and ammonium sulfate precipitation.

Excipient-free and/or buffer-free adalimumab may also be purified from commercially-available Humira® preparations using standard methods.

When pharmaceutical compositions containing antibodies (e.g. adalimumab), including aqueous and lyophilized formulations, are produced or formulated in high concentrations, the composition and/or antibody typically become unstable. Instabilities include: unfavorable physical and chemical modification such as aggregation, fragmentation, degradation, oxidation, and acidification. This can result in reduced activity of adalimumab, formation of particles, including sub-visible particles. Particle formation, adalimumab aggregation, and adalimumab degradation can cause undesirable immune responses, including formation of anti-drug antibodies, when the adalimumab formulation is administered to the subject. Additionally, simply raising the concentration of adalimumab to a high concentration in a preexisting formulation is expected to result in the formulation being too viscous for effective therapeutic administration.

Since adalimumab is a large complex molecule with heterogeneous charged surface, capable of various polar interactions, and there are numerous potential excipients with various properties, it is unclear which excipients, and at what concentration, will stabilize a high concentration adalimumab composition.

The numerous challenges for creating a high concentration adalimumab formulation with desired characteristics are described below.

Aggregation, Misfolding, and Fragments

When antibodies, including adalimumab, are formulated at high concentration the amount of antibody aggregation, misfolding, and/or fragmentation of the antibody can increase. Pharmaceutical compositions with unsuitable amounts of antibody aggregates, misfolds, and/or fragments are not stable. This is a problem because less active monomeric antibody is delivered to the patient, which reduces the therapeutic effect, and can also trigger immune responses in the patient (i.e. development of anti-drug antibodies or ADAs). Immune responses against the therapeutic antibody may result in pain, swelling, and early clearance of the antibody from the patient's body, which also reduces the therapeutic effect of the injection. ADA responses can be so severe that the patient must stop taking the therapeutic protein in the hope that the response stops and therapy can be started again in the future.

An embodiment of the present invention is a high concentration adalimumab composition with low levels of adalimumab aggregates, misfolds, and/or fragments. In another embodiment, the high concentration adalimumab composition has the same, or about the same, or fewer adalimumab aggregates, misfolds, and/or fragments as compared to Humira® or a non-high concentration adalimumab formulation. In a further embodiment, the composition is free or substantially free of antibody aggregates, misfolded antibodies, and/or fragmented antibodies.

In another embodiment, the high concentration adalimumab composition has an adalimumab content of about greater than 80%, 85%, or 90% monomeric adalimumab. In alternative embodiments, the adalimumab content is greater than about 92%, 95%, 96%, 97%, 98%, or 99% monomeric adalimumab.

In another embodiment, the high concentration adalimumab composition has an adalimumab content of about less than 20%, 15%, or 10% adalimumab aggregates, misfolds, and/or fragments. In more yet another embodiment, the adalimumab content is about less than 8%, 5%, 4%, 3%, 2%, or 1% adalimumab aggregates, misfolds, and/or fragments.

In one embodiment of the present invention, a high concentration adalimumab composition comprises at least one stabilizer to reduce or prevent aggregation, misfolding, and/or fragmentation of adalimumab.

Particles

A known problem in pharmaceutical antibody formulations, including formulations of adalimumab, is the tendency for such formulations to exhibit the presence of particles, including sub-visible particles. Such particles are believed to be associated with undesired immune reactions (immunogenicity) when protein formulations are administered to patients. Such immune reactions can reduce the effectiveness of the antibody, and may be harmful to the patient.

The present invention provides a high concentration adalimumab composition with the same, about the same, or fewer of particles as a Humira® or a non-high concentration adalimumab composition. The amount of sub-visible particles in the composition, determined by conventional means such as flowCAM® analysis at "T0," is (i) less than about 2500 particles/ml having a size of about 5-10µm; (ii) less than about 3500 particles having size of about 2-5µm; and/or (iii) less than about 700 particles/ml having size of about 1-2µm.

In another embodiment, the high concentration adalimumab composition comprises adalimumab and a stabilizer for preventing, inhibiting or reducing the occurrence of particles in the composition, wherein the stabilizer comprises a surfactant. In a further embodiment, the surfactant selected from the group consisting of polysorbate surfactants and poloxamer surfactants. The stabilizer comprises a polysorbate surfactant selected from the group consisting of polysorbate 80 (PS80), polysorbate 60, polysorbate 40 and polysorbate 20, or a poloxamer surfactant, such as for example Pluronic® F-68. In another embodiment, the surfactant, is present in the composition in an amount in the range of 0.0005 to 1% (w/v), and is a polysorbate (e.g., polysorbate 80) or a polaxamer surfactant (e.g., Pluronic® F-68). In another embodiment, the level of sub-visible particles present in a high concentration adalimumab composition with a surfactant represents at least about a 50% to 70% reduction in sub-visible particles in comparison to the same composition having no surfactant.

For high concentration adalimumab compositions that do not contain a surfactant, sub-visible particles may be reduced by improving adalimumab drug substance manufacturing processes, altering formulations, and improving the manufacturing and/or packaging of the final adalimumab drug product. Aqueous protein solutions have a tendency to aggregate upon mechanical stress. Mechanical stress frequently occurs during manufacturing of the pharmaceutical products (e.g. pumping and mixing) and transportation of the aqueous protein solution, e.g. in containers such as pharmaceutical vials.

Examples of improved drug substance manufacturing include virus filtration and reductions in shear stress on adalimumab compositions. Subvisible particles may be reduced by implementing a virus filtration (e.g. 20 nm filter) after the adalimumab is processed from bioreactor medium. For example, after ultrafiltration or diafiltration of adalimumab into a storage or buffer solution the adalimumab solution may be passed through a virus filter (e.g. 20 nm filter) to remove subvisible particles.

Additionally, shear stress (which may result from mixing, pumping, etc.) may lead to subvisible particle formation. Therefore, utilizing processes that minimize shear stress will reduce the amount of subvisible particles in an adalimumab composition. Reduction of shear stress may be implemented, for example, by employing gentler mixing and pumping processes during adalimumab purification, drug substance manufacturing, drug product manufacturing, and filling processes.

Improved formulations may also reduce subvisible particles. Including excipients in a high concentration adalimumab formulation that protect against degradation or fragmentation of adalimumab (precursors to subvisible particle formation) will reduce the amount of subvisible particles in the formulation. For example, a formulation containing glycine will have fewer subvisible particles than a formulation without glycine.

Formulations with low conductivity also have fewer sub-visible particles than high conductivity formulations. Compositions with a high conductivity have a high ionic content. High ion concentrations can cause oxidation and fragmentation of adalimumab resulting is formation of subvisible particles. Therefore, a high concentration adalimumab composition with a low conductivity will have fewer subvisible particles. Suitably low conductivity includes, but is not limed to: not exceeding about 10, 9, 8, 7, 6, 5, 4, 3, 2, or 1 millisiemens per centimeter ("mS/cm"), between about 1 and about 2.5 mS/cm, between about 2.5 and about 3 mS/cm, between about 3 and about 3.5 mS/cm, between about 3.5 and about 4.0 mS/cm, between about 4.0 and about 4.5 mS/cm, between about 4.5 and about 5.0 mS/cm, between about 5.0 and about 5.5 mS/cm, between about 5.5 and about 6.0 mS/cm, between about 6.0 and about 6.5 mS/cm, between about 6.5 and about 7.0 mS/cm, between about 7.0 and about 7.5 mS/cm, between about 7.5 and about 8.0 mS/cm, between about 8.0 and about 8.5 mS/cm, between about 8.5 and about 9.0 mS/cm, between about 9.0 and about 9.5 mS/cm, and between about 9.5 and about 10.0 mS/cm.

Particle inducing mechanical stress on adalimumab occurs when adalimumab interacts with an air-liquid interface in a vessel containing an air gap (e.g. gas headspace) and with a liquid-oil interface in a vessel containing an oil (e.g. silicone oil). Therefore, reducing the gas headspace and/or silicone oil present in a vessel, reduces adalimumab interaction with these interfaces and reduces the amount of subvisible particles in the adalimumab composition.

The present invention provides a vessel containing a high concentration adalimumab composition, wherein the vessel is filled at about more than 97% of the total volume of the vessel. In another embodiment, the gas headspace in a vessel containing a high concentration adalimumab composition is less than about 3%, 2%, or 1% of the total volume of the vessel. In another embodiment, a vessel containing a high concentration adalimumab composition is free, or substantially free, of an oil. In another embodiment a high concentration adalimumab composition is free, or substantially free, of an oil. In yet another embodiment, a high concentration adalimumab composition comprises less than 0.5%, 0.1%, 0.05, or 0.01% oil. In another embodiment, a vessel containing a high concentration adalimumab composition comprises baked silicon oil.

Viscosity

A problem with a high concentration adalimumab formulation that is that the viscosity increases. Viscous antibody solutions are difficult to process (e.g. fill vials and syringes) and to administer to patients. Highly viscous formulations are difficult to manufacture, draw into a syringe, and inject. The use of force in manipulating the viscous formulations leads to excessive frothing, which can lead to denaturation and inactivation of active biologics. Unless viscosity can be reduced, high concentration antibody formulations may require larger bore needles, high pressure injections, longer injection times, and special equipment or materials to counteract antibody adhesion. These changes will increase patient discomfort and the cost of manufacturing the therapeutic antibody product.

The present invention provides a high concentration adalimumab composition with a viscosity that is the same, about the same, or lower than the viscosity of Humira® or a non-high concentration adalimumab composition. In some embodiments, the high concentration adalimumab composition has an absolute viscosity of (a) about 30 cP or less, 25 cP or less, 20 cP or less, 15 cP or less, 14 cP or less, 13 cP or less, 12 cP or less, 11 cP or less, 10 cP or less, 9 cP or less, 8 cP or less, 7 cP or less, 6 cP or less, 5 cP or less, 4 cP or less, 3 cP or less, 2 cP or less, or 1 cP or less, (b) no more than about 30, 25, 20, 15, 14, 13, 12, 11, 10, 9, 8, 7, 6, 5, 4, 3, 2, or 1 cP, (c) about 30 to about 1 cP, about 20 to about 1 cP, about 10 to about 1 cP, or about 5 to about 1 cP or (d) about 30, 25, 20, 15, 14, 13, 12, 11, 10, 9, 8, 7, 6, 5, 4, 3, 2, or 1 cP.

Osmolarity

Generally, a pharmaceutical composition should be isotonic with serum, i.e., have the same or similar osmolality. This may be achieved by addition of a tonicity modifier. However, hypertonic formulations which would then be diluted in an isotonic vehicle would also be within the scope of this invention.

In any of the high concentration adalimumab compositions described herein, in some embodiments, the total osmolality, in milliosmoles per liter ("mOsm/L"), is (a) no greater than about 500, 450, 400, 350, 340, 330, 320, 310, 300, 290, 280, 270, 260, or 250 mOsm/L; or (b) about 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, or 350 mOsm/L. In another embodiment, high concentration adalimumab compositions close to isotonic, e.g. 250-350 mOsm/L.

Conductivity.

In one embodiment, the invention provides a composition comprising high concentration adalimumab with a conductivity suitable for administration to a subject. The term "conductivity," as used herein, refers to the ability of an aqueous solution to conduct an electric current between two electrodes. Generally, electrical conductivity or specific conductivity is a measure of a material's ability to conduct an electric current. In solution, the current flows by ion transport. Therefore, with an increasing amount of ions present in the aqueous solution, the solution will have a higher conductivity. The unit of measurement for conductivity is mmhos (mS/cm), and can be measured using a conductivity meter sold, e.g., by Orion Research, Inc. (Beverly, Mass.). The conductivity of a solution may be altered by changing the concentration of ions therein. For example, the concentration of ionic excipients in the solution may be altered in order to achieve the desired conductivity.

In one embodiment, the composition has a conductivity of less than 3 mS/cm. In another embodiment, the composition has a conductivity of less than 2 mS/cm. In yet another embodiment, the composition has a conductivity of less than 1 mS/cm. In one aspect of the invention, the composition has a conductivity of less than 0.5 mS/cm. Ranges intermediate to the above recited numbers, e.g., 1 to 3 mS/cm, are also intended to be encompassed by the invention. For example, ranges of values using a combination of any of the above recited values as upper and/or lower limits are intended to be included. In addition, values that fall within the recited numbers are also included in the invention, e.g., 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0 and so forth.

In another embodiment, the composition has a conductivity of (a) equal to or greater than 2.5, 3.0, 3.5, 4.0, 4.5, 5.0, 6.0, 6.5, 7.0, 7.5, 8.0, 8.5, 9.0, 9.5, or 10.0 mS/cm; (b) about 2.5 to about 10 mS/cm, about 3 to about 7 mS/cm, about 3 to about 5 mS/cm, about 3 to about 4 mS/cm, about 3.5 to about 4.5 mS/cm, or about 4 to about 5 mS/cm; or (c) about 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5 mS/cm.

In another embodiment, any of the high concentration adalimumab formulations of the present invention with a conductivity of greater than 2.5 mS/cm has a viscosity of less than 25 cP. In a further embodiment, the viscosity is about 30, 25, 20, 15, 14, 13, 12, 11, 10, 9, 8, 7, 6, 5, 4, 3, 2, or 1 cP.

Acidic Species

Reducing the amount of adalimumab charged variants (e.g., basic variants and acidic species, including variants) present in a composition is beneficial in high concentration compositions. High concentration adalimumab compositions with reduced acidic species will have improved product stability, product safety and product efficacy as compared to an adalimumab composition with a higher amount of acidic species (e.g. Humira®). These low acidic species compositions have improved therapeutic efficacy and improved biological properties, for example, increased cartilage tissue penetration, reduced cartilage destruction, reduced synovial proliferation, reduced bone erosion, increased protection against the development of arthritis as measured by arthritic scores and/or histopathology scores, reduced cell infiltration, reduced proteoglycan loss, reduced chondrocyte death, and/or increased TNFα affinity, as compared to a non-low acidic species composition. Adalimumab charge variants can be detected by various methods, such as ion exchange chromatography, for example, WCX-10 HPLC (a weak cation exchange chromatography) or IEF (isoelectric focusing).

Hydrodynamic Diameter

The term "hydrodynamic diameter" or "$D_h$," of a particle refers to the diameter of a sphere that has the density of water and the same velocity as the particle. Thus the term "hydrodynamic diameter of a protein" as used herein refers to a size determination for proteins in solution using dynamic light scattering (DLS).

In one embodiment, the present invention provides a composition comprising high concentration adalimumab, wherein the composition is free, or substantially free of, a buffer and/or ionic excipients. In a further embodiment, the $D_h$ of the adalimumab is smaller relative to the $D_h$ of the adalimumab in a buffered solution, irrespective of protein concentration. Thus, in certain embodiments, adalimumab in a composition made in accordance with the methods described herein, will have a $D_h$ which is at least 25% less than the $D_h$ of adalimumab in a buffered solution at the same given concentration. Examples of buffered solutions include, but are not limited to phosphate buffered saline (PBS). In certain embodiments, adalimumab in the composition of the invention have a $D_h$ that is at least 50% less than the $D_h$ of adalimumab in PBS in at the given concentration; at least 60% less than the $D_h$ of adalimumab in PBS at the given concentration; at least 70% less than the $D_h$ of adalimumab in PBS at the given concentration; or more than 70% less than the $D_h$ of adalimumab in PBS at the given concentration. Ranges intermediate to the above recited percentages are also intended to be part of this invention, e.g., 55%, 56%, 57%, 64%, 68%, and so forth. In addition, ranges of values using a combination of any of the above recited values as upper and/or lower limits are Intended to be included, e.g., 50% to 80%.

Typical values for monoclonal antibodies, e.g., IgG, are about 10 nm. Low-ionic formulations, like those described herein, may be characterized in that the $D_h$ of the proteins are notably lower than protein formulations comprising ionic excipients. The $D_h$ values of antibodies in aqueous formulations made using a diafiltration/ultrafiltration process using pure water as an exchange medium, are notably lower than the $D_h$ of antibodies in conventional formulations independent of protein concentration. In one embodiment, adalimumab in the compositions of the invention have a $D_h$ of less than 4 nm, or less than 3 nm.

Alternatively, contrary to previous teachings that a small $D_h$ is required for stable high concentration adalimumab formulations with suitable viscosity for injection, it has been discovered that high concentration adalimumab formulations are stable and have suitable viscosity with adalimumab molecules that have a $D_h$ of greater than about 3. In another embodiment, the adalimumab in the high concentration formulation of the present invention has a $D_h$ of (a) about 3 to about 15 nm, about 3 to about 10 nm, about 3 to about 5 nm, about 3 to about 4 nm, about 4 to about 10 nm, about 4 to about 6 nm, about 4 to about 5 nm, about 5 to about 10 nm, or about 5 to about 7 nm; or (b) about 3, 4, 5, 6, 7, 8, 9, 10, 11, 12, 13, 14, or 15 nm.

In another embodiment, any of the high concentration adalimumab formulations of the present invention with a $D_h$ of greater than 3 nm has a viscosity of less than 25 cP. In a further embodiment, the viscosity is about 30, 25, 20, 15, 14, 13, 12, 11, 10, 9, 8, 7, 6, 5, 4, 3, 2, or 1 cP.

C. Buffers and Excipients

The compositions and formulations of the invention may include buffers, stabilizers, tonicity modifiers, viscosity modifiers, pharmaceutically acceptable carriers and other commonly used inactive ingredients of the pharmaceutical compositions (unless they are specifically excluded in the description of the specific embodiments of the invention) to achieve desired characteristics of a high concentration adalimumab formulation. These include, without limitation, stability, low viscosity, osmolality, and pH balance.

Typically, buffers are required to maintain the pH of an antibody composition and to impart stability. In some embodiments, it is surprising to discover that a high concentration adalimumab composition that is free, or substantially free, of a buffer is stable. In a buffer-free composition, the buffer capacity that is typically associated with the buffer is passed to the antibody itself. However, it is not known at what concentration adalimumab begins to self-buffer and what excipients, if any, are required to create a stable high concentration adalimumab composition that is free, or substantially free, of a buffer.

While excipients are typically included in formulations to impart desirable characteristics to the formulation (e.g. stability, low viscosity), reduction in the number of excipients and/or the total amount of excipients in a formulation may be advantageous. Reduced excipient formulations may be less expensive to manufacture and have fewer side effects upon administration to a subject. Therefore, much experimentation is often required to determine if a high concentration adalimumab formulation with reduced excipients can possess desirable characteristics (e.g. stability, low viscosity). For example, a surfactant is commonly added to antibody formulations to improve stability and prevent formation of particles. However, contrary to expectations, it may be possible create a high concentration adalimumab formulation that exhibits stability which is free, or substantially free, of a surfactant. Such a formulation may optionally include one or more stabilizing excipients, such as glycine.

Here, the present invention describes, for the first time, compositions comprising a high concentration of adalimumab that are stable. Additionally, the compositions have a viscosity suitable for subcutaneous administration to a subject.

In one embodiment, the compositions of the present invention are stabilized by inclusion of a stabilizer, as described herein, in the formulation. Alternatively, compositions of the present invention are stabilized by reduction, removal, or exclusion of excipients from a formulation. For example, salts (e.g. NaCl) are excellent tonicity modifiers but may destabilize adalimumab when adalimumab is at present at a high concentration. Thus, a high concentration adalimumab composition with low amounts of a salt, or that is free, or substantially free, of a salt, may surprisingly be stable. Such a formulation may optionally include a tonicity modifier that is not a salt, such as a polyol or a sugar.

In one embodiment, the compositions of the present include a viscosity modifier, as described herein, to reduce the viscosity of the high concentration adalimumab formulation. In another embodiment, it was surprising to find, contrary to expectations, that in some cases a high concentration adalimumab formulation did not require addition of a viscosity modifying agent for effective therapeutic administration.

Additionally, the compositions may have low amounts of aggregated and/or misfolded adalimumab, contain low amounts of a salt (e.g. NaCl) as a stabilizer, contain at least one amino acid, do not contain citrate, contain histidine, are free or essentially free of surfactants and/or polyols, and/or contain a viscosity reducing excipient.

Thus, the present invention provides aqueous high concentration formulations of adalimumab that are stable (e.g. long-term storage of adalimumab), so that adalimumab is stable over the course of storage either in liquid or frozen states and that have viscosities suitable for therapeutic application. The provided formulations do not require any extra steps such as rehydrating.

Buffers

Buffers maintain pH in a desired range, e.g., between pH 4 and pH 9. Buffers may also serve to stabilize adalimumab by a variety of other mechanisms, meaning they may be used outside of the nominal buffer capacity range indicated by their respective pKa values. Suitable buffers include acetate (e.g., including, but not limited, to acetate salts at about pH 4 to 6), citrate (e.g., at about pH 5 to 6.5), histidine (e.g., at about pH 5 to 7), phosphate (e.g., at about pH 5 to 8), Tris (e.g., at about pH 7 to 8), and glycine (e.g., at about pH 8 to 9). Specific embodiments include, without limitation, sodium acetate sodium or potassium phosphate, sodium or potassium citrate, ammonium acetate, tris-(hydroxymethyl)-aminomethane (tris), various forms of acetate and diethanolamine. Other suitable buffers include succinate, tartrate, bicarbonate, borate, and maleate.

Additionally, mono- or dicarboxylic acids with a backbone of 2-6 C-atoms, or at least one salt thereof are suitable buffers. "Mono- or dicarboxylic acid" includes mono- or dicarboxylic acids which have a straight alkyl- or alkylene backbone with n C-Atoms and salts thereof. Said backbone may have side chains (e.g. methyl groups); however, the carbon atoms comprised in these chains do not count as C-Atoms of the backbone. According to this definition, cyclic sugar acids, as for example ascorbic acid, do not qualify as "mono- or dicarboxylic acid with a backbone of n C-Atoms," as they do not have a straight alkyl- or alkylene backbone. Examples of a mono- or dicarboxylic acid, or a salt thereof, include, but are not limited to: acetic acid, or acetate; glutamic acid, or glutamate; adipic acid, or adipate; malic acid, or malate; tartaric acid, or tartrate; and succinic acid, or succinate. See, WO 2012/089778, which is herein incorporated by reference in its entirety, for further examples. Mono- or dicarboxylic acid is present in an aqueous form of the formulation in a concentration of between >1 and <100 millimolar ("mM"), between >2 and <50 mM, or between >5 and <25 mM.

The concentration of the buffer in the formulation is between about 1 mM to about 1M, or about 10 mM to about 200 mM. Buffers are well known in the art and are manufactured by known methods and available from commercial suppliers.

The pH of the pharmaceutical composition is generally between pH 4 and pH 9. In one embodiment, the pH of the pharmaceutical composition is at or near physiological levels, e.g., between about 5.5 and about 7.5. A person of ordinary skill in the art will understand that the pH can be adjusted as necessary to maximize stability and solubility of adalimumab in a particular formulation. Thus, adalimumab formulations at a pH outside of physiological ranges, yet tolerable to the patient, are also within the scope of the invention.

Excipients

Excipients, also referred to as chemical additives, co-solutes, or co-solvents, include components of a pharmaceutical formulation other than the active ingredient and are typically added during formulation development for a specific purpose, e.g., to confer favorable properties to the formulation, e.g., stabilize the polypeptide while in solution (also in dried or frozen forms), etc. Excipients are well known in the art and are manufactured by known methods and available from commercial suppliers. Excipients may include, for example, tonicity modifiers, stabilizers, salts, chelating agents, sacrificial additives, polyols, and surfactants.

Examples of suitable excipients include but are not limited to sugars/polyols such as: sucrose, lactose, glycerol, xylitol, sorbitol, mannitol, maltose, inositol, trehalose, glucose; polymers such as: serum albumin (bovine serum albumin (BSA), human SA or recombinant HA), dextran, PVA, hydroxypropyl methylcellulose (HPMC), polyethyleneimine, gelatin, polyvinylpyrrolidone (PVP), hydroxyethylcellulose (HEC); non-aqueous solvents such as: polyhydric alcohols, (e.g., PEG, ethylene glycol and glycerol) dimethylsulfoxide (DMSO) and dimethylformamide (DMF); amino acids such as: proline, L-serine, sodium glutamic acid, alanine, glycine, lysine hydrochloride, sarcosine and gamma-aminobutyric acid; surfactants such as: Tween®-80 (polysorbate 80), Tween®-20 (polysorbate 20), SDS, polysorbates, poloxamers; and miscellaneous excipients such as: potassium phosphate, sodium acetate, ammonium sulfate, magnesium sulfate, sodium sulfate, trimethylamine N-oxide, betaine, CHAPS, monolaurate, 2-O-beta-mannoglycerate or any combination of the above.

Suitable excipients may be present in the compositions of the invention unless they are specifically excluded in the description of the specific embodiments of the invention.

The concentration of one or more excipients in a formulation of the invention is/are between about 0.001 to 30 weight percent, about 0.01 to 10 weight percent, or about 0.1 to 2 weight percent.

Tonicity Modifiers

A tonicity modifier is a molecule that contributes to the osmolality of a solution. Generally, a tonicity modifier is included so that the pharmaceutical composition is about isotonic with serum. Note that the tonicity modifier may also provide some degree of conformational or colloidal stabilization as well. The osmolality of a pharmaceutical composition is adjusted to maximize the active ingredient's stability and/or to minimize discomfort to the patient upon administration.

In one embodiment, the osmolality of the provided formulations is from about 180 to about 420 mOsM. However, it is to be understood that the osmolality can be either higher or lower as specific conditions require.

Examples of tonicity modifiers suitable for modifying osmolality include, but are not limited to amino acids (not including arginine) (e.g., cysteine, histidine and glycine), salts (e.g., sodium chloride, sodium sulfate, or potassium chloride) and/or sugars/polyols (e.g., sucrose, sorbitol, maltose, and lactose). To minimize oxidation of amino acid residues (e.g., Met, Cys, Trp, and Tyr) on the therapeutic antibody, a sugar or polyol, rather than a salt, is used as a tonicity modifier.

In one embodiment, the invention provides a stable aqueous formulation comprising adalimumab, and salt as a tonicity agent.

In another embodiment, the invention provides a stable aqueous formulation comprising adalimumab, and sugar or polyol as a tonicity agent. In a further embodiment, the formulation has low pH (e.g., 6.5 or less, 6.2 or less, 6.0 or less, 5.8 or less, 5.5 or less, 5.3 or less, 5.2 or less, 5.1 or less, or 5.0 or less).

In one embodiment, the concentration of the tonicity modifier in the formulation is between about 1 mM to about 1 M, or about 10 mM to about 200 mM. Tonicity modifiers are well known in the art and are manufactured by known methods and available from commercial suppliers.

Suitable tonicity modifiers may be present in the compositions of the invention unless they are specifically excluded in the description of the specific embodiments of the invention.

Stabilizers

Stabilizers are a class of excipients that include sugars, polymers, and polyols as well as amino acids, which provide some degree of stability to adalimumab and/or to a pharmaceutical composition comprising adalimumab. Stabilizers have beneficial impact (e.g. Improve or prevent loss of) on physical stability, chemical stability and/or biological activity.

Physical stability includes, but is not limited to, aggregation, adsorption, precipitation, and conformational changes. Chemical stability incudes, but is not limited to, oxidation, deamidation, disulfide exchange, polymerization, fragmentation, and hydrolysis. Biological activity includes, but is not limited to, immunogenicity, toxicity, safety, and efficacy.

Oxidation affects stability, purity and safety of therapeutic proteins. It affects the structure, activity, and rate of degradation of proteins, and is believed to contribute to a variety of pathological conditions. Oxidized proteins, including adalimumab, are often functionally inactive and their unfolding is associated with enhanced susceptibility to proteolytic degradation. Additionally, oxidation of adalimumab may alter its hydrophobicity and impact aggregation, tonicity and/or viscosity of the formulation. Oxidation of adalimumab may be catalyzed by metal and peroxide contaminants present in excipients and delivery devices. Amino acids prone to oxidation include methionine, cysteine, tryptophan, and tyrosine. Specifically, Met$^{83}$ and Met$^{256}$ on the adalimumab heavy chain are prone to oxidation and therefore reducing or preventing oxidation of these residues may improve adalimumab stability.

Protein aggregation is a common issue encountered during manufacture, storage and transportation of therapeutic proteins, including adalimumab. Types of aggregates include: soluble/insoluble, covalent/non-covalent, reversible/irreversible, and native/denatured aggregates. Aggregates of proteins may arise from several mechanisms and various stress conditions, including, but not limited to high temperature, mechanical agitation, exposure of the protein to the air-water inter-phase. The presence of adalimumab aggregates is undesirable because they may cause immunogenic reactions and/or adverse local reactions when administered to a patient.

Specific examples of stabilizers suitable for use with the invention (in the context of optimized pH/buffer systems as described above) include sucrose, maltose, lactose, raffinose, and trehalose; sorbitol, maltitol, xylitol, and mannitol may also be employed for this purpose. Additional stabilizers suitable for use with the invention include amino acids, such as (but not limited to) glycine, arginine, glutamate, and proline (either as the free base form or as a salt form). The invention further includes specific combinations of amino acids, e.g., Arg and Glu, as well as specific combinations of one or more amino acids with one or more polyols (e.g., Gly together with sorbitol or mannitol), which have particularly desirable properties.

Inclusion of polysorbate surfactants in a formulation may increase the oxidation of adalimumab. While polysorbates are effective at preventing aggregation of protein, they contain ether linkages (e.g. polyoxyethylene moieties). Unsaturated alkyl chains in polysorbates (e.g. PS 80) can spontaneously autooxidize to produce peroxides, epoxy acids, and reactive aldehydes which may oxidize adalimumab. Therefore, it is advantageous to reduce or eliminate polysorbates (e.g. PS 80) in adalimumab formulations.

Alternatively, polysorbate 20 may be a suitable polysorbate since it contains only saturated alkyl chains and is less prone to generating oxidative species.

In one embodiment, the invention provides a stable aqueous formulation comprising adalimumab that is free, or substantially free, of a polysorbate surfactant. In a further embodiment, the formulation is free, or substantially free, of a polysorbate with unsaturated alkyl chains. If a further embodiment, the adalimumab formulation that is free, or substantially free, of a polysorbate surfactant is more stable than a formulation with a polysorbate surfactant.

Adalimumab Formulations Stabilized with Sugars and/or Polyols

In one embodiment, the invention provides a stable aqueous formulation comprising adalimumab, a sugar and/or a polyol; and optionally an amino acid. Examples of sugars include sucrose, lactose, maltose, trehalose, and glucose. Examples of polyols include glycerol, sorbitol, mannitol, xylitol, and maltitol.

Experiments may be performed to determine the effects of a combination of a sugar and/or a polyol (and optionally an amino acid) on the physical stability and other properties of specific adalimumab formulations, e.g., to assess such stabilizers for their effects on any tendency of adalimumab to associate in an undesirable conformation, and therefore on any aggregation in adalimumab formulations. Any improvements in formulation properties, e.g., a reduction in aggregation, due to such stabilizers may last for extended periods, e.g., 6 months, 9 months, a year, or up to two years or more. Thus, a combination of a sugar and/or a polyol (and optionally an amino acid) may stabilize aqueous pharmaceutical compositions containing adalimumab.

Without wishing to be bound to a particular theory, the combination of a sugar and/or a polyol (and optionally an amino acid) may be synergistic for the purposes of stabilizing adalimumab because even though excluded solutes are, on average, residing in the bulk, rather than on the surface of the protein, the fact is that there will be interactions between sugars/polyols and the protein. Those interactions will likely differ between sugars and smaller polyols or amino acids. In addition, at high concentrations, the two additives will alter the thermodynamic activity of the other, thereby leading to solution behavior that will be different than what would be observed for each individual component.

The pharmaceutical compositions of the invention may be prepared by combining, a purified adalimumab, a sugar, and/or a polyol (and optionally amino acid). Further, a buffer, a tonicity modifier and an additional excipient can be added as needed. A person of ordinary skill in the art will understand that the combining of the various components to be included in the composition can be done in any appropriate order. For example, the buffer can be added first, middle or last, and the tonicity modifier can also be added first, middle or last. A person of ordinary skill in the art will also understand that some of these chemicals can be incompatible in certain combinations, and accordingly, are easily substituted with different chemicals that have similar properties but are compatible in the relevant mixture.

In some embodiments, a sugar and a polyol may act in concert, in the same way two metals form an alloy with properties not exhibited by either metal. The same approach would lead one to use amino acids, such as proline, serine, or glutamate along with a sugar to achieve a stability profile better than either excipient could provide on its own. One ratio of a sugar to a polyol (or amino acid) in the alloy is believed to be between 5:1 and 1:5.

Suitable sugars include without limitation sucrose, trehalose, lactose, raffinose, and maltose. Suitable polyols include without limitation sorbitol, mannitol, glycerol, and propylene glycol. Suitable amino acids include without limitation glycine, alanine, glutamate, proline, serine, and threonine. Sugars, polyols and amino acids are available from commercial suppliers In one embodiment, the concentration of a sugar in the provided formulations is between about 0.1% (w/v) to 40%, for example about 1% to about 20%, about 2% to about 10%, or about 5% to 9%.

In one embodiment, the concentration of a polyol in the provided formulations is between about 0.1% to 30%, for example about 1% to about 10%, or about 2% to about 5%.

The formulations of the invention may also include buffering agents, tonicity modifiers, excipients, and other commonly used inactive ingredients of the pharmaceutical compositions. For simplicity, these are discussed more fully elsewhere in the application.

Adalimumab Stabilized with Amino Acids

Amino acids, e.g., proline, L-serine, sodium glutamic acid, glutamate, alanine, histidine, tryptophan, tyrosine, arginine, glycine, lysine, sarcosine and glycine betaine, may be employed as stabilizers in certain adalimumab formulations. These compositions may use the free base form of the amino acid or any conjugate acid form such as a hydrochloride salt. Such amino acids are readily available from commercial suppliers. For example, in one embodiment, the invention provides a stable aqueous pharmaceutical composition comprising adalimumab and one or more amino acids, wherein the amino acid(s) is selected from the group consisting of serine, proline, glycine, alanine, glutamate, arginine and combinations thereof. The composition may further optionally include a sugar and/or polyol.

Experiments performed in accordance with the Examples, may be performed to assess the effects of amino acids such as serine, glycine, alanine, glutamate, histidine, and/or arginine, on the stability & other properties of specific adalimumab formulations, e.g., any tendency for adalimumab to associate in undesired ternary or quaternary complexes. Such additives may improve the properties of the adalimumab formulations, e.g., by reducing protein aggregation, fragmentation, degradation, and/or clipping. Any such improvement in properties, e.g., reduction in aggregation, may last for extended periods, e.g., 6 months, 9 months, a year, or up to two years or more. Without wishing to be bound to a particular theory, it is believed that amino acids such as serine, proline and glutamate are able to stabilize aqueous pharmaceutical compositions containing adalimumab because they are excluded from the surface of the protein, resulting in net conformation stabilization.

The formulations described above may be prepared, e.g., by combining, a purified adalimumab and one or more of the above-referenced amino acids. Further, a buffer, a tonicity modifier and an additional excipient can be added as needed. A person of ordinary skill in the art will understand that the combining of the various components to be included in the composition can be done in any appropriate order. For example, the buffer can be added first, middle or last, and the tonicity modifier can also be added first, middle or last. A person of ordinary skill in the art will also understand that some of these chemicals can be incompatible in certain combinations, and accordingly, are easily substituted with different chemicals that have similar properties but are compatible in the relevant mixture.

In one embodiment, the concentration of the amino acids in the provided formulations is between about 1 mM and about 500 mM. In another embodiment, the concentration of the amino acid(s) is between about 10 mM and about 250 mM; in related embodiments, the concentration of the amino acid(s) is about 5 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM and 100 mM.

The formulations of the invention may also include buffering agents, tonicity modifiers, excipients, pharmaceutically acceptable carriers and other commonly used inactive ingredients of the pharmaceutical compositions. These are discussed more fully elsewhere in the application.

Adalimumab Stabilized with Cyclodextrins

Cyclodextrins can be used as stabilizers for adalimumab formulations. Cyclodextrins include but are not limited to, α-cyclodextrin, β-cyclodextrin, γ-cyclodextrin, derivitized cyclodextrines (e.g. hydroxypropylated, hydroxyethylated, ethylated, and methylated), branched cyclodextrins, cyclodextrin polymers, and mixture thereof. In one embodiment the cyclodextrin is sulfobutyl ether beta-cyclodextrin (SBEβCD). In another embodiment the cyclodextrin is hydroxypropyl-beta-cyclodextrin (HPβCD).

In an embodiment of the invention, the cyclodextrin or derivative is present in amount about 0.2% to about 10%. In another embodiment, the cyclodextrin is present in an amount of about 3 to about 100 mM.

Salts

Salts, e.g., NaCl, are often part of protein (e.g., antibody) formulations. For instance, salts such as NaCl, $Na_2SO_4$, and KCl, together with specific buffer combinations as described above, can confer particularly advantageous stability properties. As detailed in the application, such salts may be used with as well as without a polyol added (e.g., mannitol and NaCl). For example, concentrations as low as 20 to 50 mM can provide decreased levels of proteolysis (such as hinge region hydrolysis), oxidation, deamidation, or other chemical instabilities. Furthermore, low levels of salt (<50 mM) may lead to improved colloidal stability. Likewise, it is known that high concentrations of certain salts (>400 mM)

can increase conformational stability. The specific effects of NaCl and other salts on adalimumab is dependent on pH, buffer composition, and stress condition.

Further, a small amount of salt (e.g. NaCl) may be necessary for stability and/or to reduce chemical instability, to reduce viscosity, or to improve colloidal stability. In specific embodiments, the salt concentration in the formulation is reduced to about 140 mM, about 130 mM, about 120 mM, about 110 mM, about 100 mM, about 90 mM, about 80 mM, about 70 mM, about 60 mM, about 50 mM, about 40 mM, about 30 mM, about 20 mM, about 10 mM, about 5 mM, about 4 mM, about 3 mM, about 2 mM, about 1 mM, or even lower.

In another embodiment, salt is present in the composition at a concentration selected from the group comprising: not exceeding about 150 mM, not exceeding about 140 mM, not exceeding about 125 mM, not exceeding about 100 mM, not exceeding about 75 mM, not exceeding about 50 mM, not exceeding about 45 mM, not exceeding about 44 mM, not exceeding about 40 mM, not exceeding about 35 mM, not exceeding about 30 mM, not exceeding about 28 mM, not exceeding about 26.35 mM, not exceeding about 25 mM, not exceeding about 22 mM, not exceeding about 20 mM, not exceeding about 15 mM, not exceeding about 13 mM, not exceeding about 10 mM, not exceeding about 9 mM, not exceeding about 8 mM, not exceeding about 7 mM, not exceeding about 6 mM, not exceeding about 5 mM, not exceeding about 4 mM, not exceeding about 3 mM, not exceeding about 2 mM, not exceeding about 1 mM, and not exceeding about 0.5 mM.

In another embodiment, salt is present in the composition at a concentration selected from the group comprising: about 150 mM, about 140 mM, about 125 mM, about 100 mM, about 75 mM, about 50 mM, about 45 mM, about 44 mM, about 40 mM, about 35 mM, about 30 mM, about 28 mM, about 26.35 mM, about 25 mM, about 22 mM, about 20 mM, about 15 mM, about 13 mM, about 10 mM, about 9 mM, about 8 mM, about 7 mM, about 6 mM, about 5 mM, about 4 mM, about 3 mM, about 2 mM, about 1 mM, and about 0.5 mM.

In a further embodiment, the salt is NaCl.

In specific embodiments, sodium chloride is replaced with $Na_2SO_4$, KCl, $MgCl_2$, $CaCl_2$), MgSO4, $ZnCl_2$, or other physiologically-acceptable salts, e.g., to reduce or eliminate the NaCl load in the formulation. In a more specific embodiment, such replacement is particularly advantageous in cases where the buffer is not a phosphate buffer. In a further embodiment, other physiologically-acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Surfactants

Surfactants can confer protection against agitation and freeze/thaw damage, as well as stabilizing a formulation during storage. As further detailed in this application, surfactants which may be employed with adalimumab formulations of the present invention include Tween®-80 (polysorbate 80, PS 80), Tween®-20 (polysorbate 20, PS 20), SDS, polysorbate, polyoxyethylene copolymer. In certain embodiments, surfactants that may be particularly advantageous, including PS 20, PS 40, PS 60, and PS 80 at different concentrations, as well as SDS and poloxamer 188 (Pluronic® F-68). Other zwitterionic or nonionic surfactants may be used as well. As above, optimal formulation employing such surfactants will employ specific buffers at specific pH ranges, and may optionally include other tonicity modifier such as NaCl, polyol, or amino acid(s).

In one embodiment, the composition of the present invention comprises a high concentration of adalimumab and a surfactant. In another embodiment the surfactant is present at a concentration selected from the group comprising: about 0.01% wt, 0.05% wt, 0.1% wt, 0.2% wt, 0.03% wt, 0.4% wt, 0.5% wt, 0.6% wt, 0.75% wt, 1% wt, from about 0.01 to about 5% wt.

Ultra-Low Interfacial Tension Surfactant Compositions

Additionally, ultra-low interfacial tension ("IFT") surfactants as disclosed in U.S. Patent Application Publication Nos. 2011/0309011 and 2015/0232738, which are hereby incorporated by reference in their entirety, may be used in the present invention. Such surfactants comprise a hydrophilic portion and a hydrophobic aliphatic group. In some embodiments, the aliphatic groups include saturated or unsaturated carbon chains, between five and twenty units in length, or five and eighteen units in length, or eight and twenty units in length, or hydrogen. The carbon chains can optionally be unsaturated and, when present, reside anywhere along the carbon chain. The hydrophilic portion of the inventive compounds can comprise one or more hydrophilic groups or substituents. Hydrophilic portions or groups can be an ionizable groups, including, for example, amines and carboxylic acids. In certain aspects of the invention, the hydrophilic group is C(O)OH. Hydrophilic groups also include hydrophilic polymers, including, but not limited to, methylcelluloses, hydroxypropyl methylcellulose (HPMC), carboxymethylcellulose (CMC), polyalkylamine, poly(ethylene glycol) or poly(ethylene glycol)/poly(propylene glycol) copolymers. Nonionic hydrophilic materials such as polyalkylamine, poly(ethylene glycol) or poly(ethylene glycol)/poly(propylene glycol) copolymers can be used to increase hydrophilicity or aid stability in salt solutions.

IFT surfactants demonstrate switchable behavior based on pH, where the surfactant is capable of sustaining an emulsion at a higher pH, but loses its emulsification properties at a lower pH. Thus, the viscosity of a composition comprising a high concentration of adalimumab and an IFT surfactant may be adjusted by tuning the pH of the composition. In embodiments, pH switchable surfactants can comprise an ionizable group and a hydrophobic portion, or an ionizable portion and a hydrophilic and a hydrophobic portion. The ionizable group on the surfactant reacts to changes in pH that impact its emulsification properties. For example, with a decrease in pH, the ionizable group will be in the protonated form and the surfactant molecule will lose its solubility in water solution, thereby losing its emulsification properties. Conversely, if the pH increases, the ionizable group will be in the ionic form and the surfactant molecule will increase its solubility in water solution, thus being capable of sustaining emulsions of materials in water. This behavior is reversible because no functional groups are cleaved in the process.

Additionally, IFTs can demonstrate switchable behavior based on changes in temperature, whereby they are able to stabilize emulsions at temperatures below their cloud points but lose their emulsification properties at temperatures above their cloud points. In embodiments, temperature switchable surfactants will have a hydrophobic portion and a hydrophilic portion mainly containing, for example, ethoxylated groups. Such surfactants can display solubility in water solutions at temperatures below the cloud point and will be able to suspend materials in water. However, upon increasing the temperature above the cloud point, the surfactants will lose solubility in water solutions and will lose their emulsification properties. The behavior is reversible because no functional groups are cleaved in the process.

In embodiments, surfactants can demonstrate switchable behavior based on changes in temperature and pH. There are trigger points for emulsification capability, and conversely viscosity reducing capability, that are determined by pH and by temperature. In certain embodiments, temperature switchable behavior can be elicited in compounds having ether groups. For example, PEG or hydroxyl-terminated ethers such as PPO and PEO (e.g., Pluronic®) can be reacted with anhydrides such as alkene succinic anhydride (8, 9, 12 units), and styrene maleic anhydride copolymers.

In one embodiment, the composition of the present invention comprises a high concentration of adalimumab and an ultra-low interfacial tension surfactant. In a further embodiment the ultra-low interfacial tension surfactant is present at a concentration selected from the group comprising: about 0.01% wt, 0.05% wt, 0.1% wt, 0.2% wt, 0.03% wt, 0.4% wt, 0.5% wt, 0.6% wt, 0.75% wt, 1% wt, from about 0.01 to about 5% wt. In a further embodiment, the pH of the composition comprising comprises a high concentration of adalimumab and an ultra-low interfacial tension surfactant is selected from the group comprising: about 6.5, 6.2, 6.0, 5.8, 5.5, 5.3, 5.2, 5.1, 5.0, 4.9, 4.8, 4.7, 4.6, 4.5, 4.4, and 4.3. In another embodiment the composition of the present invention comprising a high concentration of adalimumab and an ultra-low interfacial tension surfactant has a lower viscosity than a high concentration adalimumab composition that does not contain a ultra-low interfacial tension surfactant.

Polymers

Polymers, such as dextrans, starches, celluloses, and polyethylene glycols (PEGs) may also provide stabilization to adalimumab, presumably by being excluded from the surface of the protein due to steric effects arising from their higher molecular weight. In one embodiment, the concentration of polymer is between 0.5 and 40%, and alternatively between 1 and 15%. The formulations of the invention may include combination of polymers with sugars, polyols, or amino acids in any combination.

Under certain conditions, adalimumab may be stable even in the absence of surfactants, and/or may be stabilized with surfactants other than PS80 and at lower surfactant concentrations. For example, certain polymers (e.g., PEG and celluloses) can exhibit surfactant-like properties and may be employed to stabilize adalimumab formulations in the absence of surfactants according to the present invention. Celluloses include, but are not limited to, methylcelluloses, hydroxypropyl methylcellulose (HPMC), carboxymethylcellulose (CMC), CMC salts such as carboxymethylcellulose sodium (NaCMC), and hydroxyethylcellulose (HEC). Additional polymers which may be employed in specific adalimumab formulations include serum albumin (bovine serum albumin (BSA), human SA or recombinant HA), dextrans, poly(vinyl alcohol) (PVA), methylcelluloses, hydroxypropyl methylcellulose (HPMC), polyethyleneimine, gelatin, polyvinylpyrrolidone (PVP), hydroxyethylcellulose (HEC).

Additionally, certain polymers may reduce the viscosity of compositions comprising adalimumab. Carboxymethylcellulose is available as a low viscosity carboxymethylcellulose for which a 4% solution in water at 25° C. has a viscosity of 50-200 centipoise (cps). Viscosity of CMC is both concentration and temperature dependent. As the temperature increases, the viscosity decreases. As the concentration increases, the viscosity increases. Therefore, a low concentration of a CMC may have viscosity reducing properties. CMC is a suitable replacement for traditional surfactants (e.g. Polysorbates) to provide stabilizing properties while reducing the viscosity of the formulation.

Suitable polymers can reversibly interact with adalimumab and prevent protein formed matrix interaction in high concentration formulations. In one embodiment, the composition of the present invention contains a polymer that reversibly interacts with adalimumab. In another embodiment, the polymer prevents and/or reduces matrix interactions of adalimumab.

In one embodiment, the composition of the present invention contains a polymer to reduce the viscosity of the composition. In another embodiment, the composition is free, or substantially free, of a surfactant. In yet another embodiment, the composition comprising a polymer has a lower viscosity than a composition without a polymer. In yet another embodiment, the composition comprising a polymer has a lower viscosity than a composition comprising a surfactant. In a further embodiment, the polymer is a CMC and the surfactant is a polysorbate. In another embodiment, the CMC is present in the composition at a concentration selected from the group comprising: not exceeding about 5%, not exceeding about 4%, not exceeding about 3%, not exceeding about 2%, not exceeding about 1%, not exceeding about 1%, not exceeding about 0.75%, not exceeding about 0.5%, not exceeding about 0.25%, not exceeding about 0.1%, not exceeding about 0.05%, not exceeding about 0.025%, and not exceeding about 0.01%.

Chelating Agents

Chelating agents such as EDTA, DPTA, etc., and/or sacrificial additives (e.g., ascorbate, Met), may be employed at specific pH values and with and without buffers (that may also act as chelating agents, e.g., citrate, phosphate) to enhance the formulation properties, especially in cases where there may be some level of oxidative damage (under certain conditions, certain metals can catalyze the degradation of antibodies, especially at the hinge region). The addition of a chelating agent, such EDTA and DPTA, may be beneficial at improving the storage stability of adalimumab. Such approaches may be employed to stabilize adalimumab formulations according to the present invention.

The inclusion of chelating agents, such as EDTA, reduces the levels of metal-catalyzed oxidation for adalimumab and also decreases metal-catalyzed hydrolysis of the hinge region. Certain buffers, such as citrate, may also function as chelating agents and can serve multiple purposes in stabilization of adalimumab.

Sacrificial additives are well known to diminish certain oxidation events, such as oxidation of methionine residues. Addition of the free amino acid, methionine, or some derivative, can lead to decreased oxidation of adalimumab. Ascorbate and various thiol derivatives can serve the same purpose. Likewise, Trp and its derivatives can also serve as a sacrificial additive, even in the case of photolytic oxidation.

Amino Acids

In one embodiment, the composition of the present invention contains at least one amino acid selected based on the amino acid's ability to increase the stability of adalimumab and/or reduce solution viscosity. In one embodiment, the amino acid contains a positively charged side chain, such as R, H, and K. In another aspect, the amino acid contains a negatively charged side chain, such as D and E. In another embodiment, the amino acid contains a hydrophobic side chain, such as A, F, I, L, M, V, W, and Y. In another embodiment, the amino acid contains a polar uncharged side chain, such as S, T, N, and Q. In yet another embodiment, the amino acid does not have a side chain, i.e., G.

In one embodiment, the amino acid is not H or R. In another embodiment, the amino acid is not M. In another aspect, the amino acid is not D, E, K, R, G, H, M or A. In one embodiment, the amino acid is any one of A, N, D, Q, E, I, L, K, F, P, S, T, W, Y, or V.

Some embodiments use at least two different amino acids as stabilizers permitting increased adalimumab concentration while substantially limiting the deleterious effects of concomitant protein-protein interaction. In one embodiment, one of the two different amino acids is selected, without limitation, from the group consisting of I, M, P, S, R, K, E, and N. In another aspect, each of the two different amino acids is selected from the group consisting of S, T, N, G, A, K, F, V, L, E, H, I, and P. In yet another embodiment, each of the two different amino acids is selected, without limitation, from the group consisting of S, T, N, G, P, and A.

In an embodiment, the amino acid capable of stabilizing adalimumab in solution includes, without limitation, G, S, T, A, R, M, K, P, N or any combination thereof. In a further embodiment, the amino acid capable of reducing the viscosity of a solution containing adalimumab includes, without limitation, P. In an embodiment, a formulation capable of stabilizing adalimumab and reducing the viscosity of a solution comprises, without limitation, a combination of G, S, T, A, R, M, K, P and/or N and P.

The concentration of each of the amino acids may be at least, for instance, about 0.1 mg/mL.

Other examples of using amino acids to increase the stability of a composition and/or reduce solution viscosity, which are now applied to the high concentration adalimumab compositions herein, are found in U.S. Patent Application Publication No. 2014/0127227, which is herein incorporated by reference in its entirety.

Viscosity Modifiers

Amino Acid Compositions

In an embodiment, the high concentration adalimumab composition of the present invention comprises an amino acid to reduce viscosity of the composition. In one embodiment, and amino acid is added to the composition to a concentration of about 0.4% wt to about 1.1% wt. In another embodiment, the amino acid is present in the composition at a concentration not exceeding about 50 mM, 75 mM, 100 mM, 125 mM, 150 mM, 175 mM, 200 mM, 250 mM, 300 mM, 350 mM, 400 mM, 450 mM, or 500 mM.

In a further embodiment, the amino acid is glycine and/or arginine. Such high concentration adalimumab compositions comprising an amino acid have a reduced viscosity compared to viscosity of the same formulation without the amino acid. In a further embodiment, the viscosity of the high concentration adalimumab composition with amino acid is reduced by at least about 5%, at least about 10%, at least about 15%, at least about 20%, at least about 25%, at least about 30%, at least about 40%, or at least about 50% compared to the viscosity of the composition in the absence of the amino acid.

Calcium Acetate Compositions

In an embodiment, the adalimumab composition of the present Invention comprises a calcium salt and/or acetate salt to reduce viscosity of the composition.

Calcium salts include, but are not limited to, calcium acetate, calcium carbonate and calcium chloride. In some embodiments, the calcium salt is at a concentration of at least 0.5 mM, 1 mM, 2 mM, 3 mM, 4 mM, 5 mM, 6 mM, 7 mM, 8 mM, 9 mM or 10 mM. In certain embodiments, the concentration of calcium salt is not greater than 11 mM, 12 mM, 13 mM, 14 mM, 15 mM, 16 mM, 17 mM, 18 mM, 19 mM, 20 mM, 21 mM, 22 mM, 23 mM, 24 mM, or 25 mM. Any range featuring a combination of the foregoing endpoints is contemplated, including but not limited to from about 0.5 mM to about 10 mM, about 5 mM to about 10 mM, or about 5 mM to about 15 mM.

In certain embodiments, the calcium salt is added at low concentrations so as not to negatively impact the adalimumab formulation. For example, at calcium chloride or magnesium chloride concentrations of 20 mM or greater, proteins may form a gel at low storage temperatures (e.g., 2-8° C.). Accordingly, a concentration of a calcium salt is generally selected for which the viscosity is reduced at the intended storage temperature of the reduced viscosity formulation.

In some embodiments, a formulation described herein further comprises, in addition to the calcium salt, an acetate buffer at a concentration of at least 5 mM, 6 mM, 7 mM, 8 mM, 9 mM, 10 mM, or 15 mM. In some embodiments, the concentration is no greater than 10 mM, 15 mM, 20 mM, 25 mM, 30 mM, 35 mM, 40 mM, 45 mM or 50 mM. Any range featuring a combination of the foregoing endpoints is contemplated, including but not limited to from about 5 mM to about 15 mM, or from about 5 mM to about 10 mM. In another embodiment, the buffer is added to a concentration that maintains pH around 5-6 or 5-5.5 or 4.5-5.5. When the calcium salt in the formulation is calcium acetate, in some embodiments, the total concentration of acetate is about 10 mM to about 50 mM, or about 20 mM to about 40 mM.

Other examples of using calcium acetate to reduce viscosity, which are now applied to the high concentration adalimumab compositions herein, are disclosed in US 2013/0202620 which is herein incorporated by reference in its entirety.

Magnesium Chloride Compositions

The viscosity of an adalimumab composition can be reduced by the addition of a viscosity reducing agent to the composition. In some cases, the viscosity reducing agent is added at a relatively low concentration. The viscosity of a composition comprising a viscosity reducing agent is reduced compared to the viscosity of a composition lacking the viscosity reducing agent.

In one embodiment, the viscosity reducing agent is a salt such as calcium chloride, magnesium chloride, sodium phosphate, or arginine hydrochloride. In the present invention, the viscosity reducing agent is added to the adalimumab composition to a final concentration of between about 0.5 mM and about 100 mM. In one embodiment, the viscosity reducing agent is added to the adalimumab composition to a final concentration of between about 5 mM and about 20 mM. In another embodiment, the viscosity reducing agent is added to an adalimumab composition to a final concentration of between 0.5 mM and 14 mM. In certain embodiments, the viscosity reducing agent is added to an adalimumab composition to a final concentration of between about 0.5 mM and not greater than 20 mM, or 19 mM, or 18 mM, or 17 mM, or 16 M, or 15 mM, or 14 mM, or 13 mM, or 12 mM, or 11 mM, or 10 mM. In general, when the viscosity reducing agent is added to an adalimumab composition to a final concentration of between about 0.5 mM and about 25 mM, the viscosity reducing agent is calcium chloride or magnesium chloride, but not sodium chloride, or sodium biphosphate. In certain embodiments, the viscosity reducing agent is added at low concentrations so as not to negatively impact an adalimumab composition. For example, at calcium chloride or magnesium chloride concentrations of 20 mM or greater, proteins may form a gel at low storage temperatures (e.g., 2-8° C.). Accordingly, a concentration of a viscosity reducing agent is generally selected for which the viscosity is reduced at the intended storage temperature of the reduced viscosity formulation.

Other examples of using viscosity reducing agents, including calcium chloride or magnesium chloride, but not sodium chloride, and sodium biphosphate, to reduce viscosity, which are now applied to the high concentration adalimumab compositions herein, are disclosed in U.S. Pat. No. 7,758,860 which is herein incorporated by reference in its entirety.

Creatine, Creatinine, and Carnitine Compositions

In an embodiment, the invention provides a method for stabilizing or reducing viscosity of high concentration adalimumab compositions by adding an excipient selected from the group consisting of creatinine, creatine, carnitine, or mixtures thereof, in an amount effective to stabilize and/or reduce viscosity. The invention also provides stable or reduced-viscosity adalimumab compositions containing effective amounts or concentrations of an excipient selected from the group consisting of creatinine, creatine, carnitine, or mixtures thereof. In some embodiments, the excipient is present at a viscosity-reducing (weight:volume) concentration; in other embodiments, the excipient is present at an aggregation-reducing concentration.

In exemplary embodiments, the concentration of creatine/creatinine is about 10 micromolar ("µM") to about 300 mM, or about 10 µM to about 50 mM, or about 1 µM to about 750 mM. In exemplary embodiments the concentration of creatine/creatinine is at least about 1, 2, 3, 4, 5, 6, 7, 8, 9, 10, 25, 50, 75, 100, 250, 500, or 750 µM. In further exemplary embodiments the concentration of creatine/creatinine is at least about 1, 2, 3, 4, 5, 6, 8, 10, 15, 20, 25, 30, 35, 40, 45, 50, 60, 70, 75, or 100 mM. In any of the preceding embodiments the concentration of creatine/creatinine is up to about 50, 75, 100, 150, 200, 250, 300, 350, 400, 450, 500, 550, 600, 650, 700 or 750 mM.

In other exemplary embodiments, the concentration of carnitine is about 5 to about 300 mM, or about 25 to about 400 mM, or about 100 to about 300 mM. In further exemplary embodiments, the concentration of carnitine is at least about 5, 10, 15, 20, 25, 30, 35, 40, 45, 50, 75, or 100 mM, and/or up to about 100, 150, 200, 250, 300, 350, 400, 450, 500, 550, 600, 650, 700, 750, 800, 850, 900, or 950 mM, or 1, 1.5, 2, 2.5, or 3 molar ("M").

In exemplary embodiments, the concentration of creatine/creatinine is at least about 4 ng per mg adalimumab, up to about 1.25 mg per mg adalimumab. In some embodiments, the concentration of creatine/creatinine is at least about 4, 10, 25, 50, 75, 100, 250, 500, or 750 nanograms ("ng") per milligram ("mg") adalimumab. In yet other embodiments, the concentration of creatine/creatinine is at least about 1, 5, 10, 20, 30, 40, 50, 60, 70, 80, 90 or 100 µg per mg adalimumab. In any of the preceding embodiments, the concentration of creatine/creatinine is up to about 150, 200, 250, 300, 350, 400, 450, 500, 550, 600, 650, 700, 750, 800, 850, 900, 950, 1000 or 1250 microgram ("µg") per mg adalimumab.

In other exemplary embodiments, the concentration of carnitine is at least about 2 µg per mg adalimumab, up to about 7 mg per mg adalimumab. In some embodiments, the concentration of carnitine is at least about 5, 10, 15, 20, 25, 30, 35, 40, 45, or 50 µg per mg adalimumab. In any of the preceding embodiments, the concentration of carnitine can be up to about 400, 450, 500, 550, 600, 650, 700, 750, 800, 850, 900, or 950 µg or up to about 1, 2, 3, 4, 5, 6, or 7 mg per mg adalimumab.

Other examples of using excipients, including creatine, creatinine, carnitine, and mixtures thereof, to reduce viscosity, which are now applied to the high concentration adalimumab compositions herein, are disclosed in U.S. Pat. No. 8,383,114 which is herein incorporated by reference in its entirety.

Polar Solvent Compositions

In one embodiment, the invention provides a composition comprising adalimumab and a polar solvent. In another embodiment, the polar solvent comprises dimethyl sulfoxide (DMSO) or dimethylacetamide (DMA). In yet another embodiment, the composition comprising adalimumab and a polar solvent has a reduced viscosity compared to an adalimumab composition lacking a polar solvent.

In some embodiments, DMSO or DMA in the adalimumab composition is in an amount of between about any of 0.1% to 2.5%, 0.1% to 5%, 0.1% to 7.5%, 0.1% to 10%, 1% to 2.5%, 1% to 5%, 1% to 7.5%, 1% to 10%, 1% to 15%, 1% to 20%, 1% to 25%, 1% to 30%, 1% to 40%, or 1% to 50% of the composition. In some embodiments, DMSO or DMA of the adalimumab composition comprising DMSO or DMA is in an amount of about any of 1%, 1.5%, 2%, 2.5%, 3%, 3.5%, 4%, 4.5%, 5%, 6%, 7%, 8%, 9%, or 10%. In some embodiments, DMSO or DMA is DMSO. In some embodiments, DMSO or DMA is DMA. In some embodiments, DMSO or DMA is a combination of DMSO and DMA.

Other examples of using polar solvents, including DMSO and DMA, and mixtures thereof, to reduce viscosity, which are now applied to the high concentration adalimumab compositions herein, are disclosed in U.S. Patent Application Publication No. 2013/0236448 which is herein incorporated by reference in its entirety.

Lauryldimethyiamineoxide Compostions

In one embodiment, the invention provides a composition comprising a high concentration of adalimumab and a lauryldimethyiamineoxide and/or of one of its amine oxide analogs. Lauryldimethyiamineoxide and/or of one of its amine oxide analogs has the ability to stabilize adalimumab compositions. In another embodiment, the composition comprising adalimumab and a lauryldimethyiamineoxide and/or of one of its amine oxide analogs has improved stability compared to a composition (i) lacking a lauryldimethyiamineoxide and/or of one of its amine oxide analogs, (ii) or comprising polysorbates. In a further embodiment, the stabilizing effect of lauryldimethyiamineoxide and/or of one of its amine oxide analogs is independent of the pH and tonic strength of the composition. In yet another embodiment, active concentrations of the lauryldimethyiamineoxide and/ or of one of its amine oxide analogs are independent of the adalimumab concentration in the composition. In a further embodiment, the concentrations of the lauryldimethyiamineoxide and/or of one of its amine oxide analogs is lower than that of other surfactants. In another embodiment, the present invention provides a stable composition comprising adalimumab and a lauryldimethyiamineoxide and/or of one of its amine oxide analogs wherein the concentration of the lauryldimethyiamineoxide and/or of one of its amine oxide analogs is less than the concentration of a surfactant in a stable composition comprising adalimumab and a surfactant.

In one embodiment, the concentration of the lauryldimethyiamineoxide and/or of one of its amine oxide analogs in the composition is equal to about 1.5 times its critical micelle concentration (CMC). In another embodiment, the concentration of the lauryldimethyiamineoxide and/or of one of its amine oxide analogs in the composition is an amount effective to stabilize adalimumab.

Composition comprising a high concentration of adalimumab and a lauryldimethyiamineoxide and/or of one of its amine oxide analogs which appear clear are stable compositions and compositions which are turbid lack the same degree of stability as clear compositions. Clarity and turbidity of compositions are determined by methods known to one of skill in the art and include visual inspection and light scattering measurements.

Alkyl amine oxide compounds include, but are not limited to, N,-Dimethyidecyiamine N-oxide (Amine oxide 1, CAS 2605-79-0, Sigma-Aldrich, CMC=10 mM), N,M-Lauryldimethylamine N-oxide (Amine oxide 2, CAS 1643-20-5, Sigma-Aldrich, CMC=1 mM), N,N-Dimethyltetradecylamine N-oxide (Amine oxide 3, CAS 3332-27-2, Sigma-Aldrich, CMC=0.14 mM) and I-2-(dimethylnitroryi)ethyidodecanamide (Amine oxide 4, CAS 86321-42-8, Sigma-Aldrich, CMC=1.8 mM).

Lauryldimethyiamineoxide and/or of one of its amine oxide analogs is further defined in WO 2014/045081, which is incorporated herein in its entirety.

Amino Acid Analogs

In one embodiment, the high concentration adalimumab composition of the present invention contains at least one amino acid analog selected based on its ability to reduce solution viscosity. In another embodiment, the amino acid analog is selected from the group consisting of arginine (either arginine-HCl or arginine in the presence of a succinate counterion, e.g., arginine succinate), arginine dipeptide, arginine tripeptide, polyarginine, homoarginine, 2-amino-3-guanidino-propionic acid, guanidine, ornithine, agmatine, guanidobutyric acid, urea, citrulline, N-hydroxy-L-nor-arginine, nitroarginine methyl ester, argininamide, arginine methyl ester, arginine ethyl ester, lysine, lysinamide, lysine methyl ester, histidine, histidine methyl ester, histamine, alanine, alaninamide, alanine methyl ester, putrescine, cadaverine, spermidine, spermine, and methionine. Examples of amino acid analogs are found in U.S. Patent Application Publication No. 2013/0058958, which is herein incorporated by reference in its entirety.

In one embodiment, the amino acid analog is the sole viscosity modifying agent. In another embodiment, the amino acid analog is used in combination with other modifying agents. In one embodiment, the amino acid analog, is present in the composition at a concentration of about 10 mM, about 20 mM, about 30 mM, about 40 mM, about 44 mM, about 50 mM, about 100 mM, about 150 mM, about 200 mM, about 250 mM, about 300 mM, about 400 mM, about 500 mM, about 1 M, at least 10 mM, at least 20 mM, at least 30 mM, at least 40 mM, at least 44 mM, at least 50 mM, at least 100 mM, at least 150 mM, at least 200 mM, at least 250 mM, at least 300 mM, at least 400 mM, at least 500 mM, at least 1 M, between about 10 mM and about 1M.

In another embodiment, combinations of viscosity modifying agents present in the composition have a total concentration of about 10 mM, about 20 mM, about 30 mM, about 40 mM, about 44 mM, about 50 mM, about 100 mM, about 150 mM, about 200 mM, about 250 mM, about 300 mM, about 400 mM, about 500 mM, about 1 M, at least 10 mM, at least 20 mM, at least 30 mM, at least 40 mM, at least 44 mM, at least 50 mM, at least 100 mM, at least 150 mM, at least 200 mM, at least 250 mM, at least 300 mM, at least 400 mM, at least 500 mM, at least 1 M, between about 10 mM and about 1M.

In another embodiment, the high concentration adalimumab composition in which an amino acid analog is present has a viscosity equal to or less than: 50 cP; 20 cP; 15 cP; 14 cP; 13 cP; 12 cP; 11 cP; 10 cP; 9 cP; 8 cP; 7 cP; 6 cP; 5 cP; 4 cP; 3 cP; 2 cP; or 1 cP.

In another embodiment, the formulations of the present invention contain an excipient selected from the group consisting of hindered amines, anionic aromatics, functionalized amino acids, oligopeptides, short-chain organic acids, and low molecular weight aliphatic polyacids. These viscosity modifying agents are present at concentration between about 5 mg/mL and about 300 mg/mL. Examples are disclosed in WO 2015/196091 A1 and WO 2015/196187 A1, which are herein incorporated by reference in their entirety.

Preservatives

In one embodiment, the invention provides a composition comprising adalimumab and a preservative. A "preservative" is a compound which can be included in the composition to essentially reduce bacterial action therein, thus facilitating the production of a multi-use composition, for example. Examples of preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzelthonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. In one embodiment, the preservative is benzyl alcohol.

D. Stable High Concentration Adalimumab Compositions

Embodiments of the adalimumab formulations of the present invention were categorized in four separate groups, referred to herein as "Block 1" through "Block 4." Numerous experiments were prepared for the embodiments of each Block. In these examples, formulations were exposed to storage conditions to demonstrate stability. Accelerated storage conditions include 1 week at 40° C., 2 weeks at 40° C., and 4 weeks at 25° C. The chemical and physical stability of the composition and/or the adalimumab protein is measured at a time point, including time zero (t=0) by SEC, RP, CEX, MFI, pH, conductivity, and viscosity. Additional analyses include DLS, UV, CE-IEF, CE-SDS, other methods described herein, and those known to one of skill in the art.

Compositions and adalimumab, in accordance with embodiments described herein, have desirable properties, such as desirable solubility, viscosity, tonicity, syringeabilty, conductivity, and stability. Lyophilates in accordance with embodiments described herein have desirable properties, as well, such as desirable stability and reconstitution.

In one embodiment, wherein adalimumab is present in the composition at a concentration selected from the group comprising greater than about 50 mg/mL, at least about 100 mg/mL, between about 100 to 300 mg/mL, between about 100 to 200 mg/mL, and between about 100 to 150 mg/mL, between about 100 to 125 mg/mL, about 100 mg/mL, about 125 mg/mL, about 150 mg/mL, about 175 mg/mL, about 200 mg/mL, about 214 mg/mL, about 225 mg/mL, about 250 mg/mL, about 275 mg/mL, and about 300 mg/mL.

In one embodiment, the present invention provides a composition comprising a high concentration of adalimumab, wherein the composition is stable. In another embodiment, the composition exhibits long term stability.

In one embodiment, the composition is stable at room temperature for at least ten days. In another embodiment, the composition is stable for at least three months. In another embodiment, the composition is stable for at least six months. In yet another embodiment, the composition is stable for at least one year.

In one embodiment, a composition of the present invention has reduced pain upon injection to a subject as compared to an adalimumab composition comprising citrate. In a further embodiment, an adalimumab composition comprising citrate is Humira®. In yet another embodiment, a composition of the present invention has reduced pain upon injection to a subject as compared to Humira®. In another embodiment, injection of a composition of the present invention into a subject results in a Pain Visual Analog Scale (VAS) score of less than 1.0. In a further embodiment, the VAS scale is from 0 (no pain) to 10 (excruciating pain).

In another embodiment, a composition of the present invention has fewer sub-visible particles than Humira®. In yet another embodiment, a composition of the present invention has fewer adalimumab fragments and/or aggregates than Humira®.

In another embodiment, a composition of the present invention has a conductivity of equal to or greater than about 2.5 mS/cm.

In another embodiment, a composition of the present invention has a Dh equal to or greater than about 3 nm.

In another embodiment, a composition of the present invention has a viscosity of less than about 50 cP.

In another embodiment, a composition of the present invention has an osmolality of about 250 to about 350 mOsm/L.

In another embodiment, a composition of the present invention is stable at room temperature for at least about 10 days.

Block 1

The present invention provides a composition comprising a high concentration of adalimumab, wherein the composition is free, or substantially free of, a citrate buffer and the composition exhibits long term stability. Examples of Block 1 formulations are set forth in the Example 1, below.

In one embodiment, wherein adalimumab is present in the composition at a concentration selected from the group comprising greater than about 50 mg/mL, at least about 100 mg/mL, between about 100 to 300 mg/mL, between about 100 to 200 mg/mL, and between about 100 to 150 mg/mL, between about 100 to 125 mg/mL, about 100 mg/mL, about 125 mg/mL, about 150 mg/mL, about 175 mg/mL, about 200 mg/mL, about 214 mg/mL, about 225 mg/mL, about 250 mg/mL, about 275 mg/mL, and about 300 mg/mL.

In one embodiment, some compositions optionally do not contain a buffer. These compositions are self-buffering as result of high concentrations of adalimumab and polyol. In a further embodiment, the composition is optionally free, or substantially free of, a buffer. For example, Block 1 formulations 1A-26 and 1B-26 do not contain a buffer, but are self-buffering as result of high concentrations of adalimumab and a polyol.

In one embodiment, compositions contain a buffer, which is not a citrate buffer. In a one embodiment, the buffer is histidine or succinate. In a further embodiment, histidine is present at a concentration not exceeding about 60 mM. In another embodiment, histidine is present at a concentration of about 20 mM. In a yet another embodiment, histidine is present at a concentration of about 30 mM. In another embodiment, succinate is present at a concentration not exceeding about 30 mM. In a still another embodiment, succinate is present at a concentration of about 15 mM.

In one embodiment the composition comprising high concentration of adalimumab has a pH from about 4 to 8. In another embodiment, the pH is between about 5 and 6. In yet another embodiment, the pH is between about 5.2 and 5.4.

In another embodiment, the composition comprising a high concentration of adalimumab further comprises a stabilizer. In a further embodiment, the stabilizer is an amino acid. In a yet another embodiment, the amino acid is selected from the group comprising histidine, glycine, and arginine. In an embodiment, histidine is present at a concentration not exceeding about 60 mM. In another embodiment, histidine is present at a concentration of about 30 mM. In one embodiment, glycine is present at a concentration not exceeding about 300 mM. In another embodiment, glycine is present at a concentration from about 90 to 240 mM. In one embodiment, arginine is present at a concentration not exceeding about 200 mM. In another embodiment, arginine is present at a concentration from about 25 to 140 mM.

In another embodiment, the amino acid is A, N, D, Q, E, I, L, K, F, P, S, T, W, Y, or V. In yet another embodiment, the composition comprises at least two different amino acids. In one embodiment, the two different amino acids are selected from the group consisting of H, G, I, M, P, S, R, K, E, and N. In another embodiment the two different amino acids are selected from the group consisting of R, S, T, N, G, A, K, F, V, L, E, H, I, and P. In another embodiment, the two different amino acids are selected from the group consisting of H, R, 5, T, N, G, P, and A.

In one embodiment, the composition comprising a high concentration of adalimumab further comprises a polyol. In another embodiment, the polyol is mannitol. In yet another embodiment, mannitol is present at a concentration not exceeding about 300 mM. In still another embodiment, mannitol is present at a concentration from about 150 to 240 mM.

In one embodiment, the composition comprising a high concentration of adalimumab further comprises a salt. In another embodiment, the salt stabilizes the adalimumab, modifies the tonicity of the composition, and/or reduces the viscosity of the composition. In further embodiment, the salt is NaCl. In another embodiment, NaCl is present at a concentration not exceeding about 200 mM. In yet embodiment, NaCl is present at a concentration from about 13 to 140 mM.

In one embodiment, the composition comprising a high concentration of adalimumab further comprises a surfactant. In another embodiment, the surfactant is polysorbate 80 (PS 80). In yet another embodiment, PS 80 is present at a concentration not exceeding about 0.5 wt %. In still another embodiment, PS 80 is present at a concentration from about 0.01 to 0.1 wt %.

Block 2

The present invention provides a composition comprising a high concentration of adalimumab, wherein the composition has reduced excipients as compared to Humira® and the composition exhibits long term stability. The term "reduced excipients" means a reduction in the number of excipients present in the composition, a reduction in the amount of a single excipient or combinations of excipients, and/or the reduction in the total amount of excipients in the composition. For example, each 0.8 mL composition of Humira® contains adalimumab 40 mg, citric acid monohydrate 1.04 mg, dibasic sodium phosphate dihydrate 1.22 mg, mannitol 9.6 mg, monobasic sodium phosphate dihydrate 0.69 mg, polysorbate 80 0.8 mg, sodium chloride 4.93 mg, sodium citrate 0.24 mg and Water for Injection, USP. Sodium hydroxide is added as necessary to adjust pH. In alternate units, Humira® contains adalimumab 50 mg/mL, sodium chloride 105 mM, sodium phosphate 14.1 mM, sodium citrate 7.2 mM, mannitol 1.2%, polysorbate 80 0.1%, at pH 5.2. An alternative adalimumab composition contains adalimumab 50 mg/mL, sodium chloride 44 mM, glycine 160 mM, histidine 30 mM, polysorbate 80 0.1%, at pH 5.3.

The present invention includes a composition comprising a high concentration of adalimumab, wherein the composition has less than the amount of citric acid monohydrate, dibasic sodium phosphate dihydrate, mannitol, monobasic sodium phosphate dihydrate, polysorbate 80, sodium chloride, and/or sodium citrate present in Humira®. In an alternate embodiment, the composition has less than the amount of sodium chloride, sodium phosphate, sodium citrate, mannitol, and/or polysorbate 80 present in Humira®.

In one embodiment, the present invention provides a composition comprising a high concentration of adalimumab wherein the composition exhibits long term stability and is free, or substantially free, of a citrate buffer, a phosphate buffer, or both a citrate buffer and a phosphate buffer.

In another embodiment, the present invention provides a composition comprising a high concentration of adalimumab wherein the composition exhibits long term stability and is free, or substantially free, of a polyol, a surfactant, or both a polyol and a surfactant. In a further embodiment, the composition is optionally free, or substantially free of, a buffer. Such compositions are self-buffering as result of high concentrations of adalimumab alone or in combination with other non-buffer excipients (e.g. a polyol).

In another embodiment, the composition is buffered with an amino acid. In a further embodiment, the amino acid is selected from the group comprising histidine and glycine.

In one embodiment, wherein adalimumab is present in the composition at a concentration selected from the group comprising greater than about 50 mg/mL, at least about 100 mg/mL, between about 100 to 300 mg/mL, between about 100 to 200 mg/mL, and between about 100 to 150 mg/mL, between about 100 to 125 mg/mL, about 100 mg/mL, about 125 mg/mL, about 150 mg/mL, about 175 mg/mL, about 200 mg/mL, about 214 mg/mL, about 225 mg/mL, about 250 mg/mL, about 275 mg/mL, and about 300 mg/mL.

In one embodiment, the composition comprises a buffer, but is free, or substantially free of, polyol and surfactant. In another embodiment, the composition comprises a buffer and a polyol, but is free, or substantially free of, surfactant. In yet another embodiment, the composition comprises a buffer and a surfactant, but Is free, or substantially free of, polyol.

In one embodiment, the composition further comprises a buffer selected from the group comprising citrate, sodium phosphate, succinate, histidine, and potassium phosphate. In a one embodiment, citrate is present at a concentration not exceeding about 50 mM. In another embodiment, citrate is present at a concentration from about 8 to 20 mM. In one embodiment, sodium phosphate is present at a concentration not exceeding about 50 mM. In another embodiment, sodium phosphate is present at a concentration from about 10 to 20 mM. In one embodiment, succinate is present at a concentration not exceeding about 50 mM. In another embodiment, succinate is present at a concentration from about 10 to 20 mM. In one embodiment, histidine is present at a concentration not exceeding about 75 mM. In another embodiment, histidine is present at a concentration from about 10 to 50 mM. In one embodiment, potassium phosphate is present at a concentration not exceeding about 100 mM. In another embodiment, potassium phosphate is present at a concentration from about 15 to 75 mM.

In one embodiment the composition comprising high concentration of adalimumab has a pH from about 3 to 8. In another embodiment, the pH is between about 3 and 6. In yet another embodiment, the pH is between about 3.5 and 5.3.

In one embodiment, the composition comprising a high concentration of adalimumab further comprises a polyol. In another embodiment, the polyol is mannitol. In yet another embodiment, mannitol is present at a concentration not exceeding about 300 mM. In still another embodiment, mannitol is present at a concentration from about 65 to 240 mM.

In one embodiment, the composition comprising a high concentration of adalimumab further comprises a stabilizer. In another embodiment, the stabilizer is an amino acid. In a yet another embodiment, the amino acid is selected from the group comprising histidine, glycine, arginine, and methionine. In another embodiment, the amino acid buffers the high concentration adalimumab composition. In one embodiment, histidine is present at a concentration not exceeding about 60 mM. In another embodiment, histidine is present at a concentration from about 10 to 50 mM. In one embodiment, glycine is present at a concentration not exceeding about 300 mM. In another embodiment, glycine is present at a concentration from about 50 to 240 mM. In one embodiment, arginine is present at a concentration not exceeding about 200 mM. In another embodiment, arginine is present at a concentration from about 25 to 150 mM. In one embodiment, methionine is present at a concentration not exceeding about 100 mM. In another embodiment, methionine is present at a concentration from about 10 to 50 mM.

In one embodiment, the amino acid is A, N, D, Q, E, I, L, K, F, P, S, T, W, Y, or V. In other embodiment, the composition comprises at least two different amino acids. In one embodiment, the two different amino acids are selected from the group consisting of H, G, I, M, P, S, R, K, E, and N. In another embodiment the two different amino acids are selected from the group consisting of R, S, T, N, G, A, K, F, V, L, E, H, I, and P. In another embodiment, the two different amino acids are selected from the group consisting of H, R, S, T, N, G, P, and A.

In one embodiment, the composition comprising a high concentration of adalimumab further comprises a salt. In another embodiment, the salt stabilizes the adalimumab and/or reduces the viscosity of the composition. In yet another embodiment, the salt is selected from the group comprising NaCl, $Na_2SO_4$, and $MgCl_2$. In one embodiment, NaCl is present at a concentration not exceeding about 200 mM. In another embodiment, NaCl is present at a concentration from about 15 to 150 mM. In one embodiment, $Na_2SO_4$ is present at a concentration not exceeding about 150 mM. In another embodiment, $Na_2SO_4$ is present at a concentration from about 15 to 100 mM. In one embodiment, $MgCl_2$ is present at a concentration not exceeding about 50 mM. In another embodiment, $MgCl_2$ is present at a concentration of about 25 mM.

In one embodiment, the composition comprising a high concentration of adalimumab further comprises a chelating agent. In another embodiment, the chelating agent is selected from the group comprising EDTA and DPTA. In one embodiment, EDTA is present at a concentration not exceeding about 0.5 wt %. In another embodiment, EDTA is present at a concentration from about 0.01 to 0.1 wt %.

In one embodiment, the composition comprising a high concentration of adalimumab further comprises a surfactant. In another embodiment, the surfactant is selected from the group comprising polysorbate 80 (PS 80), polysorbate 20 (PS 20), and Pluronic® F-68 (F68). In one embodiment, PS 80 is present at a concentration not exceeding about 0.5 wt %. In another embodiment, PS 80 is present at a concentration from about 0.01 to 0.1 wt %. In one embodiment, PS 20 is present at a concentration not exceeding about 0.1 wt %. In another embodiment, PS 20 is present at a concentration from about 0.01 to 0.05 wt %. In one embodiment, F68 is present at a concentration not exceeding about 0.5 wt %. In another embodiment, F68 is present at a concentration from about 0.05 to 0.1 wt %.

Block 3

The present invention provides an improved composition comprising a high concentration of adalimumab, wherein the composition exhibits long term stability. As discussed above, creating an adalimumab composition with long term stability depends on discovering the excipient(s), and specific concentration of those excipients, which impart stability to the specific amount of adalimumab (i.e. the concentration) in the composition. Additionally, adalimumab compositions are created to exhibit other desirable characteristics, such as low viscosity and neutral osmolality (e.g. isotonic), for adalimumab at the concentration in the composition.

Therefore, one does not expect that increasing the concentration of adalimumab in a low concentration composition (e.g. 50 mg/mL), without changing excipient composition or concentrations, to a high concentration level (e.g. 100 mg/mL or greater) results in composition with long term stability or other desirable characteristics (e.g. viscosity, osmolality).

Therefore, high concentration compositions of adalimumab (e.g. 100 mg/mL or greater) must be specifically formulated and tested to establish long term stability. Due to the complex physical, ionic, and chemical interactions between adalimumab and excipients, one cannot expect to develop a high concentration adalimumab composition with long term stability simply by increasing the concentration of adalimumab in a low concentration composition (e.g. 50 mg/mL), without changing excipient composition or concentrations, to a high concentration level.

In one embodiment, the present invention comprises a composition comprising a high concentration of adalimumab and a surfactant, wherein the composition exhibits long term stability.

In one embodiment, wherein adalimumab is present in the composition at a concentration selected from the group comprising greater than about 50 mg/mL, at least about 100 mg/mL, between about 100 to 300 mg/mL, between about 100 to 200 mg/mL, and between about 100 to 150 mg/mL, between about 100 to 125 mg/mL, about 100 mg/mL, about 125 mg/mL, about 150 mg/mL, about 175 mg/mL, about 200 mg/mL, about 214 mg/mL, about 225 mg/mL, about 250 mg/mL, about 275 mg/mL, and about 300 mg/mL.

In one embodiment, the surfactant is selected from the group comprising polysorbate 80 (PS 80), polysorbate 20 (PS 20), and Pluronic® F-68 (F68). In another embodiment, the surfactant is PS 80. In one embodiment, PS 80 is present at a concentration not exceeding about 0.5 wt %. In another embodiment, PS 80 is present at a concentration from about 0.01 to 0.1 wt %. In yet another embodiment, PS 80 is present at a concentration of about 0.1 wt %.

In one embodiment, the composition further comprises a buffer. In another embodiment, the buffer is selected from the group comprising histidine, pyrophosphate (NaPyro), sodium phosphate, citric acid, citrate, sodium acetate, acetate (e.g. acetic acid), and succinate.

"Pyrophosphate," as used herein, is an anion, salt, or ester of pyrophosphoric acid. Pyrophosphate is also sometimes referred to as diphosphate, as pyrophosphate contains two phosphate groups covalently bound together. The difference in number of phosphate groups between phosphate and pyrophosphate results in a different number of available negative charges. A phosphate molecule can have up to three negative charges, whereas a pyrophosphate can have up to four negative charges. Pyrophosphates, in general, are highly water soluble and stable at isotonic and physiological pH. As described herein, pyrophosphates also make good complexing agents, and can be useful to improve the stability of certain compounds, including therapeutic agents such as a therapeutic polypeptide or a therapeutic polysaccharide. In some embodiments, the pharmaceutical compositions described herein are substantially free of phosphate molecules. For example, a pharmaceutical composition described herein can have less than 5000 ppm (0.5%) or less than 2500 ppm (0.25%) or less than 1000 ppm (0.1%) of phosphate, e.g., at the time of formulation.

In some embodiments, the pyrophosphate is a salt. Exemplary salts include sodium, potassium, calcium and magnesium salts. In some embodiments the pyrophosphate is sodium pyrophosphate. Aqueous compositions described herein can have, e.g., 5 mM-250 mM pyrophosphate, 5 mM-200 mM pyrophosphate, 5 mM-150 mM pyrophosphate, 5 mM-100 mM pyrophosphate; and a concentration of pyrophosphate not exceeding 15, mM, 20 mM, 25 mM, 30 mM, 35 mM, 50 mM, 75 mM, 100 mM, or 150 mM.

In one embodiment, histidine is present at a concentration not exceeding about 75 mM. In another embodiment, histidine is present at a concentration of about 25 mM. In one embodiment, sodium pyrophosphate is present at a concentration not exceeding about 50 mM. In another embodiment, sodium pyrophosphate is present at a concentration from about 5 to 25 mM. In yet another embodiment, sodium pyrophosphate is present at a concentration of about 14.1 mM. In one, sodium phosphate is present at a concentration not exceeding about 25 mM. In another, sodium phosphate is present at a concentration from about 6 to 14.5 mM. In one embodiment, citric acid is present at a concentration not exceeding about 10 mM. In another embodiment, citric acid is present at a concentration from about 0.5 to 5 mM. In yet another embodiment, citric acid is present at a concentration of about 1 mM. In one embodiment, citrate is present at a concentration not exceeding about 15 mM. In another embodiment, citrate is present at a concentration from about 2.4 to 7 mM. In one embodiment, sodium acetate is present at a concentration not exceeding about 50 mM. In another embodiment, sodium acetate is present at a concentration from about 0.05 to 5 mM. In still another embodiment, sodium acetate is present at a concentration of about 1 mM. In one embodiment, acetate is present at a concentration not exceeding about 50 mM. In another embodiment, acetate is present at a concentration from about 15 to 20 mM. In one embodiment, succinate is present at a concentration not exceeding about 50 mM. In another embodiment, succinate is present at a concentration from about 4 to 25 mM.

In one embodiment the composition comprising a high concentration of adalimumab has a pH from about 3 to 8. In another embodiment, the pH is between about 5 and 7. In yet another embodiment, the pH is between about 5.2 and 6.5.

In one embodiment, the composition comprising a high concentration of adalimumab further comprises a stabilizer. In another embodiment, the stabilizer is an amino acid. In a yet another embodiment, the amino acid is selected from the group comprising histidine, glycine, and arginine. In one embodiment, histidine is present at a concentration not exceeding about 60 mM. In another embodiment, histidine is present at a concentration from about 10 to 50 mM. In yet another embodiment, histidine is present at a concentration of about 25 mM. In one embodiment, glycine is present at a concentration not exceeding about 300 mM. In another embodiment, glycine is present at a concentration from about 50 to 240 mM. In one embodiment, arginine is present at a concentration not exceeding about 200 mM. In another embodiment, arginine is present at a concentration from about 2 to 50 mM. In yet another embodiment, arginine is present at a concentration from about 10 to 24 mM.

In one embodiment, the amino acid is A, N, D, C, E, I, L, K, F, P, S, T, W, Y, or V. In other embodiment, the composition comprises at least two different amino acids. In one embodiment, the two different amino acids are selected from the group consisting of H, G, I, M, P, S, R, K, E, and N. In another embodiment the two different amino acids are selected from the group consisting of R, S, T, N, G, A, K, F, V, L, E, H, I, and P. In another embodiment, the two different amino acids are selected from the group consisting of H, R, S, T, N, G, P, and A.

In one embodiment, the composition comprising a high concentration of adalimumab further comprises a salt. In another embodiment, the salt stabilizes the adalimumab and/or reduces the viscosity of the composition. In another embodiment, the salt is selected from the group comprising NaCl, and adipate. In one embodiment, NaCl is present at a concentration not exceeding about 200 mM. In another embodiment, NaCl is present at a concentration from about 26.35 to 105 mM. In one embodiment, adipate is present at a concentration from not exceeding about 150 mM. In another embodiment, adipate is present at a concentration from about 5 to 50 mM. In yet another embodiment, adipate is present at a concentration of about 23 mM.

In one embodiment, the composition comprising a high concentration of adalimumab further comprises a polyol. In another embodiment, the polyol is selected from the group comprising mannitol, trehalose, and sorbitol. In one embodiment, mannitol is present at a concentration not exceeding about 350 mM. In another embodiment, mannitol is present at a concentration from about 66 to 240 mM. In one embodiment, trehalose is present at a concentration not exceeding about 350 mM. In another embodiment, trehalose is present at a concentration from about 107 to 240 mM. In one embodiment, sorbitol is present at a concentration not exceeding about 100 mM. In another embodiment, sorbitol is present at a concentration from about 1 to 25 mM. In yet another embodiment, sorbitol is present at a concentration of about 10 mM.

Block 4

The present invention provides a composition comprising a high concentration of adalimumab, an acetate buffer, optionally a tonicity agent, and optionally a surfactant, wherein the composition exhibits long term stability. In one embodiment, acetate is present at a concentration not exceeding about 75 mM. In another embodiment, acetate is present at a concentration from about 10 to 30 mM.

In another embodiment, the present invention provides a composition comprising a high concentration of adalimumab, a tonicity agent and optionally a surfactant, wherein the composition is free, or substantially free, of acetate, and exhibits long term stability.

In one embodiment, wherein adalimumab is present in the composition at a concentration selected from the group comprising greater than about 50 mg/mL, at least about 100 mg/mL, between about 100 to 300 mg/mL, between about 100 to 200 mg/mL, and between about 100 to 150 mg/mL, between about 100 to 125 mg/mL, about 100 mg/mL, about 125 mg/mL, about 150 mg/mL, about 175 mg/mL, about 200 mg/mL, about 214 mg/mL, about 225 mg/mL, about 250 mg/mL, about 275 mg/mL, and about 300 mg/mL.

In one embodiment the composition comprising a high concentration of adalimumab has a pH from about 3 to 8. In another embodiment, the pH is between about 4 and 7. In yet another embodiment, the pH is between about 4.5 and 6.

In one embodiment, the composition comprising a high concentration of adalimumab further comprises a polyol. In another embodiment, the polyol is selected from the group comprising trehalose, mannitol, sorbitol, and xylitol. In one embodiment, trehalose is present at a concentration not exceeding about 350 mM. In another embodiment, trehalose is present at a concentration from about 65 to 230 mM. In one embodiment, mannitol is present at a concentration from not exceeding about 400 mM. In another embodiment, mannitol is present at a concentration from about 65 to 270 mM. In one embodiment, sorbitol is present at a concentration not exceeding about 500 mM. In another embodiment, sorbitol is present at a concentration from about 100 to 300 mM. In yet another embodiment, sorbitol is present at a concentration of about 270 mM. In one embodiment, xylitol is present at a concentration not exceeding about 500 mM. In another embodiment, xylitol is present at a concentration from about 100 to 300 mM. In yet another embodiment, xylitol is present at a concentration of about 270 mM.

In one embodiment, the composition comprising a high concentration of adalimumab further comprises a stabilizer. In another embodiment, the stabilizer is an amino acid. In a yet another embodiment, the amino acid is selected from the group comprising histidine, glycine, and arginine. In another embodiment, the amino acid is A, N, D, Q, E, I, L, K, F, P, S, T, W, Y, or V. In another embodiment, the composition comprises at least two different amino acids. In one embodiment, the two different amino acids are selected from the group consisting of H, G, I, M, P, S, R, K, E, and N. In another embodiment the two different amino acids are selected from the group consisting of R, S, T, N, G, A, K, F, V, L, E, H, I, and P. In yet another embodiment, the two different amino acids are selected from the group consisting of H, R, S, T, N, G, P, and A.

In one embodiment, the composition comprising a high concentration of adalimumab further comprises a salt. In another embodiment, the salt stabilizes the adalimumab and/or reduces the viscosity of the composition. In one embodiment, the salt is NaCl. In another embodiment, NaCl is present at a concentration not exceeding about 300 mM. In yet another embodiment, NaCl is present at a concentration from about 100 to 140 mM.

In one embodiment, the composition comprising a high concentration of adalimumab further comprises a surfactant. In another embodiment, the surfactant is polysorbate 80 (PS 80). In one embodiment, PS 80 is present at a concentration not exceeding about 0.5 wt %. In another embodiment, PS 80 is present at a concentration from about 0.01 to 0.1 wt %.

In one embodiment, the composition comprising a high concentration of adalimumab further comprises a preservative. In another embodiment, the preservative is benzyl alcohol. In one embodiment, benzyl alcohol is present at a concentration not exceeding about 0.2 wt %. In another embodiment, benzyl alcohol is present at a concentration from about 0.5 to 1.5 wt %. In yet another embodiment, benzyl alcohol is present at a concentration of about 0.9 wt %.

Modification of Adalimumab Formulations

The high concentration formulations of the present invention exhibit long term stability. For example, a formulation is stable after 1 week at 40° C., 2 weeks at 40° C., and/or 4 weeks at 25° C. In further embodiments, the formulations of the present invention can be modified as discussed to below to achieved desired properties.

Stability

To improve the stability of a high concentration adalimumab formulation, the amount of a stabilizer present in the formulation is increased and/or a stabilizer is added to the formulation. Stabilizers include those described herein.

To improve the stability of a high concentration adalimumab formulation, the amount of a polyol present in the formulation is increased and/or a polyol is added to the formulation. Stabilizing polyols include sucrose, maltose, lactose, raffinose, and trehalose, sorbitol, maltitol, xylitol, and mannitol. Polyols are present at a concentration of about 0.4% wt to about 1.1% wt. Such high concentration adalimumab formulations comprising a polyol have long term stability and/or increased stability compared to the stability of the same formulation without the polyol.

To improve the stability of a high concentration adalimumab formulation, the amount of at least one amino acid present in the formulation is increased and/or at least one amino acid is added to the formulation. Stabilizing amino acids include serine, proline, glycine, alanine, glutamate, arginine, and combinations thereof. The concentration of the amino acids in the formulation is between about 1 mM and about 500 mM. Such high concentration adalimumab formulations comprising at least one amino acid have long term stability and/or increased stability compared to the stability of the same formulation without at least one amino acid.

Alternatively, high concentration adalimumab formulations exhibit increased stability when the amount of salt (e.g. NaCl) present is reduced. NaCl is reduced to an amount not exceeding about 50 mM, not exceeding about 44 mM, not exceeding about 28 mM, not exceeding about 26.35 mM, not exceeding about 10 mM, or not exceeding about 5 mM. Alternatively, the salt present in a high concentration adalimumab formulation is reduced so that the formulation is free, or substantially free, of a salt.

Thus, a high concentration adalimumab formulation is stable after 1 week at 40° C., 2 weeks at 40° C., and/or 4 weeks at 25° C.

Viscosity

To improve the viscosity of high concentration adalimumab formulations, the amount of a viscosity modifier present in the formulation is increased and/or a viscosity modifier is added to the formulation. Viscosity modifiers include those described herein.

To improve the viscosity of a high concentration adalimumab formulation, the amount of a viscosity reducing amino acid present in the formulation is increased and/or a viscosity reducing amino acid is added to the formulation. Viscosity reducing amino acids include glycine, proline and/or arginine. Amino acids are present at a concentration of about 0.4% wt to about 1.1% wt. High concentration adalimumab compositions comprising an amino acid have a reduced viscosity compared to the viscosity of the same formulation without the amino acid.

Thus, a high concentration adalimumab formulation has a viscosity of less than about 15 cP or a viscosity suitable for subcutaneous injection.

Amino Acid Combinations

To improve the stability and/or the viscosity of a high concentration adalimumab formulation, the amount of at least one amino acid present in the formulation is increased and/or at least one amino acid is added to the formulation. The stability and the viscosity of a high concentration adalimumab formulation are improved by adding or increasing the amount of a stabilizing amino acid and by adding or increasing the amount of a viscosity reducing amino acid. Stabilizing amino acids include G, S, T, A, R, M, K, P, N and any combination thereof. Viscosity reducing amino acids include P, R, G, and any combination thereof. Combinations of amino acids that stabilize adalimumab and reduce the viscosity of formulation include, but are not limited to, G, S, T, A, R, M, K, P, and/or N and P.

Thus, a high concentration adalimumab formulation with a combination of amino acids is stable after 1 week at 40° C., 2 weeks at 40° C., and/or 4 weeks at 25° C.; and has a viscosity of less than about 15 cP or a viscosity suitable for subcutaneous injection.

Generally speaking, while embodiments above have adalimumab concentrations of 100 mg/mL and 150 mg/mL, and require no different or increased amounts stabilizer or viscosity modifying excipients compared to corresponding formulation containing 50 mg/mL of adalimumab, it was uncertain if this is the case for formulations with adalimumab concentrations in excess of 150 mg/mL (e.g. 200, 225, 250 mg/mL). It was previously thought that in order to achieve acceptable stability and viscosity at these concentrations, it was necessary to exclude ionic excipients from formulations or necessary to supplement with added or increased amounts of either stabilizers, viscosity modifiers, or both. Here it is shown that these high concentration adalimumab formulations have suitable viscosity, even with ionic excipients in the formulation, and are stable without excessive amounts of stabilizing agents. It was not previously appreciated in the art that the high concentration formulations of the present invention would be suitable for administration to a patient.

E. Materials and Methods

In the Examples below, the chemical and physical stability of the adalimumab protein and the formulation comprising a high concentration of adalimumab is measured using, e.g., SEC, RP, UV, pH, CE-IEF and CE-SDS. However, other analytical methods may also be employed, for example, biophysical techniques such as those described by Jiskoot and Crommelin (Methods for Structural Analysis of Protein Pharmaceuticals, Springer, New York, 2005). Specific examples of such techniques are described below and further include spectroscopic analyses (e.g., second derivative ultraviolet spectroscopy, circular dichroism, Fourier Transform infrared spectroscopy, Raman spectroscopy, fluorescence and phosphorescence spectroscopy), thermal analyses (e.g., differential scanning calorimetry), and size based analyses (e.g., analytical ultracentrifuge, light scattering).

One of skill in the art can readily determine which of these or other suitable techniques may be used in specific situations when assessing the physical characteristics (e.g., stability, aggregation, oxidation, etc.) of the adalimumab protein in particular formulations.

Processing of Humira

Experiments using adalimumab present in commercially available Humira® may be processed according to the following procedures or to those known by one of skill in the art. Humira® material was dialyzed as follows: 100 µL of Humira® was placed into Mini Dialysis units with a 3.5 MWCO and dialyzed in 1 L of formulation buffer for 24 hours at 4 to 8'C. A few samples did experience a small increase in volume due to the dialysis, but never to extent that the concentration of the polysorbate 80 dropped below the CMC (critical micelle concentration).

The protein concentration for each formulation was measured by UV absorbance spectroscopy, using a calculated experimental molar absorptivity based on reported concentration of Humira®, 50 mg/mL. For a number of the formulations the protein concentration was adjusted by using a spin concentrator. The sample was placed in the spin concentrator and rotated at 14,000 RPM for 30 to 60 secs. The protein concentration was then checked with UV. After the targeted protein concentration around 50 mg/mL was reached the samples were filtered through a 0.22 µM sterile filter into sterile vials in a biosafety hood. The samples were then placed on stability at 40° C. for one and two weeks.

Processing of a Proprietary Adalimumab Protein

The formulation studies described herein used a proprietary adalimumab biosimilar protein which did not contain polysorbate 80. The material was dialyzed using 7,000 MWCO Slide-A-Lyzer® in different formulation buffers for 24 hours at a temperature range between 4 to 8° C. After dialysis the protein concentration was measured by UV and sample pH was measured. The target concentration of samples was 50±2.5 mg/mL, which was adjusted if the sample concentration fell out of the above range. Some of the samples did experience an increase in sample volume do to dilution, requiring the concentration of the protein to increase. For these samples the protein concentration was Increased by using spin concentrators, usually at 14,000 rpm for 30 to 60 secs. The pH of a number of samples were adjusted using 1M NaOH or 1M HCl to reach the target pH of 5.2.

After the targeted protein concentration and pH of the samples were determined to be within experimental parameters, the samples were filtered through a 0.22 µM sterile filter into sterile vials in a biosafety hood. The samples were then placed on stability at 40° C. for one week and 25° C. for two weeks.

Stability Time Points

A high concentration adalimumab composition is evaluated by for stability by exposing it to storage conditions over time. Storage conditions may be real-time or accelerated. Conditions include, but are not limited to, 1 week at 40° C. (t1/40 C), 6-10 days at 30° C., 2 weeks at 40° C. (t2/40 C), 4 weeks at 25° C. (t4/25 C), 9 weeks at 25° C. (t9/25 C), 13 weeks at 25° C. (t13/25 C), 13 weeks at 5° C. (t13/5 C), and 26 weeks at 5° C. (t26/5 C). Analyses of a high concentration adalimumab composition at a given time point are compared to analyses of the composition at time 0 (t0), before the composition was exposed to storage conditions.

Analytical Methods

Stability of high concentration adalimumab compositions can be measured using any of a variety of well-known methods, such as visual observation, turbidity measurement at 600-700 nm, light scattering, particle counting, electrophoresis, chromatographic methods like size-exclusion, ion-exchange, hydrophobic interaction, and/or reversed phase, structural analyses like CD, FTIR, fluorescence, DSC, and/or UV/VIS, and biological activity assays. Instability can be indicated by any of soluble aggregates, precipitates (insoluble aggregates), gelation, changes in pH, loss of activity. Aggregation can be measured by SEC-HPLC methods, dynamic light scattering, analytical ultracentrifuge, and by electrophoresis. Stresses relevant for the stability studies include storage at elevated temperature, agitation, freeze-thawing, light exposure, etc.

Generally, high levels of monomeric, therapeutically active, adalimumab is present in stable compositions. Conversely, compositions with low levels of adalimumab aggregates and/or degraded adalimumab (e.g. fragments) are also stable.

Size Exclusion Chromatography (SEC)

Size Exclusion Chromatography (SEC) is used to analyze the amount of monomer adalimumab in a composition. SEC is also useful in determining the amount of adalimumab aggregates and/or fragments in a composition.

Cation Exchange Chromatography (CEX)

Cation Exchange Chromatography (CEX) is also used to analyze the amount of monomer adalimumab in a composition. CEX is also useful in determining the amount of adalimumab aggregates and/or fragments in a composition. CEX method parameters known by one of skill in the art may be used for the analysis of adalimumab compositions.

Reverse Phase Chromatography (RP)

Reverse Phase Chromatography (RP) is also used to analyze the amount of monomer adalimumab in a composition. RP is also useful in determining the amount of adalimumab aggregates and/or fragments in a composition. RP method parameters known by one of skill in the art may be used for the analysis of adalimumab compositions.

Asymmetric Flow Field Flow Fractionation (AF4)

Asymmetric flow field flow fractionation (AF4) is a type of asymmetric field flow fractionation. AF4 is a method capable of rapid fractionation and high resolution characterization of various particles including bio-molecules (Giddings, J. C.; Yang, F. J.; Myers, M. N., Flow-field-flow fractionation: a versatile new separation method, 193 *Science* 1244-1245 (1976); Giddings, J. C.; Yang, F. J.; Myers, M. N., Theoretical and experimental characterization of flow field-flow fractionation, 48 *Anal. Chem.* 1126-1132 (1976)). AF4 is capable of separating particles ranging from a few nanometers to a few micrometers. Proteins, aggregates thereof, and fragments thereof are readily separated due to the difference in mobility in a flow field. Field flow fractionation separation occurs in a thin flow channel (comparable to a chromatographic separation column). An aqueous or organic solvent carries the sample through this channel. The flow through the channel, the first force exerted on the sample, is laminar due to the low channel height. A second force is generated perpendicular to the channel flow. In AF4, one side of the flow channel is a membrane and the second force is fluid flow across the channel through the membrane. Particle separation occurs in this system as a result of these two forces. First, the velocity gradient due to the laminar flow within the channel causes particles in the center of the channel to move more quickly along the channel and be separated from those closer to the sides of the channel. Second, the second force forces the sample toward the membrane. Size separation occurs because the smaller molecules diffuse back toward the center of the channel more quickly than larger particles and hence are separated from the larger particles due to the quicker solvent flow toward the center of the channel.

An AF4 set-up may have a number of different detectors, which allow for determining the molar mass, root mean squared radius (of gyration), and second virial coefficient of the eluting compounds. AF4 analysis provides information on the diffusion coefficients, hydrodynamic radius and the shape of the molecules.

UV Absorbance Spectroscopy

UV spectroscopy is used to measure the protein concentration in the samples. Analysis parameters known by one of skill in the art may be used for the analysis of adalimumab compositions.

Mixed Mode Chromatography (MMC)

MMC is a chromatography method generally utilizes at least two different forces to bind proteins and separate a desired protein product from undesired materials that may be present in a composition containing the desired protein along with undesired impurities. These forces can include, for example, electrostatic forces and hydrophobic forces. Therefore, MMC is useful for evaluating the stability of adalimumab by determining the amount of adalimumab monomer present in a formulation.

Two examples of mixed mode resins are Capto® MMC and Capto® Adhere (available from GE Healthcare). Capto® MMC utilizes a ligand attached to a solid support matrix that may interact with the analyte by cation exchange (with its carboxylic group), hydrogen bonding, and hydrophobic interactions. Capto® Adhere is similar to Capto® MMC in that it also employs a ligand which is attached to a solid support matrix. The ligand, N-benzyl-N-methyl ethanol amine, also interacts with the analyte by anion exchange, hydrogen bonding, and hydrophobic interactions. MMC parameters known by one of skill in the art may be used for the evaluation of adalimumab compositions.

Micro-Flow Imaging (MFI)

Micro-Flow Imaging (MFI) is an imaging technology that is used to detect and measure subvisible and visible particulate matter in solutions. The technology captures digital images of particles suspended in a fluid as they pass through a sensing zone, which are automatically analysed to provide a digital archive of particle parameters aspect ratio and intensity. Furthermore, the results are described as the size and count of the particles. MFI is useful for detecting protein, rubber, and polystyrene particles, silicone, and oil droplets in a formulation. Analysis parameters known by one of skill in the art may be used for the analysis of adalimumab compositions.

Reverse Phase-High Performance Liquid Chromatography (RP-HPLC)

RP-HPLC is useful for evaluating the stability of adalimumab in formulations. RP-HPLC analyses detect the amount of adalimumab, and fragments and/or aggregates thereof, present in a formulation. RP method parameter known by one of skill in the art may be used for the analysis of adalimumab compositions.

CE-IEF Analysis

Capillary isoelectric focusing (cIEF) methods known by one of skill in the art may be used for the analysis of adalimumab compositions. For example, cIEF may be conducted as described in the PA 800 plus Application Guide published by Beckman Coulter. A more detailed description can be found in a research article published by Mack et al. The pI markers and adalimumab are detected with absorbance at 280 nm during the mobilization step. The pI of adalimumab is calculated from the resultant regression equation of pI vs. first peak moment obtained from the pI standards.

CE-SDS Analysis

Analysis by CE-SDS methods known by one of skill in the art may be used for the analysis antibody fragment in adalimumab compositions. For example, CE-SDS is conducted under reducing conditions utilizing a method adapted from the SOP published by Beckman-Coulter for determining IgG purity/heterogeneity. Antibody fragments are detected using absorbance at 214 nm (4 Hz acquisition) and time-normalized areas reported for measured peaks.

pH

The pH of a composition is measured according to methods known in the art. For example, the pH of a sample is measured using a mico-pH probe. Before the start of analysis the pH probe is calibrated with three pH standards. The pH values of samples are measured by transferring 60 µL of each sample to 100 uL PCR tube. The micro-pH probe is then submerged into the sample and after the value stabilized it is recorded.

Conductivity

Conductivity of a composition is measured according to methods known in the art. Conductivity meters and cells may be used to determine the conductivity of the aqueous formulation, and should be calibrated to a standard solution before use. Examples of conductivity meters available in the art include MYRON L® Digital (Cole Parmer®), Conductometer (Metrohm AG), and Series 3105/3115 Integrated Conductivity Analyzers (Kemotron).

Hydrodynamic Diameter

The term "hydrodynamic diameter of a protein" as used herein refers to a size determination for proteins in solution using dynamic light scattering (DLS). A DIS-measuring instrument measures the time-dependent fluctuation in the intensity of light scattered from the proteins in solution at a fixed scattering angle. Protein $D_h$ is determined from the intensity autocorrelation function of the time-dependent fluctuation in intensity. Scattering intensity data are processed using DLS instrument software to determine the value for the hydrodynamic diameter and the size distribution of the scattering molecules, i.e. the protein specimen. The hydrodynamic diameter of the protein in solution may be measured using dynamic light scattering (DLS), which is an established analytical method for determining the $D_h$ of proteins.

Viscosity

Viscosity can be measured by methods known to one of skill in the art, including the use of various types of viscometers and rheometers. In a further embodiment, the viscometer is a U-tube viscometer, a falling piston viscometer, a rotational viscometer or a bubble viscometer. In an embodiment, the rheometer is a Rheotans, a CaBer, an Acoustic, a Falling Plate, a Capillary/Contraction Flow, a FiSER or a Sentmanat. In a further embodiment, viscosity is measured with a Zahn cup, in which the efflux time is determined or a Ford viscosity cup.

Viscosity of compositions can be measured using any of a variety of well-known methods, such as viscometry, Instron, and measurements of injectability and syringeability.

Solubility

Solubility, such as that of proteins, in compositions can be measured using any of a variety of well-known methods. For example, a protein solution is concentrated to a desired concentration or above using ultrafiltration. The concentration in the clear supernatant is determined for solubility. Protein beyond solubility will either precipitate or form a gel.

Freeze-Thaw Conditions

Compositions for freeze-thaw analyses are prepared on the day of analysis to match with t=0. The samples are frozen at −80° C. between 3 to 7 minutes. The frozen sample are then thawed at room temperature until all the ice has thawed. The freeze and thaw cycle may be repeated (e.g. 5 times) for each sample.

Agitation

To evaluate the stability of adalimumab, formulations are subjected to agitation studies. For example, compositions are agitated at 150 rpm for 24 hours at 4° C. on a rockerplate. A control is prepared and placed next to the rocker plate for each sample that is agitated.

F. Methods of Treatment

In another embodiment, the invention provides a method of treating a subject comprising administering a therapeutically effective amount of the pharmaceutical compositions of the invention to a subject, wherein the subject has a disease or disorder that can be beneficially treated with adalimumab.

In a one embodiment, the subject is a mammal. In another embodiment, the mammal is a human. The term "patient" is used to identify a subject with a disease or disorder that can be beneficially treated with adalimumab. In one embodiment, the patient is a mammal. In yet another embodiment, the patient is a human.

Diseases or disorders that can be treated with the provided compositions include but are not limited to rheumatoid arthritis, psoriatic arthritis, ankylosing spondylitis, juvenile idiopathic arthritis (JIA), Wegener's disease (granulomatosis), Crohn's disease (or inflammatory bowel disease), ulcerative colitis, hidradenitis suppurativa, Behcet's disease, sarcoidosis (e.g. cutaneous sarcoidosis), chronic obstructive pulmonary disease (COPD), diabetic retinopathy, giant cell arteritis, Hepatitis C, endometriosis, asthma, cachexia, psoriasis, axial spondyloarthropathy, uveitis and atopic dermatitis. Additional diseases or disorders that can be treated with the compositions of the present invention include those described in U.S. Pat. Nos. 6,090,382 and 8,216,583 the relevant portions of which are incorporated herein by reference.

The provided pharmaceutical compositions may be administered to a subject in need of treatment by injection systemically, such as by intravenous injection; or by injection or application to the relevant site, such as by direct injection, or direct application to the site when the site is exposed in surgery; or by topical application.

In one embodiment, the invention provides a method of treatment and/or prevention of rheumatoid arthritis comprises administering to a mammal in need thereof a therapeutically effective amount of one of the provided adalimumab compositions.

The therapeutically effective amount of the adalimumab in the provided compositions will depend on the condition to be treated, the severity of the condition, prior therapy, and the patient's clinical history and response to the therapeutic agent. The proper dose can be adjusted according to the judgment of the attending physician such that it can be administered to the patient one time or over a series of administrations.

In one embodiment, the effective adalimumab amount per adult dose is from about 1-500 milligrams per square meter ("mg/m$^2$"), or from about 1-200 mg/m$^2$, or from about 1-40 mg/m$^2$ or about 5-25 mg/m$^2$.

Alternatively, a flat dose may be administered, whose amount may range from 2-500 mg/dose, 2-100 mg/dose or from about 10-80 mg/dose.

In certain embodiments, the composition comprises a dose of about 30-90 mg of adalimumab, or antigen binding portion thereof. In one embodiment, the composition comprises about 40 mg of adalimumab, or antigen binding portion thereof. In one embodiment, the composition comprises about 50 mg of adalimumab, or antigen binding portion thereof. In one embodiment, the composition comprises about 60 mg of adalimumab, or antigen binding portion thereof. In one embodiment, the composition comprises about 70 mg of adalimumab, or antigen binding portion thereof. In one embodiment, the composition comprises about 80 mg of adalimumab, or antigen binding portion thereof. In one embodiment, the composition comprises about 90 mg of adalimumab, or antigen binding portion thereof. In one embodiment, the composition comprises 60-85 mg. In another embodiment, the composition comprises 70-90 mg. In yet a further embodiment, the composition contains 30-110 mg. In one embodiment, the composition contains 70-110 mg.

In one embodiment, the composition is administered to the subject according to a periodicity selected from the group consisting of weekly, biweekly, every three weeks, and monthly. In one embodiment, the composition of the invention contains 30-90 mg of adalimumab, or antigen-binding portion thereof, and is administered on a biweekly dosing regimen. In another embodiment, the composition of the invention contains 30-90 mg of adalimumab, or antigen-binding portion thereof, and is administered according to a monthly dosing regimen. In one embodiment, the composition of the invention contains 60-85 mg of adalimumab, or antigen-binding portion thereof, and is administered on a biweekly dosing regimen. In another embodiment, the composition of the invention contains 60-85 mg of adalimumab, or antigen-binding portion thereof, and is administered according to a monthly dosing regimen.

If the dose is to be administered more than one time per week, an exemplary dose range is the same as the foregoing described dose ranges or lower. In another embodiment, the dose is administered two or more times per week at a per dose range of 25-100 mg/dose.

In another embodiment, an acceptable dose for administration by injection contains 80-100 mg/dose, or alternatively, containing 80 mg per dose.

The dose can be administered weekly, biweekly, or separated by several weeks (for example 2 to 8).

In one embodiment, adalimumab is administered at 40 mg by a single subcutaneous (SC) injection.

In some instances, an improvement in a patient's condition will be obtained by administering a dose of up to about 100 mg of the pharmaceutical composition one to three times per week over a period of at least three weeks. Treatment for longer periods may be necessary to induce the desired degree of improvement. For incurable chronic conditions the regimen may be continued indefinitely. For pediatric patients (ages 4-17), a suitable regimen may involve administering a dose of 0.4 milligrams per kilogram ("mg/kg") to 5 mg/kg of adalimumab, one or more times per week.

In another embodiment, the pharmaceutical formulations of the invention may be prepared in a bulk formulation, and as such, the components of the pharmaceutical composition are adjusted to be higher than would be required for administration and diluted appropriately prior to administration.

The pharmaceutical compositions can be administered as a sole therapeutic or in combination with additional therapies as needed. Thus, in one embodiment, the provided methods of treatment and/or prevention are used in combination with administering a therapeutically effective amount of another active agent. The other active agent may be administered before, during, or after administering the pharmaceutical compositions of the present invention. Another active agent may be administered either as a part of the provided compositions, or alternatively, as a separate formulation.

Administration of the provided pharmaceutical compositions can be achieved in various ways, including parenteral, oral, buccal, nasal, rectal, intraperitoneal, intradermal, transdermal, subcutaneous, intravenous, intra-arterial, intracardiac, intraventricular, intracranial, intratracheal, intrathecal administration, intramuscular injection, intravitreous injection, and topical application.

The pharmaceutical compositions of this invention are particularly useful for parenteral administration, i.e., subcutaneously, intramuscularly, intravenously, intraperitoneal, intracerobrospinal, intra-articular, intrasynovial, and/or intrathecal. Parenteral administration can be by bolus injection or continuous infusion. Pharmaceutical compositions for injection may be presented in single or multi unit dosage form, e.g., single unit dosage containers (e.g. a syringe), in ampoules or in multi-dose containers, with an added preservative. In addition, a number of recent drug delivery approaches have been developed and the pharmaceutical compositions of the present invention are suitable for administration using these new methods, e.g., Inject-Ease®, Genject®, injector pens such as GenPen®, and needleless devices such as MedUector® and BioJector®. The present pharmaceutical composition can also be adapted for yet to be discovered administration methods. See also Langer, 1990, *Science*, 249:1527-1533.

Another aspect of the invention provides a pre-filled syringe or autoinjector device, comprising any of the subject compositions described herein. In certain embodiments, the composition stored in the pre-filled syringe or autoinjector device contains about 40 mg of adalimumab. In certain embodiments, the composition stored in the pre-filled syringe or autoinjector device contains about 80 mg of adalimumab.

In one embodiment, the pre-filled syringe or autoinjector device comprises a needle with a bore size selected from the group comprising: 29-31 gauge, 31 gauge or higher, 28, 29, 30, 31, and 32, 33, and 34. The needle may be a regular-wall or a thin-wall needle.

In one embodiment the pre-filled syringe or autoinjector device administers a high concentration adalimumab composition to a subject in less than about 10, 9, 8, 7, 6, 5, 4.5, 4, 3.5, 3, 2.5, or 2 seconds.

The provided pharmaceutical compositions can also be formulated as a depot preparation. Such long acting formulations may be administered by implantation (for example subcutaneously or intramuscularly) or by intramuscular injection. Thus, for example, the formulations may be modified with suitable polymeric or hydrophobic materials (for example as an emulsion in an acceptable oil) or ion exchange resins, or as sparingly soluble derivatives, for example, as a sparingly soluble salt.

The pharmaceutical compositions may, if desired, be presented in a vial, pack or dispenser device which may contain one or more unit dosage forms containing the active ingredient. In one embodiment, the dispenser device can comprise a syringe having a single dose of the liquid formulation ready for injection. The syringe can be accompanied by instructions for administration.

In another embodiment, the present invention is directed to a kit or container, which contains an aqueous pharmaceutical composition of the invention. The concentration of the polypeptide in the aqueous pharmaceutical composition can vary over a wide range, but is generally within the range of from about 0.05 to about 20,000 micrograms per milliliter (µg/ml) of aqueous formulation. The kit can also be accompanied by instructions for use.

In addition to the formulations referenced in the formulation studies of Blocks 1 through 4, the additional embodiments and examples are provided as further embodiments of the invention.

To the extent there is any conflict between terms in the instant application and an incorporated reference, the instant application controls.

The following embodiments and Examples are provided solely for illustrative purposes and are not meant to limit the invention in any way.

EXEMPLARY EMBODIMENTS

A. An aqueous pharmaceutical composition comprising a stable high concentration of adalimumab, wherein: (a) the composition has a concentration of adalimumab greater than 50 mg/mL; (b) the composition has stability comparable to or better than a commercially sold adalimumab formulation having a concentration of adalimumab selected from: (i) not greater than about 50 mg/mL; or (ii) not greater than about 100 mg/mL; and (c) the composition has viscosity approximately equal to, or less than, that of a commercially sold adalimumab formulation having a concentration of adalimumab selected from: (i) not greater than about 50 mg/ml; or (ii) not greater than about 100 mg/mL.

B. The composition of embodiment A., wherein adalimumab is present in the composition at a concentration selected from: greater than 50 mg/mL and less than 100 g/mL; at least 100 mg/mL; 100 to 300 mg/ml; 100 to 200 mg/ml; 100 to 150 mg/mL; 100 to 125 mg/mL; 75 mg/mL; 100 mg/mL; 125 mg/mL, 150 mg/ml; 175 mg/mL; 200 mg/mL; 225 mg/mL; 250 mg/ml; 275 mg/mL; and 300 mg/mL.

C. The composition of embodiment A., wherein the conductivity of the composition is greater than 2.5 mS/cm.

D. The composition of embodiment A., wherein the composition comprises an ionic excipient.

FURTHER EXEMPLARY EMBODIMENTS

1. An aqueous pharmaceutical composition comprising a stable high concentration of adalimumab, wherein:
(a) the composition has a concentration of adalimumab greater than 50 mg/ml;
(b) the composition has long term stability comparable to or better than a commercially sold adalimumab formulation having a concentration of adalimumab selected from:
(i) not greater than about 50 mg/mL; or
(ii) not greater than about 100 mg/ml; and
(c) the composition has viscosity approximately equal to, or less than, that of a commercially sold adalimumab formulation having a concentration of adalimumab selected from:
(i) not greater than about 50 mg/mL; or
(ii) not greater than about 100 mg/mL.

2. The high concentration composition of embodiment 1, wherein adalimumab is present in the composition at a concentration selected from: greater than 50 mg/mL and less than 100 g/mL; at least 100 mg/mL; 100 to 300 mg/mL; 100 to 200 mg/ml; 100 to 150 mg/mL; 100 to 125 mg/mL; 75 mg/mL; 100 mg/mL; 125 mg/mL, 150 mg/mL; 175 mg/mL; 200 mg/mL; 225 mg/mL; 250 mg/mL; 275 mg/ml; and 300 mg/ml.

3. The high concentration composition of embodiment 2, comprising at least one buffer.

4. The high concentration composition of embodiment 1, wherein the composition is free, or substantially free, of buffer.

5. The high concentration composition of embodiment 4, wherein the following buffers are not present in the composition: phosphate buffer, pyrophosphate buffer, citrate buffer, acetate buffer, glutamate buffer, gluconate buffer, histidine buffer, succinate buffer, adipate buffer, maleate buffer and tartrate buffer.

6. The high concentration composition of embodiment 3, wherein the buffer is at least one, or a combination, of phosphate, pyrophosphate, citrate, acetate, glutamate, gluconate, histidine, succinate, adipate, maleate, and tartrate.

7. The high concentration composition of embodiment 2, comprising at least one buffer, wherein the composition (a) is free or essentially free of citrate buffer; or (b) is free or essentially free of phosphate buffer; or (c) is free or essentially free of a buffer composition comprising citrate buffer and phosphate buffer.

8. The high concentration composition of any of embodiment 3, 6, or 7, wherein the buffer is or comprises succinate.

9. The high concentration composition of any of embodiment 3, 6, or 7, wherein the buffer is or comprises histidine.

10. The high concentration composition of embodiment 3 or 6, wherein the composition comprises a combination of two buffers where the combination is selected from (a) a combination of histidine buffer and succinate buffer; (b) a combination of citrate buffer and phosphate buffer; (c) a combination of citrate buffer and pyrophosphate buffer; and (d) a combination of phosphate buffer plus either histidine buffer or succinate buffer.

11. The high concentration composition of embodiment 10, wherein the buffer combination is succinate and histidine.

12. The high concentration composition of embodiment 10, wherein the buffer combination is citrate and pyrophosphate.

13. The high concentration composition of any of embodiments 1 to 12, wherein the composition has a pH of 3 to 8; 4 to 8; or 5 to 6.

14. The high concentration composition of any of embodiments 1 to 13, wherein the composition has a viscosity equal to or less than: 20 cP; 15 cP; 14 cP; 13 cP; 12 cP; 11 cP; 10 cP; 9 cP; 8 cP; 7 cP; 6 cP; 5 cP; 4 cP; 3 cP; 2 cP; or 1 cP.

15. The high concentration composition of any of embodiments 1 to 14, further comprising at least one tonicity agent, wherein the tonicity agent comprises salts, amino acids, sugars, and polyols.

16. The high concentration composition of any of embodiments 1 to 14, further comprising at least one tonicity agent, wherein the tonicity agent is not a salt.

17. The high concentration composition of embodiment 15, wherein the salt comprises NaCl, KCl, $Na_2SO_4$, $MgCl_2$, $CaCl_2$, and adipate.

18. The high concentration composition of embodiment 17, wherein the salt is present at a concentration selected from: 40 to 140 mM; not exceeding about 150; not exceeding about 100 mM; not exceeding about 50 mM, not exceeding about 44 mM, not exceeding about 28 mM, not exceeding about 26.35 mM, not exceeding about 10 mM, and not exceeding about 5 mM.

19. The high concentration composition of any of embodiments 1 to 18, wherein the composition is isotonic or has an osmolality of about 180 to about 420 mOsM.

20. The high concentration composition of any of embodiments 1 to 19, wherein the composition comprises at least one polyol.

21. The high concentration composition of embodiment 20, wherein the polyol is selected from glycerol, xylitol, inositol, mannitol, sorbitol, trehalose and combinations thereof.

22. The high concentration composition of embodiment 21, wherein the polyol is mannitol at a concentration not exceeding about 300 mM.

23. The high concentration composition of any of embodiments 1 to 22, further comprising at least one sugar.

24. The high concentration composition of embodiment 23, wherein the sugar comprises sucrose, lactose, glucose, and maltose, and combinations thereof.

25. The high concentration composition of any of embodiments 1 to 24, further comprising at least one amino acid.

26. The high concentration composition of embodiment 25, wherein the amino acid is selected from the group consisting of histidine, glycine, methionine, serine, proline, and arginine.

27. The high concentration composition of embodiment 25, wherein the amino acid is histidine.

28. The high concentration composition of embodiment 25, wherein the amino acid is glycine.

29. The high concentration composition of embodiment 25, wherein the amino acid is arginine.

30. The high concentration composition of embodiment 25, wherein the amino acids are a combination of glycine and arginine.

31. The high concentration composition of any of embodiments 1 to 30, wherein the composition further comprises at least one surfactant.

32. The high concentration composition of embodiment 31, wherein the surfactant is selected from the group consisting of polysorbate 20, polysorbate 80, SDS, poloxamer 188 (Pluronic® F68) and combinations thereof.

Embodiments 33 to 39 Reserved

40. The high concentration composition of embodiment 1 to 32, wherein the concentration of adalimumab is selected from:
(a) 51 mg/mL, 52 mg/mL, 53 mg/mL, 54 mg/mL, 55 mg/mL, 56 mg/mL, 57 mg/mL, 58 mg/mL, 59 mg/mL, 60 mg/mL, 61 mg/mL, 62 mg/mL, 63 mg/mL, 64 mg/mL, 65 mg/mL, 66 mg/mL, 67 mg/mL, 68 mg/mL, 69 mg/mL, 70 mg/mL, 71 mg/mL, 72 mg/mL, 73 mg/mL, 74 mg/mL, 75 mg/mL, 76 mg/mL, 77 mg/mL, 78 mg/mL, 79 mg/mL, 80 mg/mL, 81 mg/mL, 82 mg/mL, 83 mg/mL, 84 mg/mL, 85 mg/mL, 86 mg/mL, 87 mg/mL, 88 mg/mL, 89 mg/mL, 90 mg/mL, 91 mg/mL, 92 mg/mL, 93 mg/mL, 94 mg/mL, 95 mg/mL, 96 mg/mL, 97 mg/mL, 98 mg/mL, 99 mg/mL, 100 mg/mL, 101 mg/mL, 102 mg/mL, 103 mg/mL, 104 mg/mL, 105 mg/mL, 106 mg/mL, 107 mg/mL, 108 mg/mL, 109 mg/mL, 110 mg/mL, 111 mg/mL, 112 mg/mL, 113 mg/mL, 114 mg/mL, 115 mg/mL, 116 mg/mL, 117 mg/mL, 118 mg/mL, 119 mg/mL, 120 mg/mL, 121 mg/mL, 122 mg/mL, 123 mg/mL, 124 mg/mL, 125 mg/mL, 126 mg/mL, 127 mg/mL, 128 mg/mL, 129 mg/mL, 130 mg/mL, 131 mg/mL, 132 mg/mL, 133 mg/mL, 134 mg/mL, 135 mg/mL, 136 mg/mL, 137 mg/mL, 138 mg/mL, 139 mg/mL, 140 mg/mL, 141 mg/mL, 142 mg/mL, 143 mg/mL, 144 mg/mL, 145 mg/mL, 146 mg/mL, 147 mg/mL, 148 mg/mL, 149 mg/mL, 150 mg/mL, 151 mg/mL, 152 mg/mL, 153 mg/mL, 154 mg/mL, 155 mg/mL, 156 mg/mL, 157 mg/mL, 158 mg/mL, 159 mg/mL, 160 mg/mL, 161 mg/mL, 162 mg/mL, 163 mg/mL, 164 mg/mL, 165 mg/mL, 166 mg/mL, 167 mg/mL, 168 mg/mL, 169 mg/mL, 170 mg/mL, 171 mg/mL, 172 mg/mL, 173 mg/mL, 174 mg/mL, 175 mg/mL, 176 mg/mL, 177 mg/mL, 178 mg/mL, 179 mg/mL, 180 mg/mL, 181 mg/mL, 182 mg/mL, 183 mg/mL, 184 mg/mL, 185 mg/mL, 186 mg/mL, 187 mg/mL, 188 mg/mL, 189 mg/mL, 190 mg/mL, 191 mg/mL, 192 mg/mL, 193 mg/mL, 194 mg/mL, 195 mg/mL, 196 mg/mL, 197 mg/mL, 198 mg/mL, 199 mg/mL, 200 mg/mL; or (b) 201 mg/mL, 202 mg/mL, 203 mg/mL, 204 mg/mL, 205 mg/mL, 206 mg/mL, 207 mg/mL, 208 mg/mL, 209 mg/mL, 210 mg/mL, 211 mg/mL, 212 mg/mL, 213 mg/mL, 214 mg/mL, 215 mg/mL, 216 mg/mL, 217 mg/mL, 218 mg/mL, 219 mg/mL, 220 mg/mL, 221 mg/mL, 222 mg/mL, 223 mg/mL, 224 mg/mL, 225 mg/mL, 226 mg/mL, 227 mg/mL, 228 mg/mL, 229 mg/mL, 230 mg/mL, 231 mg/mL, 232 mg/mL, 233 mg/mL, 234 mg/mL, 235 mg/mL, 236 mg/mL, 237 mg/mL, 238 mg/mL, 239 mg/mL, 240 mg/mL, 241 mg/mL, 242 mg/mL, 243 mg/mL, 244 mg/mL, 245 mg/mL, 246 mg/mL, 247 mg/mL, 248 mg/mL, 249 mg/mL, 250 mg/mL, 251 mg/mL, 252 mg/mL, 253 mg/mL, 254 mg/mL, 255 mg/mL, 256 mg/mL, 257 mg/mL, 258 mg/mL, 259 mg/mL, 260 mg/mL, 261 mg/mL, 262 mg/mL, 263 mg/mL, 264 mg/mL, 265 mg/mL, 266 mg/mL, 267 mg/mL, 268 mg/mL, 269 mg/mL, 270 mg/mL, 271 mg/mL, 272 mg/mL, 273 mg/mL, 274 mg/mL, 275 mg/mL, 276 mg/mL, 277 mg/mL, 278 mg/mL, 279 mg/mL, 280 mg/mL, 281 mg/mL, 282 mg/mL, 283 mg/mL, 284 mg/mL, 285 mg/mL, 286 mg/mL, 287 mg/mL, 288 mg/mL, 289 mg/mL, 290 mg/mL, 291 mg/mL, 292 mg/mL, 293 mg/mL, 294 mg/mL, 295 mg/mL, 296 mg/mL, 297 mg/mL, 298 mg/mL, 299 mg/mL, and 300 mg/mL.

41. The high concentration composition of any of embodiments 1 to 40, comprising:
(a) a buffer;
(b) a stabilizer selected from the group consisting of polyols, amino acids and salts; and
(c) a surfactant,
wherein the composition has a conductivity greater than 2.5, 3, 4, 5, 6, or 7 mS/cm; an osmolarity from about 100 to 400 mOsM, and wherein the hydrodynamic diameter of the adalimumab is greater than 2, 3, 4, 5, 6, 7, 8, 9 10 or 11.

42. The high concentration composition of embodiment 41, wherein:
(a) the buffer is selected from phosphate, citrate, acetate, pyrophosphate, histidine, succinate, adipate, and combinations thereof;
(b) the salt, if present, is selected from sodium chloride and sodium sulfate;
(c) the amino acid, if present, is selected from arginine, glycine, proline, serine and methionine, and combinations thereof; and
(d) the surfactant is a polysorbate surfactant.

43. The high concentration composition of embodiment 1-42, wherein the concentration of adalimumab is (a) 100, 125, 150, 175 or 200 mg/mL; or (b) 200 to 300 mg/mL.

44. The high concentration composition of any of embodiments 1 to 43, wherein at least one member, or a combination thereof, selected from the following list is present and contributes to stabilization of the composition: a polyol, a sugar, an amino acid, a salt, creatine, creatinine, carnitine, lauryldimethylamineoxide (and amine oxide analogs), a polymer, a chelating agent, a polar solvent and a surfactant.

45. The high concentration composition of any of embodiments 1 to 44, wherein at least one of member, or combination thereof, selected from the following list contributes to reducing viscosity of the composition: an amino acid, a calcium salt, an acetate salt, magnesium chloride, sodium phosphate, arginine hydrochloride, creatine, creatinine, carnitine, an ultra-low interfacial tension surfactant, and a polar solvent.

46. The high concentration composition of embodiment 1 to 45, comprising at least one amino acid, wherein at least one amino acid stabilizes the composition and at least one other, different, amino acid reduces the viscosity of the composition.

47. The high concentration composition of embodiment 46, wherein one of the two different amino acids contains a polar uncharged side chain and the other contains a hydrophobic side chain.

48. The high concentration composition of embodiment 46, wherein one of the two different amino acids contains a polar uncharged side chain and the other is selected from the group consisting of G and P.

49. The high concentration composition of embodiment 46, wherein the stabilizing amino acid is selected from the group consisting of S, A, G, T, and V, and the viscosity reducing amino acid is elected from the group consisting of S, A, G, T, V, R, E, and P.

50. The high concentration composition of embodiment 46, wherein the stabilizing amino acid is selected from the group consisting of R, D, K, V, T, P, and I, and the viscosity reducing amino acid selected from the group consisting of P, H, K, M, G, F, E, T, 5, N, and I.

51. The high concentration composition of embodiment 46, wherein the stabilizing amino acid is selected from the group consisting of R, H, M, K, and F, and the viscosity reducing amino acid selected from the group consisting of H, M, T, and V.

52. The high concentration composition of embodiment 46, wherein the stabilizing amino acid is G, and the viscosity reducing amino acid is P.

53. The high concentration composition of embodiment 46, wherein the stabilizing amino acid is S, and the viscosity reducing amino acid is P.

54. The high concentration composition of any of embodiments 1 to 43, wherein the composition comprises at least two amino acids that stabilize the composition.

55. The high concentration composition of embodiment 54, wherein stabilizing amino acids are a combination of two amino acids selected from the combinations consisting of A and G, A and M, G and M, G and T, M and T, M and 5, S and T, A and N, A and Q, N and Q, A and S, N and S, Q and S, and Q and T.

56. The high concentration composition of embodiment 54, wherein the stabilizing amino acids are a combination of three amino acids selected from the combinations consisting of A, G, and M; G, M, and T; M, S, and T; A, N, and; A, N, and S; and Q, S, and T.

57. The high concentration composition of any of embodiments 1 to 43, wherein the composition comprises at least two amino acids that reduce the viscosity of the composition.

58. The high concentration composition of embodiment 57, wherein the viscosity reducing amino acids are a combination of two amino acids selected from the combinations consisting of P and G, and P and S.

59. The high concentration composition of any of embodiments 1 to 43, wherein the composition further comprises at least one salt.

60. The high concentration composition of embodiment 59, wherein the salt stabilizes or contributes to stabilization of the composition.

61. The high concentration composition of embodiment 60, wherein the salt is selected from the group consisting of NaCl, KCl, Na2SO4, MgCl2, CaCl2, and adipate.

62. The high concentration composition of embodiment 61, wherein the salt is present at a concentration selected from the group consisting of: not exceeding about 200 mM, not exceeding about 50 mM, not exceeding about 44 mM, not exceeding about 28 mM, not exceeding about 26.35 mM, not exceeding about 10 mM, and not exceeding about 5 mM.

63. The high concentration composition of embodiment 61, wherein the salt is $MgCl_2$ and the composition has a viscosity of about 15 cP or less.

64. The high concentration composition of any of embodiments 1 to 43, wherein the composition further comprises at least one lauryldimethylamineoxide and/or of one of its amine oxide analogs.

65. The high concentration composition of embodiment 64, wherein the lauryldimethylamineoxide and/or of one of its amine oxide analogs stabilizes adalimumab and/or the composition.

66. The high concentration composition of any of embodiments 1 to 43, wherein the composition further comprises at least one or a combination of creatinine, creatine and carnitine.

67. The high concentration composition of embodiment 66, wherein the creatinine, creatine, and carnitine stabilize or contribute to stabilization of the composition.

68. The high concentration composition of any of embodiments 1 to 43, wherein the composition further comprises at least one polymer.

69. The high concentration composition of embodiment 68, wherein the polymer is selected from celluloses, 40 kD Dextran, betaine, PVP, and glycerol.

70. The high concentration composition of embodiment 69, wherein the cellulose polymer is selected from the group consisting of: methylcelluloses and ethylcellulose.

71. The high concentration composition of embodiment 70, wherein the methylcellulose is selected from the group consisting of: hydroxypropyl methylcellulose (HPMC), carboxymethylcellulose (CMC), and sodium carboxymethylcellulose (NaCMC).

72. The high concentration composition of any of embodiments 68 to 71, wherein the polymer stabilizes or contributes to stabilization of the composition.

73. The high concentration composition of any of embodiments 68 to 72, wherein the polymer reduces the viscosity of the composition.

74. The high concentration composition of any of embodiments 68 to 73, wherein the polymer reversibly interacts with adalimumab and prevents protein-formed matrix interaction.

75. The high concentration composition of any of embodiments 1 to 74, wherein the composition further comprises at least one chelating agent.

76. The high concentration composition of embodiment 75, wherein the chelating agent is selected from the group consisting of EDTA, and DPTA.

77. The high concentration composition of any of embodiments 1 to 76, wherein the composition further comprises at least one sacrificial additive.

78. The high concentration composition of embodiment 77, wherein the sacrificial additive is selected from the group consisting of Met, N-Ac-Trp, ascorbate.

79. The high concentration composition of any of embodiments 1 to 78, comprising a surfactant, wherein the surfactant (a) stabilizes or contributes to stabilization of the composition, (b) reduces the viscosity of the composition, or (c) both reduces the viscosity of the composition and stabilizes or contributes to stabilization of the composition.

80. The high concentration composition of embodiment 79, wherein the surfactant is selected from the group consisting of polysorbate 20, polysorbate 80, SDS, poloxamer 188 (Pluronic® F68).

81. The high concentration composition of embodiment 79, wherein the surfactant is an ultra-low interfacial tension surfactant.

82. The high concentration composition of embodiment 81, wherein the surfactant comprises a hydrophilic portion and a hydrophobic aliphatic group.

83. The high concentration composition of embodiment 82, wherein the aliphatic group comprises saturated and/or unsaturated carbon chains.

84. The high concentration composition of embodiment 82, wherein the hydrophilic portion comprises one or more hydrophilic groups or substituents.

85. The high concentration composition of embodiment 82, wherein the hydrophilic portion is an ionizable group.

86. The high concentration composition of embodiment 85, wherein the ionizable group comprises amines and carboxylic acids.

87. The high concentration composition of embodiment 84, wherein the hydrophilic group is a hydrophilic polymer.

88. The high concentration composition of embodiment 87, wherein the hydrophilic polymer is selected from the group consisting of: methylcelluloses, hydroxypropyl methylcellulose (HPMC), carboxymethylcellulose (CMC), polyalkylamine, poly(ethylene glycol), and poly(ethylene glycol)/poly(propylene glycol) copolymers.

89. The high concentration composition of any of embodiments 1 to 88, comprising Polysorbate 80 at a concentration not exceeding about 0.1% wt.

90. The high concentration composition of any of embodiments 1 to 89, comprising at least one preservative.

91. The high concentration composition of embodiment 90, wherein the preservative is selected from the group consisting of octadecyldimethylbenzyl ammonium chloride, hexamethonium chloride, benzalkonium chloride, benzelthonium chloride, aromatic alcohols and alkyl parabens.

92. The high concentration composition of embodiment 91, wherein the aromatic alcohol is selected from the group consisting of phenol, butyl and benzyl alcohol.

93. The high concentration composition of embodiment 92, wherein the alkyl paraben is selected from the group consisting of methyl or propyl paraben, catechol, resorcinol, cyclohexanol, 3-pentanol, and m-cresol.

94. The high concentration composition of any of embodiments 1 to 93, wherein the composition further comprises a polar solvent.

95. The high concentration composition of embodiment 94, wherein the polar solvent is selected from the group consisting of dimethyl sulfoxide (DMSO) and dimethylacetamide (DMA).

96. The high concentration composition of any of embodiments 1 to 95, wherein:

(a) adalimumab is present at a concentration greater than 50 mg/mL and less than or equal to about 200-250 mg/mL; and (b) said high concentration composition, and a comparator adalimumab composition comprising adalimumab at a concentration of no more than about 50 mg/mL, are the same or essentially the same with respect to the identity and concentration of excipients contained therein; and both the high concentration formulation and the comparator have stability comparable to or better than, and viscosity comparable to or lower than, a commercially sold Humira® formulation having no greater than about 50 mg/mL or no greater than about 100 mg/mL 97. The high concentration composition of any of embodiments 1 to 95, wherein:
(a) adalimumab is present at a concentration greater than 50 mg/mL and less than or equal to about 200-250 mg/mL; and
(b) said high concentration composition, and a comparator adalimumab composition comprising adalimumab at a concentration of no more than about 50 mg/mL, are the same or essentially the same with respect to the identity and concentration of excipients contained therein; and both the high concentration formulation and the comparator have (i) stability comparable to or better than a commercially sold Humira® formulation having no greater than about 50 mg/mL or no greater than about 100 mg/mL, and (ii) viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP.

98. The high concentration composition of any of embodiments 1 to 95, wherein:
(a) adalimumab is present at a concentration greater than 50 mg/mL and less than or equal to about 200-250 mg/mL; and
(b) the high concentration composition is able to exhibit stability and viscosity at least comparable to or better than a commercially sold Humira® composition containing no greater than about 50 mg/mL, or no greater than about 100 mg/mL, without need to incorporate in such high concentration composition either (i) any viscosity reducing agents or stabilizing agents not found in a comparator adalimumab composition comprising adalimumab at a concentration of no more than about 50 mg/mL; or (ii) amounts of viscosity modifying agents or stabilizing agents different from that found in the comparator composition.

99. The high concentration composition of any of embodiments 1 to 95, wherein:
(a) adalimumab is present at a concentration greater than 50 mg/mL and less than or equal to about 200-250 mg/mL; and
(b) the high concentration composition is able to exhibit stability at least comparable to or better than a commercially sold Humira® composition containing no greater than about 50 mg/mL, or no greater than about 100 mg/mL and viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP, without need to incorporate in such high concentration composition either (i) any viscosity reducing agents or stabilizing agents not found in a comparator adalimumab composition comprising adalimumab at a concentration of no more than about 50 mg/mL; or (ii) amounts of viscosity modifying agents or stabilizing agents different from that found in the comparator composition.

100. The high concentration composition of any of embodiments 1 to 95, wherein
(a) adalimumab is present at a concentration greater than or equal to about 200-250 mg/mL;
(b) the high concentration composition, and a comparator adalimumab composition comprising adalimumab at a concentration of not more than about 50 mg/mL, compare to one another in the following respects:
(I) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein the high concentration composition has viscosity less than or approximately equal to that of commercially sold Humira® containing adalimumab at a concentration not greater than about 50 mg/mL or not greater than about 100 mg/mL; and/or
(ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein the high concentration composition has stability equal to or better than a commercially sold Humira® formulation comprising adalimumab at a concentration not greater than about 50 mg/mL or not greater than about 100 mg/mL; and
(c) the high concentration composition is not able to exhibit stability and viscosity at least comparable to or better than a commercially sold Humira® composition containing no greater than about 50 mg/mL, or no greater than about 100 mg/mL, unless the high concentration composition comprises (i) said viscosity reducing agent or stabilizing agent not found in the comparator composition; or (ii) said increased amount of viscosity modifying agent or stabilizing agent.

101. The high concentration composition of any of embodiments 1 to 95, wherein
(a) adalimumab is present at a concentration greater than or equal to about 200-250 mg/mL;
(b) the high concentration composition, and a comparator adalimumab composition comprising adalimumab at a concentration of not more than about 50 mg/mL, compare to one another in the following respects:
(i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein the high concentration composition has viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP; and/or
(ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein the high concentration composition has stability equal to or better than a commercially sold Humira® formulation comprising adalimumab at a concentration not greater than about 50 mg/mL or not greater than about 100 mg/mL; and
(c) the high concentration composition is not able to exhibit stability at least comparable to or better than a commercially sold Humira® composition containing no greater than about 50 mg/mL or no greater than about 100 mg/mL, and viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP, unless the high concentration composition comprises (i) said viscosity reducing agent or stabilizing agent not found in the comparator composition; or (ii) said increased amount of viscosity modifying agent or stabilizing agent.

102. The high concentration composition of any of embodiments 1 to 95, wherein
(a) adalimumab is present at a concentration greater than or equal to about 200-250 mg/mL;
(b) the high concentration composition, and a comparator adalimumab composition comprising adalimumab at a concentration of not more than about 50 mg/mL, compare to one another in the following respects:

(i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein both the high concentration composition, and the comparator, have viscosity less than or approximately equal to that of commercially sold Humira® containing adalimumab at a concentration not greater than about 50 mg/mL or not greater than about 100 mg/mL; and/or (ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein both the high concentration composition, and the comparator, have stability equal to or better than a commercially sold Humira® formulation comprising adalimumab at a concentration not greater than about 50 mg/mL or not greater than about 100 mg/mL; and (c) the high concentration composition is not able to exhibit stability and viscosity at least comparable to or better than a commercially sold Humira® composition containing no greater than about 50 mg/mL, or no greater than about 100 mg/mL, unless the high concentration composition comprises (i) said viscosity reducing agent or stabilizing agent not found in the comparator composition; or (ii) said increased amount of viscosity modifying agent or stabilizing agent.

103. The high concentration composition of any of embodiments 1 to 95, wherein (a) adalimumab is present at a concentration greater than or equal to about 200-250 mg/mL;

(b) the high concentration composition, and a comparator adalimumab composition comprising adalimumab at a concentration of not more than about 50 mg/mL, compare to one another in the following respects:

(i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein both the high concentration composition, and the comparator, have viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP; and/or (ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein both the high concentration composition, and the comparator, have stability equal to or better than a commercially sold Humira® formulation comprising adalimumab at a concentration not greater than about 50 mg/mL or not greater than about 100 mg/mL; and (c) the high concentration composition is not able to exhibit stability at least comparable to or better than a commercially sold Humira® composition containing no greater than about 50 mg/mL or no greater than about 100 mg/mL, and viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP, unless the high concentration composition comprises (i) said viscosity reducing agent or stabilizing agent not found in the comparator composition; or (ii) said increased amount of viscosity modifying agent or stabilizing agent.

104. The high concentration composition of any of embodiments 1 to 103 having long term stability, wherein the composition comprises one or more ionic excipients, wherein said excipients contribute to the composition having conductivity greater than 2.5, 3, 4, 5, 6, 7 or 8; osmolarity of 140 to about 400; and a hydrodynamic diameter of the adalimumab of greater than 4, 5, 6, 7, 8, 9, 10 or 11; and wherein the composition, upon administration to a subject, results in a degree of pain or discomfort no worse than, or better than, that of an AbbVie-supplied Humira® composition, having a concentration of adalimumab greater than 50 mg/mL.

105. The high concentration composition of any of embodiments 1 to 104, wherein said composition is substantially free of protein aggregates and/or high molecular weight species.

106. The high concentration composition of any of embodiments 1 to 105, wherein the composition has an absolute viscosity of about 15 cP or less.

107. The high concentration composition of any of embodiments 1 to 106, wherein the composition has an osmolality of about 180 to about 420 mOsM.

108. The high concentration composition of any of embodiments 1 to 107, wherein the composition has a conductivity selected from the group comprising: between about 1 and about 2.5 mS/cm, between about 2.5 and about 3 mS/cm, between about 3 and about 3.5 mS/cm, greater than about 2.5 mS/cm, at least about 3.0 mS/cm, about 3.0 mS/cm, about 3.5 mS/cm, about 4 mS/cm, about 4.4 mS/cm, and about 4.5 mS/cm.

109. The high concentration composition of any of embodiments 1 to 108, wherein the adalimumab has a hydrodynamic diameter selected from the group comprising greater than about 2.5 nm, greater than about 3 nm, greater than about 4 nm, greater than about 4 nm, about 2.5 to about 3 nm, about 3 nm to about 3.5 nm, about 3.5 to about 4 nm, about 3 nm, about 4 nm, about 5 nm, about 6 nm, about 7 nm, about 8 nm, about 9 nm, and about 10 nm.

110. The high concentration composition of any of embodiments 1 to 109, wherein the composition has reduced pain upon injection to a subject as compared to an adalimumab composition comprising citrate.

111. The high concentration composition of any of embodiments 1 to 110, wherein the composition has sizes and amounts of sub-visible particles comparable to, or better than that of a commercially sold Humira® containing adalimumab at concentrations between about 50 and 111 mg/mL.

112. The high concentration composition of any of embodiments 1 to 111, wherein the composition has approximately the same or fewer adalimumab fragments and/or aggregates than commercially sold Humira® containing adalimumab at concentrations between about 50 and 100 mg/mL.

113. The high concentration composition of any of embodiments 1 to 112, wherein the composition has an adalimumab monomer content of at least about 85% monomer.

114. The high concentration composition of any of embodiments 1 to 113, wherein the composition has an adalimumab monomer content of at least about 90% monomer.

115 The high concentration composition of any of embodiments 1 to 114, wherein the composition has an adalimumab monomer content of at least about 95% monomer.

116. The high concentration composition of any of embodiments 1 to 115, wherein the composition is stable at room temperature for at least 10 days.

117. The high concentration composition of any of embodiments 1 to 116, wherein the composition is stable under conditions selected from the group comprising: at least 1 week at 40° C., at least 6-10 days at 30° C., at least 2 weeks at 40° C., at least 4 weeks at 25° C., at least 9 weeks at 25° C., at least 13 weeks at 25° C., at least 13 weeks at 5° C., and at least 26 weeks at 5° C.

118. The high concentration composition of any of embodiments 1 to 117, wherein the composition is stable for at least three months.

119. The high concentration composition of any of embodiments 1 to 118, wherein the composition is stable for at least six months.

120. The high concentration composition of any of embodiments 1 to 119 wherein the composition is stable for at least one year.

121. The high concentration composition of any of embodiments 1 to 99, prepared by modifying a pre-existing adalimumab formulation having a pH of 5 to 6 and no more than about 50 mg/mL, wherein the modification consists solely of increasing the concentration of adalimumab in the pre-existing formulation to concentration selected from (i) greater than 50 mg/mL and less than or equal to about 200-250 mg/mL; and (ii) about 100 to 250 mg/mL, without altering the identity or concentration of any excipients present in the pre-existing formulation.

122. A prefilled syringe containing the high concentration composition of any of embodiments 1 to 121.

123. A prefilled syringe containing the high concentration composition of any of embodiments 1 to 122 wherein the composition is optionally free of surfactant, and is present in a defined containment volume of the syringe, said containment volume being essentially free of any portion thereof in which the composition is absent.

124. The prefilled syringe of any of embodiments 122-123 wherein the high concentration composition does not have a polysorbate or polaxamer surfactant.

125. The prefilled syringe of any of embodiments 122-124 where the high concentration composition does not have a surfactant.

126. The prefilled syringe of any of embodiments 122-125 wherein the high concentration composition is isotonic, has conductivity greater than 2.5, 3, 4, 5, 6, 7, or 8, and is free of surfactant; or free of polyol; or free of both.

127. The prefilled syringe of any of embodiments 122-126 wherein the high concentration composition does not contain any of the following buffers: phosphate, pyrophosphate, acetate, citrate, histidine, succinate, adipate, maleate, glutamate, gluconate, or tartrate.

128. The prefilled syringe of any of embodiments 122 to 127 wherein the high concentration composition is self-buffering based substantially only on the buffer capacity afforded by the adalimumab.

129. A method for preparing a high concentration formulation of any of embodiments 1-99 having a concentration of adalimumab greater than about 50 mg/mL and less than or equal to about 200-250 mg/mL, and a pH of 5 to 6, said method comprising the step of: preparing an adalimumab formulation that is modified over a known adalimumab formulation, said known formulation having a pH of 5 to 6 and comprising no more than about 50 mg/mL, wherein the modification consists solely of increasing the adalimumab concentration of the known formulation to a concentration selected from (i) greater than 50 mg/mL and less than or equal to about 200-250 mg/mL; and (ii) about 100 to about 200-250 mg/mL, without modifying the identity or concentration of any excipients present in the known formulation.

Reserved: Embodiments 130 to 200

201. An aqueous pharmaceutical composition comprising a stable high concentration of adalimumab, wherein:
(A) the composition has a concentration of adalimumab greater than 50 mg/mL;
(B) the composition has long term stability comparable to or better than a commercially sold adalimumab formulation having a concentration of adalimumab selected from:
(i) not greater than about 50 mg/mL; or
(ii) not greater than about 100 mg/mL; and
(C) the composition has viscosity approximately equal to, or less than, that of a commercially sold adalimumab formulation having a concentration of adalimumab selected from:
(i) not greater than about 50 mg/mL; or
(ii) not greater than about 100 mg/mL;
(D) wherein the composition comprises:
(i) adalimumab;
(ii) a buffer selected from one, or a combination of phosphate buffer, histidine buffer, gluconate buffer, succinate buffer, acetate buffer, adipate buffer, glutamate buffer, maleate buffer and tartrate buffer, and combinations thereof;
(iii) a stabilizer, or combination of stabilizers, selected from one or a combination of
(a) polyols;
(b) amino acids; and
(c) salts;
(iii) optionally, a surfactant, or combination of surfactants, selected from the group consisting of:
(a) polysorbate surfactants; and
(b) polaxamer surfactants;
and wherein the composition is free of citrate buffer and has a pH between 3 to 8, 4 to 8 and 5 to 6.

202. The high concentration composition of embodiment 201, wherein adalimumab is present in the composition at a concentration selected from: greater than 50 mg/mL and less than 100 g/mL; at least 100 mg/ml; 100 to 300 mg/ml; 100 to 200 mg/mL; 100 to 150 mg/ml; 100 to 125 mg/ml; 75 mg/ml; 100 mg/ml; 125 mg/ml, 150 mg/mL; 175 mg/ml; 200 mg/ml; 225 mg/ml; 250 mg/ml; 275 mg/mL; and 300 mg/mL.

203. The high concentration composition of embodiment 202, wherein the buffer consists solely of histidine, succinate, or a combination of histidine and succinate; the amino acid is selected from glycine, arginine, methionine or combinations thereof; the polyol is selected from mannitol, sorbitol and trehalose or combinations thereof; and the optional surfactant is polysorbate 80.

204. The high concentration composition of any of embodiments 201 to 203 comprising, consisting essentially of, or consisting of 30 mM histidine 160 mM glycine, 44 mM NaCl, and 0.1% polysorbate 80.

205. The high concentration composition of any of embodiments 201 to 203 comprising, consisting essentially of, or consisting of embodiment 116 comprising 30 mM histidine 160 mM mannitol, 44 mM NaCl, and 0.1% polysorbate 80.

206. The high concentration composition of any of embodiments 201 to 203 comprising, consisting essentially of, or consisting of 30 mM histidine, 192 mM glycine, 27 mM NaCl, and 0.1% polysorbate 80.

207. The high concentration composition of any of embodiments 201 to 203 comprising, consisting essentially of, or consisting of 30 mM histidine at pH 5.2, 192 mM mannitol, 27 mM NaCl, and 0.1% polysorbate 80.

208. The high concentration composition of any of embodiments 201 to 203 comprising, consisting essentially of, or consisting of 30 mM histidine at pH 5.2, 216 mM glycine, 13 mM NaCl, and 0.1% polysorbate 80.

209. The high concentration composition of any of embodiments 201 to 203 comprising, consisting essentially of, or consisting of 30 mM histidine at pH 5.2, 216 mM mannitol, 13 mM NaCl, and 0.1% polysorbate 80.

210. The high concentration composition of any of embodiments 201 to 203 comprising, consisting essentially of, or consisting of 30 mM histidine at pH 5.2, 90 mM glycine, 150 mM mannitol, 13 mM NaCl, and 0.1% polysorbate 80.

211. The high concentration composition of any of embodiments 201 to 203 comprising, consisting essentially of, or consisting of 30 mM histidine at pH 5.2, 240 mM glycine, 13 mM NaCl, and does not contain the surfactant.

212. The high concentration composition of any of embodiments 201 to 203 comprising, consisting essentially of, or consisting of 30 mM histidine at pH 5.2, 120 mM glycine, 80 mM arginine, and 0.1% polysorbate 80.

213. The high concentration composition of any of embodiments 201 to 203 comprising, consisting essentially of, or consisting of 15 mM succinate and 30 mM histidine at pH 5.2, 90 mM glycine, 80 mM arginine, and 0.1% polysorbate 80.

214. The high concentration composition of any of embodiments 201 to 203 comprising, consisting essentially of, or consisting of 30 mM histidine at pH 5.2, 240 mM mannitol, 13 mM NaCl, and 0.1% polysorbate 80.

215. The high concentration composition of any of embodiments 201 to 203 comprising, consisting essentially of, or consisting of 30 mM histidine at pH 5.2, 50 mM arginine, 160 mM mannitol, 13 mM NaCl, and 0.1% polysorbate 80.

216. The high concentration composition of any of embodiments 201 to 203 comprising, consisting essentially of, or consisting of 30 mM histidine at pH 5.2, 90 mM glycine, 100 mM arginine, and 0.1% polysorbate 80.

217. The high concentration composition of any of embodiments 201 to 203 comprising, consisting essentially of, or consisting of 30 mM histidine at pH 5.4, 120 mM glycine, 80 mM arginine, and 0.1% polysorbate 80.

218. The high concentration composition of any of embodiments 201 to 203 comprising, consisting essentially of, or consisting of 30 mM histidine at pH 5.2, 120 mM glycine 50 mM NaCl, and 0.01% polysorbate 80.

219. The high concentration composition of any of embodiments 201 to 203 comprising, consisting essentially of, or consisting of 30 mM histidine at pH 5.3, 160 mM glycine, 44 mM NaCl, and 0.1% polysorbate 80.

220. The high concentration composition of any of embodiments 201 to 203 comprising, consisting essentially of, or consisting of 30 mM histidine at pH 5.3, 160 mM glycine, 160 mM mannitol, 44 mM NaCl, and 0.1% polysorbate 80.

221. The high concentration composition of any of embodiments 201 to 203 comprising, consisting essentially of, or consisting of 30 mM histidine at pH 5.3, 160 mM glycine, 44 mM NaCl, and 0.1% polysorbate 80.

222. The high concentration composition of any of embodiments 201 to 203 comprising, consisting essentially of, or consisting of 30 mM histidine at pH 5.3, 160 mM glycine, 160 mM mannitol, 44 mM NaCl, and 0.1% polysorbate 80.

223. The high concentration composition of any of embodiments 201 to 203 comprising, consisting essentially of, or consisting of 231 mM mannitol, and 0.1% polysorbate 80.

224. The high concentration composition of any of embodiments 201 to 203 comprising, consisting essentially of, or consisting of 30 mM histidine at pH 5.3, 160 mM glycine, 44 mM arginine, 4 mM NaCl, and 0.1% polysorbate 80.

225. The high concentration composition of any of embodiments 201 to 203 comprising, consisting essentially of, or consisting of 30 mM histidine at pH 5.3, 140 mM arginine, 140 mM NaCl, and 0.1% polysorbate 80.

226. The high concentration composition of any of embodiments 201 to 203 comprising, consisting essentially of, or consisting of 30 mM histidine at pH 5.3, 240 mM glycine, and 0.1% polysorbate 80.

227. The high concentration composition of any of embodiments 201 to 203 comprising, consisting essentially of, or consisting of 30 mM histidine at pH 5.3, 160 mM glycine, 25 mM arginine, 25 mM NaCl, and 0.1% polysorbate 80.

228. The high concentration composition of any of embodiments 1 to 13, wherein the composition has a viscosity equal to or less than: 20 cP; 15 cP; 14 cP; 13 cP; 12 cP; 11 cP; 10 cP; 9 cP; 8 cP; 7 cP; 6 cP; 5 cP; 4 cP; 3 cP; 2 cP; or 1 cP.

Reserved: Embodiments 229 to 235

236. The high concentration composition of embodiment 201 to 228 the concentration of adalimumab is selected from (a) 51 mg/mL, 52 mg/mL, 53 mg/mL, 54 mg/mL, 55 mg/mL, 56 mg/mL, 57 mg/mL, 58 mg/mL, 59 mg/mL, 60 mg/mL, 61 mg/mL, 62 mg/mL, 63 mg/mL, 64 mg/mL, 65 mg/mL, 66 mg/mL, 67 mg/mL, 68 mg/mL, 69 mg/mL, 70 mg/mL, 71 mg/mL, 72 mg/mL, 73 mg/mL, 74 mg/mL, 75 mg/mL, 76 mg/mL, 77 mg/mL, 78 mg/mL, 79 mg/mL, 80 mg/mL, 81 mg/mL, 82 mg/mL, 83 mg/mL, 84 mg/mL, 85 mg/mL, 86 mg/mL, 87 mg/mL, 88 mg/mL, 89 mg/mL, 90 mg/mL, 91 mg/mL, 92 mg/mL, 93 mg/mL, 94 mg/mL, 95 mg/mL, 96 mg/mL, 97 mg/mL, 98 mg/mL, 99 mg/mL, 100 mg/mL, 101 mg/mL, 102 mg/mL, 103 mg/mL, 104 mg/mL, 105 mg/mL, 106 mg/mL, 107 mg/mL, 108 mg/mL, 109 mg/mL, 110 mg/mL, 111 mg/mL, 112 mg/mL, 113 mg/mL, 114 mg/mL, 115 mg/mL, 116 mg/mL, 117 mg/mL, 118 mg/mL, 119 mg/mL, 120 mg/mL, 121 mg/mL, 122 mg/mL, 123 mg/mL, 124 mg/mL, 125 mg/mL, 126 mg/mL, 127 mg/mL, 128 mg/mL, 129 mg/mL, 130 mg/mL, 131 mg/mL, 132 mg/mL, 133 mg/mL, 134 mg/mL, 135 mg/mL, 136 mg/mL, 137 mg/mL, 138 mg/mL, 139 mg/mL, 140 mg/mL, 141 mg/mL, 142 mg/mL, 143 mg/mL, 144 mg/mL, 145 mg/mL, 146 mg/mL, 147 mg/mL, 148 mg/mL, 149 mg/mL, 150 mg/mL, 151 mg/mL, 152 mg/mL, 153 mg/mL, 154 mg/mL, 155 mg/mL, 156 mg/mL, 157 mg/mL, 158 mg/mL, 159 mg/mL, 160 mg/mL, 161 mg/mL, 162 mg/mL, 163 mg/mL, 164 mg/mL, 165 mg/mL, 166 mg/mL, 167 mg/mL, 168 mg/mL, 169 mg/mL, 170 mg/mL, 171 mg/mL, 172 mg/mL, 173 mg/mL, 174 mg/mL, 175 mg/mL, 176 mg/mL, 177 mg/mL, 178 mg/mL, 179 mg/mL, 180 mg/mL, 181 mg/mL, 182 mg/mL, 183 mg/mL, 184 mg/mL, 185 mg/mL, 186 mg/mL, 187 mg/mL, 188 mg/mL, 189 mg/mL, 190 mg/mL, 191 mg/mL, 192 mg/mL, 193 mg/mL, 194 mg/mL, 195 mg/mL, 196 mg/mL, 197 mg/mL, 198 mg/mL, 199 mg/mL, and 200 mg/mL;
and (b) 201 mg/mL, 202 mg/mL, 203 mg/mL, 204 mg/mL, 205 mg/mL, 206 mg/mL, 207 mg/mL, 208 mg/mL, 209 mg/mL, 210 mg/mL, 211 mg/mL, 212 mg/mL, 213 mg/mL, 214 mg/mL, 215 mg/mL, 216 mg/mL, 217 mg/mL, 218 mg/mL, 219 mg/mL, 220 mg/mL, 221 mg/mL, 222 mg/mL, 223 mg/mL, 224 mg/mL, 225 mg/mL, 226 mg/mL, 227 mg/mL, 228 mg/mL, 229 mg/mL, 230 mg/mL, 231 mg/mL, 232 mg/mL, 233 mg/mL, 234 mg/mL, 235 mg/mL, 236 mg/mL, 237 mg/mL, 238 mg/mL, 239 mg/mL, 240 mg/mL, 241 mg/mL, 242 mg/mL, 243 mg/mL, 244 mg/mL, 245 mg/mL, 246 mg/mL, 247 mg/mL, 248 mg/mL, 249 mg/mL, 250 mg/mL, 251 mg/mL, 252 mg/mL, 253 mg/mL, 254 mg/mL, 255 mg/mL, 256 mg/mL, 257 mg/mL, 258 mg/mL, 259 mg/mL, 260 mg/mL, 261 mg/mL, 262 mg/mL, 263 mg/mL, 264 mg/mL, 265 mg/mL, 266 mg/mL, 267 mg/mL, 268 mg/mL, 269 mg/mL, 270 mg/mL, 271 mg/mL, 272 mg/mL, 273 mg/mL, 274 mg/mL, 275 mg/mL, 276 mg/mL, 277 mg/mL, 278 mg/mL, 279 mg/mL, 280 mg/mL, 281 mg/mL, 282 mg/mL, 283 mg/mL, 284 mg/mL, 285 mg/mL, 286 mg/mL, 287 mg/mL, 288 mg/mL, 289 mg/mL, 290 mg/mL, 291 mg/mL, 292 mg/mL, 293 mg/mL, 294 mg/mL, 295 mg/mL, 296 mg/mL, 297 mg/mL, 298 mg/mL, 299 mg/mL, and 300 mg/mL.

237. The high concentration composition of any of embodiments 201 to 236 wherein the composition has a conductivity greater than 2.5, 3, 4, 5, 6, or 7 mS/cm; an osmolarity from about 100 to 400 mOsM, and wherein the hydrodynamic diameter of the adalimumab is greater than 2, 3, 4, 5, 6, 7, 8, 9 10 or 11.

238. The high concentration composition of embodiments 201 to 237, wherein the concentration of adalimumab is (a) 100, 125, 150, 175 or 200 mg/mL; or (b) between about 200 d 300 mg/mL.

239. The high concentration composition of any of embodiments 201 to 238, wherein at least one member, or combination thereof, selected from the following list is present and contributes to stabilization of the composition: a polyol, a sugar, an amino acid, a salt, creatine, creatinine, carnitine, lauryldimethyiamineoxide (and amine oxide analogs), a polymer, a chelating agent, a polar solvent and/or a surfactant.

240. The high concentration composition of any of embodiments 201 to 238, wherein at least one of member, or combination thereof, selected from the following list is present and contributes to reducing the viscosity of the composition: an amino acid, a calcium salt, an acetate salt, magnesium chloride, sodium phosphate, arginine hydrochloride, creatine, creatinine, carnitine, an ultra-low interfacial tension surfactant, and a polar solvent.

241. The high concentration composition of embodiment 201 to 238, comprising at least one amino acid, wherein at least one amino acid stabilizes the composition and at least one other, different, amino acid reduces the viscosity of the composition.

242. The high concentration composition of embodiment 241, wherein one of the two different amino acids contains a polar uncharged side chain and the other contains a hydrophobic side chain.

243. The high concentration composition of embodiment 241, wherein one of the two different amino acids contains a polar uncharged side chain and the other is selected from the group consisting of G and P.

244. The high concentration composition of embodiment 241, wherein the stabilizing amino acid is selected from the group consisting of S, A, G, T, and V, and the viscosity reducing amino acid is elected from the group consisting of S, A, G, T, V, R, E, and P.

245. The high concentration composition of embodiment 241, wherein the stabilizing amino acid is selected from the group consisting of R, D, K, V, T, P, and I, and the viscosity reducing amino acid selected from the group consisting of P, H, K, M, G, F, E, T, S, N, and I.

246. The high concentration composition of embodiment 241, wherein the stabilizing amino acid is selected from the group consisting of R, H, M, K, and F, and the viscosity reducing amino acid selected from the group consisting of H, M, T, and V.

247. The high concentration composition of embodiment 241, wherein the stabilizing amino acid is G, and the viscosity reducing amino acid is P.

248. The high concentration composition of embodiment 241, wherein the stabilizing amino acid is S, and the viscosity reducing amino acid is P.

249. The high concentration composition of any of embodiments 201 to 238, wherein the composition comprises at least two amino acids that stabilize the composition.

250. The high concentration composition of embodiment 249, wherein stabilizing amino acids are a combination of two amino acids selected from the combinations consisting of A and G, A and M, G and M, G and T, M and T, M and S, S and T, A and N, A and Q, N and Q, A and S, N and S, Q and S, and Q and T.

251. The high concentration composition of embodiment 249, wherein the stabilizing amino acids are a combination of three amino acids selected from the combinations consisting of A, G, and M; G, M, and T; M, S, and T; A, N, and Q A, N, and S; and 0, 5, and T.

252. The high concentration composition of any of embodiments 201 to 238, wherein the composition comprises at least two amino acids that reduce the viscosity of the composition.

253. The high concentration composition of embodiment 252, wherein the viscosity reducing amino acids are a combination of two amino acids selected from the combinations consisting of P and G, and P and S.

254. The high concentration composition of any of embodiments 201 to 238, wherein the composition further comprises at least one salt.

255. The high concentration composition of embodiment 254, wherein the salt stabilizes or contributes to stabilization of the composition.

256. The high concentration composition of embodiment 255, wherein the salt is selected from the group consisting of NaCl, KCl, Na2SO4, MgCl2, CaCl2, and adipate.

257. The high concentration composition of embodiment 256, wherein the salt is present at a concentration selected from the group consisting of: not exceeding about 200 mM, not exceeding about 50 mM, not exceeding about 44 mM, not exceeding about 28 mM, not exceeding about 26.35 mM, not exceeding about 10 mM, and not exceeding about 5 mM.

258. The high concentration composition of embodiment 257, wherein the salt is MgCl2 and the composition has a viscosity of about 15 cP or less.

260. The high concentration composition of any of embodiments 201 to 238, wherein the composition further comprises at least one lauryldimethylamineoxide and/or of one of its amine oxide analogs.

261. The high concentration composition of embodiment 260, wherein the lauryldimethylamineoxide and/or of one of its amine oxide analogs stabilizes adalimumab and/or the composition.

262. The high concentration composition of any of embodiments 201 to 239, wherein the composition further comprises at least one or a combination of creatinine, creatine and carnitine.

263. The high concentration composition of embodiment 262, wherein the creatinine, creatine, and carnitine stabilize or contribute to stabilization of the composition.

264. The high concentration composition of any of embodiments 201 to 238, wherein the composition further comprises at least one polymer.

265. The high concentration composition of embodiment 264, wherein the polymer is selected from celluloses, 40 kD Dextran, betaine, PVP, and glycerol.

266. The high concentration composition of embodiment 265, wherein the cellulose polymer is selected from the group consisting of: methylcelluloses and ethlycelluloses.

267. The high concentration composition of embodiment 266, wherein the methylcellulose is selected from the group consisting of: hydroxypropyl methylcellulose (HPMC), carboxymethylcellulose (CMC), and sodium carboxymethylcellulose (NaCMC).

268. The high concentration composition of any of embodiments 264 to 267, wherein the polymer stabilizes or contributes to stabilization of the composition.

269. The high concentration composition of any of embodiments 264 to 268, wherein the polymer reduces the viscosity of the composition.

270. The high concentration composition of any of embodiments 264 to 269, wherein the polymer reversibly interacts with adalimumab and prevents protein-formed matrix interaction.

271. The high concentration composition of any of embodiments 201 to 270, wherein the composition further comprises at least one chelating agent.

272. The high concentration composition of embodiment 271, wherein the chelating agent is selected from the group consisting of EDTA, and DPTA.

273. The high concentration composition of any of embodiments 201 to 272, wherein the composition further comprises at least one sacrificial additive.

274. The high concentration composition of embodiment 273, wherein the sacrificial additive is selected from the group consisting of Met, N-Ac-Trp, ascorbate.

275. The high concentration composition of any of embodiments 201 to 274, comprising a surfactant, wherein the surfactant (a) stabilizes or contributes to stabilization of the composition, (b) reduces the viscosity of the composition, or (c) both reduces the viscosity of the composition and stabilizes or contributes to stabilization of the composition.

276. The high concentration composition of embodiment 275, wherein the surfactant is selected from the group consisting of polysorbate 20, polysorbate 80, SDS, poloxamer 188 (Pluronic® F68).

277. The high concentration composition of embodiment 275, wherein the surfactant is an ultra-low interfacial tension surfactant.

278. The high concentration composition of embodiment 277, wherein the surfactant comprises a hydrophilic portion and a hydrophobic aliphatic group.

279. The high concentration composition of embodiment 278, wherein the aliphatic group comprises saturated and/or unsaturated carbon chains.

280. The high concentration composition of embodiment 278, wherein the hydrophilic portion comprises one or more hydrophilic groups or substituents.

281. The high concentration composition of embodiment 278, wherein the hydrophilic portion is an ionizable group.

282. The high concentration composition of embodiment 281, wherein the ionizable group comprises amines and carboxylic acids.

283. The high concentration composition of embodiment 280, wherein the hydrophilic group is a hydrophilic polymer.

284. The high concentration composition of embodiment 283, wherein the hydrophilic polymer is selected from the group consisting of: methylcelluloses, hydroxypropyl methylcellulose (HPMC), carboxymethylcellulose (CMC), polyalkylamine, poly(ethylene glycol), and poly(ethylene glycol)/poly(propylene glycol) copolymers.

285. The high concentration composition of any of embodiments 201 to 284, comprising Polysorbate 80 at a concentration not exceeding about 0.1% wt.

286. The high concentration composition of any of embodiments 201 to 285, comprising at least one preservative.

287. The high concentration composition of embodiment 286, wherein the preservative is selected from the group consisting of octadecyldimethylbenzyl ammonium chloride, hexamethonium chloride, benzalkonium chloride, benzelthonium chloride, aromatic alcohols and alkyl parabens.

288. The high concentration composition of embodiment 287, wherein the aromatic alcohol is selected from the group consisting of phenol, butyl and benzyl alcohol.

289. The high concentration composition of embodiment 288, wherein the alkyl paraben is selected from the group consisting of methyl or propyl paraben, catechol, resorcinol, cyclohexanol, 3-pentanol, and m-cresol.

290. The high concentration composition of any of embodiments 201 to 289, wherein the composition further comprises a polar solvent.

291. The high concentration composition of embodiment 290, wherein the polar solvent is selected from the group consisting of dimethyl sulfoxide (DMSO) and dimethylacetamide (DMA).

292. The high concentration composition of any of embodiments 201 to 291, wherein:
(a) adalimumab Is present at a concentration greater than 50 mg/mL and less than or equal to about 200-250 mg/ml; and
(b) said high concentration composition, and a comparator adalimumab composition comprising adalimumab at a concentration of no more than about 50 mg/mL, are the same or essentially the same with respect to the identity and concentration of excipients contained therein; and both the high concentration formulation and the comparator have stability comparable to or better than, and viscosity comparable to or lower than, a commercially sold Humira® formulation having no greater than about 50 mg/mL or no greater than about 100 mg/mL 293. The high concentration composition of any of embodiments 201 to 291, wherein:
(a) adalimumab is present at a concentration greater than 50 mg/mL and less than or equal to about 200-250 mg/mL; and
(b) said high concentration composition, and a comparator adalimumab composition comprising adalimumab at a concentration of no more than about 50 mg/mL, are the same or essentially the same with respect to the identity and concentration of excipients contained therein; and both the high concentration formulation and the comparator have (i) stability comparable to or better than a commercially sold Humira® formulation having no greater than about 50 mg/mL or no greater than about 100 mg/mL, and (ii) viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP.

294. The high concentration composition of any of embodiments 201 to 291, wherein:
(a) adalimumab is present at a concentration greater than 50 mg/mL and less than or equal to about 200-250 mg/ml; and
(b) the high concentration composition is able to exhibit stability and viscosity at least comparable to or better than a commercially sold Humira® composition containing no greater than about 50 mg/ml, or no greater than about 100 mg/mL, without need to incorporate in such high concentration composition either (i) any viscosity reducing agents or stabilizing agents not found in a comparator adalimumab composition comprising adalimumab at a concentration of no more than about 50 mg/mL; or (ii) amounts of viscosity modifying agents or stabilizing agents different from that found in the comparator composition.

295. The high concentration composition of any of embodiments 201 to 291, wherein:
(a) adalimumab is present at a concentration greater than 50 mg/mL and less than or equal to about 200-250 mg/mL; and
(b) the high concentration composition is able to exhibit stability at least comparable to or better than a commercially sold Humira® composition containing no greater than about 50 mg/mL, or no greater than about 100 mg/mL and viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP, without need to incorporate in such high concentration composition either (i) any viscosity reducing agents or stabilizing agents not found in a comparator adalimumab composition comprising adalimumab at a concentration of no more than about 50 mg/mL; or (ii) amounts of viscosity modifying agents or stabilizing agents different from that found in the comparator composition.

296. The high concentration composition of any of embodiments 201 to 291, wherein
(a) adalimumab is present at a concentration greater than or equal to about 200-250 mg/mL;
(b) the high concentration composition, and a comparator adalimumab composition comprising adalimumab at a concentration of not more than about 50 mg/mL, compare to one another in the following respects:
(i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein the high concentration composition has viscosity less than or approximately equal to that of commercially sold Humira® containing adalimumab at a concentration not greater than about 50 mg/mL or not greater than about 100 mg/mL; and/or
(ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein the high concentration composition has stability equal to or better than a commercially sold Humira® formulation comprising adalimumab at a concentration not greater than about 50 mg/mL or not greater than about 100 mg/mL; and
(c) the high concentration composition is not able to exhibit stability and viscosity at least comparable to or better than a commercially sold Humira® composition containing no greater than about 50 mg/mL, or no greater than about 100 mg/mL, unless the high concentration composition comprises (i) said viscosity reducing agent or stabilizing agent not found in the comparator composition; or (ii) said increased amount of viscosity modifying agent or stabilizing agent.

297. The high concentration composition of any of embodiments 201 to 291, wherein
(a) adalimumab is present at a concentration greater than or equal to about 200-250 mg/mL;
(b) the high concentration composition, and a comparator adalimumab composition comprising adalimumab at a concentration of not more than about 50 mg/mL, compare to one another in the following respects:
(i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein the high concentration composition has viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP; and/or
(ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein the high concentration composition has stability equal to or better than a commercially sold Humira® formulation comprising adalimumab at a concentration not greater than about 50 mg/mL or not greater than about 100 mg/mL; and
(c) the high concentration composition is not able to exhibit stability at least comparable to or better than a commercially sold Humira® composition containing no greater than about 50 mg/mL or no greater than about 100 mg/mL, and viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP, unless the high concentration composition comprises (i) said viscosity reducing agent or stabilizing agent not found in the comparator composition; or (ii) said increased amount of viscosity modifying agent or stabilizing agent.

298. The high concentration composition of any of embodiments 201 to 291, wherein
(a) adalimumab is present at a concentration greater than or equal to about 200-250 mg/mL;
(b) the high concentration composition, and a comparator adalimumab composition comprising adalimumab at a concentration of not more than about 50 mg/mL, compare to one another in the following respects:
(i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein both the high concentration composition, and the comparator, have viscosity less than or approximately equal to that of commercially sold Humira® containing adalimumab at a concentration not greater than about 50 mg/mL or not greater than about 100 mg/mL; and/or
(ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein both the high concentration composition, and the comparator, have stability equal to or better than a commercially sold Humira® formulation comprising adalimumab at a concentration not greater than about 50 mg/mL or not greater than about 100 mg/mL; and (c) the high concentration composition is not able to exhibit stability and viscosity at least comparable to or better than a commercially sold Humira® composition containing no greater than about 50 mg/mL, or no greater than about 100 mg/mL, unless the high concentration composition comprises (i) said viscosity reducing agent or stabilizing agent not found in the comparator composition; or (ii) said increased amount of viscosity modifying agent or stabilizing agent.

299. The high concentration composition of any of embodiments 201 to 291, wherein
(a) adalimumab is present at a concentration greater than or equal to about 200-250 mg/mL;
(b) the high concentration composition, and a comparator adalimumab composition comprising adalimumab at a concentration of not more than about 50 mg/mL, compare to one another in the following respects:
(i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein both the high concentration composition, and the comparator, have viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP; and/or
(ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein both the high concentration composition, and the comparator, have stability equal to or better than a commercially sold Humira® formulation comprising adalimumab at a concentration not greater than about 50 mg/mL or not greater than about 100 mg/mL; and
(c) the high concentration composition is not able to exhibit stability at least comparable to or better than a commercially sold Humira® composition containing no greater than about 50 mg/mL or no greater than about 100 mg/mL, and viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP, unless the high concentration composition comprises (i) said viscosity reducing agent or stabilizing agent not found in the comparator composition; or (ii) said increased amount of viscosity modifying agent or stabilizing agent.

300. The high concentration composition of any of embodiments 201 to 299 having long term stability, wherein the composition comprises one or more ionic excipients, wherein said excipients contribute to the composition having conductivity greater than 2.5, 3, 4, 5, 6, 7 or 8; osmolarity of 140 to about 400; and a hydrodynamic diameter of the adalimumab of greater than 4, 5, 6, 7, 8, 9, 10 or 11; and wherein the composition, upon administration to a subject, results in a degree of pain or discomfort no worse than, or better than, that of an AbbVie-supplied Humira® composition, having a concentration of adalimumab greater than 50 mg/mL.

302. The high concentration composition of any of embodiments 201 to 301, wherein said composition is substantially free of protein aggregates and/or high molecular weight species.

303. The high concentration composition of any of embodiments 201 to 302, wherein the composition has an absolute viscosity of about 15 cP or less.

304. The high concentration composition of any of embodiments 201 to 303, wherein the composition has an osmolality of about 180 to about 420 mOsM.

305. The high concentration composition of any of embodiments 201 to 304, wherein the composition has a conductivity selected from the group comprising: between about 1 and about 2.5 mS/cm, between about 2.5 and about 3 mS/cm, between about 3 and about 3.5 mS/cm, greater than about 2.5 mS/cm, at least about 3.0 mS/cm, about 3.0 mS/cm, about 3.5 mS/cm, about 4 mS/cm, about 4.4 mS/cm, and about 4.5 mS/cm.

306. The high concentration composition of any of embodiments 201 to 305, wherein the adalimumab has a hydrodynamic diameter selected from the group comprising greater than about 2.5 nm, greater than about 3 nm, greater than about 4 nm, greater than about 4 nm, about 2.5 to about 3 nm, about 3 nm to about 3.5 nm, about 3.5 to about 4 nm, about 3 nm, about 4 nm, about 5 nm, about 6 nm, about 7 nm, about 8 nm, about 9 nm, and about 10 nm.

307. The high concentration composition of any of embodiments 201 to 306, wherein the composition has reduced pain upon injection to a subject as compared to an adalimumab composition comprising citrate.

308. The high concentration composition of any of embodiments 201 to 307, wherein the composition has sizes and amounts of sub-visible particles comparable to, or better than that of a commercially sold Humira® containing adalimumab at concentrations between about 50 and 100 mg/mL.

309. The high concentration composition of any of embodiments 201 to 308, wherein the composition has approximately the same or fewer adalimumab fragments and/or aggregates than commercially sold Humira® containing adalimumab at concentrations between about 50 and 100 mg/mL.

310. The high concentration composition of any of embodiments 201 to 309, wherein the composition has an adalimumab monomer content of at least about 85% monomer.

311. The high concentration composition of any of embodiments 201 to 310, wherein the composition has an adalimumab monomer content of at least about 90% monomer.

312 The high concentration composition of any of embodiments 201 to 311, wherein the composition has an adalimumab monomer content of at least about 95% monomer.

313. The high concentration composition of any of embodiments 201 to 312, wherein the composition is stable at room temperature for at least 10 days.

314. The high concentration composition of any of embodiments 201 to 313, wherein the composition is stable under conditions selected from the group comprising: at least 1 week at 40'C, at least 6-10 days at 30° C., at least 2 weeks at 40° C., at least 4 weeks at 25° C., at least 9 weeks at 25° C., at least 13 weeks at 25° C., at least 13 weeks at 5° C., and at least 26 weeks at 5'C.

315. The high concentration composition of any of embodiments 201 to 314, wherein the composition is stable for at least three months.

316. The high concentration composition of any of embodiments 201 to 315, wherein the composition is stable for at least six months.

317. The high concentration composition of any of embodiments 201 to 316 wherein the composition is stable for at least one year.

318. The high concentration composition of any of embodiments 201 to 317, having a pH of 5 to 6, and prepared by modifying a pre-existing adalimumab formulation having a pH of 5 to 6 and no more than about 50 mg/mL, wherein the modification consists solely of increasing the concentration of adalimumab in the pre-existing formulation to concentration selected from (i) greater than 50 mg/mL and less than or equal to about 200-250 mg/mL; and (ii) about 100 to 250 mg/mL, without altering the identity or concentration of any excipients present in the pre-existing formulation.

319. A prefilled syringe containing the high concentration composition of any of embodiments 201 to 318.

320. A prefilled syringe containing the high concentration composition of any of embodiment 201 to 319 wherein the composition is optionally free of surfactant, and is present in a defined containment volume of the syringe, said containment volume being essentially free of any portion thereof in which the composition is absent.

320. The prefilled syringe of embodiments 319-320 wherein the high concentration composition does not have a polysorbate or polaxamer surfactant.

321. The prefilled syringe of any of embodiments 319 to 320 where the high concentration composition does not have a surfactant.

322. The prefilled syringe of any of embodiments 319-321 wherein the high concentration composition is isotonic, has conductivity greater than 2.5, and is free of surfactant or free of polyol or free of both.

323. The prefilled syringe of any of embodiments 319-322 wherein the high concentration composition does not contain any of the following buffers: phosphate, pyrophosphate, acetate, citrate, histidine, succinate, adipate, maleate, glutamate, gluconate, or tartrate.

324. The prefilled syringe of any of embodiments 319-323 wherein the high concentration composition is self-buffering based substantially only on the buffer capacity afforded by the adalimumab.

325. A method for preparing a high concentration formulation of any of embodiments 201-291 having a concentration of adalimumab greater than about 50 mg/mL and less than or equal to about 200-250 mg/mL, and a pH of 5 to 6, said method comprising the step of: preparing an adalimumab formulation that is modified over a known adalimumab formulation, said known formulation having a pH of 5 to 6 and comprising no more than about 50 mg/mL, wherein the modification consists solely of increasing the adalimumab concentration of the known formulation to a concentration selected from (i) greater than 50 mg/mL and less than or equal to about 200-250 mg/mL; and (ii) about 100 to about 200-250 mg/mL, without modifying the identity or concentration of any excipients present in the known formulation.

Reserved: Embodiment 325-400

401. An aqueous pharmaceutical composition comprising a stable high concentration of adalimumab, wherein:

(A) the composition has a concentration of adalimumab greater than 50 mg/mL;
(B) the composition has long term stability comparable to or better than a commercially sold adalimumab formulation having a concentration of adalimumab selected from:
(i) not greater than about 50 mg/mL; or
(ii) not greater than about 100 mg/mL; and
(C) the composition has viscosity approximately equal to, or less than, that of a commercially sold adalimumab formulation having a concentration of adalimumab selected from:
(i) not greater than about 50 mg/mL; or
(ii) not greater than about 100 mg/mL; and
(D) the composition:
(i) comprises a polyol, and is free or substantially free of surfactant; or
(ii) comprises a surfactant, and is free or substantially free of polyol; or
(iii) is free or substantially free of both surfactant and polyol; and
(E) the composition has pH 3 to 8; 4 to 8; or 5 to 6, and optionally comprises a buffer.

402. The high concentration composition of embodiment 201, wherein adalimumab is present in the composition at a concentration selected from: greater than 50 mg/mL and less than 100 g/mL; at least 100 mg/mL; 100 to 300 mg/mL; 100 to 200 mg/mL; 100 to 150 mg/mL; 100 to 125 mg/mL; 75 mg/mL; 100 mg/mL; 125 mg/mL, 150 mg/mL; 175 mg/mL; 200 mg/mL; 225 mg/mL; 250 mg/mL; 275 mg/mL; and 300 mg/mL.

403. The high concentration composition of embodiment 402 wherein comprises a polyol, and is free or substantially free of surfactant 404. The high concentration composition of embodiment 402 wherein comprises a surfactant, and is free or substantially free of polyol.

405. The high concentration composition of embodiment 402 wherein the composition is free or substantially free of both surfactant and polyol.

406. The high concentration composition of embodiment 402 wherein the composition is free or substantially free of surfactant, polyol and buffer.

407. The high concentration composition of embodiment 405, wherein the composition has pH of 5.2 and is free, or substantially free, of a surfactant, and wherein the composition further comprises 30 mM histidine, 180 mM glycine, and 40 mM NaCl.

408. The high concentration composition of embodiment 405, wherein the composition has pH of 5.2 and is free, or substantially free, of a surfactant, and wherein the composition further comprises 30 mM histidine, 25 mM arginine, and 200 mM glycine.

409. The high concentration composition of embodiment 405, wherein the composition has pH of 5.2 and is free, or substantially free, of a surfactant, and wherein the composition further comprises 30 mM histidine, 25 mM arginine, 180 mM glycine, and 20 mM NaCl.

410. The high concentration composition of embodiment 405, wherein the composition has pH of 5.2 and is free, or substantially free, of a surfactant, and wherein the composition further comprises 30 mM histidine, 25 mM arginine, 180 mM glycine, and 15 mM sodium sulfate.

411. The high concentration composition of embodiment 405, wherein the composition has pH of 5.2 and is free, or substantially free, of a surfactant, and wherein the composition further comprises 30 mM histidine, 180 mM glycine, and 30 mM potassium phosphate.

412. The high concentration composition of embodiment 405, wherein the composition has pH of 5.2 and is free, or substantially free, of a surfactant, and wherein the composition further comprises 30 mM histidine, 180 mM glycine, 15 mM NaCl, and 15 mM potassium phosphate.

413. The high concentration composition of embodiment 405, wherein the composition has pH of 5.2 and is free, or substantially free, of a surfactant, and wherein the composition further comprises 30 mM histidine, 180 mM glycine, 15 mM sodium sulfate, and 15 mM potassium phosphate.

414. The high concentration composition of embodiment 405, wherein the composition has pH of 5.2 and is free, or substantially free, of a surfactant, and wherein the composition further comprises 30 mM histidine, 25 mM arginine, 15 mM NaCl, and 75 mM potassium phosphate.

415. The high concentration composition of embodiment 405, wherein the composition has pH of 5.2 and is free, or substantially free, of a surfactant, and wherein the composition further comprises 30 mM histidine, 25 mM arginine, 140 mM glycine, and 30 mM potassium phosphate.

416. The high concentration composition of embodiment 406, wherein the composition has pH of 5.2 and is free, or substantially free, of a surfactant, and wherein the composition further comprises 240 mM glycine, and 20 mM NaCl.

417. The high concentration composition of embodiment 405, wherein the composition has pH of 5.3 and is free, or substantially free, of a surfactant, and wherein the composition further comprises 30 mM histidine, 180 mM glycine, and 30 mM sodium sulfate.

418. The high concentration composition of embodiment 405, wherein the composition has pH of 5.3 and is free, or substantially free, of a surfactant, and wherein the composition further comprises 30 mM histidine, 180 mM glycine, and 25 mM magnesium chloride.

419. The high concentration composition of embodiment 405, wherein the composition has pH of 5.3 and is free, or substantially free, of a surfactant, and wherein the composition further comprises 30 mM histidine, 60 mM glycine, and 75 mM sodium sulfate.

420. The high concentration composition of embodiment 405, wherein the composition has pH of 5.3 and is free, or substantially free, of a surfactant, and wherein the composition further comprises 30 mM histidine, 25 mM arginine, and 120 mM NaCl.

421. The high concentration composition of embodiment 403, wherein the composition has pH of 5.3 and is free, or substantially free, of a surfactant, and wherein the composition further comprises 30 mM histidine, 160 mM mannitol, and 25 mM arginine.

422. The high concentration composition of embodiment 405, wherein the composition has pH of 5.3 and is free, or substantially free, of a surfactant, and wherein the composition further comprises 30 mM histidine, and 240 mM glycine.

423. The high concentration composition of embodiment 405, wherein the composition has pH of 5.3 and is free, or substantially free, of a surfactant, and wherein the composition further comprises 30 mM histidine, 25 mM arginine, and 180 mM glycine.

424. The high concentration composition of embodiment 405, wherein the composition has pH of 5.3 and is free, or substantially free, of a surfactant, and wherein the composition further comprises 30 mM histidine, and 100 mM sodium sulfate.

425. The high concentration composition of embodiment 405, wherein the composition has pH of 5.3 and is free, or substantially free, of a surfactant, and wherein the composition further comprises 50 mM histidine, and 140 mM NaCl.

426. The high concentration composition of embodiment 404, wherein the composition has pH of 5.2 and is free, or substantially free, of a polyol, and wherein the composition further comprises 10 mM citrate, 150 mM NaCl, and 0.1% PS 80.

427. The high concentration composition of embodiment 404, wherein the composition has pH of 5.2 and is free, or substantially free, of a polyol, and wherein the composition further comprises 10 mM sodium phosphate, 150 mM NaCl, and 0.1% PS 80.

428. The high concentration composition of embodiment 404, wherein the composition has pH of 3.5 and is free, or substantially free, of a polyol, and wherein the composition further comprises 130 mM arginine, and 0.1% PS 80.

429. The high concentration composition of embodiment 404, wherein the composition has pH of 5.2 and is free, or substantially free, of a polyol, and wherein the composition further comprises 10 mM histidine, 120 mM arginine, and 120 mM glycine, and 0.1% PS 80.

430. The high concentration composition of embodiment 404, wherein the composition has pH of 5.2 and is free, or substantially free, of a polyol, and wherein the composition further comprises 10 mM histidine, 120 mM arginine, and 120 mM glycine, and 0.05% PS 80.

431. The high concentration composition of embodiment 404, wherein the composition has pH of 5.2 and is free, or substantially free, of a polyol, and wherein the composition further comprises 10 mM histidine, 120 mM arginine, and 120 mM glycine, and 0.01% PS 80.

432. The high concentration composition of embodiment 404, wherein the composition has pH of 5.2 and is free, or substantially free, of a polyol, and wherein the composition further comprises 10 mM histidine, 120 mM arginine, and 120 mM glycine, 0.05% PS 20, and 0.05% F68.

433. The high concentration composition of embodiment 404, wherein the composition has pH of 5.2 and is free, or substantially free, of a polyol, and wherein the composition further comprises 10 mM histidine, 120 mM arginine, and 120 mM glycine, and 0.1% F68.

434. The high concentration composition of embodiment 404, wherein the composition has pH of 5.2 and is free, or substantially free, of a polyol, and wherein the composition further comprises 10 mM succinate, 120 mM arginine, and 120 mM glycine, and 0.05% PS 80.

435. The high concentration composition of embodiment 404, wherein the composition has pH of 5.2 and is free, or substantially free, of a polyol, and wherein the composition further comprises 20 mM succinate, 100 mM arginine, and 150 mM glycine, and 0.05% PS 20.

436. The high concentration composition of embodiment 404, wherein the composition has pH of 5.2 and is free, or substantially free, of a polyol, and wherein the composition further comprises 20 mM histidine, 100 mM arginine, and 150 mM glycine, and 0.01% PS 80.

437. The high concentration composition of embodiment 404, wherein the composition has pH of 5.2 and is free, or substantially free, of a polyol, and wherein the composition further comprises 20 mM histidine, 120 mM arginine, and 120 mM glycine, and 0.01% PS 20.

438. The high concentration composition of embodiment 404, wherein the composition has pH of 5.2 and is free, or substantially free, of a polyol, and wherein the composition further comprises 120 mM arginine, and 120 mM glycine, and 0.1% PS 80.

439. The high concentration composition of embodiment 404, wherein the composition has pH of 5.2 and is free, or substantially free, of a polyol, and wherein the composition further comprises 10 mM succinate, 10 mM histidine, 100 mM arginine, and 120 mM glycine, and 0.1% PS 80.

440. The high concentration composition of embodiment 404, wherein the composition has pH of 5.2 and is free, or substantially free, of a polyol, and wherein the composition further comprises 30 mM histidine, and 240 mM glycine, and 0.1% PS 80.

441. The high concentration composition of embodiment 403, wherein the composition has pH of 5.2 and is free, or substantially free, of a surfactant, and wherein the composition further comprises 8 mM citrate, 18 mM sodium phosphate, 65 mM mannitol, and 100 mM NaCl.

442. The high concentration composition of embodiment 403, wherein the composition has pH of 5.2 and is free, or substantially free, of a surfactant, and wherein the composition further comprises 20 mM citrate, 65 mM mannitol, and 100 mM NaCl.

443. The high concentration composition of embodiment 403, wherein the composition has pH of 5.2 and is free, or substantially free, of a surfactant, and wherein the composition further comprises 20 mM sodium phosphate, 65 mM mannitol, and 100 mM NaCl.

444. The high concentration composition of embodiment 406, wherein the composition has pH of 3.5 and is free, or substantially free, of a surfactant, and wherein the composition further comprises 130 mM arginine.

445. The high concentration composition of embodiment 406, wherein the composition has pH of 3.5 and is free, or substantially free, of a surfactant, and wherein the composition further comprises 240 mM glycine.

446. The high concentration composition of embodiment 406, wherein the composition has pH of 5.2 and is free, or substantially free, of a surfactant, and wherein the composition further comprises 240 mM glycine.

447. The high concentration composition of embodiment 406, wherein the composition has pH of 3.5 and is free, or substantially free, of a surfactant, and wherein the composition further comprises 100 mM arginine, and 100 mM glycine.

448. The high concentration composition of embodiment 406, wherein the composition has pH of 5.2 and is free, or substantially free, of a surfactant, and wherein the composition further comprises 100 mM arginine, and 100 mM glycine.

449. The high concentration composition of embodiment 406, wherein the composition has pH of 3.5 and is free, or substantially free, of a surfactant, and wherein the composition further comprises 150 mM arginine, and 50 mM glycine.

450. The high concentration composition of embodiment 405, wherein the composition has pH of 5.2 and is free, or substantially free, of a surfactant, and wherein the composition further comprises 10 mM histidine, 150 mM arginine, and 0.1% EDTA.

451. The high concentration composition of embodiment 403, wherein the composition has pH of 5.2 and is free, or substantially free, of a surfactant, and wherein the composition further comprises 10 mM histidine, and 240 mM mannitol.

452. The high concentration composition of embodiment 403, wherein the composition has pH of 5.2 and is free, or substantially free, of a surfactant, and wherein the composition further comprises 10 mM histidine, 240 mM mannitol, and 10 mM methionine.

453. The high concentration composition of embodiment 403, wherein the composition has pH of 5.2 and is free, or substantially free, of a surfactant, and wherein the composition further comprises 10 mM histidine, 240 mM mannitol, and 50 mM methionine.

454. The high concentration composition of embodiment 403, wherein the composition has pH of 5.2 and is free, or substantially free, of a surfactant, and wherein the composition further comprises 20 mM histidine, and 240 mM mannitol.

455. The high concentration composition of embodiment 406, wherein the composition has pH of 5.2 and is free, or substantially free, of a surfactant, and wherein the composition further comprises 240 mM glycine.

456. The high concentration composition of embodiment 406, wherein the composition has pH of 5.2 and is free, or substantially free, of a surfactant, and wherein the composition further comprises 100 mM arginine, and 100 mM glycine.

457. The high concentration composition of any of embodiments 407 to 456 wherein the concentration of adalimumab in the composition is selected from: (i) greater than about 50 mg/mL and up to about 200 mg/mL; (ii) 100 mg/mL; (iii) 150 mg/ml; and (iv) 51 mg/mL, 52 mg/mL, 53 mg/mL, 54 mg/mL, 55 mg/mL, 56 mg/mL, 57 mg/mL, 58 mg/mL, 59 mg/mL, 60 mg/mL, 61 mg/mL, 62 mg/mL, 63 mg/mL, 64 mg/mL, 65 mg/mL, 66 mg/mL, 67 mg/mL, 68 mg/mL, 69 mg/mL, 70 mg/mL, 71 mg/mL, 72 mg/mL, 73 mg/mL, 74 mg/mL, 75 mg/mL, 76 mg/mL, 77 mg/mL, 78 mg/mL, 79 mg/mL, 80 mg/mL, 81 mg/mL, 82 mg/mL, 83 mg/mL, 84 mg/mL, 85 mg/mL, 86 mg/mL, 87 mg/mL, 88 mg/mL, 89 mg/mL, 90 mg/mL, 91 mg/mL, 92 mg/mL, 93 mg/mL, 94 mg/mL, 95 mg/mL, 96 mg/mL, 97 mg/mL, 98 mg/mL, 99 mg/mL, 100 mg/mL, 101 mg/mL, 102 mg/mL, 103 mg/mL, 104 mg/mL, 105 mg/mL, 106 mg/mL, 107 mg/mL, 108 mg/mL, 109 mg/mL, 110 mg/mL, 111 mg/mL, 112 mg/mL, 113 mg/mL, 114 mg/mL, 115 mg/mL, 116 mg/mL, 117 mg/mL, 118 mg/mL, 119 mg/mL, 120 mg/mL, 121 mg/mL, 122 mg/mL, 123 mg/mL, 124 mg/mL, 125 mg/mL, 126 mg/mL, 127 mg/mL, 128 mg/mL, 129 mg/mL, 130 mg/mL, 131 mg/mL, 132 mg/mL, 133 mg/mL, 134 mg/mL, 135 mg/mL, 136 mg/mL, 137 mg/mL, 138 mg/mL, 139 mg/mL, 140 mg/mL, 141 mg/mL, 142 mg/mL, 143 mg/mL, 144 mg/mL, 145 mg/mL, 146 mg/mL, 147 mg/mL, 148 mg/mL, 149 mg/mL, 150 mg/mL, 151 mg/mL, 152 mg/mL, 153 mg/mL, 154 mg/mL, 155 mg/mL, 156 mg/mL, 157 mg/mL, 158 mg/mL, 159 mg/mL, 160 mg/mL, 161 mg/mL, 162 mg/mL, 163 mg/mL, 164 mg/mL, 165 mg/mL, 166 mg/mL, 167 mg/mL, 168 mg/mL, 169 mg/mL, 170 mg/mL, 171 mg/mL, 172 mg/mL, 173 mg/mL, 174 mg/mL, 175 mg/mL, 176 mg/mL, 177 mg/mL, 178 mg/mL, 179 mg/mL, 180 mg/mL, 181 mg/mL, 182 mg/mL, 183 mg/mL, 184 mg/mL, 185 mg/mL, 186 mg/mL, 187 mg/mL, 188 mg/mL, 189 mg/mL, 190 mg/mL, 191 mg/mL, 192 mg/mL, 193 mg/mL, 194 mg/mL, 195 mg/mL, 196 mg/mL, 197 mg/mL, 198 mg/mL, 199 mg/mL, or 200 mg/mL, 458. The high concentration composition of any of embodiments 401 to 457, wherein the composition has a viscosity equal to or less than: 20 cP; 15 cP; 14 cP; 13 cP; 12 cP; 11 cP; 10 cP; 9 cP; 8 cP; 7 cP; 6 cP; 5 cP; 4 cP; 3 cP; 2 cP; or 1 cP.

459. The high concentration composition of any of embodiments 401 to 406 wherein the following buffers are not present in the composition: phosphate buffer, pyrophosphate buffer, citrate buffer, acetate buffer, glutamate buffer, gluconate buffer, histidine buffer, succinate buffer, adipate buffer, maleate buffer and tartrate buffer.

460. The high concentration composition of any of embodiments embodiment 401 to 405, wherein the buffer, when present, is at least one, or a combination, of phosphate, pyrophosphate, citrate, acetate, glutamate, gluconate, histidine, succinate, adipate, maleate, and tartrate.

461. The high concentration composition of any of embodiments 401 to 405, comprising at least one buffer, wherein the composition (a) is free or essentially free of citrate buffer; or (b) is free or essentially free of phosphate buffer; or (c) is free or essentially free of a buffer composition comprising citrate buffer and phosphate buffer.

462. The high concentration composition of any of embodiment 401 to 405, wherein the buffer is or comprises succinate.

463. The high concentration composition of any of embodiment 401 to 405, wherein the buffer is or comprises histidine.

464. The high concentration composition of embodiment 401-405, wherein the composition comprises a combination of two buffers where the combination is selected from (a) a combination of histidine buffer and succinate buffer; (b) a combination of citrate buffer and phosphate buffer; (c) a combination of citrate buffer and pyrophosphate buffer; and (d) a combination of phosphate buffer plus either histidine buffer or succinate buffer.

465. The high concentration composition of embodiment 464, wherein the buffer combination is succinate and histidine.

466. The high concentration composition of embodiment 464, wherein the buffer combination is citrate and pyrophosphate.

467. The high concentration composition of any of embodiments 459 to 466, wherein the composition has a pH of 5 to 6.

468. The high concentration composition of any of embodiments 459 to 467, comprising at least one tonicity agent, wherein the tonicity agent comprises salts, amino acids, sugars, and polyols.

469. The high concentration composition of any of embodiments 459 to 468, further comprising at least one tonicity agent, wherein the tonicity agent is not a salt.

470. The high concentration composition of embodiment 468, wherein the salt comprises NaCl, KCl, Na$_2$SO4, MgCl$_2$, CaCl$_2$), and adipate.

471. The high concentration composition of embodiment 470, wherein the salt is present at a concentration selected from: 40 to 140 mM; not exceeding about 150; not exceeding about 100 mM; not exceeding about 50 mM, not exceeding about 44 mM, not exceeding about 28 mM, not exceeding about 26.35 mM, not exceeding about 10 mM, and not exceeding about 5 mM.

472. The high concentration composition of any of embodiments 459 to 471, wherein the composition comprises at least one polyol.

473. The high concentration composition of embodiment 472, wherein the polyol is selected from glycerol, xylitol, inositol, mannitol, sorbitol, trehalose and combinations thereof.

474. The high concentration composition of embodiment 473, wherein the polyol is mannitol at a concentration not exceeding about 300 mM.

475. The high concentration composition of any of embodiments 459 to 474, comprising at least one sugar.

476. The high concentration composition of embodiment 475, wherein the sugar comprises sucrose, lactose, glucose, and maltose, and combinations thereof.

477. The high concentration composition of any of embodiments 459 to 477, comprising at least one amino acid.

478. The high concentration composition of embodiment 477, wherein the amino acid is selected from the group consisting of histidine, glycine, methionine, serine, proline, and arginine.

479. The high concentration composition of embodiment 477, wherein the amino acid is histidine.

480. The high concentration composition of embodiment 477, wherein the amino acid is glycine.

481. The high concentration composition of embodiment 477, wherein the amino acid is arginine.

482. The high concentration composition of embodiment 478, wherein the amino acid comprises a combination of glycine and arginine.

483. The high concentration composition of any of embodiments 459 to 482, wherein the surfactant, if present, is selected from the group consisting of polysorbate 20, polysorbate 80, SDS, poloxamer 188 (Pluronic® F68) and combinations thereof.

484. The high concentration composition of any of embodiments 1 to 483, wherein the composition is isotonic or has an osmolality of about 180 to about 420 mOsM.

Reserved: Embodiments 485 to 491

492. The high concentration composition of embodiment 401 to 484, wherein the concentration of adalimumab is selected from (a) 51 mg/mL, 52 mg/mL, 53 mg/mL, 54 mg/mL, 55 mg/mL, 56 mg/mL, 57 mg/mL, 58 mg/mL, 59 mg/mL, 60 mg/mL, 61 mg/mL, 62 mg/mL, 63 mg/mL, 64 mg/mL, 65 mg/mL, 66 mg/mL, 67 mg/mL, 68 mg/mL, 69 mg/mL, 70 mg/mL, 71 mg/mL, 72 mg/mL, 73 mg/mL, 74 mg/mL, 75 mg/mL, 76 mg/mL, 77 mg/mL, 78 mg/mL, 79 mg/mL, 80 mg/mL, 81 mg/mL, 82 mg/mL, 83 mg/mL, 84 mg/mL, 85 mg/mL, 86 mg/mL, 87 mg/mL, 88 mg/mL, 89 mg/ml, 90 mg/mL, 91 mg/mL, 92 mg/mL, 93 mg/mL, 94 mg/mL, 95 mg/mL, 96 mg/mL, 97 mg/mL, 98 mg/mL, 99 mg/mL, 100 mg/mL, 101 mg/mL, 102 mg/mL, 103 mg/mL, 104 mg/mL, 105 mg/mL, 106 mg/mL, 107 mg/mL, 108 mg/mL, 109 mg/mL, 110 mg/mL, 111 mg/mL, 112 mg/mL, 113 mg/mL, 114 mg/mL, 115 mg/mL, 116 mg/mL, 117 mg/mL, 118 mg/mL, 119 mg/mL, 120 mg/mL, 121 mg/mL, 122 mg/mL, 123 mg/mL, 124 mg/mL, 125 mg/mL, 126 mg/mL, 127 mg/mL, 128 mg/mL, 129 mg/mL, 130 mg/mL, 131 mg/mL, 132 mg/mL, 133 mg/mL, 134 mg/mL, 135 mg/mL, 136 mg/mL, 137 mg/mL, 138 mg/mL, 139 mg/mL, 140 mg/mL, 141 mg/mL, 142 mg/mL, 143 mg/mL, 144 mg/mL, 145 mg/mL, 146 mg/mL, 147 mg/mL, 148 mg/mL, 149 mg/mL, 150 mg/mL, 151 mg/mL, 152 mg/mL, 153 mg/mL, 154 mg/mL, 155 mg/mL, 156 mg/mL, 157 mg/mL, 158 mg/mL, 159 mg/mL, 160 mg/mL, 161 mg/mL, 162 mg/mL, 163 mg/mL, 164 mg/mL, 165 mg/mL, 166 mg/mL, 167 mg/mL, 168 mg/mL, 169 mg/mL, 170 mg/mL, 171 mg/mL, 172 mg/mL, 173 mg/mL, 174 mg/mL, 175 mg/mL, 176 mg/mL, 177 mg/mL, 178 mg/mL, 179 mg/mL, 180 mg/mL, 181 mg/mL, 182 mg/mL, 183 mg/mL, 184 mg/mL, 185 mg/mL, 186 mg/mL, 187 mg/mL, 188 mg/mL, 189 mg/mL, 190 mg/mL, 191 mg/mL, 192 mg/mL, 193 mg/mL, 194 mg/mL, 195 mg/mL, 196 mg/mL, 197 mg/mL, 198 mg/mL, 199 mg/mL, 200 mg/ml;

and (b): 201 mg/mL, 202 mg/mL, 203 mg/mL, 204 mg/mL, 205 mg/mL, 206 mg/mL, 207 mg/mL, 208 mg/mL, 209 mg/mL, 210 mg/mL, 211 mg/mL, 212 mg/mL, 213 mg/mL, 214 mg/mL, 215 mg/mL, 216 mg/mL, 217 mg/mL, 218 mg/mL, 219 mg/mL, 220 mg/mL, 221 mg/mL, 222 mg/mL, 223 mg/mL, 224 mg/mL, 225 mg/mL, 226 mg/mL, 227 mg/mL, 228 mg/mL, 229 mg/mL, 230 mg/mL, 231 mg/mL, 232 mg/mL, 233 mg/mL, 234 mg/mL, 235 mg/mL, 236 mg/mL, 237 mg/mL, 238 mg/mL, 239 mg/mL, 240 mg/mL, 241 mg/mL, 242 mg/mL, 243 mg/mL, 244 mg/mL, 245 mg/mL, 246 mg/mL, 247 mg/mL, 248 mg/mL, 249 mg/mL, 250 mg/mL, 251 mg/mL, 252 mg/mL, 253 mg/mL, 254 mg/mL, 255 mg/mL, 256 mg/mL, 257 mg/mL, 258 mg/mL, 259 mg/mL, 260 mg/mL, 261 mg/mL, 262 mg/mL, 263 mg/mL, 264 mg/mL, 265 mg/mL, 266 mg/mL, 267 mg/mL, 268 mg/mL, 269 mg/mL, 270 mg/mL, 271 mg/mL, 272 mg/mL, 273 mg/mL, 274 mg/mL, 275 mg/mL, 276 mg/mL, 277 mg/mL, 278 mg/mL, 279 mg/mL, 280 mg/mL, 281 mg/mL, 282 mg/mL, 283 mg/mL, 284 mg/mL, 285 mg/mL, 286 mg/mL, 287 mg/mL, 288 mg/mL, 289 mg/mL, 290 mg/mL, 291 mg/mL, 292 mg/mL, 293 mg/mL, 294 mg/mL, 295 mg/mL, 296 mg/mL, 297 mg/mL, 298 mg/mL, 299 mg/mL, and 300 mg/mL.

493. The high concentration composition of any of embodiments 401 to 492, comprising:
(a) a buffer consisting solely of histidine;
(b) stabilizer selected from one, or combinations, of arginine, glycine and sodium chloride; and provided that:
(i) when polyol is present, it is mannitol; and
(ii) when surfactant is present, it is PS 80;
wherein the composition has a conductivity greater than 2.5, 3, 4, 5, 6, or 7 mS/cm; an osmolarity from about 100 to 400 mOsM, and wherein the hydrodynamic diameter of the adalimumab is greater than 2, 3, 4, 5, 6, 7, 8, 9 10 or 11.

494. The high concentration composition of embodiments 401 to 493, wherein the concentration of adalimumab is (a) 100, 125, 150, 175 or 200 mg/mL; or (b) between 200 and 300 mg/mL 495. The high concentration composition of any of embodiments 401 to 494, wherein at least one member, or combination thereof, selected from the following list is present and contributes to stabilization of the composition: a polyol, a sugar, an amino acid, a salt, creatine, creatinine, carnitine, lauryldimethyiamineoxide (and amine oxide analogs), a polymer, a chelating agent, a polar solvent and/or a surfactant.

496. The high concentration composition of any of embodiments 401 to 494, wherein at least one of member, or combination thereof, selected from the following list contributes to reducing viscosity of the composition: an amino acid, a calcium salt, an acetate salt, magnesium chloride, sodium phosphate, arginine hydrochloride, creatine, creatinine, carnitine, an ultra-low Interfacial tension surfactant, and a polar solvent.

497. The high concentration composition of any of embodiment 401 to 496, comprising at least one amino acid, wherein at least one amino acid stabilizes the composition and at least one other, different, amino acid reduces the viscosity of the composition.

498. The high concentration composition of embodiment 497, wherein one of the two different amino acids contains a polar uncharged side chain and the other contains a hydrophobic side chain.

499. The high concentration composition of embodiment 497, wherein one of the two different amino acids contains a polar uncharged side chain and the other is selected from the group consisting of G and P.

500. The high concentration composition of embodiment 497, wherein the stabilizing amino acid is selected from the group consisting of S, A, G, T, and V, and the viscosity reducing amino acid is elected from the group consisting of S, A, G, T, V, R, E, and P.

501. The high concentration composition of embodiment 497, wherein the stabilizing amino acid is selected from the group consisting of R, D, K, V, T, P, and I, and the viscosity reducing amino acid selected from the group consisting of P, H, K, M, G, F, E, T, S, N, and I.

502. The high concentration composition of embodiment 497, wherein the stabilizing amino acid is selected from the group consisting of R, H, M, K, and F, and the viscosity reducing amino acid selected from the group consisting of H, M, T, and V.

503. The high concentration composition of embodiment 497, wherein the stabilizing amino acid is G, and the viscosity reducing amino acid is P.

504. The high concentration composition of embodiment 497, wherein the stabilizing amino acid is S, and the viscosity reducing amino acid is P.

505. The high concentration composition of any of embodiments 401 to 504, wherein the composition comprises at least two amino acids that stabilize the composition.

506. The high concentration composition of embodiment 505, wherein stabilizing amino acids are a combination of two amino acids selected from the combinations consisting of A and G, A and M, G and M, G and T, M and T, M and S, S and T, A and N, A and Q, N and, A and S, N and S, Q and S, and Q and T.

507. The high concentration composition of embodiment 505, wherein the stabilizing amino acids are a combination of three amino acids selected from the combinations consisting of A, G, and M; G, M, and T; M, S, and T; A, N, and Q; A, N, and S; and Q, S, and T.

508. The high concentration composition of any of embodiments 401-507, wherein the composition comprises at least two amino acids that reduce the viscosity of the composition.

509. The high concentration composition of embodiment 508, wherein the viscosity reducing amino acids are a combination of two amino acids selected from the combinations consisting of P and G, and P and S.

510. The high concentration composition of any of embodiments 401 to 238, wherein the composition comprises at least one salt that contributes to stabilization of the composition.

511. The high concentration composition of embodiment 510, wherein the salt is selected from the group consisting of NaCl, KCl, Na2SO4, MgCl2, CaCl2, and adipate.

512. The high concentration composition of embodiment 511, wherein the salt is present at a concentration selected from the group consisting of: not exceeding about 200 mM, not exceeding about 50 mM, not exceeding about 44 mM, not exceeding about 28 mM, not exceeding about 26.35 mM, not exceeding about 10 mM, and not exceeding about 5 mM.

513. The high concentration composition of embodiment 511, wherein the salt is MgCl2 and the composition has a viscosity of about 15 cP or less.

514. The high concentration composition of any of embodiments 401 to 513, wherein the composition comprises at least one lauryldimethylamineoxide and/or of one of its amine oxide analogs, to contribute to stabilization of the composition.

515. The high concentration composition of any of embodiments 401 to 514, wherein the composition comprises at least one or a combination of creatinine, creatine and carnitine, to contribute to stabilization of the composition.

516. The high concentration composition of any of embodiments 401 to 515, wherein the composition comprises at least one polymer that contributes to stabilization, or reduction in viscosity, of the composition.

517. The high concentration composition of embodiment 516, wherein the polymer is selected from celluloses, 40 kD Dextran, betaine, PVP, and glycerol.

518. The high concentration composition of embodiment 517, wherein the cellulose polymer is selected from the group consisting of: methylcelluloses and ethylcelluloses.

519. The high concentration composition of embodiment 518, wherein the methylcellulose is selected from the group consisting of: hydroxypropyl methylcellulose (HPMC), carboxymethylcellulose (CMC), and sodium carboxymethylcellulose (NaCMC).

520. The high concentration composition of any of embodiments 516 to 519, wherein the polymer contributes to stabilization of the composition.

521. The high concentration composition of any of embodiments 516 to 520, wherein the polymer contributes to stabilization of the composition.

522. The high concentration composition of any of embodiments 517 to 521, wherein the polymer reversibly interacts with adalimumab and prevents protein-formed matrix interaction.

523. The high concentration composition of any of embodiments 401 to 522, wherein the composition comprises at least one chelating agent.

524. The high concentration composition of embodiment 523, wherein the chelating agent is selected from the group consisting of EDTA, and DPTA.

525. The high concentration composition of any of embodiments 401 to 524, wherein the composition comprises at least one sacrificial additive.

526. The high concentration composition of embodiment 525, wherein the sacrificial additive is selected from the group consisting of Met, N-Ac-Trp, ascorbate.

527. The high concentration composition of any of embodiments 401 to 526, wherein surfactant, if present therein, (a) stabilizes or contributes to stabilization of the composition, (b) reduces the viscosity of the composition, or (c) both reduces the viscosity of the composition and stabilizes or contributes to stabilization of the composition.

528. The high concentration composition of embodiment 527, wherein the surfactant is selected from the group consisting of polysorbate 20, polysorbate 80, SDS, poloxamer 188 (Pluronic® F68).

529. The high concentration composition of embodiment 527, wherein the surfactant is an ultra-low interfacial tension surfactant.

530. The high concentration composition of embodiment 529, wherein the surfactant comprises a hydrophilic portion and a hydrophobic aliphatic group.

531. The high concentration composition of embodiment 530, wherein the aliphatic group comprises saturated and/or unsaturated carbon chains.

532. The high concentration composition of embodiment 530, wherein the hydrophilic portion comprises one or more hydrophilic groups or substituents.

533. The high concentration composition of embodiment 532, wherein the hydrophilic portion is an ionizable group.

534. The high concentration composition of embodiment 533, wherein the ionizable group comprises amines and carboxylic acids.

535. The high concentration composition of embodiment 532, wherein the hydrophilic group is a hydrophilic polymer.

536. The high concentration composition of embodiment 535, wherein the hydrophilic polymer is selected from the group consisting of: methylcelluloses, hydroxypropyl methylcellulose (HPMC), carboxymethylcellulose (CMC), polyalkylamine, poly(ethylene glycol), and poly(ethylene glycol)/poly(propylene glycol) copolymers.

537. The high concentration composition of any of embodiments 401 to 536 where surfactant is not excluded, and wherein the surfactant is present at a concentration not exceeding about 0.1% wt.

538. The high concentration composition of any of embodiments 401 to 537, comprising at least one preservative.

539. The high concentration composition of embodiment 538, wherein the preservative is selected from the group consisting of octadecyldimethylbenzyl ammonium chloride, hexamethonium chloride, benzalkonium chloride, benzelthonium chloride, aromatic alcohols and alkyl parabens.

540. The high concentration composition of embodiment 539, wherein the aromatic alcohol is selected from the group consisting of phenol, butyl and benzyl alcohol.

541. The high concentration composition of embodiment 539, wherein the alkyl paraben is selected from the group consisting of methyl or propyl paraben, catechol, resorcinol, cyclohexanol, 3-pentanol, and m-cresol.

542. The high concentration composition of any of embodiments 401 to 541, wherein the composition comprises a polar solvent.

543. The high concentration composition of embodiment 542, wherein the polar solvent is selected from the group consisting of dimethyl sulfoxide (DMSO) and dimethylacetamide (DMA).

544. The high concentration composition of any of embodiments 401 to 543, wherein:
(a) adalimumab is present at a concentration greater than 50 mg/mL and less than or equal to about 200-250 mg/mL; and
(b) said high concentration composition, and a comparator adalimumab composition comprising adalimumab at a concentration of no more than about 50 mg/mL, are the same or essentially the same with respect to the identity and concentration of excipients contained therein; and both the high concentration formulation and the comparator have stability comparable to or better than, and viscosity comparable to or lower than, a commercially sold Humira® formulation having no greater than about 50 mg/ml or no greater than about 100 mg/mL.

545. The high concentration composition of any of embodiments 401 to 543, wherein:
(a) adalimumab is present at a concentration greater than 50 mg/mL and less than or equal to about 200-250 mg/ml; and
(b) said high concentration composition, and a comparator adalimumab composition comprising adalimumab at a concentration of no more than about 50 mg/mL, are the same or essentially the same with respect to the identity and concentration of excipients contained therein; and both the high concentration formulation and the comparator have (i) stability comparable to or better than a commercially sold Humira® formulation having no greater than about 50 mg/ml or no greater than about 100 mg/mL, and (ii) viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP.

546. The high concentration composition of any of embodiments 401 to 543, wherein:
(a) adalimumab is present at a concentration greater than 50 mg/mL and less than or equal to about 200-250 mg/ml; and (b) the high concentration composition is able to exhibit stability and viscosity at least comparable to or better than a commercially sold Humira® composition containing no greater than about 50 mg/mL, or no greater than about 100 mg/mL, without need to incorporate in such high concentration composition either (i) any viscosity reducing agents or stabilizing agents not found in a comparator adalimumab composition comprising adalimumab at a concentration of no more than about 50 mg/mL; or (ii) amounts of viscosity modifying agents or stabilizing agents different from that found in the comparator composition.

547. The high concentration composition of any of embodiments 401 to 543, wherein:
(a) adalimumab is present at a concentration greater than 50 mg/mL and less than or equal to about 200-250 mg/mL; and
(b) the high concentration composition is able to exhibit stability at least comparable to or better than a commercially sold Humira® composition containing no greater than about 50 mg/mL, or no greater than about 100 mg/mL and viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP, without need to incorporate in such high concentration composition either (i) any viscosity reducing agents or stabilizing agents not found in a comparator adalimumab composition comprising adalimumab at a concentration of no more than about 50 mg/mL; or (ii) amounts of viscosity modifying agents or stabilizing agents different from that found in the comparator composition.

548. The high concentration composition of any of embodiments 401 to 543, wherein
(a) adalimumab is present at a concentration greater than or equal to about 200-250 mg/mL;
(b) the high concentration composition, and a comparator adalimumab composition comprising adalimumab at a concentration of not more than about 50 mg/mL, compare to one another in the following respects:
(i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein the high concentration composition has viscosity less than or approximately equal to that of commercially sold Humira® containing adalimumab at a concentration not greater than about 50 mg/mL or not greater than about 100 mg/mL; and/or
(ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein the high concentration composition has stability equal to or better than a commercially sold Humira® formulation comprising adalimumab at a concentration not greater than about 50 mg/mL or not greater than about 100 mg/mL; and
(c) the high concentration composition is not able to exhibit stability and viscosity at least comparable to or better than a commercially sold Humira® composition containing no greater than about 50 mg/mL, or no greater than about 100 mg/mL, unless the high concentration composition comprises (i) said viscosity reducing agent or stabilizing agent not found in the comparator composition; or (ii) said increased amount of viscosity modifying agent or stabilizing agent.

549. The high concentration composition of any of embodiments 401 to 543, wherein
(a) adalimumab is present at a concentration greater than or equal to about 200-250 mg/mL;
(b) the high concentration composition, and a comparator adalimumab composition comprising adalimumab at a concentration of not more than about 50 mg/mL, compare to one another in the following respects:
(i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein the high concentration composition has viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP; and/or
(ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein the high concentration composition has stability equal to or better than a commercially sold Humira® formulation comprising adalimumab at a concentration not greater than about 50 mg/mL or not greater than about 100 mg/mL; and
(c) the high concentration composition is not able to exhibit stability at least comparable to or better than a commercially sold Humira® composition containing no greater than about 50 mg/mL or no greater than about 100 mg/mL, and viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP, unless the high concentration composition comprises (i) said viscosity reducing agent or stabilizing agent not found in the comparator composition; or (ii) said increased amount of viscosity modifying agent or stabilizing agent.

550. The high concentration composition of any of embodiments 401 to 543, wherein
(a) adalimumab is present at a concentration greater than or equal to about 200-250 mg/mL;
(b) the high concentration composition, and a comparator adalimumab composition comprising adalimumab at a concentration of not more than about 50 mg/mL, compare to one another in the following respects:
(i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein both the high concentration composition, and the comparator, have viscosity less than or approximately equal to that of commercially sold Humira® containing adalimumab at a concentration not greater than about 50 mg/mL or not greater than about 100 mg/mL; and/or
(ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein both the high concentration composition, and the comparator, have stability equal to or better than a commercially sold Humira® formulation comprising adalimumab at a concentration not greater than about 50 mg/mL or not greater than about 100 mg/mL; and (c) the high concentration composition is not able to exhibit stability and viscosity at least comparable to or better than a commercially sold Humira® composition containing no greater than about 50 mg/mL, or no greater than about 100 mg/mL, unless the high concentration composition comprises (i) said viscosity reducing agent or stabilizing agent not found in the comparator composition; or (ii) said increased amount of viscosity modifying agent or stabilizing agent.

551. The high concentration composition of any of embodiments 401 to 543, wherein (a) adalimumab is present at a concentration greater than or equal to about 200-250 mg/mL;

(b) the high concentration composition, and a comparator adalimumab composition comprising adalimumab at a concentration of not more than about 50 mg/mL, compare to one another in the following respects:

(i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein both the high concentration composition, and the comparator, have viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP; and/or (ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein both the high concentration composition, and the comparator, have stability equal to or better than a commercially sold Humira® formulation comprising adalimumab at a concentration not greater than about 50 mg/mL or not greater than about 100 mg/mL; and (c) the high concentration composition is not able to exhibit stability at least comparable to or better than a commercially sold Humira® composition containing no greater than about 50 mg/mL or no greater than about 100 mg/mL, and viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP, unless the high concentration composition comprises (i) said viscosity reducing agent or stabilizing agent not found in the comparator composition; or (ii) said increased amount of viscosity modifying agent or stabilizing agent.

552. The high concentration composition of any of embodiments 401 to 551 having long term stability, wherein the composition comprises one or more ionic excipients, wherein said excipients contribute to the composition having conductivity greater than 2.5, 3, 4, 5, 6, 7 or 8; osmolarity of 140 to about 400; and a hydrodynamic diameter of the adalimumab of greater than 4, 5, 6, 7, 8, 9, 10 or 11; and wherein the composition, upon administration to a subject, results in a degree of pain or discomfort no worse than, or better than, that of an AbbVie-supplied Humira® composition, having a concentration of adalimumab greater than 50 mg/mL.

553. The high concentration composition of any of embodiments 401 to 552, wherein said composition is substantially free of protein aggregates and/or high molecular weight species.

554. The high concentration composition of any of embodiments 401 to 553, wherein the composition has an absolute viscosity of about 15 cP or less.

555. The high concentration composition of any of embodiments 401 to 554, wherein the composition has an osmolality of about 180 to about 420 mOsM.

556. The high concentration composition of any of embodiments 401 to 555, wherein the composition has a conductivity selected from the group comprising: between about 1 and about 2.5 mS/cm, between about 2.5 and about 3 mS/cm, between about 3 and about 3.5 mS/cm, greater than about 2.5 mS/cm, at least about 3.0 mS/cm, about 3.0 mS/cm, about 3.5 mS/cm, about 4 mS/cm, about 4.4 mS/cm, and about 4.5 mS/cm.

557. The high concentration composition of any of embodiments 401 to 556, wherein the adalimumab has a hydrodynamic diameter selected from the group comprising greater than about 2.5 nm, greater than about 3 nm, greater than about 4 nm, greater than about 4 nm, about 2.5 to about 3 nm, about 3 nm to about 3.5 nm, about 3.5 to about 4 nm, about 3 nm, about 4 nm, about 5 nm, about 6 nm, about 7 nm, about 8 nm, about 9 nm, and about 10 nm.

558. The high concentration composition of any of embodiments 401 to 557, wherein the composition has reduced pain upon injection to a subject as compared to an adalimumab composition comprising citrate.

559. The high concentration composition of any of embodiments 401 to 558, wherein the composition has sizes and amounts of sub-visible particles comparable to, or better than that of a commercially sold Humira® containing adalimumab at concentrations between about 50 and 100 mg/mL.

560. The high concentration composition of any of embodiments 401 to 559, wherein the composition has approximately the same or fewer adalimumab fragments and/or aggregates than commercially sold Humira® containing adalimumab at concentrations between about 50 and 100 mg/mL.

561. The high concentration composition of any of embodiments 401 to 560, wherein the composition has an adalimumab monomer content of at least about 85% monomer.

562. The high concentration composition of any of embodiments 401 to 561, wherein the composition has an adalimumab monomer content of at least about 90% monomer.

563 The high concentration composition of any of embodiments 401 to 562, wherein the composition has an adalimumab monomer content of at least about 95% monomer.

564. The high concentration composition of any of embodiments 401 to 563, wherein the composition is stable at room temperature for at least 10 days.

565. The high concentration composition of any of embodiments 401 to 564, wherein the composition is stable under conditions selected from the group comprising: at least 1 week at 40'C, at least 6-10 days at 30° C., at least 2 weeks at 40° C., at least 4 weeks at 25° C., at least 9 weeks at 25° C., at least 13 weeks at 25° C., at least 13 weeks at 5° C., and at least 26 weeks at 5° C.

566. The high concentration composition of any of embodiments 401 to 565, wherein the composition is stable for at least three months.

567. The high concentration composition of any of embodiments 401 to 566, wherein the composition is stable for at least six months.

568. The high concentration composition of any of embodiments 401 to 567 wherein the composition is stable for at least one year.

571. The high concentration composition of any of embodiments 401 to 570, having a pH of 5 to 6, and prepared by modifying a pre-existing adalimumab formulation having a pH of 5 to 6 and no more than about 50 mg/mL, wherein the modification consists solely of increasing the concentration of adalimumab in the pre-existing formulation to concentration selected from (i) greater than 50 mg/mL and less than or equal to about 200-250 mg/mL; and (ii) about 100 to about 250 mg/mL, without altering the identity or concentration of any excipients present in the pre-existing formulation.

572. A prefilled syringe containing the high concentration composition of any of embodiments 201 to 571.

573. A prefilled syringe containing the high concentration composition of embodiment 572 wherein the composition is optionally free of surfactant, and is present in a defined containment volume of the syringe, said containment volume being essentially free of any portion thereof in which the composition is absent.

574. The prefilled syringe of embodiments 572-573 wherein the high concentration composition does not have a polysorbate or polaxamer surfactant.

575. The prefilled syringe of any of embodiments 572-574 where the high concentration composition does not have a surfactant.

576. The prefilled syringe of any of embodiments 572-575 wherein the high concentration composition is isotonic, has conductivity greater than 2.5, and is free of surfactant or free of polyol or free of both.

577. The prefilled syringe of any of embodiments 572-576 wherein the high concentration composition does not contain any of the following buffers: phosphate, pyrophosphate, acetate, citrate, histidine, succinate, adipate, maleate, glutamate, gluconate, or tartrate.

578. The prefilled syringe of any of embodiments 572-577 wherein the high concentration is self-buffering based on the buffer capacity afforded by the adalimumab.

579. A method for preparing a high concentration formulation of any of embodiments 401-571 having a concentration of adalimumab greater than about 50 mg/mL and less than or equal to about 200-250 mg/mL, and a pH of 5 to 6, said method comprising the step of: preparing an adalimumab formulation that is modified over a known adalimumab formulation, said known formulation having a pH of 5 to 6 and comprising no more than about 50 mg/mL, wherein the modification consists solely of increasing the adalimumab concentration of the known formulation to a concentration selected from (i) greater than 50 mg/mL and less than or equal to 200-250 mg/mL; and (ii) about 100 to about 200-250 mg/mL, without modifying the identity or concentration of any excipients present in the known formulation.

Reserved: Embodiment 580 to 600

601. An aqueous pharmaceutical composition comprising a stable high concentration of adalimumab, wherein:
(a) the composition has a concentration of adalimumab greater than 50 mg/mL;
(b) the composition has long term stability comparable to or better than a commercially sold adalimumab formulation having a concentration of adalimumab selected from:
(i) not greater than about 50 mg/mL; or
(ii) not greater than about 100 mg/mL; and
(c) the composition has viscosity approximately equal to, or less than, that of a commercially sold adalimumab composition having a concentration of adalimumab selected from:
(i) not greater than about 50 mg/mL; or
(ii) not greater than about 100 mg/mL.
(d) the composition comprises a buffer;
(e) the composition comprises a polyol that is one, or a combination of mannitol, sorbitol, and trehalose; and
(f) the composition comprises a surfactant.

602. The high concentration composition of embodiment 1, wherein adalimumab is present in the composition at a concentration selected from: greater than 50 mg/mL and less than 100 g/mL; at least 100 mg/mL; 100 to 300 mg/mL; 100 to 200 mg/mL; 100 to 150 mg/mL; 100 to 125 mg/mL; 75 mg/mL; 100 mg/mL; 125 mg/mL, 150 mg/mL; 175 mg/mL; 200 mg/mL; 225 mg/mL; 250 mg/mL; 275 mg/mL; and 300 mg/mL.

603. The high concentration composition of embodiment 602 comprising a buffer comprising a mono- or dicarboxylic acid and salts thereof, a stabilizer, a tonicity agent, a polysorbate surfactant, and optionally, a chelating agent, wherein the composition exhibits long term stability.

604. The high concentration composition of embodiment 603, wherein the buffer is adipate at a concentration of about 10 to about 27 mM.

605. The high concentration composition of embodiment 603, wherein the stabilizer comprises a polyol.

606. The high concentration composition of embodiment 605, wherein the polyol is mannitol at a concentration of about 55 to about 77 mM.

607. The high concentration composition of embodiment 603, wherein the tonicity agent is an inorganic salt.

608. The high concentration composition of embodiment 607, wherein the inorganic salt is NaCl at a concentration of about 85 to about 120 mM.

609. The high concentration composition of embodiment 603, wherein the polysorbate surfactant is at a concentration not exceeding about 10 mg/mL or not exceeding about 0.1% wt.

610. The high concentration composition of embodiment 603, wherein the composition has a pH of about 4.0 to about 8.0 and/or a osmolality of about 250 to about 350 mOsm.

611. The high concentration composition of embodiment 603, wherein the composition has a pH of 5.2 and comprises 23 mM adipate as a buffer, 66 mM mannitol as a stabilizer, 105 mM NaCl as a tonicity agent, and 0.1% PS 80 as a surfactant.

612. The high concentration composition of embodiment 603, wherein the buffer is acetate at a concentration of about 8 to about 25 mM.

613. The high concentration composition of embodiment 603, wherein the buffer comprises citrate at a concentration of about 1 to about 15 mM.

614. The high concentration composition of embodiment 613, wherein the composition has a pH of 5.2 and comprises 20 mM acetate and 2.4 mM citrate as a buffer, 66 mM mannitol as a stabilizer, 105 mM NaCl as a tonicity agent, and 0.1% PS 80 as a surfactant.

615. The high concentration composition of embodiment 613, wherein the composition has a pH of 5.2 and comprises 23 mM adipate and 1.4 mM citrate as a buffer, 66 mM mannitol as a stabilizer, 105 mM NaCl as a tonicity agent, and 0.1% PS 80 as a surfactant.

616. The high concentration composition of embodiment 603, wherein the buffer comprises phosphate at a concentration of about 1 to about 15 mM.

617. The high concentration composition of embodiment 603, wherein the composition has a pH of 5.2 and comprises 23 mM adipate, 1.4 mM citrate, and 2.8 mM phosphate, 66 mM mannitol as a stabilizer, 105 mM NaCl as a tonicity agent, and 0.1% PS 80 as a surfactant.

618. The high concentration composition of embodiment 603, wherein the composition has a pH of 5.2 and comprises 20 mM acetate, 2.4 mM citrate, and 2.8 mM phosphate as a buffer, 66 mM mannitol as a stabilizer, 105 mM NaCl as a tonicity agent, and 0.1% PS 80 as a surfactant.

619. The high concentration composition of embodiment 603, wherein the composition has a pH of 5.2 and comprises 17 mM acetate as a buffer, 66 mM mannitol as a stabilizer, 103 mM NaCl as a tonicity agent, and 0.1% PS 80 as a surfactant.

620. The high concentration composition of embodiment 602 comprising a high concentration of adalimumab, a succinate buffer, a tonicity agent, a polysorbate surfactant, and a stabilizer selected from amino acids, cyclodextrins, and polyols, wherein the composition exhibits long term stability.

621. The high concentration composition of embodiment 620, wherein the succinate is present at a concentration of about 1 to about 50 mM.

622. The high concentration composition of embodiment 620, wherein the tonicity agent is an inorganic salt.

623. The high concentration composition of embodiment 622, wherein the salt is NaCl at a concentration of about 10 to about 200 mM.

624. The high concentration composition of embodiment 620, wherein the amino acid is arginine at a concentration of about 1 to about 50 mM.

625. The high concentration composition of embodiment 620, wherein the cyclodextrin is selected from α-cyclodextrin, β-cyclodextrin, γ-cyclodextrin, their hydroxypropylated, hydroxyethylated, ethylated and methylated derivatives thereof, Sulfobutyl ether beta-cyclodextrin (SBE-beta-CD), a branched cyclodextrins, cyclodextrin polymers and suitable mixture thereof 626. The high concentration composition of embodiment 625, wherein the cyclodextrin is present at a concentration of about 0.2% to about 10%.

627. The high concentration composition of embodiment 625, wherein the cyclodextrin is hydroxypropylated cyclo beta-dextrin (HP-β-CD).

628. The high concentration composition of embodiment 620, wherein the polyol is sorbitol at a concentration of about 1 to about 50 mM.

629. The high concentration composition of embodiment 620, wherein the polysorbate is present at a concentration not exceeding about 10 mg/mL or not exceeding about 0.1% wt.

630. The high concentration composition of embodiment 620, wherein the composition has a pH of 5.2 and comprises 10 mM succinate, 100 mM NaCl, 10 mM sorbitol, 24 mM arginine, and 0.1% PS 80 surfactant.

631. The high concentration composition of embodiment 602 comprising acetate buffer and an amino acid wherein the composition exhibits long term stability.

632. The high concentration composition of embodiment 602, wherein the composition is free, or substantially free, of a citrate buffer, a phosphate buffer, or both citrate and phosphate buffers.

633. The high concentration composition of embodiment 602, wherein the acetate is present at a concentration of about 10 to about 200 mM.

634. The high concentration composition of embodiment 602, wherein the polyol is trehalose at a concentration of about 50 to about 1000 mM.

635. The high concentration composition of embodiment 602, wherein the amino acid is arginine at a concentration of about 1 to about 100 mM.

636. The high concentration composition of embodiment 602, wherein the surfactant is a polysorbate at a concentration not exceeding about 10 mg/mL or not exceeding about 0.1% wt.

637. The high concentration composition of embodiment 636, wherein the composition has a pH of 6.5 and comprises 15 mM acetate, 240 mM trehalose, and 10 mM arginine.

638. The high concentration composition of embodiment 637 comprising 0.1% PS 80.

639. The high concentration composition of embodiment 602 comprising succinate buffer, wherein the composition exhibits long term stability.

640. The high concentration composition of embodiment 639, wherein the composition is free, or substantially free, of a citrate buffer, a phosphate buffer, or both citrate and phosphate buffers.

641. The high concentration composition of embodiment 639, wherein the succinate is present at a concentration of about 10 to about 200 mM.

642. The high concentration composition of embodiment 639, wherein the polyol is trehalose at a concentration of about 50 to about 1000 mM.

643. The high concentration composition of embodiment 639, wherein the surfactant is a polysorbate at a concentration not exceeding about 10 mg/mL or not exceeding about 0.1% wt.

644. The high concentration composition of embodiment 639, wherein the composition has a pH of 6.25 and comprises 25 mM succinate, and 215 mM trehalose.

645. The high concentration composition of embodiment 644 comprising 0.1% PS 80.

646. The high concentration composition of embodiment 602, comprising an amino acid wherein the composition exhibits long term stability.

647. The high concentration composition of embodiment 646, wherein the composition is free, or substantially free, of a citrate buffer, a phosphate buffer, or both citrate and phosphate buffers.

648. The high concentration composition of embodiment 646, wherein the amino acid is histidine at a concentration of about 10 to about 200 mM.

649. The high concentration composition of embodiment 646, wherein the polyol is mannitol at a concentration of about 50 to about 1000 mM.

650. The high concentration composition of embodiment 646, wherein the surfactant is a polysorbate at a concentration not exceeding about 10 mg/mL or not exceeding about 0.1% wt.

651. The high concentration composition of embodiment 646, wherein the composition has a pH of 6.25 and comprises 25 mM histidine, and 240 mM mannitol.

652. The high concentration composition of embodiment 602 comprising a phosphate buffer and optionally a salt, wherein the composition exhibits long term stability.

653. The high concentration composition of embodiment 652 comprising a succinate buffer.

654. The high concentration composition of embodiment 652, wherein the pH is about 5.4 to about 5.6.

655. The high concentration composition of embodiment 652, wherein the salt is NaCl at a concentration of about 10 to about 200 mM.

656. The high concentration composition of embodiment 652, wherein the polyol acts as a stabilizer.

657. The high concentration composition of embodiment 652, wherein the polyol is mannitol at a concentration of about 5 to about 300 mM or trehalose at a concentration of about 5 to about 300 mM.

658. The high concentration composition of embodiment 652, wherein the surfactant is a polysorbate at a concentration not exceeding about 10 mg/mL or not exceeding about 0.1% wt.

659. The high concentration composition of embodiment 652, wherein the composition has a pH of 5.3 and comprises 10 mM sodium phosphate, 88 mM NaCl, 107 mM trehalose, and 0.1% PS 80.

660. The high concentration composition of embodiment 653, wherein the composition has a pH of 5.3 and comprises 6 mM sodium phosphate, 4 mM succinate, 88 mM NaCl, 107 mM trehalose, and 0.1% PS 80.

661. The high concentration composition of embodiment 602 comprising pyrophosphate, wherein the composition exhibits long term stability.

662. The high concentration composition of embodiment 661, wherein the composition is free, or substantially free, of phosphate.

663. The high concentration composition of embodiment 661, wherein the pyrophosphate is present at a concentration of about 5 to about 250 mM.

664. The high concentration composition of embodiment 661, further comprising a salt.

665. The high concentration composition of embodiment 664, wherein the buffer is citric acid at a concentration not exceeding about 200 mM and/or citrate at a concentration not exceeding about 200 mM.

666. The high concentration composition of embodiment 664, wherein the salt is NaCl at a concentration of about 10 to about 200 mM.

667. The high concentration composition of embodiment 664, wherein the polyol is mannitol at a concentration of about 5 to about 300 mM or sorbitol at a concentration of about 5 to about 300 mM.

668. The high concentration composition of embodiment 664, wherein the surfactant is a polysorbate at a concentration not exceeding about 10 mg/mL or not exceeding about 0.1% wt.

669. The high concentration composition of embodiment 662 or 664, wherein the composition has a pH of 5.2 and comprises 14.1 mM sodium pyrophosphate, 1 mM citric acid, 6.8 mM citrate, 105 mM NaCl, and 66 mM mannitol, and 0.1% PS 80.

670. The high concentration composition of embodiment 602 comprising an acetate buffer, and a salt, wherein the composition exhibits long term stability.

671. The high concentration composition of embodiment 670, wherein the acetate buffer is an acetate salt.

672. The high concentration composition of embodiment 670, wherein the acetate buffer is sodium acetate.

673. The high concentration composition of embodiment 672, wherein the acetate buffer is present at a concentration of about 0.7 to about 1.3 mM.

674. The high concentration composition of embodiment 670, comprising acetic acid.

675. The high concentration composition of embodiment 670, wherein the acetic acid is present at a concentration of about 16 to about 22 mM.

676. The high concentration composition of embodiment 670, wherein the polyol is mannitol.

677. The high concentration composition of embodiment 676, wherein the mannitol is present at a concentration of about 200 to about 500 mM.

678. The high concentration composition of embodiment 670, wherein the salt is sodium chloride.

679. The high concentration composition of embodiment 670, wherein the salt is present a concentration not exceeding 28 mM.

680. The high concentration composition of embodiment 670, wherein the surfactant is a polysorbate.

681. The high concentration composition of embodiment 680, wherein the polysorbate is present at a concentration of about 0.07 to about 0.15% wt.

682. The high concentration composition of embodiments 670 to 681, wherein the composition has a pH of about 5.1 to about 5.3.

683. The high concentration composition of embodiment 670, wherein the composition has a pH of 5.2 and comprises 1 mM sodium acetate, 19 mM acetic acid, 26.35 mM NaCl, 203 mM mannitol, and 0.1% PS 80.

684. The high concentration composition of embodiment 602, wherein the buffer is at least one, or a combination, of phosphate, pyrophosphate, citrate, acetate, glutamate, gluconate, histidine, succinate, adipate, maleate, and tartrate.

685. The high concentration composition of embodiment 602, comprising at least one buffer, wherein the composition (a) is free or essentially free of citrate buffer; or (b) is free or essentially free of phosphate buffer; or (c) is free or essentially free of a buffer composition comprising citrate buffer and phosphate buffer.

686. The high concentration composition of embodiment 602, wherein the buffer is or comprises succinate.

687. The high concentration composition of embodiment 602, wherein the buffer is or comprises histidine.

688. The high concentration composition of embodiment 602, wherein the composition comprises a combination of two buffers where the combination is selected from (a) a combination of histidine buffer and succinate buffer; (b) a combination of citrate buffer and phosphate buffer; (c) a combination of citrate buffer and pyrophosphate buffer; and (d) a combination of phosphate buffer plus either histidine buffer or succinate buffer.

689. The high concentration composition of embodiment 602, wherein the buffer combination is succinate and histidine.

690. The high concentration composition of embodiment 602, wherein the buffer combination is citrate and pyrophosphate.

691. The high concentration composition of any of embodiments 684 to 690, wherein the composition has a pH of 3 to 8; 4 to 8; or 5 to 6.

692. The high concentration composition of any of embodiments 684 to 691, wherein the composition has a viscosity equal to or less than: 20 cP; 15 cP; 14 cP; 13 cP; 12 cP; 11 cP; 10 cP; 9 cP; 8 cP; 7 cP; 6 cP; 5 cP; 4 cP; 3 cP; 2 cP; or 1 cP.

693. The high concentration composition of any of embodiments 684 to 692, further comprising at least one ingredient acting as a tonicity agent, said ingredient being a salt, an amino acid, a sugar, or a polyol.

694. The high concentration composition of any of embodiments 684 to 692, further comprising at least one tonicity agent, wherein the tonicity agent is not a salt.

695. The high concentration composition of embodiment 693, wherein the salt is one, or a combination of NaCl, KCl, Na2SO4, MgCl2, CaCl2, and adipate.

696. The high concentration composition of embodiment 695, wherein the salt is present at a concentration selected from: 40 to 140 mM; not exceeding about 150; not exceeding about 100 mM; not exceeding about 50 mM, not exceeding about 44 mM, not exceeding about 28 mM, not exceeding about 26.35 mM, not exceeding about 10 mM, and not exceeding about 5 mM.

697. The high concentration composition of any of embodiments 684 to 696, wherein the composition is isotonic or has an osmolality of about 180 to about 420 mOsM.

698. The high concentration composition of embodiments 684 to 697, wherein the polyol is or comprises mannitol at a concentration not exceeding about 300 mM.

699. The high concentration composition of any of embodiments 684 to 698, comprising at least one sugar.

700. The high concentration composition of embodiment 699, wherein the sugar comprises sucrose, lactose, glucose, and maltose, and combinations thereof.

701. The high concentration composition of any of embodiments 684 to 700, further comprising at least one amino acid.

702. The high concentration composition of embodiment 701, wherein the amino acid is selected from the group consisting of histidine, glycine, methionine, serine, proline, and arginine.

703. The high concentration composition of embodiment 701, wherein the amino acid is histidine.

704. The high concentration composition of embodiment 701, wherein the amino acid is glycine.

705. The high concentration composition of embodiment 701, wherein the amino acid is arginine.

706. The high concentration composition of embodiment 701, wherein the amino acids are a combination of glycine and arginine.

707. The high concentration composition of any of embodiments 684 to 706, wherein the surfactant is selected from the group consisting of polysorbate 20, polysorbate 80, SDS, poloxamer 188 (Pluronic® F68) and combinations thereof.

Reserved: Embodiment 708-714

715. The high concentration composition of embodiment 601 to 707 wherein the concentration of adalimumab is selected from
(a) 51 mg/mL, 52 mg/mL, 53 mg/mL, 54 mg/mL, 55 mg/mL, 56 mg/mL, 57 mg/mL, 58 mg/mL, 59 mg/mL, 60 mg/mL, 61 mg/mL, 62 mg/mL, 63 mg/mL, 64 mg/mL, 65 mg/mL, 66 mg/mL, 67 mg/mL, 68 mg/mL, 69 mg/mL, 70 mg/mL, 71 mg/mL, 72 mg/mL, 73 mg/mL, 74 mg/mL, 75 mg/mL, 76 mg/mL, 77 mg/mL, 78 mg/mL, 79 mg/mL, 80 mg/mL, 81 mg/mL, 82 mg/mL, 83 mg/mL, 84 mg/mL, 85 mg/mL, 86 mg/mL, 87 mg/mL, 88 mg/mL, 89 mg/mL, 90 mg/mL, 91 mg/mL, 92 mg/mL, 93 mg/mL, 94 mg/mL, 95 mg/mL, 96 mg/mL, 97 mg/mL, 98 mg/mL, 99 mg/mL, 100 mg/mL, 101 mg/mL, 102 mg/mL, 103 mg/mL, 104 mg/mL, 105 mg/mL, 106 mg/mL, 107 mg/mL, 108 mg/mL, 109 mg/mL, 110 mg/mL, 111 mg/mL, 112 mg/mL, 113 mg/mL, 114 mg/mL, 115 mg/mL, 116 mg/mL, 117 mg/mL, 118 mg/mL, 119 mg/mL, 120 mg/mL, 121 mg/mL, 122 mg/mL, 123 mg/mL, 124 mg/mL, 125 mg/mL, 126 mg/mL, 127 mg/mL, 128 mg/mL, 129 mg/mL, 130 mg/mL, 131 mg/mL, 132 mg/mL, 133 mg/mL, 134 mg/mL, 135 mg/mL, 136 mg/mL, 137 mg/mL, 138 mg/mL, 139 mg/mL, 140 mg/mL, 141 mg/mL, 142 mg/mL, 143 mg/mL, 144 mg/mL, 145 mg/mL, 146 mg/mL, 147 mg/mL, 148 mg/mL, 149 mg/mL, 150 mg/mL, 151 mg/mL, 152 mg/mL, 153 mg/mL, 154 mg/mL, 155 mg/mL, 156 mg/mL, 157 mg/mL, 158 mg/mL, 159 mg/mL, 160 mg/mL, 161 mg/mL, 162 mg/mL, 163 mg/mL, 164 mg/mL, 165 mg/mL, 166 mg/mL, 167 mg/mL, 168 mg/mL, 169 mg/mL, 170 mg/mL, 171 mg/mL, 172 mg/mL, 173 mg/mL, 174 mg/mL, 175 mg/mL, 176 mg/mL, 177 mg/mL, 178 mg/mL, 179 mg/mL, 180 mg/mL, 181 mg/mL, 182 mg/mL, 183 mg/mL, 184 mg/mL, 185 mg/mL, 186 mg/mL, 187 mg/mL, 188 mg/mL, 189 mg/mL, 190 mg/mL, 191 mg/mL, 192 mg/mL, 193 mg/mL, 194 mg/mL, 195 mg/mL, 196 mg/mL, 197 mg/mL, 198 mg/mL, 199 mg/mL, and 200 mg/mL.
and (b) 201 mg/mL, 201 mg/mL, 202 mg/mL, 203 mg/mL, 204 mg/mL, 205 mg/mL, 206 mg/mL, 207 mg/mL, 208 mg/mL, 209 mg/mL, 210 mg/mL, 211 mg/mL, 212 mg/mL, 213 mg/mL, 214 mg/mL, 215 mg/mL, 216 mg/mL, 217 mg/mL, 218 mg/mL, 219 mg/mL, 220 mg/mL, 221 mg/mL, 222 mg/mL, 223 mg/mL, 224 mg/mL, 225 mg/mL, 226 mg/mL, 227 mg/mL, 228 mg/mL, 229 mg/mL, 230 mg/mL, 231 mg/mL, 232 mg/mL, 233 mg/mL, 234 mg/mL, 235 mg/mL, 236 mg/mL, 237 mg/mL, 238 mg/mL, 239 mg/mL, 240 mg/mL, 241 mg/mL, 242 mg/mL, 243 mg/mL, 244 mg/mL, 245 mg/mL, 246 mg/mL, 247 mg/mL, 248 mg/mL, 249 mg/mL, 250 mg/mL, 251 mg/mL, 252 mg/mL, 253 mg/mL, 254 mg/mL, 255 mg/mL, 256 mg/mL, 257 mg/mL, 258 mg/mL, 259 mg/mL, 260 mg/mL, 261 mg/mL, 262 mg/mL, 263 mg/mL, 264 mg/mL, 265 mg/mL, 266 mg/mL, 267 mg/mL, 268 mg/mL, 269 mg/mL, 270 mg/mL, 271 mg/mL, 272 mg/mL, 273 mg/mL, 274 mg/mL, 275 mg/mL, 276 mg/mL, 277 mg/mL, 278 mg/mL, 279 mg/mL, 280 mg/mL, 281 mg/mL, 282 mg/mL, 283 mg/mL, 284 mg/mL, 285 mg/mL, 286 mg/mL, 287 mg/mL, 288 mg/mL, 289 mg/mL, 290 mg/mL, 291 mg/mL, 292 mg/mL, 293 mg/mL, 294 mg/mL, 295 mg/mL, 296 mg/mL, 297 mg/mL, 298 mg/mL, 299 mg/mL, and 300 mg/mL.

716. The high concentration composition of any of embodiments 601 to 715 wherein the composition has a conductivity greater than 2.5, 3, 4, 5, 6, or 7 mS/cm; an osmolarity from about 100 to 400 mOsM, and wherein the hydrodynamic diameter of the adalimumab is greater than 2, 3, 4, 5, 6, 7, 8, 9 10 or 11.

717. The high concentration composition of embodiment 601 to 683, wherein the concentration of adalimumab is (a) 100, 125, 150, 175 or 200 mg/mL; or (b) greater than 200 mg/mL.

718. The high concentration composition of any of embodiments 601 to 717, wherein at least one member, or a combination thereof, selected from the following list is present and contributes to stabilization of the composition: a polyol, a sugar, an amino acid, a salt, creatine, creatinine, carnitine, lauryldimethyiamineoxide (and amine oxide analogs), a polymer, a chelating agent, a polar solvent and a surfactant.

719. The high concentration composition of any of embodiments 601 to 718, wherein at least one of member, or combination thereof, selected from the following list contributes to reducing viscosity of the composition: an amino acid, a calcium salt, an acetate salt, magnesium chloride, sodium phosphate, arginine hydrochloride, creatine, creatinine, carnitine, an ultra-low interfacial tension surfactant, and a polar solvent.

720. The high concentration composition of embodiment 601 to 719, comprising at least one amino acid, wherein at least one amino acid stabilizes the composition and at least one other, different, amino acid reduces the viscosity of the composition.

721. The high concentration composition of embodiment 720, wherein one of the two different amino acids contains a polar uncharged side chain and the other contains a hydrophobic side chain.

722. The high concentration composition of embodiment 720, wherein one of the two different amino acids contains a polar uncharged side chain and the other is selected from the group consisting of G and P.

723. The high concentration composition of embodiment 720, wherein the stabilizing amino acid is selected from the group consisting of S, A, G, T, and V, and the viscosity reducing amino acid is elected from the group consisting of S, A, G, T, V, R, E, and P.

724. The high concentration composition of embodiment 720, wherein the stabilizing amino acid is selected from the group consisting of R, D, K, V, T, P, and I, and the viscosity reducing amino acid selected from the group consisting of P, H, K, M, G, F, E, T, S, N, and I.

725. The high concentration composition of embodiment 720, wherein the stabilizing amino acid is selected from the group consisting of R, H, M, K, and F, and the viscosity reducing amino acid selected from the group consisting of H, M, T, and V.

726. The high concentration composition of embodiment 720, wherein the stabilizing amino acid is G, and the viscosity reducing amino acid is P.

727. The high concentration composition of embodiment 720, wherein the stabilizing amino acid is S, and the viscosity reducing amino acid is P.

728. The high concentration composition of any of embodiments 601 to 727, wherein the composition comprises at least two amino acids that stabilize the composition.

729. The high concentration composition of embodiment 728, wherein stabilizing amino acids are a combination of two amino acids selected from the combinations consisting of A and G, A and M, G and M, G and T, M and T, M and S, S and T, A and N, A and Q, N and Q, A and S, N and S, Q and S, and Q and T.

730. The high concentration composition of embodiment 728, wherein the stabilizing amino acids are a combination of three amino acids selected from the combinations consisting of A, G, and M; G, M, and T; M, S, and T; A, N, and Q; A, N, and S; and Q, S, and T.

731. The high concentration composition of any of embodiments 601 to 730, wherein the composition comprises at least two amino acids that reduce the viscosity of the composition.

732. The high concentration composition of embodiment 731, wherein the viscosity reducing amino acids are a combination of two amino acids selected from the combinations consisting of P and G, and P and S.

733. The high concentration composition of any of embodiments 601 to 732, wherein the composition further comprises at least one salt.

734. The high concentration composition of embodiment 733, wherein the salt stabilizes or contributes to stabilization of the composition.

735. The high concentration composition of embodiment 734, wherein the salt is selected from the group consisting of NaCl, KCl, Na$_2$SO$_4$, MgCl$_2$, CaCl$_2$), and adipate.

736. The high concentration composition of embodiment 735, wherein the salt is present at a concentration selected from the group consisting of: not exceeding about 200 mM, not exceeding about 50 mM, not exceeding about 44 mM, not exceeding about 28 mM, not exceeding about 26.35 mM, not exceeding about 10 mM, and not exceeding about 5 mM.

737. The high concentration composition of embodiment 735, wherein the salt is MgCl$_2$ and the composition has a viscosity of about 15 cP or less.

738. The high concentration composition of any of embodiments 601 to 737, wherein the composition comprises at least one lauryldimethylamineoxide and/or of one of its amine oxide analogs.

739. The high concentration composition of embodiment 738, wherein the lauryldimethylamineoxide and/or of one of its amine oxide analogs stabilizes adalimumab and/or the composition.

740. The high concentration composition of any of embodiments 601 to 739, wherein the composition comprises at least one or a combination of creatinine, creatine and carnitine.

741. The high concentration composition of embodiment 740, wherein the creatinine, creatine, and carnitine stabilize or contribute to stabilization of the composition.

742. The high concentration composition of any of embodiments 601 to 741, wherein the composition further comprises at least one polymer.

743. The high concentration composition of embodiment 742, wherein the polymer is selected from celluloses, 40 kD Dextran, betaine, PVP, and glycerol.

744. The high concentration composition of embodiment 743, wherein the cellulose polymer is selected from the group consisting of: methylcelluloses and ethlycelluloses.

745. The high concentration composition of embodiment 744, wherein the methylcellulose is selected from the group consisting of: hydroxypropyl methylcellulose (HPMC), carboxymethylcellulose (CMC), and sodium carboxymethylcellulose (NaCMC).

746. The high concentration composition of any of embodiments 742 to 7456, wherein the polymer stabilizes or contributes to stabilization of the composition.

747. The high concentration composition of any of embodiments 742 to 746, wherein the polymer reduces the viscosity of the composition.

748. The high concentration composition of any of embodiments 742 to 747, wherein the polymer reversibly interacts with adalimumab and prevents protein-formed matrix interaction.

749. The high concentration composition of any of embodiments 601 to 748, wherein the composition further comprises at least one chelating agent.

750. The high concentration composition of embodiment 749, wherein the chelating agent is selected from the group consisting of EDTA, and DPTA.

751. The high concentration composition of any of embodiments 601 to 750, wherein the composition further comprises at least one sacrificial additive.

752. The high concentration composition of embodiment 751, wherein the sacrificial additive is selected from the group consisting of Met, N-Ac-Trp, ascorbate.

753. The high concentration composition of any of embodiments 601 to 752 wherein the surfactant (a) stabilizes or contributes to stabilization of the composition, (b) reduces the viscosity of the composition, or (c) both reduces the viscosity of the composition and stabilizes or contributes to stabilization of the composition.

754. The high concentration composition of embodiment 6011 to 753, wherein, with respect to those embodiments that do not specify PS80, the surfactant is selected from the group consisting of polysorbate 20, polysorbate 80, SDS, poloxamer 188 (Pluronic® F68).

755. The high concentration composition of embodiment 753, wherein the surfactant is an ultra-low interfacial tension surfactant.

756. The high concentration composition of embodiment 755, wherein the surfactant comprises a hydrophilic portion and a hydrophobic aliphatic group.

757. The high concentration composition of embodiment 756, wherein the aliphatic group comprises saturated and/or unsaturated carbon chains.

758. The high concentration composition of embodiment 756, wherein the hydrophilic portion comprises one or more hydrophilic groups or substituents.

759. The high concentration composition of embodiment 756, wherein the hydrophilic portion is an ionizable group.

760. The high concentration composition of embodiment 759, wherein the ionizable group comprises amines and carboxylic acids.

761. The high concentration composition of embodiment 758, wherein the hydrophilic group is a hydrophilic polymer.

762. The high concentration composition of embodiment 761, wherein the hydrophilic polymer is selected from the group consisting of: methylcelluloses, hydroxypropyl methylcellulose (HPMC), carboxymethylcellulose (CMC), polyalkylamine, poly(ethylene glycol), and poly(ethylene glycol)/poly(propylene glycol) copolymers.

763. The high concentration composition of any of embodiments 601 to 762, comprising Polysorbate 80 at a concentration not exceeding about 0.1% wt.

764. The high concentration composition of any of embodiments 601 to 763, comprising at least one preservative.

765. The high concentration composition of embodiment 764, wherein the preservative is selected from the group consisting of octadecyldimethylbenzyl ammonium chloride, hexamethonium chloride, benzalkonium chloride, benzelthonium chloride, aromatic alcohols and alkyl parabens.

766. The high concentration composition of embodiment 765, wherein the aromatic alcohol is selected from the group consisting of phenol, butyl and benzyl alcohol.

767. The high concentration composition of embodiment 766, wherein the alkyl paraben is selected from the group consisting of methyl or propyl paraben, catechol, resorcinol, cyclohexanol, 3-pentanol, and m-cresol.

768. The high concentration composition of any of embodiments 601 to 767, wherein the composition further comprises a polar solvent.

769. The high concentration composition of embodiment 94, wherein the polar solvent is selected from the group consisting of dimethyl sulfoxide (DMSO) and dimethylacetamide (DMA).

770. The high concentration composition of any of embodiments 601 to 769, wherein:
(a) adalimumab is present at a concentration greater than 50 mg/mL and less than or equal to about 200-250 mg/mL; and
(b) said high concentration composition, and a comparator adalimumab composition comprising adalimumab at a concentration of no more than about 50 mg/mL, are the same or essentially the same with respect to the identity and concentration of excipients contained therein; and both the high concentration formulation and the comparator have stability comparable to or better than, and viscosity comparable to or lower than, a commercially sold Humira® formulation having no greater than about 50 mg/mL or no greater than about 100 mg/mL.

771. The high concentration composition of any of embodiments 601 to 769, wherein:
(a) adalimumab is present at a concentration greater than 50 mg/mL and less than or equal to about 200-250 mg/mL; and
(b) said high concentration composition, and a comparator adalimumab composition comprising adalimumab at a concentration of no more than about 50 mg/mL, are the same or essentially the same with respect to the identity and concentration of excipients contained therein; and both the high concentration formulation and the comparator have (i) stability comparable to or better than a commercially sold Humira® formulation having no greater than about 50 mg/mL or no greater than about 100 mg/mL, and (ii) viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP.

772. The high concentration composition of any of embodiments 601 to 769, wherein:
(a) adalimumab is present at a concentration greater than 50 mg/mL and less than or equal to about 200-250 mg/mL; and
(b) the high concentration composition is able to exhibit stability and viscosity at least comparable to or better than a commercially sold Humira® composition containing no greater than about 50 mg/mL, or no greater than about 100 mg/mL, without need to incorporate in such high concentration composition either (i) any viscosity reducing agents or stabilizing agents not found in a comparator adalimumab composition comprising adalimumab at a concentration of no more than about 50 mg/mL; or (ii) amounts of viscosity modifying agents or stabilizing agents different from that found in the comparator composition.

773. The high concentration composition of any of embodiments 601 to 769, wherein:
(a) adalimumab is present at a concentration greater than 50 mg/mL and less than or equal to about 200-250 mg/mL; and
(b) the high concentration composition is able to exhibit stability at least comparable to or better than a commercially sold Humira® composition containing no greater than about 50 mg/mL, or no greater than about 100 mg/mL and viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP, without need to incorporate in such high concentration composition either (i) any viscosity reducing agents or stabilizing agents not found in a comparator adalimumab composition comprising adalimumab at a concentration of no more than about 50 mg/mL; or (ii) amounts of viscosity modifying agents or stabilizing agents different from that found in the comparator composition.

774. The high concentration composition of any of embodiments 601 to 769, wherein
(a) adalimumab is present at a concentration greater than or equal to about 200-250 mg/mL;
(b) the high concentration composition, and a comparator adalimumab composition comprising adalimumab at a concentration of not more than about 50 mg/mL, compare to one another in the following respects:
(i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein the high concentration composition has viscosity less than or approximately equal to that of commercially sold Humira® containing adalimumab at a concentration not greater than about 50 mg/mL or not greater than about 100 mg/mL; and/or (ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein the high concentration composition has stability equal to or better than a commercially sold Humira® formulation comprising adalimumab at a concentration not greater than about 50 mg/mL or not greater than about 100 mg/mL; and (c) the high concentration composition is not able to exhibit stability and viscosity at least comparable to or better than a commercially sold Humira® composition containing no greater than about 50 mg/mL, or no greater than about 100 mg/mL, unless the high concentration composition comprises (i) said viscosity reducing agent or stabilizing agent not found in the comparator composition; or (ii) said increased amount of viscosity modifying agent or stabilizing agent.

775. The high concentration composition of any of embodiments 601 to 769, wherein
(a) adalimumab is present at a concentration greater than or equal to about 200-250 mg/mL;
(b) the high concentration composition, and a comparator adalimumab composition comprising adalimumab at a concentration of not more than about 50 mg/mL, compare to one another in the following respects:
(i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein the high concentration composition has viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP; and/or
(ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein the high concentration composition has stability equal to or better than a commercially sold Humira® formulation comprising adalimumab at a concentration not greater than about 50 mg/mL or not greater than about 100 mg/mL; and
(c) the high concentration composition is not able to exhibit stability at least comparable to or better than a commercially sold Humira® composition containing no greater than about 50 mg/mL or no greater than about 100 mg/mL, and viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP, unless the high concentration composition comprises (i) said viscosity reducing agent or stabilizing agent not found in the comparator composition; or (ii) said increased amount of viscosity modifying agent or stabilizing agent.

776. The high concentration composition of any of embodiments 601 to 769, wherein
(a) adalimumab is present at a concentration greater than or equal to about 200-250 mg/mL;
(b) the high concentration composition, and a comparator adalimumab composition comprising adalimumab at a concentration of not more than about 50 mg/mL, compare to one another in the following respects:
(i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein both the high concentration composition, and the comparator, have viscosity less than or approximately equal to that of commercially sold Humira® containing adalimumab at a concentration not greater than about 50 mg/mL or not greater than about 100 mg/mL; and/or
(ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein both the high concentration composition, and the comparator, have stability equal to or better than a commercially sold Humira® formulation comprising adalimumab at a concentration not greater than about 50 mg/mL or not greater than about 100 mg/mL; and
(c) the high concentration composition is not able to exhibit stability and viscosity at least comparable to or better than a commercially sold Humira® composition containing no greater than about 50 mg/mL, or no greater than about 100 mg/mL, unless the high concentration composition comprises (i) said viscosity reducing agent or stabilizing agent not found in the comparator composition; or (ii) said increased amount of viscosity modifying agent or stabilizing agent.

777. The high concentration composition of any of embodiments 601 to 769, wherein
(a) adalimumab is present at a concentration greater than or equal to about 200-250 mg/mL;
(b) the high concentration composition, and a comparator adalimumab composition comprising adalimumab at a concentration of not more than about 50 mg/mL, compare to one another in the following respects:
(i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein both the high concentration composition, and the comparator, have viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP; and/or
(ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein both the high concentration composition, and the comparator, have stability equal to or better than a commercially sold Humira® formulation comprising adalimumab at a concentration not greater than about 50 mg/mL or not greater than about 100 mg/mL; and
(c) the high concentration composition is not able to exhibit stability at least comparable to or better than a commercially sold Humira® composition containing no greater than about 50 mg/mL or no greater than about 100 mg/mL, and viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP, unless the high concentration composition comprises (i) said viscosity reducing agent or stabilizing agent not found in the comparator composition; or (ii) said increased amount of viscosity modifying agent or stabilizing agent.

778. The high concentration composition of any of embodiments 601 to 777 having long term stability, wherein the composition comprises one or more ionic excipients, wherein said excipients contribute to the composition having conductivity greater than 2.5, 3, 4, 5, 6, 7 or 8; osmolarity of 140 to about 400; and a hydrodynamic diameter of the adalimumab of greater than 4, 5, 6, 7, 8, 9, 10 or 11; and wherein the composition, upon administration to a subject, results in a degree of pain or discomfort no worse than, or better than, that of an AbbVie-supplied Humira® composition, having a concentration of adalimumab greater than 50 mg/mL.

779. The high concentration composition of any of embodiments 601 to 778, wherein said composition is substantially free of protein aggregates and/or high molecular weight species.

780. The high concentration composition of any of embodiments 601 to 779, wherein the composition has an absolute viscosity of about 15 cP or less.

781. The high concentration composition of any of embodiments 601 to 780, wherein the composition has an osmolality of about 180 to about 420 mOsM.

782. The high concentration composition of any of embodiments 601 to 781, wherein the composition has a conductivity selected from the group comprising: between about 1 and about 2.5 mS/cm, between about 2.5 and about 3 mS/cm, between about 3 and about 3.5 mS/cm, greater than about 2.5 mS/cm, at least about 3.0 mS/cm, about 3.0 mS/cm, about 3.5 mS/cm, about 4 mS/cm, about 4.4 mS/cm, and about 4.5 mS/cm.

783. The high concentration composition of any of embodiments 601 to 782, wherein the adalimumab has a hydrodynamic diameter selected from the group comprising greater than about 2.5 nm, greater than about 3 nm, greater than about 4 nm, greater than about 4 nm, about 2.5 to about 3 nm, about 3 nm to about 3.5 nm, about 3.5 to about 4 nm, about 3 nm, about 4 nm, about 5 nm, about 6 nm, about 7 nm, about 8 nm, about 9 nm, and about 10 nm.

784. The high concentration composition of any of embodiments 601 to 783, wherein the composition has reduced pain upon injection to a subject as compared to an adalimumab composition comprising citrate.

785. The high concentration composition of any of embodiments 601 to 784, wherein the composition has sizes and amounts of sub-visible particles comparable to, or better than that of a commercially sold Humira® containing adalimumab at concentrations between about 601 to 781 mg/mL.

786. The high concentration composition of any of embodiments 601 to 785, wherein the composition has approximately the same or fewer adalimumab fragments and/or aggregates than commercially sold Humira® containing adalimumab at concentrations between about 50 and 100 mg/mL.

787. The high concentration composition of any of embodiments 601 to 786, wherein the composition has an adalimumab monomer content of at least about 85% monomer.

788. The high concentration composition of any of embodiments 601 to 787, wherein the composition has an adalimumab monomer content of at least about 90% monomer.

789. The high concentration composition of any of embodiments 601 to 788, wherein the composition has an adalimumab monomer content of at least about 95% monomer.

790. The high concentration composition of any of embodiments 601 to 789, wherein the composition is stable at room temperature for at least 10 days.

791. The high concentration composition of any of embodiments 601 to 790, wherein the composition is stable under conditions selected from the group comprising: at least 1 week at 40° C., at least 6-10 days at 30° C., at least 2 weeks at 40° C., at least 4 weeks at 25° C., at least 9 weeks at 25° C., at least 13 weeks at 25° C., at least 13 weeks at 5° C., and at least 26 weeks at 5° C.

792. The high concentration composition of any of embodiments 601 to 791, wherein the composition is stable for at least three months.

793. The high concentration composition of any of embodiments 601 to 792, wherein the composition is stable for at least six months.

794. The high concentration composition of any of embodiments 601 to 792 wherein the composition is stable for at least one year.

795. The high concentration composition of any of embodiments 601 to 794, having a pH of 5 to 6, and prepared by modifying a pre-existing adalimumab formulation having a pH of 5 to 6 and no more than about 50 mg/mL, wherein the modification consists solely of increasing the concentration of adalimumab in the pre-existing formulation to concentration selected from (i) greater than 50 mg/mL and less than or equal to about 200-250 mg/mL; and (ii) about 100 to 250 mg/mL, without altering the identity or concentration of any excipients present in the pre-existing formulation.

796. A prefilled syringe containing the high concentration composition of any of embodiments 601 to 795.

797. A prefilled syringe of embodiment 796 wherein the composition is optionally free of surfactant, and is present in a defined containment volume of the syringe, said containment volume being essentially free of any portion thereof in which the composition is absent.

798. The prefilled syringe of embodiments 796-797 wherein the high concentration composition does not have a polysorbate or polaxamer surfactant.

799. The prefilled syringe of any of embodiments 796-798 where the high concentration composition does not have a surfactant.

799A. The prefilled syringe of any of embodiments 796-799 wherein the high concentration composition is isotonic, has conductivity greater than 2.5, and is free of surfactant or free of polyol or free of both.

799B. The prefilled syringe of any of embodiments 796-799A wherein the high concentration composition does not contain any of the following buffers: phosphate, pyrophosphate, acetate, citrate, histidine, succinate, adipate, maleate, glutamate, gluconate, or tartrate.

799C. The prefilled syringe of any of embodiments 796-799B wherein the high concentration composition is self-buffering based substantially only on the buffer capacity afforded by the adalimumab.

799D. A method for preparing a high concentration formulation of any of embodiments 601-795 having a concentration of adalimumab greater than about 50 mg/mL and less than or equal to about 200-250 mg/mL, and a pH of 5 to 6, said method comprising the step of: preparing an adalimumab formulation that is modified over a known adalimumab formulation, said known formulation having a pH of 5 to 6 and comprising no more than about 50 mg/mL, wherein the modification consists solely of increasing the adalimumab concentration of the known formulation to a concentration selected from (i) greater than 50 mg/mL and less than or equal to about 200-250 mg/mL; and (ii) about 100 to about 200-250 mg/mL, without modifying the identity or concentration of any excipients present in the known formulation.

Reserved: Embodiment 800

801. An aqueous pharmaceutical composition comprising a stable high concentration of adalimumab, wherein:
(a) the composition has a concentration of adalimumab greater than 50 mg/mL;
(b) the composition has long term stability comparable to or better than a commercially sold adalimumab pharmaceutical composition having a concentration of adalimumab selected from:
(I) not greater than about 50 mg/mL; or
(ii) not greater than about 100 mg/mL; and
(c) the composition has viscosity approximately equal to, or less than, that of a commercially sold adalimumab pharmaceutical composition having a concentration of adalimumab selected from:
(i) not greater than about 50 mg/mL; or
(ii) not greater than about 100 mg/mL.
(d) the composition comprises an acetate buffer;
(e) the composition comprises a polyol that is one, or a combination of mannitol, sorbitol, and trehalose; and
(f) the composition comprises a surfactant.

802. The high concentration composition of embodiment 1, wherein adalimumab is present in the composition at a concentration selected from: greater than 50 mg/mL and less than 100 g/mL; at least 100 mg/mL; 100 to 300 mg/mL; 100 to 200 mg/mL; 100 to 150 mg/mL; 100 to 125 mg/mL; 75 mg/mL; 100 mg/mL; 125 mg/mL, 150 mg/mL; 175 mg/mL; 200 mg/mL; 225 mg/mL; 250 mg/mL; 275 mg/mL; and 300 mg/mL.

803. The high concentration composition of embodiment 802, wherein the acetate buffer is present at a concentration of about 1 to about 50 mM.

804. The high concentration composition of embodiment 802, wherein the polyol, or a salt, or both act as tonicity agents.

805. The high concentration composition of embodiment 802 wherein the polyol acts as a tonicity agent, and wherein the composition is free or essentially free of sodium chloride.

806. The high concentration composition of embodiment 804, wherein the polyol is at a concentration selected from the group comprising: about 1% to about 15% wt; about 67 to 270 mM; at least about 135 mM; at least about 500 moles of polyol per mole of adalimumab.

807. The high concentration composition of embodiment 804, wherein the salt is NaCl.

808. The high concentration composition of embodiment 804, wherein the salt is present at a concentration not exceeding about 200 mM.

809. The high concentration composition of embodiment 802, wherein the surfactant is present at a concentration of about 0.001% to about 0.5% wt.

810. The high concentration composition of embodiment 802, wherein the composition is free, or substantially free, of a preservative.

811. The high concentration composition of embodiment 802, wherein the composition further comprises a preservative.

812. The high concentration composition of embodiment 810, wherein the preservative is selected from the group comprising, benzyl alcohol, phenol, m-cresol, chlorobutanol, and benzethonium Cl.

813. The high concentration composition of embodiment 810, wherein the preservative is present at a concentration of about 0.1% to about 2% wt.

814. The high concentration composition of embodiment 802, wherein the composition has a pH of about 4.0 to 8.

816. The high concentration formulation of any of embodiments 802 to 814 comprising acetic acid.

817. The high concentration composition of embodiment 802, wherein the composition has a pH of 4 to 8 and comprises 30 mM acetate and 140 mM NaCl.

818. The high concentration composition of embodiment 802, wherein the composition has a pH of 5 to 6 and comprises 30 mM acetate and 270 mM mannitol.

819. The high concentration composition of embodiment 802, wherein the composition has a pH of 5 to 6 and comprises 140 mM NaCl.

820. The high concentration composition of embodiment 802, wherein the composition has a pH of 5 to 6 and comprises 20 mM acetate, 270 mM sorbitol, and 0.05% polysorbate 80.

821. The high concentration composition of embodiment 802, wherein the composition has a pH of 5 to 6 and comprises 20 mM acetate, 270 mM xylitol, and 0.05% polysorbate 80.

822. The high concentration composition of embodiment 802, wherein the composition has a pH of 5 to 6 and comprises 20 mM acetate, 270 mM sorbitol, and 0.9% benzyl alcohol.

823. The high concentration composition of embodiment 802, wherein the composition has a pH of 5 to 6 and comprises 20 mM acetate and 230 mM trehalose.

824. The high concentration composition of embodiment 802, wherein the composition has a pH of 4 to 8 and comprises 10 mM acetate, 65 mM trehalose, and 100 mM NaCl.

825. The high concentration composition of embodiment 802, wherein the composition has a pH of 5 to 6 and comprises 10 mM acetate, 270 mM sorbitol, and 0.9% benzyl alcohol.

826. The high concentration composition of embodiment 802, wherein the composition has a pH of 5 to 6 and comprises 30 mM acetate, 140 mM NaCl, and 0.9% benzyl alcohol.

827. The high concentration composition of embodiment 802, wherein the composition has a pH of 5 to 6 and comprises 10 mM acetate, 270 mM mannitol, and 0.1% polysorbate 80.

828. The high concentration composition of embodiment 802, wherein the composition has a pH of 5 to 6 and comprises 65 mM mannitol, 100 mM NaCl, and 0.1% polysorbate 80.

829. The high concentration composition of embodiment 802, wherein the composition has a pH of 5 to 6 and comprises 10 mM acetate, 140 mM NaCl, 0.1% polysorbate 80, and 0.9% benzyl alcohol.

830. The high concentration composition of embodiment 802, wherein the composition has a pH of 5 to 6 and comprises 10 mM acetate, 230 mM trehalose, 0.1% polysorbate 80, and 0.9% benzyl alcohol.

834. The high concentration composition of any of embodiments 818, 820, 821, 822, 823, 825, 827, and 830, wherein the composition is free of sodium chloride; or lacks a tonicifying amount of sodium chloride.

Reserved: Embodiment 835 to 841

842. The high concentration composition of embodiment 835 to 836 wherein the concentration of adalimumab is selected from:
51 mg/mL, 52 mg/mL, 53 mg/mL, 54 mg/mL, 55 mg/mL, 56 mg/mL, 57 mg/mL, 58 mg/mL, 59 mg/mL, 60 mg/mL, 61 mg/mL, 62 mg/mL, 63 mg/mL, 64 mg/mL, 65 mg/mL, 66 mg/mL, 67 mg/mL, 68 mg/mL, 69 mg/mL, 70 mg/mL, 71 mg/mL, 72 mg/mL, 73 mg/mL, 74 mg/mL, 75 mg/mL, 76 mg/mL, 77 mg/mL, 78 mg/mL, 79 mg/mL, 80 mg/mL, 81 mg/mL, 82 mg/mL, 83 mg/mL, 84 mg/mL, 85 mg/mL, 86 mg/mL, 87 mg/mL, 88 mg/mL, 89 mg/mL, 90 mg/mL, 91 mg/mL, 92 mg/mL, 93 mg/mL, 94 mg/mL, 95 mg/mL, 96 mg/mL, 97 mg/mL, 98 mg/mL, 99 mg/mL, 100 mg/mL, 101 mg/mL, 102 mg/mL, 103 mg/mL, 104 mg/mL, 105 mg/mL, 106 mg/mL, 107 mg/mL, 108 mg/mL, 109 mg/mL, 110 mg/mL, 111 mg/mL, 112 mg/mL, 113 mg/mL, 114 mg/mL, 115 mg/mL, 116 mg/mL, 117 mg/mL, 118 mg/mL, 119 mg/mL, 120 mg/mL, 121 mg/mL, 122 mg/mL, 123 mg/mL, 124 mg/mL, 125 mg/mL, 126 mg/mL, 127 mg/mL, 128 mg/mL, 129 mg/mL, 130 mg/mL, 131 mg/mL, 132 mg/mL, 133 mg/mL, 134 mg/mL, 135 mg/mL, 136 mg/mL, 137 mg/mL, 138 mg/mL, 139 mg/mL, 140 mg/mL, 141 mg/mL, 142 mg/mL, 143 mg/mL, 144 mg/mL, 145 mg/mL, 146 mg/mL, 147 mg/mL, 148 mg/mL, 149 mg/mL, 150 mg/mL, 151 mg/mL, 152 mg/mL, 153 mg/mL, 154 mg/mL, 155 mg/mL, 156 mg/mL, 157 mg/mL, 158 mg/mL, 159 mg/mL, 160 mg/mL, 161 mg/mL, 162 mg/mL, 163 mg/mL, 164 mg/mL, 165 mg/mL, 166 mg/mL, 167 mg/mL, 168 mg/mL, 169 mg/mL, 170 mg/mL, 171 mg/mL, 172 mg/mL, 173 mg/mL, 174 mg/mL, 175 mg/mL, 176 mg/mL, 177 mg/mL, 178 mg/mL, 179 mg/mL, 180 mg/mL, 181 mg/mL, 182 mg/mL, 183 mg/mL, 184 mg/mL, 185 mg/mL, 186 mg/mL, 187 mg/mL, 188 mg/mL, 189 mg/mL, 190 mg/mL, 191 mg/mL, 192 mg/mL, 193 mg/mL, 194 mg/mL, 195 mg/mL, 196 mg/mL, 197 mg/mL, 198 mg/mL, 199 mg/mL, and 200 mg/mL.

843. The high concentration composition of embodiment 837-841 wherein the concentration of adalimumab is selected from:
201 mg/mL, 202 mg/mL, 203 mg/mL, 204 mg/mL, 205 mg/mL, 206 mg/mL, 207 mg/mL, 208 mg/mL, 209 mg/mL, 210 mg/mL, 211 mg/mL, 212 mg/mL, 213 mg/mL, 214 mg/mL, 215 mg/mL, 216 mg/mL, 217 mg/mL, 218 mg/mL, 219 mg/mL, 220 mg/mL, 221 mg/mL, 222 mg/mL, 223 mg/mL, 224 mg/mL, 225 mg/mL, 226 mg/mL, 227 mg/mL, 228 mg/mL, 229 mg/mL, 230 mg/mL, 231 mg/mL, 232 mg/mL, 233 mg/mL, 234 mg/mL, 235 mg/mL, 236 mg/mL, 237 mg/mL, 238 mg/mL, 239 mg/mL, 240 mg/mL, 241 mg/mL, 242 mg/mL, 243 mg/mL, 244 mg/mL, 245 mg/mL, 246 mg/mL, 247 mg/mL, 248 mg/mL, 249 mg/mL, 250 mg/mL, 251 mg/mL, 252 mg/mL, 253 mg/mL, 254 mg/mL, 255 mg/mL, 256 mg/mL, 257 mg/mL, 258 mg/mL, 259 mg/mL, 260 mg/mL, 261 mg/mL, 262 mg/mL, 263 mg/mL, 264 mg/mL, 265 mg/mL, 266 mg/mL, 267 mg/mL, 268 mg/mL, 269 mg/mL, 270 mg/mL, 271 mg/mL, 272 mg/mL, 273 mg/mL, 274 mg/mL, 275 mg/mL, 276 mg/mL, 277 mg/mL, 278 mg/mL, 279 mg/mL, 280 mg/mL, 281 mg/mL, 282 mg/mL, 283 mg/mL, 284 mg/mL, 285 mg/mL, 286 mg/mL, 287 mg/mL, 288 mg/mL, 289 mg/mL, 290 mg/mL, 291 mg/mL, 292 mg/mL, 293 mg/mL, 294 mg/mL, 295 mg/mL, 296 mg/mL, 297 mg/mL, 298 mg/mL, 299 mg/mL, and 300 mg/mL.

844. The high concentration composition of any of embodiments 801 to 843 wherein the composition has a conductivity greater than 2.5, 3, 4, 5, 6, or 7 mS/cm; an osmolarity from about 100 to 400 mOsM, and wherein the hydrodynamic diameter of the adalimumab is greater than 2, 3, 4, 5, 6, 7, 8, 9 10 or 11.

845. The high concentration composition of embodiment 801 to 844, wherein the concentration of adalimumab is (a) 100, 125, 150, 175 or 200 mg/mL; or (b) 200 mg/mL to 300 mg/mL.

846. The high concentration composition of any of embodiments 801 to 845, wherein at least one member, or a combination thereof, selected from the following list is present and contributes to stabilization of the composition: a polyol, a sugar, an amino acid, a salt, creatine, creatinine, carnitine, lauryldimethylamineoxide (and amine oxide analogs), a polymer, a chelating agent, a polar solvent and a surfactant.

847. The high concentration composition of any of embodiments 801 to 846, wherein at least one of member, or combination thereof, selected from the following list is present and contributes to reducing viscosity of the composition: an amino acid, a calcium salt, an acetate salt, magnesium chloride, sodium phosphate, arginine hydrochloride, creatine, creatinine, carnitine, an ultra-low Interfacial tension surfactant, and a polar solvent.

848. The high concentration composition of embodiment 801 to 847, comprising at least one amino acid, wherein at least one amino acid stabilizes the composition and at least one other, different, amino acid reduces the viscosity of the composition.

849. The high concentration composition of embodiment 848, wherein one of the two different amino acids contains a polar uncharged side chain and the other contains a hydrophobic side chain.

850. The high concentration composition of embodiment 848, wherein one of the two different amino acids contains a polar uncharged side chain and the other is selected from the group consisting of G and P.

851. The high concentration composition of embodiment 848, wherein the stabilizing amino acid is selected from the group consisting of S, A, G, T, and V, and the viscosity reducing amino acid is elected from the group consisting of S, A, G, T, V, R, E, and P.

852. The high concentration composition of embodiment 848, wherein the stabilizing amino acid is selected from the group consisting of R, D, K, V, T, P, and I, and the viscosity reducing amino acid selected from the group consisting of P, H, K, M, G, F, E, T, S, N, and I.

853. The high concentration composition of embodiment 848, wherein the stabilizing amino acid is selected from the group consisting of R, H, M, K, and F, and the viscosity reducing amino acid selected from the group consisting of H, M, T, and V.

854. The high concentration composition of embodiment 848, wherein the stabilizing amino acid is G, and the viscosity reducing amino acid is P.

855. The high concentration composition of embodiment 848, wherein the stabilizing amino acid is S, and the viscosity reducing amino acid is P.

8. The high concentration composition of any of embodiments 601 to 727, wherein the composition comprises at least two amino acids that stabilize the composition.

856. The high concentration composition of embodiment 856, wherein stabilizing amino acids are a combination of two amino acids selected from the combinations consisting of A and G, A and M, G and M, G and T, M and T, M and S, S and T, A and N, A and C, N and, A and S, N and S, Q and S, and Q and T.

857. The high concentration composition of embodiment 856, wherein the stabilizing amino acids are a combination of three amino acids selected from the combinations consisting of A, G, and M; G, M, and T; M, S, and T; A, N, and Q; A, N, and S; and Q, S, and T.

858. The high concentration composition of any of embodiments 801 to 857, wherein the composition comprises at least two amino acids that reduce the viscosity of the composition.

859. The high concentration composition of embodiment 858, wherein the viscosity reducing amino acids are a combination of two amino acids selected from the combinations consisting of P and G, and P and S.

860. The high concentration composition of any of embodiments 801 to 859, wherein the composition further comprises at least one salt.

861. The high concentration composition of embodiment 860, wherein the salt stabilizes or contributes to stabilization of the composition.

862. The high concentration composition of embodiment 861, wherein the salt is selected from the group consisting of NaCl, KCl, Na2SO4, MgCl2, CaCl2, and adipate.

863. The high concentration composition of embodiment 862, wherein the salt is present at a concentration selected from the group consisting of: not exceeding about 200 mM, not exceeding about 50 mM, not exceeding about 44 mM, not exceeding about 28 mM, not exceeding about 26.35 mM, not exceeding about 10 mM, and not exceeding about 5 mM.

864. The high concentration composition of embodiment 862, wherein the salt is MgCl2 and the composition has a viscosity of about 15 cP or less.

865. The high concentration composition of any of embodiments 801 to 864, wherein the composition comprises at least one lauryldimethylamineoxide and/or of one of its amine oxide analogs.

866. The high concentration composition of embodiment 865, wherein the lauryldimethylamineoxide and/or of one of its amine oxide analogs stabilizes adalimumab and/or the composition.

867. The high concentration composition of any of embodiments 801 to 739, wherein the composition comprises at least one or a combination of creatinine, creatine and carnitine.

868. The high concentration composition of embodiment 867, wherein the creatinine, creatine, and carnitine stabilize or contribute to stabilization of the composition.

869. The high concentration composition of any of embodiments 801 to 868, wherein the composition further comprises at least one polymer.

870. The high concentration composition of embodiment 869, wherein the polymer is selected from celluloses, 40 kD Dextran, betaine, PVP, and glycerol.

871. The high concentration composition of embodiment 870, wherein the cellulose polymer is selected from the group consisting of: methylcelluloses and ethlycelluloses.

872. The high concentration composition of embodiment 871, wherein the methylcellulose is selected from the group consisting of: hydroxypropyl methylcellulose (HPMC), carboxymethylcellulose (CMC), and sodium carboxymethylcellulose (NaCMC).

873. The high concentration composition of any of embodiments 869 to 872, wherein the polymer stabilizes or contributes to stabilization of the composition.

874. The high concentration composition of any of embodiments 869 to 873, wherein the polymer reduces the viscosity of the composition.

875. The high concentration composition of any of embodiments 869 to 874, wherein the polymer reversibly interacts with adalimumab and prevents protein-formed matrix interaction.

876. The high concentration composition of any of embodiments 801 to 875, wherein the composition further comprises at least one chelating agent.

877. The high concentration composition of embodiment 876, wherein the chelating agent is selected from the group consisting of EDTA, and DPTA.

878. The high concentration composition of any of embodiments 801 to 877, wherein the composition further comprises at least one sacrificial additive.

879. The high concentration composition of embodiment 878, wherein the sacrificial additive is selected from the group consisting of Met, N-Ac-Trp, ascorbate.

880. The high concentration composition of any of embodiments 601 to 879 wherein the surfactant (a) stabilizes or contributes to stabilization of the composition, (b) reduces the viscosity of the composition, or (c) both reduces the viscosity of the composition and stabilizes or contributes to stabilization of the composition.

881. The high concentration composition of embodiment 701 to 880, wherein, with respect to those embodiments that do not specify PS80, the surfactant is selected from the group consisting of polysorbate 20, polysorbate 80, SDS, poloxamer 188 (Pluronic® F68).

882. The high concentration composition of embodiment 880, wherein the surfactant is an ultra-low interfacial tension surfactant.

883. The high concentration composition of embodiment 882, wherein the surfactant comprises a hydrophilic portion and a hydrophobic aliphatic group.

884. The high concentration composition of embodiment 883, wherein the aliphatic group comprises saturated and/or unsaturated carbon chains.

885. The high concentration composition of embodiment 883, wherein the hydrophilic portion comprises one or more hydrophilic groups or substituents.

886. The high concentration composition of embodiment 883, wherein the hydrophilic portion is an ionizable group.

887. The high concentration composition of embodiment 886, wherein the ionizable group comprises amines and carboxylic acids.

888. The high concentration composition of embodiment 885, wherein the hydrophilic group is a hydrophilic polymer.

889. The high concentration composition of embodiment 888, wherein the hydrophilic polymer is selected from the group consisting of: methylcelluloses, hydroxypropyl methylcellulose (HPMC), carboxymethylcellulose (CMC), polyalkylamine, poly(ethylene glycol), and poly(ethylene glycol)/poly(propylene glycol) copolymers.

890. The high concentration composition of any of embodiments 801 to 889, comprising Polysorbate 80 at a concentration not exceeding about 0.1% wt.

891. The high concentration composition of any of embodiments 801 to 890, comprising at least one preservative.

892. The high concentration composition of embodiment 891, wherein the preservative is selected from the group consisting of octadecyldimethylbenzyl ammonium chloride, hexamethonium chloride, benzalkonium chloride, benzelthonium chloride, aromatic alcohols and alkyl parabens.

891. The high concentration composition of embodiment 892, wherein the aromatic alcohol is selected from the group consisting of phenol, butyl and benzyl alcohol.

892. The high concentration composition of embodiment 892, wherein the alkyl paraben is selected from the group consisting of methyl or propyl paraben, catechol, resorcinol, cyclohexanol, 3-pentanol, and m-cresol.

893. The high concentration composition of any of embodiments 801 to 892, wherein the composition further comprises a polar solvent.

894. The high concentration composition of embodiment 893, wherein the polar solvent is selected from the group consisting of dimethyl sulfoxide (DMSO) and dimethylacetamide (DMA).

895. The high concentration composition of any of embodiments 801 to 894, wherein:
(a) adalimumab is present at a concentration greater than 50 mg/mL and less than or equal to about 200-250 mg/mL; and
(b) said high concentration composition, and a comparator adalimumab composition comprising adalimumab at a concentration of no more than about 50 mg/mL, are the same or essentially the same with respect to the identity and concentration of excipients contained therein; and both the high concentration formulation and the comparator have stability comparable to or better than, and viscosity comparable to or lower than, a commercially sold Humira® formulation having no greater than about 50 mg/mL or no greater than about 100 mg/mL.

896. The high concentration composition of any of embodiments 801 to 894, wherein:
(a) adalimumab is present at a concentration greater than 50 mg/mL and less than or equal to about 200-250 mg/mL; and
(b) said high concentration composition, and a comparator adalimumab composition comprising adalimumab at a concentration of no more than about 50 mg/mL, are the same or essentially the same with respect to the identity and concentration of excipients contained therein; and both the high concentration formulation and the comparator have (i) stability comparable to or better than a commercially sold Humira® formulation having no greater than about 50 mg/mL or no greater than about 100 mg/mL, and (ii) viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP.

897. The high concentration composition of any of embodiments 801 to 894, wherein:
(a) adalimumab is present at a concentration greater than 50 mg/mL and less than or equal to about 200-250 mg/mL; and
(b) the high concentration composition is able to exhibit stability and viscosity at least comparable to or better than a commercially sold Humira® composition containing no greater than about 50 mg/mL, or no greater than about 100 mg/mL, without need to incorporate in such high concentration composition either (i) any viscosity reducing agents or stabilizing agents not found in a comparator adalimumab composition comprising adalimumab at a concentration of no more than about 50 mg/mL; or (ii) amounts of viscosity modifying agents or stabilizing agents different from that found in the comparator composition.

898. The high concentration composition of any of embodiments 801 to 894, wherein:
(a) adalimumab is present at a concentration greater than 50 mg/ml and less than or equal to about 200-250 mg/mL; and
(b) the high concentration composition is able to exhibit stability at least comparable to or better than a commercially sold Humira® composition containing no greater than about 50 mg/mL, or no greater than about 100 mg/ml and viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP, without need to incorporate in such high concentration composition either (I) any viscosity reducing agents or stabilizing agents not found in a comparator adalimumab composition comprising adalimumab at a concentration of no more than about 50 mg/ml; or (ii) amounts of viscosity modifying agents or stabilizing agents different from that found in the comparator composition.

899. The high concentration composition of any of embodiments 801 to 894, wherein
(a) adalimumab is present at a concentration greater than or equal to about 200-250 mg/mL;
(b) the high concentration composition, and a comparator adalimumab composition comprising adalimumab at a concentration of not more than about 50 mg/mL, compare to one another in the following respects:
(i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein the high concentration composition has viscosity less than or approximately equal to that of commercially sold Humira® containing adalimumab at a concentration not greater than about 50 mg/mL or not greater than about 100 mg/mL; and/or
(ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein the high concentration composition has stability equal to or better than a commercially sold Humira® formulation comprising adalimumab at a concentration not greater than about 50 mg/mL or not greater than about 100 mg/mL; and
(c) the high concentration composition is not able to exhibit stability and viscosity at least comparable to or better than a commercially sold Humira® composition containing no greater than about 50 mg/mL, or no greater than about 100 mg/mL, unless the high concentration composition comprises (i) said viscosity reducing agent or stabilizing agent not found in the comparator composition; or (ii) said increased amount of viscosity modifying agent or stabilizing agent.

900. The high concentration composition of any of embodiments 801 to 894, wherein
(a) adalimumab is present at a concentration greater than or equal to about 200-250 mg/mL;
(b) the high concentration composition, and a comparator adalimumab composition comprising adalimumab at a concentration of not more than about 50 mg/mL, compare to one another in the following respects:
(i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein the high concentration composition has viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP; and/or (ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein the high concentration composition has stability equal to or better than a commercially sold Humira® formulation comprising adalimumab at a concentration not greater than about 50 mg/mL or not greater than about 100 mg/mL; and (c) the high concentration composition is not able to exhibit stability at least comparable to or better than a commercially sold Humira® composition containing no greater than about 50 mg/mL or no greater than about 100 mg/mL, and viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP, unless the high concentration composition comprises (i) said viscosity reducing agent or stabilizing agent not found in the comparator composition; or (ii) said increased amount of viscosity modifying agent or stabilizing agent.

901. The high concentration composition of any of embodiments 801 to 894, wherein
(a) adalimumab is present at a concentration greater than or equal to about 200-250 mg/mL;
(b) the high concentration composition, and a comparator adalimumab composition comprising adalimumab at a concentration of not more than about 50 mg/mL, compare to one another in the following respects:
(i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein both the high concentration composition, and the comparator, have viscosity less than or approximately equal to that of commercially sold Humira® containing adalimumab at a concentration not greater than about 50 mg/mL or not greater than about 100 mg/mL; and/or
(ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein both the high concentration composition, and the comparator, have stability equal to or better than a commercially sold Humira® formulation comprising adalimumab at a concentration not greater than about 50 mg/mL or not greater than about 100 mg/mL; and
(c) the high concentration composition is not able to exhibit stability and viscosity at least comparable to or better than a commercially sold Humira® composition containing no greater than about 50 mg/mL, or no greater than about 100 mg/mL, unless the high concentration composition comprises (i) said viscosity reducing agent or stabilizing agent not found in the comparator composition; or (ii) said increased amount of viscosity modifying agent or stabilizing agent.

902. The high concentration composition of any of embodiments 801 to 894, wherein
(a) adalimumab is present at a concentration greater than or equal to about 200-250 mg/mL;
(b) the high concentration composition, and a comparator adalimumab composition comprising adalimumab at a concentration of not more than about 50 mg/mL, compare to one another in the following respects:
(i) the high concentration composition comprises (A) a viscosity modifying agent not present in the comparator composition, and/or (B) an increased amount of a viscosity modifying agent present in the comparator, and/or (C) both a viscosity modifying agent not present in the comparator, and an increased amount of a viscosity modifying agent present in the comparator; wherein both the high concentration composition, and the comparator, have viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP; and/or
(ii) the high concentration composition comprises (A) a stabilizing agent not present in the comparator, and/or (B) an increased amount of a stabilizing agent present in the comparator, and/or (C) both a stabilizing agent not present in the comparator, and an increased amount of a stabilizing agent present in the comparator; and wherein both the high concentration composition, and the comparator, have stability equal to or better than a commercially sold Humira® formulation comprising adalimumab at a concentration not greater than about 50 mg/mL or not greater than about 100 mg/mL; and
(c) the high concentration composition is not able to exhibit stability at least comparable to or better than a commercially sold Humira® composition containing no greater than about 50 mg/mL or no greater than about 100 mg/mL, and viscosity equal to or less than: 20 cP, 15 cP, 14 cP, 13 cP, 12 cP, 11 cP, 10 cP, 9 cP, 8 cP, 7 cP, 6 cP, 5 cP, 4 cP, 3 cP, 2 cP, or 1 cP, unless the high concentration composition comprises (i) said viscosity reducing agent or stabilizing agent not found in the comparator composition; or (ii) said increased amount of viscosity modifying agent or stabilizing agent.

903. The high concentration composition of any of embodiments 801 to 902 having long term stability, wherein the composition comprises one or more ionic excipients, wherein said excipients contribute to the composition having conductivity greater than 2.5, 3, 4, 5, 6, 7 or 8; osmolarity of 140 to about 400; and a hydrodynamic diameter of the adalimumab of greater than 4, 5, 6, 7, 8, 9, 10 or 11; and wherein the composition, upon administration to a subject, results in a degree of pain or discomfort no worse than, or better than, that of an AbbVie-supplied Humira® composition, having a concentration of adalimumab greater than 50 mg/mL 904. The high concentration composition of any of embodiments 801 to 903, wherein said composition is substantially free of protein aggregates and/or high molecular weight species.

905. The high concentration composition of any of embodiments 801 to 904, wherein the composition has an absolute viscosity of about 15 cP or less.

906. The high concentration composition of any of embodiments 801 to 905, wherein the composition has an osmolality of about 180 to about 420 mOsM.

907. The high concentration composition of any of embodiments 801 to 906, wherein the composition has a conductivity selected from the group comprising: between about 1 and about 2.5 mS/cm, between about 2.5 and about 3 mS/cm, between about 3 and about 3.5 mS/cm, greater than about 2.5 mS/cm, at least about 3.0 mS/cm, about 3.0 mS/cm, about 3.5 mS/cm, about 4 mS/cm, about 4.4 mS/cm, and about 4.5 mS/cm.

908. The high concentration composition of any of embodiments 801 to 907, wherein the adalimumab has a hydrodynamic diameter selected from the group comprising greater than about 2.5 nm, greater than about 3 nm, greater than about 4 nm, greater than about 4 nm, about 2.5 to about 3 nm, about 3 nm to about 3.5 nm, about 3.5 to about 4 nm, about 3 nm, about 4 nm, about 5 nm, about 6 nm, about 7 nm, about 8 nm, about 9 nm, and about 10 nm.

909. The high concentration composition of any of embodiments 801 to 908, wherein the composition has reduced pain upon injection to a subject as compared to an adalimumab composition comprising citrate.

910. The high concentration composition of any of embodiments 801 to 909, wherein the composition has sizes and amounts of sub-visible particles comparable to, or better than that of a commercially sold Humira® containing adalimumab at concentrations between about 601 to 781 mg/mL.

911. The high concentration composition of any of embodiments 801 to 910, wherein the composition has approximately the same or fewer adalimumab fragments and/or aggregates than commercially sold Humira® containing adalimumab at concentrations between about 50 and 100 mg/mL.

912. The high concentration composition of any of embodiments 801 to 911, wherein the composition has an adalimumab monomer content of at least about 85% monomer.

913. The high concentration composition of any of embodiments 801 to 912, wherein the composition has an adalimumab monomer content of at least about 90% monomer.

914 The high concentration composition of any of embodiments 801 to 913, wherein the composition has an adalimumab monomer content of at least about 95% monomer.

915. The high concentration composition of any of embodiments 801 to 914, wherein the composition is stable at room temperature for at least 10 days.

916. The high concentration composition of any of embodiments 801 to 915, wherein the composition is stable under conditions selected from the group comprising: at least 1 week at 40° C., at least 6-10 days at 30° C., at least 2 weeks at 40'C, at least 4 weeks at 25° C., at least 9 weeks at 25° C., at least 13 weeks at 25° C., at least 13 weeks at 5° C., and at least 26 weeks at 5° C.

917. The high concentration composition of any of embodiments 801 to 916, wherein the composition is stable for at least three months.

918. The high concentration composition of any of embodiments 801 to 917, wherein the composition is stable for at least six months.

919. The high concentration composition of any of embodiments 801 to 918 wherein the composition is stable for at least one year.

920. The high concentration composition of any of embodiments 801 to 919, having a pH of 5 to 6, and prepared by modifying a pre-existing adalimumab formulation having a pH of 5 to 6 and no more than about 50 mg/mL, wherein the modification consists solely of increasing the concentration of adalimumab in the pre-existing formulation to concentration selected from (i) greater than 50 mg/mL and less than or equal to about 200-250 mg/mL; and (ii) about 100 to 250 mg/mL, without altering the identity or concentration of any excipients present in the pre-existing formulation.

921. A prefilled syringe containing the high concentration composition of any of embodiments 801 to 920.

922. A prefilled syringe containing the high concentration composition of embodiment 921 wherein the composition is optionally free of surfactant, and is present in a defined containment volume of the syringe, said containment volume being essentially free of any portion thereof in which the composition is absent.

923. The prefilled syringe of embodiments 921-922 wherein the high concentration composition does not have a polysorbate or polaxamer surfactant.

924. The prefilled syringe of any of embodiments 921-923 where the high concentration composition does not have a surfactant.

925. The prefilled syringe of any of embodiments 921-924 wherein the high concentration composition is isotonic, has conductivity greater than 2.5, and is free of surfactant or free of polyol or free of both.

926. The prefilled syringe of any of embodiments 921-925 wherein the high concentration composition does not contain any of the following buffers: phosphate, pyrophosphate, acetate, citrate, histidine, succinate, adipate, maleate, glutamate, gluconate, or tartrate.

927. The prefilled syringe of any of embodiments 921-926 wherein the high concentration is self-buffering based on the buffer capacity afforded by the adalimumab.

928. A method for preparing a high concentration formulation of any of embodiments 801-920 having a concentration of adalimumab greater than about 50 mg/mL and less than or equal to about 200-250 mg/mL, and a pH of 5 to 6, said method comprising the step of: preparing an adalimumab formulation that is modified over a known adalimumab formulation, said known formulation having a pH of 5 to 6 and comprising no more than about 50 mg/mL, wherein the modification consists solely of increasing the adalimumab concentration of the known formulation to a concentration selected from (i) greater than 50 mg/mL and less than or equal to about 200-250 mg/mL; and (ii) about 100 to 250 mg/mL, without modifying the identity or concentration of any excipients present in the known formulation:

Reserved: Embodiments 929 to 1000

1001. A stable, aqueous pharmaceutical composition comprising adalimumab at a concentration of 100 to 250 mg/ml wherein:

(a) the composition has (I) long term stability comparable to or better than; (ii) viscosity approximately equal to or less than; and (iii) discomfort upon administration lesser than; a commercially sold adalimumb formulation having a concentration of adalimumab not greater than about 50 mg/ml that comprises a combination of citrate and phosphate buffers; mannitol; sodium chloride and PS 80; and (b) the high concentration composition has reduced excipients as compared to the commercially sold adalimumab formulation, said reduction in excipients meeting at least one of the following criteria:

(i) the composition replaces the phosphate and citrate with a different buffer system that does not comprise citrate; and/or (ii) the composition is free of surfactant; and/or (iii) the composition is free of polyol;

1002. The high concentration composition of embodiment 1001 in which all three criteria are met and the composition has an adalimumab concentration selected from 51 mg/mL, 52 mg/mL, 53 mg/mL, 54 mg/mL, 55 mg/mL, 56 mg/mL, 57 mg/ml, 58 mg/ml, 59 mg/ml, 60 mg/mL, 61 mg/ml, 62 mg/mL, 63 mg/ml, 64 mg/mL, 65 mg/ml, 66 mg/mL, 67 mg/mL, 68 mg/mL, 69 mg/ml, 70 mg/mL, 71 mg/ml, 72 mg/ml, 73 mg/mL, 74 mg/mL, 75 mg/mL, 76 mg/mL, 77 mg/mL, 78 mg/ml, 79 mg/mL, 80 mg/mL, 81 mg/mL, 82 mg/mL, 83 mg/mL, 84 mg/mL, 85 mg/mL, 86 mg/mL, 87 mg/mL, 88 mg/mL, 89 mg/mL, 90 mg/mL, 91 mg/mL, 92 mg/mL, 93 mg/mL, 94 mg/mL, 95 mg/mL, 96 mg/mL, 97 mg/mL, 98 mg/mL, 99 mg/mL, 100 mg/ml, 101 mg/ml, 102 mg/mL, 103 mg/ml, 104 mg/mL, 105 mg/mL, 106 mg/mL, 107 mg/mL, 108 mg/mL, 109 mg/mL, 110 mg/mL, 111 mg/mL, 112 mg/mL, 113 mg/mL, 114 mg/mL, 115 mg/mL, 116 mg/mL, 117 mg/mL, 118 mg/mL, 119 mg/mL, 120 mg/mL, 121 mg/mL, 122 mg/mL, 123 mg/mL, 124 mg/mL, 125 mg/mL, 126 mg/mL, 127 mg/mL, 128 mg/mL, 129 mg/mL, 130 mg/mL, 131 mg/mL, 132 mg/mL, 133 mg/mL, 134 mg/mL, 135 mg/mL, 136 mg/mL, 137 mg/mL, 138 mg/mL, 139 mg/mL, 140 mg/mL, 141 mg/mL, 142 mg/mL, 143 mg/mL, 144 mg/mL, 145 mg/mL, 146 mg/mL, 147 mg/mL, 148 mg/mL, 149 mg/mL, 150 mg/mL, 151 mg/mL, 152 mg/mL, 153 mg/mL, 154 mg/mL, 155 mg/mL, 156 mg/mL, 157 mg/mL, 158 mg/mL, 159 mg/mL, 160 mg/mL, 161 mg/mL, 162 mg/mL, 163 mg/mL, 164 mg/mL, 165 mg/mL, 166 mg/mL, 167 mg/mL, 168 mg/mL, 169 mg/mL, 170 mg/mL, 171 mg/mL, 172 mg/mL, 173 mg/mL, 174 mg/mL, 175 mg/mL, 176 mg/mL, 177 mg/mL, 178 mg/mL, 179 mg/mL, 180 mg/mL, 181 mg/mL, 182 mg/mL, 183 mg/mL, 184 mg/mL, 185 mg/mL, 186 mg/mL, 187 mg/mL, 188 mg/mL, 189 mg/mL, 190 mg/mL, 191 mg/mL, 192 mg/mL, 193 mg/mL, 194 mg/mL, 195 mg/mL, 196 mg/mL, 197 mg/mL, 198 mg/mL, 199 mg/mL, and 200 mg/mL.

1003. The high concentration composition of embodiment 1001-1002 comprising at least one amino acid selected from one, or combinations, of arginine, glycine, serine, glutamine, proline, and methionine.

1004. The high concentration composition of embodiment 1003 wherein the amino acid is arginine, glycine or a combination thereof.

1005. The high concentration composition of embodiment 1001 to 1004 comprising sodium chloride or sodium sulfate.

1006. The high concentration composition of embodiment 1001-1002 comprising, consisting of, or consisting essentially of (i) adalimumab, (ii) at least one of sodium chloride and sodium sulfate; (iii) at least one of glycine and arginine; and (iv) at least one of histidine buffer and succinate buffer.

1007. The high concentration composition of embodiment 1006 having a concentration of adalimumab of 100, 125, 150, 175 or 200 mg/mL.

1008. The high concentration composition of embodiments 1001 to 1007, wherein the composition has resistance to aggregation and/or particle formation comparable or better than that of a commercially sold adalimumab composition.

1009. The high concentration composition of any of embodiments 1001 to 1008, wherein the composition is suitable for subcutaneous injection.

1011. The high concentration composition of any of embodiments 1001 to 1009, wherein the composition is suitable for subcutaneous injection and causes no greater degree of pain or discomfort upon administration to a subject than said Humira® composition.

1012. The composition of any of embodiments 1001 to 1009, prepared by modifying a pre-existing adalimumab formulation having no more than about 50 mg/mL, wherein the modification consists solely of increasing the concentration of adalimumab in the pre-existing formulation to a range of about 100 to 200 mg/mL, without altering the identity or concentration of any excipients present in the pre-existing formulation.

1013. A prefilled syringe containing the high concentration composition of any of embodiments 1001 to 1012.

1014. the prefilled syringe of embodiment 1013 wherein the composition is optionally free of surfactant, and is present in a defined containment volume of the syringe, said containment volume being essentially free of any portion thereof in which the composition is absent.

1015. The prefilled syringe of embodiments 1013 to 1014 wherein the high concentration composition does not have a polysorbate or polaxamer surfactant.

1016. The prefilled syringe of any of embodiments 1013-1015 where the high concentration composition does not have a surfactant.

1017. The prefilled syringe of any of embodiments 1013-1016 wherein the high concentration composition is isotonic, has conductivity greater than 2.5, and is free of surfactant or free of polyol or free of both.

1018. The prefilled syringe of any of embodiments 1013-1017 wherein the high concentration composition does not contain any of the following buffers: phosphate, pyrophosphate, acetate, citrate, histidine, succinate, adipate, maleate, glutamate, gluconate, or tartrate.

1019. The prefilled syringe of any of embodiments 1013-1018 wherein the high concentration is self-buffering based on the buffer capacity afforded by the adalimumab.

1020. A method for preparing a high concentration formulation of any of embodiments 1013-1012 having a concentration of adalimumab greater than about 50 mg/mL and less than or equal to about 200-250 mg/mL, and a pH of 5 to 6, said method comprising the step of: preparing an adalimumab formulation that is modified over a known adalimumab formulation, said known formulation having a pH of 5 to 6 and comprising no more than about 50 mg/mL, wherein the modification consists solely of increasing the adalimumab concentration of the known formulation to a concentration selected from (i) greater than 50 mg/mL and less than or equal to about 200-250 mg/mL; and (ii) about 100 to 250 mg/mL, without modifying the identity or concentration of any excipients present in the known formulation.

Reserved: Embodiment 1021 to 1100

1101. An aqueous pharmaceutical composition of any of embodiments 1 to 1100, wherein the composition is suitable for subcutaneous injection.

1102. An aqueous pharmaceutical composition of embodiment 1101, wherein the composition is suitable for subcutaneous self-administration by a subject or subcutaneous automatic-administration by a device.

1103. An aqueous pharmaceutical composition of any of embodiments 1 to 1100, wherein the composition is about 1.5 mL, 1.0 mL, 0.8 mL, 0.5 mL, 0.4 mL, or 0.2 mL.

1104. An article of manufacture comprising a vessel containing an aqueous pharmaceutical composition of any of embodiments 1 to 1100.

1105. A device for administering adalimumab to a subject comprising, a needle and a vessel containing an aqueous pharmaceutical composition of any of embodiments 1 to 1100.

1106. A device of embodiment 1105, wherein the needle is a thin-wall needle or a standard needle.

1107. A device of embodiment 1106, wherein the needle has a gauge of 28 or less.

1108. A device of embodiment 1106, wherein the needle has a gauge selected from the group comprising 25, 26, 27, 28, 29, 30, 31, and 32.

1109. A device of embodiment 1105, wherein the aqueous pharmaceutical composition further comprises a viscosity modifier.

1110. A device of embodiment 1105, wherein the aqueous pharmaceutical composition is free, or substantially free, of surfactant.

1111. A device of embodiment 1105, wherein the vessel is free, or substantially free, of a gas headspace.

1112. A device of embodiment 1105, wherein the gas headspace in the vessel is less than about: 10%, 9%, 8%, 7%, 6%, 5%, 4%, 3%, 2%, or 1% of the volume of the vessel.

1113. A device of embodiment 1105 wherein the needle has a gauge of 28 or less; the aqueous pharmaceutical composition further comprises a viscosity modifier, and is free, or substantially free, of surfactant; and optionally, the vessel is free, or substantially free, of gas headspace.

EXAMPLES

Example 1. Viscosity and Stability Screening of High Concentration Adalimumab Formulations Block AA Study Design Block AA formulations were created to evaluate the viscosity of high concentration adalimumab formulations at pH 5.3. E.g. 100, 150, 200, 225, and 250 mg/mL adalimumab. Upon demonstration of acceptable viscosity, formulations with similar concentrations of adalimumab will be evaluated for stability.

All Block AA formulations comprise a high concentration of adalimumab and are free, or substantially free, of a citrate buffer. Further, these formulations are free, or substantially free, of a phosphate buffer. Some formulations are free of stabilizers, tonicity agents, viscosity agents, salt, polyols, and/or surfactants.

Adalimumab was concentrated to 225 mg/mL to allow for addition of a 3× excipient spike (dilutes protein to 150 mg/mL). Protein (in His buffer, pH 5.25) was concentrated to 225 mg/mL using centrifugal spin concentrators.

| Block 1A Table | | | | | | | | |
|---|---|---|---|---|---|---|---|---|
| Form No | protien (mg/ml) | His (mM) | NaCl (mM) | Gly (nM) | Arg (mM) | Mannitol (mM) | Trehalose (mM) | PS80 (w/v %) |
| AA-1 | 150 | 20 | 44 | 160 | 0 | 0 | 0 | 0.10% |
| AA-2 | 150 | 20 | 44 | 160 | 0 | 0 | 0 | 0.00% |
| AA-3 | 100 | 20 | 44 | 160 | 0 | 0 | 0 | 0.10% |
| AA-4 | 100 | 20 | 44 | 160 | 0 | 0 | 0 | 0.00% |
| AA-5 | 150 | 20 | 140 | 0 | 0 | 0 | 0 | 0.10% |
| AA-6 | 150 | 20 | 140 | 0 | 0 | 0 | 0 | 0.00% |
| AA-7 | 150 | 20 | 44 | 130 | 25 | 0 | 0 | 0.10% |
| AA-8 | 150 | 20 | 44 | 0 | 160 | 0 | 0 | 0.10% |
| AA-9 | 100 | 20 | 44 | 130 | 25 | 0 | 0 | 0.10% |
| AA-10 | 100 | 20 | 44 | 130 | 25 | 0 | 0 | 0.00% |
| AA-11 | 150 | 20 | 44 | 0 | 0 | 160 | 0 | 0.10% |
| AA-12 | 150 | 20 | 44 | 0 | 0 | 0 | 160 | 0.10% |
| AA-13 | 100 | 20 | 44 | 0 | 0 | 160 | 0 | 0.10% |
| AA-14 | 100 | 20 | 44 | 0 | 0 | 160 | 0 | 0.00% |
| AA-15 | 200 | 30 | 0 | 0 | 0 | 0 | 0 | 0.00% |
| AA-16 | 225 | 30 | 0 | 0 | 0 | 0 | 0 | 0.00% |
| AA-17 | 250 | 30 | 0 | 0 | 0 | 0 | 0 | 0.00% |

Concentration, pH, and Viscosity Screens

High concentration of adalimumab formulations were evaluated to determine the adalimumab concentration, pH, and viscosity. Viscosities were evaluated at shear rates for 500 l/s, except for formulation AA-1 which was evaluated at 1000 l/s. Results for Block AA formulations are described below.

| Block AA Formulations at 150 mg/mL or greater | | | |
|---|---|---|---|
| Form No | Measured protein conc. (mg/mL) | Measured pH | Viscosity (mPs · s) |
| AA-1 | 155.0 | 5.35 | 5.0 |
| AA-2 | 154.2 | 5.35 | 5.9 |
| AA-5 | 155.2 | 5.39 | 6.8 |
| AA-6 | 154.1 | 5.4 | 7.1 |
| AA-7 | 154.3 | 5.36 | 6.2 |
| AA-8 | 155.9 | 5.38 | 5.7 |
| AA-11 | 154.8 | 5.34 | 6.0 |
| AA-12 | 155.5 | 5.34 | 6.7 |
| AA-15 | 195.6 | — | 11.3 |
| AA-16 | 227.0 | — | 26.4 |
| AA-17 | 248.4 | — | 44.6 |

All formulations were within 4% of their target concentration. All 150 mg/mL formulations were well below 20 mPa·s. In fact, all were below 7.2 mPa·s. Even as the concentration of adalimumab was raised to 200, 225, and 250 mg/mL, the viscosity remained below 50 mPa·s.

| Block AA Formulations at 100 mg/mL | | | |
|---|---|---|---|
| Form No | Nominal protein conc. (mg/mL) | Measured pH | Viscosity (mPs · s) |
| AA-3 | 100 | 5.32 | 2.42 |
| AA-4 | 100 | 5.40 | 2.63 |
| AA-9 | 100 | 5.41 | 2.79 |
| AA-10 | 100 | 5.41 | 2.52 |
| AA-13 | 100 | 5.40 | 2.54 |
| AA-14 | 100 | 5.41 | 2.53 |

All 100 mg/mL formulations were well below 20 mPa·s. In fact, all were below 3.0 mPa·s.

These results demonstate that high concentration adalimumab formulations have viscosities that are suitable for injection.

Stability Studies

Formulations AA-1 through AA-14 were examined in a 4 week stability study. Samples were stored for 2 weeks at 40° C. and for 4 weeks at 25° C. Various measurements were taken at t0, t2 (2 weeks at 40° C.), and t4 (4 weeks at 25° C.). Measurements included MFI, viscosity, conductivity, pH, A280, RP, SEC, and CEX.

Block AA Viscosity and Conductivity at t0

| Form No | Target Conc. (mg/mL) | Measured Conc. (mg/mL) | Viscosity (mPa·s) | Conductivity (mS/cm) |
|---|---|---|---|---|
| AA-1 | 150 | 155.0 | 5.0 | 6.38 |
| AA-2 | 150 | 154.2 | 5.9 | 6.21 |
| AA-3 | 100 | 103.6 | 2.4 | 6.41 |
| AA-4 | 100 | 102.0 | 2.6 | 6.39 |
| AA-5 | 150 | 155.2 | 6.8 | 14.00 |
| AA-6 | 150 | 154.1 | 7.1 | 13.97 |
| AA-7 | 150 | 154.3 | 6.2 | 7.46 |
| AA-8 | 150 | 155.9 | 5.7 | 14.28 |
| AA-9 | 100 | 100.8 | 2.8 | 7.93 |
| AA-10 | 100 | 100.0 | 2.5 | 7.92 |
| AA-11 | 150 | 154.8 | 6.0 | 5.64 |
| AA-12 | 150 | 155.5 | 6.7 | 5.30 |
| AA-13 | 100 | 98.5 | 2.5 | 5.96 |
| AA-14 | 100 | 98.5 | 2.5 | 5.99 |

Viscosities were evaluated at shear rates for 500 1/s, except for formulation AA-1 which was evaluated at 1000 1/s. At t0, all high concentration adalimumab formulations had acceptable concentrations of adalimumab and low viscosities. As a result of the formulations containing ionic excipients (e.g. buffer, salt), all high concentration adalimumab formulations had a conductivity of greater than 3.0 mS/cm.

Block AA pH stability

| Form No | t0 pH | t2 pH | t4 pH |
|---|---|---|---|
| AA-1 | 5.42 | 5.39 | 5.40 |
| AA-2 | 5.43 | 5.39 | 5.42 |
| AA-3 | 5.32 | 5.29 | 5.30 |
| AA-4 | 5.40 | 5.35 | 5.38 |
| AA-5 | 5.48 | 5.44 | 5.47 |
| AA-6 | 5.47 | 5.44 | 5.45 |
| AA-7 | 5.44 | 5.42 | 5.41 |
| AA-8 | 5.45 | 5.43 | 5.41 |
| AA-9 | 5.41 | 5.38 | 5.37 |
| AA-10 | 5.41 | 5.39 | 5.37 |
| AA-11 | 5.42 | 5.40 | 5.39 |
| AA-12 | 5.42 | 5.39 | 5.39 |
| AA-13 | 5.40 | 5.37 | 5.35 |
| AA-14 | 5.41 | 5.37 | 5.35 |

The pH of all high concentration adalimumab formulations was stable.

Concentration Stability Studies

Concentration of adalimumab was measured by A280. The experimental procedure included correcting for scattering by subtracting (directly) A320. Samples diluted to ~0.3 mg/mL in water for A280 measurement.

Block AA concentrations at t0, t2, and t4

| Form No | Conc t0 (mg/mL) | Conc t2 (mg/mL) | Conc t4 (mg/mL) |
|---|---|---|---|
| AA-1 | 153.3 | 150.5 | 149.8 |
| AA-2 | 151.3 | 148.9 | 141.6 |
| AA-3 | 103.6 | 102.7 | 103.5 |
| AA-4 | 102.0 | 101.7 | 101.3 |
| AA-5 | 150.4 | 149.3 | 151.9 |
| AA-6 | 147.3 | 148.1 | 149.2 |
| AA-7 | 150.1 | 148.9 | 151.6 |
| AA-8 | 151.1 | 150.8 | 150.4 |
| AA-9 | 100.8 | 100.7 | 103.1 |
| AA-10 | 100.0 | 100.6 | 101.8 |
| AA-11 | 148.1 | 149.5 | 150.9 |
| AA-12 | 148.2 | 149.1 | 151.3 |
| AA-13 | 98.5 | 102.2 | 104.8 |
| AA-14 | 98.5 | 100.6 | 101.0 |

The concentration of adalimumab in all high concentration adalimumab formulations was stable.

CEX Stability Studies

Stability of adalimumab in high concentration formulations was evaluated by CEX. The tables below list the relative peak areas for the main peak (MP), the acidic region (pre-MP), and the basic region (post-MP). The delta (Δ) is the difference in relative peak area between t0 and t2 or t4.

Block AA CEX t0 and t2

| Form No | t0 MP | t2 MP | Δ MP | t0 Acidic | t2 Acidic | Δ Acidic | t0 Basic | t2 Basic | Δ Basic |
|---|---|---|---|---|---|---|---|---|---|
| AA-1 | 75.44 | 62.21 | 13.23 | 17.33 | 26.94 | 9.60 | 7.23 | 10.85 | 3.62 |
| AA-2 | 75.51 | 63.96 | 11.55 | 17.28 | 25.25 | 7.97 | 7.21 | 10.79 | 3.58 |
| AA-3 | 75.54 | 61.93 | 13.61 | 17.24 | 26.83 | 9.59 | 7.22 | 11.24 | 4.02 |
| AA-4 | 75.33 | 63.33 | 12.01 | 17.46 | 25.76 | 8.30 | 7.21 | 10.92 | 3.71 |
| AA-5 | 75.53 | 64.09 | 11.44 | 17.25 | 24.82 | 7.57 | 7.22 | 11.10 | 3.87 |
| AA-6 | 75.47 | 64.66 | 10.81 | 17.32 | 24.26 | 6.93 | 7.20 | 11.08 | 3.88 |
| AA-7 | 75.52 | 62.05 | 13.47 | 17.28 | 26.78 | 9.50 | 7.20 | 11.17 | 3.96 |
| AA-8 | 75.69 | 64.12 | 11.57 | 17.10 | 24.63 | 7.52 | 7.20 | 11.25 | 4.05 |
| AA-9 | 75.26 | 62.90 | 12.35 | 17.55 | 26.04 | 8.49 | 7.20 | 11.06 | 3.86 |
| AA-10 | 75.31 | 63.77 | 11.54 | 17.48 | 25.25 | 7.77 | 7.21 | 10.99 | 3.77 |
| AA-11 | 75.52 | 63.57 | 11.95 | 17.20 | 25.36 | 8.17 | 7.28 | 11.06 | 3.78 |
| AA-12 | 75.46 | 62.60 | 12.86 | 17.34 | 26.46 | 9.12 | 7.20 | 10.94 | 3.74 |
| AA-13 | 75.51 | 63.26 | 12.25 | 17.28 | 25.58 | 8.30 | 7.21 | 11.16 | 3.95 |
| AA-14 | 75.29 | 63.75 | 11.54 | 17.47 | 25.13 | 7.67 | 7.25 | 11.12 | 3.87 |

| Block AA CEX t0 and t4 | | | | | | | | | |
|---|---|---|---|---|---|---|---|---|---|
| Form No | t0 MP | t4 MP | Δ MP | t0 Acidic | t4 Acidic | Δ Acidic | t0 Basic | t4 Basic | Δ Basic |
| AA-1 | 75.44 | 71.36 | 4.08 | 17.33 | 20.08 | 2.75 | 7.23 | 8.57 | 1.34 |
| AA-2 | 75.51 | 72.18 | 3.33 | 17.28 | 19.30 | 2.02 | 7.21 | 8.52 | 1.31 |
| AA-3 | 75.54 | 71.58 | 3.96 | 17.24 | 19.77 | 2.53 | 7.22 | 8.65 | 1.43 |
| AA-4 | 75.33 | 72.22 | 3.12 | 17.46 | 19.27 | 1.81 | 7.21 | 8.51 | 1.31 |
| AA-5 | 75.53 | 72.42 | 3.10 | 17.25 | 19.01 | 1.76 | 7.22 | 8.57 | 1.34 |
| AA-6 | 75.47 | 72.72 | 2.75 | 17.32 | 18.74 | 1.42 | 7.20 | 8.54 | 1.33 |
| AA-7 | 75.52 | 71.84 | 3.67 | 17.28 | 19.66 | 2.38 | 7.20 | 8.50 | 1.30 |
| AA-8 | 75.69 | 72.26 | 3.44 | 17.10 | 19.10 | 2.00 | 7.20 | 8.65 | 1.44 |
| AA-9 | 75.26 | 71.82 | 3.44 | 17.55 | 19.64 | 2.09 | 7.20 | 8.54 | 1.34 |
| AA-10 | 75.31 | 72.37 | 2.94 | 17.48 | 19.14 | 1.66 | 7.21 | 8.48 | 1.27 |
| AA-11 | 75.52 | 72.44 | 3.08 | 17.20 | 18.97 | 1.77 | 7.28 | 8.59 | 1.31 |
| AA-12 | 75.46 | 71.90 | 3.56 | 17.34 | 16.56 | 2.21 | 7.20 | 8.54 | 1.34 |
| AA-13 | 75.51 | 72.24 | 3.27 | 17.28 | 19.20 | 1.92 | 7.21 | 8.56 | 1.35 |
| AA-14 | 75.29 | 72.57 | 2.72 | 17.47 | 18.90 | 1.44 | 7.25 | 8.53 | 1.28 |

The CEX results show surprisingly that high concentration adalimumab formulations with surfactant (e.g. 0.1% Polysorbate 80) degraded faster than identical formulations without surfactant.

High concentration adalimumab formulations with NaCl; NaCl and Arg; and NaCl and Mannitol formulations had the smallest change in the main peak after storage for 4 weeks 25° C. Slight Increases were seen in both acidic and basic regions of CEX chromatogram for formulations. This may be a result of deamidation, leading to acidic peak increases, and clipping or aggregates leading to basic peak increases. Despite these small changes, all that high concentration adalimumab formulations demonstrated suitable stability.

SEC Stability Studies

Stability of adalimumab in high concentration formulations was evaluated by SEC. The tables below list the relative peak areas for the main peak (MP), high molecular weight species (HMW), and low molecular weight species (LMW). The delta (Δ) is the difference in relative peak area between t0 and t2 or t4.

| Block AA SEC t0 and t2 | | | | | | | | | |
|---|---|---|---|---|---|---|---|---|---|
| Form No | t0 MP | t2 MP | Δ MP | HMW t0 | HMW t2 | Δ HMW | LMW t0 | LMW t2 | Δ LMW |
| AA-1 | 99.34 | 98.05 | 1.28 | 0.12 | 0.55 | 0.43 | 0.54 | 1.40 | 0.86 |
| AA-2 | 99.35 | 98.33 | 1.02 | 0.11 | 0.36 | 0.25 | 0.54 | 1.31 | 0.77 |
| AA-3 | 99.36 | 98.17 | 1.19 | 0.08 | 0.36 | 0.28 | 0.56 | 1.47 | 0.91 |
| AA-4 | 99.34 | 98.43 | 0.91 | 0.09 | 0.24 | 0.15 | 0.57 | 1.33 | 0.76 |
| AA-5 | 99.32 | 98.12 | 1.21 | 0.13 | 0.50 | 0.37 | 0.55 | 1.38 | 0.83 |
| AA-6 | 99.34 | 98.26 | 1.09 | 0.12 | 0.42 | 0.30 | 0.54 | 1.33 | 0.79 |
| AA-7 | 99.34 | 98.10 | 1.24 | 0.11 | 0.48 | 0.37 | 0.54 | 1.42 | 0.88 |
| AA-8 | 99.37 | 98.18 | 1.19 | 0.09 | 0.42 | 0.33 | 0.53 | 1.40 | 0.87 |
| AA-9 | 99.30 | 98.30 | 0.99 | 0.09 | 0.32 | 0.23 | 0.61 | 1.38 | 0.76 |
| AA-10 | 99.31 | 98.44 | 0.87 | 0.08 | 0.23 | 0.15 | 0.61 | 1.33 | 0.72 |
| AA-11 | 99.35 | 98.24 | 1.11 | 0.12 | 0.45 | 0.33 | 0.53 | 1.31 | 0.78 |
| AA-12 | 99.29 | 98.23 | 1.06 | 0.12 | 0.46 | 0.34 | 0.58 | 1.31 | 0.72 |
| AA-13 | 99.23 | 98.36 | 0.88 | 0.10 | 0.30 | 0.20 | 0.67 | 1.34 | 0.67 |
| AA-14 | 99.33 | 98.42 | 0.92 | 0.11 | 0.25 | 0.14 | 0.56 | 1.33 | 0.77 |

| Block AA SEC t0 and t2 | | | | | | | | | |
|---|---|---|---|---|---|---|---|---|---|
| Form No | t0 MP | t4 MP | Δ MP | HMW t0 | HMW t4 | Δ HMW | LMW t0 | LMW t4 | Δ LMW |
| AA-1 | 99.34 | 98.6 | 0.38 | 0.12 | 0.29 | 0.17 | 0.54 | 0.75 | 0.21 |
| AA-2 | 99.35 | 99.06 | 0.29 | 0.11 | 0.22 | 0.11 | 0.54 | 0.72 | 0.18 |
| AA-3 | 99.36 | 99.03 | 0.33 | 0.08 | 0.18 | 0.10 | 0.56 | 0.79 | 0.23 |
| AA-4 | 99.34 | 99.13 | 0.21 | 0.09 | 0.15 | 0.07 | 0.57 | 0.72 | 0.15 |
| AA-5 | 99.32 | 98.97 | 0.35 | 0.13 | 0.29 | 0.16 | 0.55 | 0.74 | 0.19 |
| AA-6 | 99.34 | 99.01 | 0.34 | 0.12 | 0.25 | 0.13 | 0.54 | 0.74 | 0.21 |
| AA-7 | 99.34 | 99.00 | 0.35 | 0.11 | 0.25 | 0.14 | 0.54 | 0.75 | 0.21 |
| AA-8 | 99.37 | 99.03 | 0.35 | 0.09 | 0.21 | 0.12 | 0.53 | 0.76 | 0.23 |
| AA-9 | 99.30 | 99.05 | 0.25 | 0.09 | 0.18 | 0.09 | 0.61 | 0.77 | 0.16 |
| AA-10 | 99.31 | 99.10 | 0.21 | 0.08 | 0.15 | 0.07 | 0.61 | 0.75 | 0.14 |
| AA-11 | 99.35 | 99.02 | 0.32 | 0.12 | 0.25 | 0.13 | 0.53 | 0.72 | 0.19 |
| AA-12 | 99.29 | 99.01 | 0.28 | 0.12 | 0.27 | 0.14 | 0.58 | 0.72 | 0.14 |

| Block AA SEC t0 and t2 | | | | | | | | |
|---|---|---|---|---|---|---|---|---|
| Form No | t0 MP | t4 MP | Δ MP | HMW t0 | HMW t4 | Δ HMW | LMW t0 | LMW t4 | Δ LMW |
| AA-13 | 99.23 | 99.09 | 0.14 | 0.10 | 0.18 | 0.08 | 0.67 | 0.73 | 0.06 |
| AA-14 | 99.33 | 99.06 | 0.27 | 0.11 | 0.16 | 0.05 | 0.56 | 0.78 | 0.22 |

Note: the header row above has 10 columns but the Form No column is separate. Reading: Form No, t0 MP, t4 MP, Δ MP, HMW t0, HMW t4, Δ HMW, LMW t0, LMW t4, Δ LMW.

The SEC results show surprisingly that high concentration adalimumab formulations with surfactant (e.g. 0.1% Polysorbate 80) degraded faster than identical formulations without surfactant.

Only small changes were observed in these formulations demonstrating that the high concentration adalimumab formulations are stable.

Particle Stability Studies

Stability of adalimumab in high concentration formulations was evaluated by measuring the size and number of particles by MFI. Sample of 1.3 mL (nominal) were evaluated by MFI analysis.

| Block AA MFi t0 | | | | | | |
|---|---|---|---|---|---|---|
| | Total (particles/mL) | | | Circularity <0.9; Particles/mL | | |
| Form No | ≥5 μm | ≥10 μm | ≥25 μm | ≥5 μm | ≥10 μm | ≥25 μm |
| AA-1 | 95 | 15 | 0 | 54 | 8 | 0 |
| AA-2 | 2066 | 660 | 77 | 2002 | 638 | 76 |
| AA-3 | 174 | 13 | 0 | 89 | 9 | 0 |
| AA-4 | 1651 | 807 | 117 | 1630 | 803 | 117 |
| AA-5 | 95 | 4 | 0 | 47 | 4 | 0 |
| AA-6 | 4455 | 824 | 97 | 4446 | 824 | 97 |
| AA-7 | 88 | 2 | 0 | 53 | 0 | 0 |
| AA-8 | 136 | 0 | 0 | 81 | 0 | 0 |
| AA-9 | 172 | 9 | 0 | 111 | 6 | 0 |
| AA-10 | 1576 | 1003 | 311 | 1576 | 1003 | 311 |
| AA-11 | 68 | 8 | 0 | 35 | 6 | 0 |
| AA-12 | 72 | 6 | 0 | 46 | 6 | 0 |
| AA-13 | 128 | 0 | 0 | 79 | 0 | 0 |
| AA-14 | 202 | 57 | 4 | 197 | 57 | 4 |

Unexpectedly high particles counts (≥10 μm=4878 particles/mL) were observed in formulation AA-6 at 4 weeks. While this formulation does not contain a surfactant, other formulations without surfactant (e.g. AA-2, AA-4, AA-10, AA-14) did not have high particle counts. In fact, particle counts for particles ≥10 μm and ≥25 μm were generally low in all high concentration adalimumab formulations. These results demonstrating that the high concentration adalimumab formulations are stable.

In conclusion, high concentration adalimumab formulations have suitable viscosity for administration via a needle (e.g. subcutaneous administration) and are stable as demonstrated by pH, IEX, SEC, and MFI analyses.

Example 2. Stable High Concentration Adalimumab Formulations—Block 1

Block 1 Study Design

All Block 1 formulations comprise a high concentration of adalimumab and are free, or substantially free, of a citrate buffer. Further, these formulations are free, or substantially free, of a phosphate buffer. The majority of Block1 formulations contain a buffer, either succinate or histidine. Optionally, some formulations (e.g. 1A-26 and 1B-26) do not contain a buffer, but are self-buffering as result of high concentrations of adalimumab and polyol.

Examples of Block 1 formulations are set forth In the tables below. Block 1A formulations comprise adalimumab at about 100 mg/mL and Block 1B formulations comprise adalimumab at about 150 mg/mL. Blocks 1A and 1B also include 50 mg/mL formulations as controls (1A-22, 1A-23, 1B-22, and 1B-23).

| Block AA MFi t4 | | | | | | | | |
|---|---|---|---|---|---|---|---|---|
| | Total (particles/mL) | | | | Circularity <0.9; Particles/mL | | | |
| Form No | ≥2 μm | ≥5 μm | ≥10 μm | ≥25 μm | ≥2 μm | ≥5 μm | ≥10 μm | ≥25 μm |
| AA-1 | 2396 | 299 | 5 | 0 | 1860 | 177 | 0 | 0 |
| AA-2 | 14171 | 4334 | 1235 | 95 | 14121 | 4325 | 1233 | 95 |
| AA-3 | 5605 | 563 | 27 | 0 | 4210 | 271 | 10 | 0 |
| AA-4 | 12094 | 2692 | 614 | 108 | 12032 | 2684 | 614 | 108 |
| AA-5 | 2704 | 344 | 16 | 0 | 2130 | 190 | 7 | 0 |
| AA-6 | 38864 | 14784 | 4878 | 371 | 38713 | 14750 | 4874 | 371 |
| AA-7 | 1910 | 191 | 12 | 3 | 1500 | 95 | 7 | 3 |
| AA-8 | 4005 | 400 | 12 | 2 | 3254 | 216 | 3 | 2 |
| AA-9 | 3450 | 286 | 14 | 2 | 2604 | 144 | 7 | 2 |
| AA-10 | 12582 | 2662 | 570 | 65 | 12513 | 2657 | 570 | 65 |
| AA-11 | 1931 | 236 | 5 | 0 | 1528 | 153 | 5 | 0 |
| AA-12 | 1484 | 156 | 7 | 5 | 1225 | 102 | 7 | 5 |
| AA-13 | 4456 | 419 | 9 | 0 | 3415 | 201 | 2 | 0 |
| AA-14 | 10522 | 2185 | 395 | 35 | 10493 | 2178 | 395 | 35 |

Block 1A Table

| Form. No. | pH | protien (mg/mL) | Succinate (mM) | His (mM) | Gly (mM) | Arg (mM) | mannitol (mM) | NaCl (mM) | PS 80 (wt %) |
|---|---|---|---|---|---|---|---|---|---|
| 1A-1 | 5.2 | 100 | 0 | 30 | 160 | 0 | 0 | 44 | 0.1 |
| 1A-2 | 5.2 | 100 | 0 | 30 | 160 | 0 | 0 | 44 | 0.02 |
| 1A-3 | 5.2 | 100 | 0 | 30 | 0 | 0 | 160 | 44 | 0.1 |
| 1A-4 | 5.2 | 100 | 0 | 30 | 0 | 0 | 160 | 44 | 0.02 |
| 1A-5 | 5.2 | 100 | 0 | 30 | 192 | 0 | 0 | 27 | 0.1 |
| 1A-6 | 5.2 | 100 | 0 | 30 | 192 | 0 | 0 | 27 | 0.02 |
| 1A-7 | 5.2 | 100 | 0 | 30 | 0 | 0 | 192 | 27 | 0.1 |
| 1A-8 | 5.2 | 100 | 0 | 30 | 0 | 0 | 192 | 27 | 0.02 |
| 1A-9 | 5.2 | 100 | 0 | 30 | 216 | 0 | 0 | 13 | 0.1 |
| 1A-10 | 5.2 | 100 | 0 | 30 | 216 | 0 | 0 | 13 | 0.02 |
| 1A-11 | 5.2 | 100 | 0 | 30 | 0 | 0 | 216 | 13 | 0.1 |
| 1A-12 | 5.2 | 100 | 0 | 30 | 0 | 0 | 216 | 13 | 0.02 |
| 1A-13 | 5.2 | 100 | 0 | 30 | 90 | 0 | 150 | 13 | 0.1 |
| 1A-14 | 5.2 | 100 | 0 | 30 | 240 | 0 | 0 | 13 | 0 |
| 1A-15 | 5.2 | 100 | 0 | 30 | 120 | 80 | 0 | 0 | 0.1 |
| 1A-16 | 5.2 | 100 | 15 | 30 | 90 | 80 | 0 | 0 | 0.1 |
| 1A-17 | 5.2 | 100 | 0 | 30 | 0 | 0 | 240 | 13 | 0.1 |
| 1A-18 | 5.2 | 100 | 0 | 30 | 0 | 50 | 160 | 13 | 0.1 |
| 1A-19 | 5.2 | 100 | 0 | 30 | 90 | 100 | 0 | 0 | 0.1 |
| 1A-20 | 5.4 | 100 | 0 | 30 | 120 | 80 | 0 | 0 | 0.1 |
| 1A-21 | 5.2 | 100 | 0 | 30 | 120 | 0 | 0 | 50 | 0.01 |
| 1A-22 | 5.3 | 50 | 0 | 30 | 160 | 0 | 0 | 44 | 0.1 |
| 1A-23 | 5.3 | 50 | 0 | 30 | 160 | 0 | 160 | 44 | 0.1 |
| 1A-24 | 5.3 | 100 | 0 | 30 | 160 | 0 | 0 | 44 | 0.1 |
| 1A-25 | 5.3 | 100 | 0 | 30 | 160 | 0 | 160 | 44 | 0.1 |
| 1A-26 | 5.3 | 100 | 0 | 0 | 0 | 0 | 231 | 0 | 0.1 |
| 1A-27 | 5.3 | 100 | 0 | 30 | 160 | 44 | 0 | 44 | 0.1 |
| 1A-28 | 5.3 | 100 | 0 | 30 | 0 | 140 | 0 | 140 | 0.1 |
| 1A-29 | 5.3 | 100 | 0 | 30 | 240 | 0 | 0 | 0 | 0.1 |
| 1A-30 | 5.3 | 100 | 0 | 30 | 160 | 25 | 0 | 25 | 0.1 |
| 1A-31 | 5.3 | 100 | 0 | 200 | 200 | 0 | 0 | 44 | 0.1 |
| 1A-32 | 5.3 | 100 | 0 | 20 | 200 | 0 | 0 | 44 | 0.02 |
| 1A-33 | 5.3 | 100 | 0 | 20 | 0 | 0 | 200 | 44 | 0.1 |
| 1A-34 | 5.3 | 100 | 0 | 20 | 0 | 0 | 200 | 44 | 0.02 |
| 1A-35 | 5.3 | 100 | 0 | 20 | 230 | 0 | 0 | 27 | 0.1 |
| 1A-36 | 5.3 | 100 | 0 | 20 | 230 | 0 | 0 | 27 | 0.02 |
| 1A-37 | 5.3 | 100 | 0 | 20 | 0 | 0 | 230 | 27 | 0.1 |
| 1A-38 | 5.3 | 100 | 0 | 20 | 0 | 0 | 230 | 27 | 0.02 |
| 1A-39 | 5.3 | 100 | 0 | 20 | 255 | 0 | 0 | 13 | 0.1 |
| 1A-40 | 5.3 | 100 | 0 | 20 | 255 | 0 | 0 | 13 | 0.02 |
| 1A-41 | 5.3 | 100 | 0 | 20 | 0 | 0 | 255 | 13 | 0.1 |
| 1A-42 | 5.3 | 100 | 0 | 20 | 0 | 0 | 255 | 13 | 0.02 |

Block 1B Table

| Form. No. | pH | protien (mg/mL) | Succinate (mM) | His (mM) | Gly (mM) | Arg (mM) | mannitol (mM) | NaCl (mM) | PS 80 (wt %) |
|---|---|---|---|---|---|---|---|---|---|
| 1B-1 | 5.2 | 150 | 0 | 30 | 160 | 0 | 0 | 44 | 0.1 |
| 1B-2 | 5.2 | 150 | 0 | 30 | 160 | 0 | 0 | 44 | 0.02 |
| 1B-3 | 5.2 | 150 | 0 | 30 | 0 | 0 | 160 | 44 | 0.1 |
| 1B-4 | 5.2 | 150 | 0 | 30 | 0 | 0 | 160 | 44 | 0.02 |
| 1B-5 | 5.2 | 150 | 0 | 30 | 192 | 0 | 0 | 27 | 0.1 |
| 1B-6 | 5.2 | 150 | 0 | 30 | 192 | 0 | 0 | 27 | 0.02 |
| 1B-7 | 5.2 | 150 | 0 | 30 | 0 | 0 | 192 | 27 | 0.1 |
| 1B-8 | 5.2 | 150 | 0 | 30 | 0 | 0 | 192 | 27 | 0.02 |
| 1B-9 | 5.2 | 150 | 0 | 30 | 216 | 0 | 0 | 13 | 0.1 |
| 1B-10 | 5.2 | 150 | 0 | 30 | 216 | 0 | 0 | 13 | 0.02 |
| 1B-11 | 5.2 | 150 | 0 | 30 | 0 | 0 | 216 | 13 | 0.1 |
| 1B-12 | 5.2 | 150 | 0 | 30 | 0 | 0 | 216 | 13 | 0.02 |
| 1B-13 | 5.2 | 150 | 0 | 30 | 90 | 0 | 150 | 13 | 0.1 |
| 1B-14 | 5.2 | 150 | 0 | 30 | 240 | 0 | 0 | 13 | 0 |
| 1B-15 | 5.2 | 150 | 0 | 30 | 120 | 80 | 0 | 0 | 0.1 |
| 1B-16 | 5.2 | 150 | 15 | 30 | 90 | 80 | 0 | 0 | 0.1 |
| 1B-17 | 5.2 | 150 | 0 | 30 | 0 | 0 | 240 | 13 | 0.1 |
| 1B-18 | 5.2 | 150 | 0 | 30 | 0 | 50 | 160 | 13 | 0.1 |
| 1B-19 | 5.2 | 150 | 0 | 30 | 90 | 100 | 0 | 0 | 0.1 |
| 1B-20 | 5.4 | 150 | 0 | 30 | 120 | 80 | 0 | 0 | 0.1 |
| 1B-21 | 5.2 | 150 | 0 | 30 | 120 | 0 | 0 | 50 | 0.01 |
| 1B-22 | 5.3 | 50 | 0 | 30 | 160 | 0 | 0 | 44 | 0.1 |
| 1B-23 | 5.3 | 50 | 0 | 30 | 160 | 0 | 160 | 44 | 0.1 |

-continued

Block 1B Table

| Form. No. | pH | protien (mg/mL) | Succinate (mM) | His (mM) | Gly (mM) | Arg (mM) | mannitol (mM) | NaCl (mM) | PS 80 (wt %) |
|---|---|---|---|---|---|---|---|---|---|
| 1B-24 | 5.3 | 150 | 0 | 30 | 160 | 0 | 0 | 44 | 0.1 |
| 1B-25 | 5.3 | 150 | 0 | 30 | 160 | 0 | 160 | 44 | 0.1 |
| 1B-26 | 5.3 | 150 | 0 | 0 | 0 | 0 | 231 | 0 | 0.1 |
| 1B-27 | 5.3 | 150 | 0 | 30 | 160 | 44 | 0 | 44 | 0.1 |
| 1B-28 | 5.3 | 150 | 0 | 30 | 0 | 140 | 0 | 140 | 0.1 |
| 1B-29 | 5.3 | 150 | 0 | 30 | 240 | 0 | 0 | 0 | 0.1 |
| 1B-30 | 5.3 | 150 | 0 | 30 | 160 | 25 | 0 | 25 | 0.1 |
| 1B-31 | 5.3 | 150 | 0 | 200 | 200 | 0 | 0 | 44 | 0.1 |
| 1B-32 | 5.3 | 150 | 0 | 20 | 200 | 0 | 0 | 44 | 0.02 |
| 1B-33 | 5.3 | 150 | 0 | 20 | 0 | 0 | 200 | 44 | 0.1 |
| 1B-34 | 5.3 | 150 | 0 | 20 | 0 | 0 | 200 | 44 | 0.02 |
| 1B-35 | 5.3 | 150 | 0 | 20 | 230 | 0 | 0 | 27 | 0.1 |
| 1B-36 | 5.3 | 150 | 0 | 20 | 230 | 0 | 0 | 27 | 0.02 |
| 1B-37 | 5.3 | 150 | 0 | 20 | 0 | 0 | 230 | 27 | 0.1 |
| 1B-38 | 5.3 | 150 | 0 | 20 | 0 | 0 | 230 | 27 | 0.02 |
| 1B-39 | 5.3 | 150 | 0 | 20 | 255 | 0 | 0 | 13 | 0.1 |
| 1B-40 | 5.3 | 150 | 0 | 20 | 255 | 0 | 0 | 13 | 0.02 |
| 1B-41 | 5.3 | 150 | 0 | 20 | 0 | 0 | 255 | 13 | 0.1 |
| 1B-42 | 5.3 | 150 | 0 | 20 | 0 | 0 | 255 | 13 | 0.02 |

The formulations in Block 1A Table and Block 1B Table do not contain a citrate buffer or a phosphate buffer. It is expected that high concentration adalimumab formulations in Block 1A (100 mg/mL) and 1B (150 mg/mL) exhibit stability and viscosity comparable to, or better, other formulations at 50 mg/mL or 100 mg/mL (e.g. commercial adalimumab formulations). However, if desired, further improvements in stability or viscosity may be achieved by adding additional stabilizers or viscosity modifiers.

Characterization and Stability Studies

Block 1 formulations were examined in a 4 week stability study. Samples were stored for 2 weeks at 40° C. and for 4 weeks at 25° C. Various measurements were taken at t0, t2 (2 weeks at 40° C.), and t4 (4 weeks at 25° C.). Measurements included MFI, viscosity, conductivity, pH, A280, RP, SEC, and CEX.

Block 1 Viscosity and Conductivity at t0

| Form No | Viscosity (mPa · S) | Conductivity (mS/cm) |
|---|---|---|
| 1A-31 | 2.26 | 5.81 |
| 1A-32 | 2.32 | 5.91 |
| 1A-33 | 2.62 | 5.51 |
| 1A-34 | 2.61 | 5.50 |
| 1A-35 | 2.38 | 4.55 |
| 1A-36 | 2.35 | 4.61 |
| 1A-37 | 2.65 | 4.12 |
| 1A-38 | 2.67 | 4.12 |
| 1A-39 | 2.36 | 3.33 |
| 1A-40 | 2.34 | 3.34 |
| 1A-41 | 2.67 | 3.04 |
| 1A-42 | 2.64 | 3.05 |

Viscosities were evaluated at shear rates for 500 l/s at 25° C. At t0, all high concentration adalimumab formulations had low viscosities. As a result of the formulations containing ionic excipients (e.g. buffer, salt), all high concentration adalimumab formulations had a conductivity of 3.0 mS/cm or greater.

Block 1 pH stability

| Form No | t0 pH | t2 pH | t4 pH |
|---|---|---|---|
| 1A-31 | 5.43 | 5.44 | 5.43 |
| 1A-32 | 5.45 | 5.45 | 5.44 |
| 1A-33 | 5.45 | 5.44 | 5.46 |
| 1A-34 | 5.43 | 5.43 | 5.42 |
| 1A-35 | 5.41 | 5.40 | 5.40 |
| 1A-36 | 5.43 | 5.42 | 5.41 |
| 1A-37 | 5.42 | 5.43 | 5.42 |
| 1A-38 | 5.43 | 5.44 | 5.43 |
| 1A-39 | 5.41 | 5.41 | 5.40 |
| 1A-40 | 5.40 | 5.42 | 5.39 |
| 1A-41 | 5.42 | 5.38 | 5.40 |
| 1A-42 | 5.42 | 5.43 | 5.40 |

The pH of all high concentration adalimumab formulations was stable.

Concentration Stability Studies

Concentration of adalimumab was measured by A280. The experimental procedure included correcting for scattering by subtracting (directly) A320. Samples diluted to 0.3 mg/mL in water for A280 measurement.

Block 1 concentrations at t0, t2, and t4

| Form No | Conc t0 (mg/mL) | Conc t2 (mg/mL) | Conc t4 (mg/mL) |
|---|---|---|---|
| 1A-31 | 97.1 | 98.2 | 97.2 |
| 1A-32 | 99.4 | 97.5 | 98.8 |
| 1A-33 | 98.5 | 97.1 | 98.3 |
| 1A-34 | 97.2 | 98.1 | 98.0 |
| 1A-35 | 98.6 | 98.5 | 99.3 |
| 1A-36 | 97.9 | 98.1 | 98.9 |
| 1A-37 | 97.4 | 97.4 | 98.6 |
| 1A-38 | 97.3 | 98.0 | 98.8 |
| 1A-39 | 97.1 | 98.7 | 98.5 |
| 1A-40 | 97.3 | 97.9 | 97.6 |
| 1A-41 | 98.3 | 98.6 | 98.1 |
| 1A-42 | 97.8 | 98.4 | 98.6 |

The concentration of adalimumab in all high concentration adalimumab formulations was stable.

CEX Stability Studies

Stability of adalimumab in high concentration formulations was evaluated by CEX. The tables below list the relative peak areas for the main peak (MP), the acidic region (pre-MP), and the basic region (post-MP). The delta (Δ) is the difference in relative peak area between t0 and t2 or t4.

| Block 1 CEX t0 and t2 | | | | | | | | |
|---|---|---|---|---|---|---|---|---|
| Form No | t0 MP | t2 MP | Δ MP | t0 Acidic | t2 Acidic | Δ Acidic | t0 Basic | t2 Basic | Δ Basic |
| 1A-31 | 75.06 | 60.06 | 15.01 | 17.94 | 29.12 | 11.18 | 6.99 | 10.82 | 3.83 |
| 1A-32 | 75.03 | 61.96 | 13.07 | 17.99 | 27.27 | 9.29 | 6.98 | 10.77 | 3.78 |
| 1A-33 | 75.02 | 61.74 | 13.29 | 17.96 | 27.26 | 9.30 | 7.02 | 11.00 | 3.98 |
| 1A-34 | 75.03 | 62.98 | 12.05 | 17.95 | 26.06 | 8.11 | 7.01 | 10.96 | 3.94 |
| 1A-35 | 75.22 | 59.34 | 15.88 | 17.82 | 29.81 | 11.98 | 6.96 | 10.85 | 3.90 |
| 1A-36 | 75.04 | 61.46 | 13.58 | 17.97 | 27.75 | 9.78 | 6.99 | 10.79 | 3.80 |
| 1A-37 | 75.18 | 62.10 | 13.08 | 17.84 | 26.95 | 9.11 | 6.98 | 10.96 | 3.97 |
| 1A-38 | 75.12 | 63.10 | 12.03 | 17.87 | 26.11 | 8.23 | 7.01 | 10.80 | 3.79 |
| 1A-39 | 74.89 | 59.71 | 15.18 | 18.01 | 29.81 | 11.81 | 7.10 | 10.48 | 3.37 |
| 1A-40 | 75.07 | 61.51 | 13.55 | 17.94 | 27.92 | 9.98 | 6.99 | 10.57 | 3.57 |
| 1A-41 | 75.16 | 61.32 | 13.83 | 17.82 | 27.78 | 9.96 | 7.02 | 10.90 | 3.87 |
| 1A-42 | 75.22 | 62.66 | 12.56 | 17.80 | 26.53 | 8.73 | 6.98 | 10.81 | 3.83 |

| Block 1 CEX t0 and t4 | | | | | | | | |
|---|---|---|---|---|---|---|---|---|
| Form No | t0 MP | t4 MP | Δ MP | t0 Acidic | t4 Acidic | Δ Acidic | t0 Basic | t4 Basic | Δ Basic |
| 1A-31 | 75.06 | 70.82 | 4.25 | 17.94 | 20.97 | 3.03 | 6.99 | 8.21 | 1.22 |
| 1A-32 | 75.03 | 71.85 | 3.18 | 17.99 | 19.98 | 2.00 | 6.98 | 8.17 | 1.18 |
| 1A-33 | 75.02 | 71.75 | 3.27 | 17.96 | 19.99 | 2.03 | 7.02 | 8.26 | 1.24 |
| 1A-34 | 75.03 | 72.22 | 2.81 | 17.95 | 19.58 | 1.63 | 7.01 | 8.20 | 1.18 |
| 1A-35 | 75.22 | 70.84 | 4.37 | 17.82 | 20.95 | 3.12 | 6.96 | 8.21 | 1.25 |
| 1A-36 | 75.04 | 71.87 | 3.16 | 17.97 | 20.02 | 2.05 | 6.99 | 8.10 | 1.11 |
| 1A-37 | 75.18 | 71.93 | 3.25 | 17.84 | 19.89 | 2.06 | 6.98 | 8.17 | 1.19 |
| 1A-38 | 75.12 | 72.24 | 2.88 | 17.87 | 19.56 | 1.69 | 7.01 | 8.20 | 1.20 |
| 1A-39 | 74.89 | 70.94 | 3.95 | 18.01 | 20.97 | 2.96 | 7.10 | 8.09 | 0.99 |
| 1A-40 | 75.07 | 71.53 | 3.54 | 17.94 | 20.36 | 2.42 | 6.99 | 8.11 | 1.12 |
| 1A-41 | 75.16 | 71.92 | 3.24 | 17.82 | 19.89 | 2.07 | 7.02 | 8.19 | 1.17 |
| 1A-42 | 75.22 | 72.14 | 3.08 | 17.80 | 19.67 | 1.87 | 6.98 | 8.20 | 1.21 |

The CEX results show surprisingly that high concentration adalimumab formulations with higher surfactant concentration (e.g. 0.1% Polysorbate 80) degraded faster than identical formulations with lower concentrations (e.g. 0.02% Polysorbate 80). For example, formulations 1A-31, 1A1-35 and 1A-39 (all with glycine and 0.1% Polysorbate 80) had the largest change in charge variant make-up vs. t0 (at both time-points, t2 and t4). In contrast, formulations 1A-34 and 1A-38 (both with mannitol and 0.02% Polysorbate 80) had the smallest change in charge variant make-up vs. t0 (at both time-points, t2 and t4).

In general, high concentration adalimumab formulations with glycine had a larger change in charge variant makeup than comparable mannitol formulations. Slight increases were seen in both acidic and basic regions of CEX chromatogram for formulations. This may be a result of deamidation, leading to acidic peak Increases, and clipping or aggregates leading to basic peak increases. Despite these small changes, all that high concentration adalimumab formulations demonstrated suitable stability.

SEC Stability Studies

Stability of adalimumab in high concentration formulations was evaluated by SEC. The tables below list the relative peak areas for the main peak (MP), high molecular weight species (HMW), and low molecular weight species (LMW). The delta (Δ) is the difference in relative peak area between t0 and t2 or t4.

| Block 1 SEC t0 and t2 | | | | | | | | |
|---|---|---|---|---|---|---|---|---|
| Form No | t0 MP | t2 MP | Δ MP | HMW t0 | HMW t2 | Δ HMW | LMW t0 | LMW t2 | Δ LMW |
| 1A-31 | 99.53 | 98.36 | 1.18 | 0.14 | 0.49 | 0.35 | 0.33 | 1.16 | 0.83 |
| 1A-32 | 99.54 | 98.53 | 1.01 | 0.12 | 0.36 | 0.24 | 0.34 | 1.11 | 0.77 |
| 1A-33 | 99.50 | 98.34 | 1.15 | 0.14 | 0.46 | 0.32 | 0.36 | 1.20 | 0.83 |
| 1A-34 | 99.54 | 98.67 | 0.87 | 0.14 | 0.32 | 0.19 | 0.32 | 1.01 | 0.68 |
| 1A-35 | 99.50 | 98.29 | 1.21 | 0.13 | 0.50 | 0.36 | 0.37 | 1.21 | 0.84 |
| 1A-36 | 99.55 | 98.55 | 1.00 | 0 13 | 0.35 | 0.22 | 0.32 | 1.10 | 0.78 |
| 1A-37 | 99.53 | 98.50 | 1.02 | 0.13 | 0.41 | 0.28 | 0.34 | 1.08 | 0.74 |
| 1A-38 | 99.55 | 98.65 | 0.90 | 0.14 | 0.31 | 0.17 | 0.31 | 1.04 | 0.73 |
| 1A-39 | 99.54 | 98.47 | 1.07 | 0.12 | 0.43 | 0.32 | 0.34 | 1.09 | 0.75 |

Block 1 SEC t0 and t2

| Form No | t0 MP | t2 MP | Δ MP | HMW t0 | HMW t2 | Δ HMW | LMW t0 | LMW t2 | Δ LMW |
|---|---|---|---|---|---|---|---|---|---|
| 1A-40 | 99.55 | 98.57 | 0.98 | 0.11 | 0.33 | 0.22 | 0.33 | 1.10 | 0.76 |
| 1A-41 | 99.49 | 98.46 | 1.03 | 0.13 | 0.41 | 0.28 | 0.38 | 1.12 | 0.75 |
| 1A-42 | 99.55 | 98.64 | 0.91 | 0.12 | 0.30 | 0.17 | 0.33 | 1.06 | 0.74 |

Block 1 SEC t0 and t4

| Form No | t0 MP | t4 MP | Δ MP | HMW t0 | HMW t4 | Δ HMW | LMW t0 | LMW t4 | Δ LMW |
|---|---|---|---|---|---|---|---|---|---|
| 1A-31 | 99.53 | 99.19 | 0.35 | 0.14 | 0.24 | 0.10 | 0.33 | 0.57 | 0.24 |
| 1A-32 | 99.54 | 99.33 | 0.21 | 0.12 | 0.21 | 0.09 | 0.34 | 0.47 | 0.12 |
| 1A-33 | 99.50 | 99.28 | 0.22 | 0.14 | 0.24 | 0.10 | 0.36 | 0.48 | 0.12 |
| 1A-34 | 99.54 | 99.26 | 0.29 | 0.14 | 0.22 | 0.09 | 0.32 | 0.52 | 0.20 |
| 1A-35 | 99.50 | 99.21 | 0.29 | 0.13 | 0.24 | 0.11 | 0.37 | 0.54 | 0.17 |
| 1A-36 | 99.55 | 99.26 | 0.29 | 0 13 | 0.21 | 0.08 | 0.32 | 0.53 | 0.21 |
| 1A-37 | 99.53 | 99.25 | 0.28 | 0.13 | 0.23 | 0.10 | 0.34 | 0.52 | 0.18 |
| 1A-38 | 99.55 | 99.34 | 0.21 | 0.14 | 0.19 | 0.05 | 0.31 | 0.47 | 0.16 |
| 1A-39 | 99.54 | 99.24 | 0.30 | 0.12 | 0.24 | 0.12 | 0.34 | 0.52 | 0.18 |
| 1A-40 | 99.55 | 99.30 | 0.25 | 0.11 | 0.19 | 0.07 | 0.33 | 0.51 | 0.17 |
| 1A-41 | 99.49 | 99.23 | 0.26 | 0.13 | 0.23 | 0.10 | 0.38 | 0.55 | 0.17 |
| 1A-42 | 99.55 | 99.26 | 0.29 | 0.12 | 0.22 | 0.10 | 0.33 | 0.52 | 0.19 |

The SEC results show surprisingly that high concentration adalimumab formulations with surfactant (e.g. 0.1% Polysorbate 80) degraded faster than identical formulations with lower concentrations (e.g. 0.02% Polysorbate 80). No statistical differences between samples at 25° C.

Overall, only small changes were observed in these formulations demonstrating that the high concentration adalimumab formulations are stable.

Reverse Phase Stability Studies

Stability of adalimumab in high concentration formulations was evaluated by reverse phase chromatography (RP). The tables below list the relative peak areas for the main peak (MP), pre-peaks (Pre), and post-peaks (Post). The delta (Δ) is the difference in relative peak area between t0 and t2 or t4; reported as an absolute value.

Block 1 RP t0 and t4

| Form No | t0 MP | t2 MP | Δ MP | Pre t0 | Pre t2 | Δ Pre | Post t0 | Post t2 | Δ Post |
|---|---|---|---|---|---|---|---|---|---|
| 1A-31 | 90.69 | 88.79 | 1.90 | 2.06 | 3.28 | 1.22 | 7.25 | 7.39 | 0.68 |
| 1A-32 | 90.55 | 89.46 | 1.09 | 2.09 | 3.15 | 1.06 | 7.36 | 7.37 | 0.03 |
| 1A-33 | 90.60 | 89.11 | 1.49 | 2.04 | 3.20 | 1.15 | 7.35 | 7.38 | 0.34 |
| 1A-34 | 90.56 | 89.50 | 1.06 | 2.05 | 3.12 | 1.07 | 7.39 | 7.40 | 0.01 |
| 1A-35 | 90.44 | 88.75 | 1.69 | 2.15 | 3.30 | 1.15 | 7.41 | 7.38 | 0.54 |
| 1A-36 | 90.54 | 89.79 | 0.75 | 2.10 | 2.62 | 0.51 | 7.36 | 7.25 | 0.23 |
| 1A-37 | 90.54 | 89.11 | 1.44 | 2.03 | 3.17 | 1.13 | 7.42 | 7.51 | 0.30 |
| 1A-38 | 90.69 | 89.48 | 1.21 | 2.08 | 3.11 | 1.02 | 7.23 | 7.34 | 0.19 |
| 1A-39 | 90.61 | 88.86 | 1.75 | 2.03 | 3.32 | 1.29 | 7.36 | 7.50 | 0.46 |
| 1A-40 | 90.58 | 89.36 | 1.22 | 2.05 | 3.25 | 1.20 | 7.38 | 7.31 | 0.02 |
| 1A-41 | 90.73 | 89.10 | 1.64 | 2.02 | 3.21 | 1.20 | 7.25 | 7.36 | 0.44 |
| 1A-42 | 90.71 | 89.43 | 1.27 | 2.02 | 3.16 | 1.14 | 7.28 | 7.31 | 0.13 |

Block 1 RP t0 and t4

| Form No | t0 MP | t4 MP | Δ MP | Pre t0 | Pre t4 | Δ Pre | Post t0 | Post t4 | Δ Post |
|---|---|---|---|---|---|---|---|---|---|
| 1A-31 | 90.69 | 90.26 | 0.43 | 2.06 | 2.35 | 0.29 | 7.25 | 7.39 | 0.14 |
| 1A-32 | 90.55 | 90.32 | 0.23 | 2.09 | 2.30 | 0.22 | 7.36 | 7.37 | 0.01 |
| 1A-33 | 90.60 | 90.32 | 0.28 | 2.04 | 2.30 | 0.26 | 7.35 | 7.38 | 0.02 |
| 1A-34 | 90.56 | 90.26 | 0.30 | 2.05 | 2.34 | 0.29 | 7.39 | 7.40 | 0.01 |
| 1A-35 | 90.44 | 90.13 | 0.31 | 2.15 | 2.48 | 0.34 | 7.41 | 7.38 | 0.03 |
| 1A-36 | 90.54 | 90.46 | 0.07 | 2.10 | 2.29 | 0.19 | 7.36 | 7.25 | 0.12 |
| 1A-37 | 90.54 | 90.17 | 0.38 | 2.03 | 2.32 | 0.28 | 7.42 | 7.51 | 0.09 |
| 1A-38 | 90.69 | 90.41 | 0.28 | 2.08 | 2.25 | 0.16 | 7.23 | 7.34 | 0.11 |
| 1A-39 | 90.61 | 90.12 | 0.49 | 2.03 | 2.38 | 0.35 | 7.36 | 7.50 | 0.14 |
| 1A-40 | 90.58 | 90.28 | 0.29 | 2.05 | 2.41 | 0.36 | 7.38 | 7.31 | 0.07 |
| 1A-41 | 90.73 | 90.30 | 0.44 | 2.02 | 2.34 | 0.32 | 7.25 | 7.36 | 0.11 |
| 1A-42 | 90.71 | 90.33 | 0.37 | 2.02 | 2.36 | 0.34 | 7.28 | 7.31 | 0.03 |

On some RP chromatograms a shoulder was observed on the trailing edge of the main peak that is integrated with the main peak. While efforts to reproducibly split it out or quantify the shoulder with good precision were unsuccessful, it did not appear to change at the t2 or t4 time points, as compared to t0. Thus, it appears that this observation does not impact stability of the high concentration adalimumab formulations.

Changes of greater than 1 In the pre-peaks at t2 was observed in many of the formulations. The magnitude of change many be slightly higher for formulations with 0.1% Polysorbate 80, but the differences are small and may not be significant.

Likewise, an increase in the relative peak area of the post peaks at t2 was observed. The magnitude of change appears to be higher for formulations with 0.1% Polysorbate 80, but the differences are small and may not be significant.

No discernable trends seen at t4, but the relative peak areas do change slightly vs t0.

Overall, RP analysis demonstrated that high concentration adalimumab formulations are stable.

Particle Stability Studies

Stability of adalimumab in high concentration formulations was evaluated by measuring the size and number of particles by MFI. Sample were evaluated by MFI analysis,

| | Block 1 MFi t0 | | | | | | | |
|---|---|---|---|---|---|---|---|---|
| | Total (particles/mL) | | | | Non-silicone Oil (particles/mL) | | | |
| Form No | ≥2 μm | ≥5 μm | ≥10 μm | ≥25 μm | ≥2 μm | ≥5 μm | ≥10 μm | ≥25 μm |
| 1A-31 | 296 | 43 | 13 | 4 | 153 | 34 | 11 | 4 |
| 1A-32 | 73 | 16 | 9 | 2 | 39 | 11 | 7 | 2 |
| 1A-33 | 216 | 39 | 14 | 4 | 143 | 27 | 14 | 4 |
| 1A-34 | 67 | 12 | 3 | 0 | 36 | 8 | 3 | 0 |
| 1A-35 | 297 | 22 | 9 | 2 | 245 | 21 | 9 | 2 |
| 1A-36 | 162 | 32 | 12 | 7 | 88 | 20 | 10 | 7 |
| 1A-37 | 314 | 74 | 11 | 0 | 255 | 65 | 11 | 0 |
| 1A-38 | 108 | 15 | 3 | 0 | 74 | 12 | 2 | 0 |
| 1A-39 | 193 | 37 | 6 | 6 | 112 | 31 | 6 | 6 |
| 1A-40 | 169 | 67 | 18 | 5 | 103 | 52 | 15 | 5 |
| 1A-41 | 152 | 21 | 7 | 3 | 100 | 16 | 5 | 3 |
| 1A-42 | 543 | 108 | 33 | 8 | 344 | 91 | 29 | 4 |

| | Block 1 MFi t4 | | | | | | | |
|---|---|---|---|---|---|---|---|---|
| | Total (particles/mL) | | | | Non-silicone Oil (particles/mL) | | | |
| Form No | ≥2 μm | ≥5 μm | ≥10 μm | ≥25 μm | ≥2 μm | ≥5 μm | ≥10 μm | ≥25 μm |
| 1A-31 | 260 | 30 | 5 | 0 | | | | |
| 1A-32 | 347 | 32 | 0 | 0 | 171 | 26 | 2 | 0 |
| 1A-33 | 4152 | 524 | 103 | 2 | 232 | 26 | 0 | 0 |
| 1A-34 | 99 | 12 | 2 | 2 | 1948 | 429 | 91 | 2 |
| 1A-35 | 1202 | 269 | 54 | 2 | 63 | 12 | 2 | 2 |
| 1A-36 | 437 | 67 | 3 | 0 | 870 | 215 | 54 | 2 |
| 1A-37 | 130 | 14 | 4 | 0 | 312 | 51 | 3 | 0 |
| 1A-38 | 234 | 13 | 0 | 0 | 62 | 8 | 4 | 0 |
| 1A-39 | 294 | 27 | 0 | 0 | 175 | 13 | 0 | 0 |
| 1A-40 | 170 | 38 | 5 | 2 | 177 | 8 | 0 | 0 |
| 1A-41 | 228 | 18 | 0 | 0 | 114 | 29 | 4 | 2 |
| 1A-42 | 54 | 14 | 2 | 2 | 145 | 17 | 0 | 0 |

The difference between total particles and non-silicone oil particles are the number of silicone oil particles.

Particle counts for particles ≥10 μm and ≥25 μm were generally low in all high concentration adalimumab formulations. All were within USP 788 guidelines. These results demonstrate that the high concentration adalimumab formulations are stable.

In conclusion, high concentration adalimumab formulations have suitable viscosity for administration via a needle (e.g. subcutaneous administration) and are stable as demonstrated by pH, CEX, SEC, RP, and MFI analyses.

Example 3. Stable High Concentration Adalimumab Formulations—Block 2

Block 2 Study Design

All Block 2 formulations have a high concentration with reduced excipients. These formulations may exclude excipients found in Humira® which one would expect to be required for a stable adalimumab formulation. Block 2 formulations may have low amounts of excipients.

Block 2 compositions comprise a high concentration of adalimumab and are free, or substantially free, of a polyol, a surfactant, or both a polyol and a surfactant. Alternatively, Block 2 compositions comprise a high concentration of adalimumab and are free, or substantially free, of manitol, xylitol, or both manitol and xylitol. Optionally, some Block 2 formulations contain a buffer.

Examples of Block 2 formulations are set forth in the tables below. Block 2A formulations comprise adalimumab at about 100 mg/mL and Block 2B formulations comprise adalimumab at about 150 mg/mL.

| | | | | | | | | | | | | | | | | | |
|---|---|---|---|---|---|---|---|---|---|---|---|---|---|---|---|---|---|
| Block 2A Table | | | | | | | | | | | | | | | | | |
| Form. No. | pH | Citrate (mM) | Na Phos (mM) | Succinate (mM) | His (mM) | Mannitol (mM) | Arg (mM) | Gly (mM) | NaCl (mM) | Na2SO4 (mM) | K Phos (mM) | MgCl2 (mM) | Met (mM) | EDTA (% w/v) | PS 80 (% w/v) | PS 20 (% w/v) | F68 (% w/v) |
| 2A-1 | 5.2 | 0 | 0 | 0 | 30 | 0 | 0 | 180 | 40 | 0 | 0 | 0 | 0 | 0 | 0 | 0 | 0 |
| 2A-2 | 5.2 | 0 | 0 | 0 | 30 | 0 | 25 | 200 | 0 | 0 | 0 | 0 | 0 | 0 | 0 | 0 | 0 |
| 2A-3 | 5.2 | 0 | 0 | 0 | 30 | 0 | 25 | 180 | 20 | 0 | 0 | 0 | 0 | 0 | 0 | 0 | 0 |
| 2A-4 | 5.2 | 0 | 0 | 0 | 30 | 0 | 25 | 180 | 0 | 15 | 0 | 0 | 0 | 0 | 0 | 0 | 0 |
| 2A-5 | 5.2 | 0 | 0 | 0 | 30 | 0 | 0 | 180 | 0 | 0 | 30 | 0 | 0 | 0 | 0 | 0 | 0 |

-continued

Block 2A Table

| Form. No. | pH | Citrate (mM) | Na Phos (mM) | Succinate (mM) | His (mM) | Mannitol (mM) | Arg (mM) | Gly (mM) | NaCl (mM) | Na2SO4 (mM) | K Phos (mM) | MgCl2 (mM) | Met (mM) | EDTA (% w/v) | PS 80 (% w/v) | PS 20 (% w/v) | F68 (% w/v) |
|---|---|---|---|---|---|---|---|---|---|---|---|---|---|---|---|---|---|
| 2A-6 | 5.2 | 0 | 0 | 0 | 30 | 0 | 0 | 180 | 15 | 0 | 15 | 0 | 0 | 0 | 0 | 0 | 0 |
| 2A-7 | 5.2 | 0 | 0 | 0 | 30 | 0 | 0 | 180 | 0 | 15 | 15 | 0 | 0 | 0 | 0 | 0 | 0 |
| 2A-8 | 5.2 | 0 | 0 | 0 | 30 | 0 | 25 | 0 | 15 | 0 | 75 | 0 | 0 | 0 | 0 | 0 | 0 |
| 2A-9 | 5.2 | 0 | 0 | 0 | 30 | 0 | 25 | 140 | 0 | 0 | 30 | 0 | 0 | 0 | 0 | 0 | 0 |
| 2A-10 | 5.2 | 0 | 0 | 0 | 0 | 0 | 0 | 240 | 20 | 0 | 0 | 0 | 0 | 0 | 0 | 0 | 0 |
| 2A-11 | 5.3 | 0 | 0 | 0 | 30 | 0 | 0 | 180 | 0 | 30 | 0 | 0 | 0 | 0 | 0 | 0 | 0 |
| 2A-12 | 5.3 | 0 | 0 | 0 | 30 | 0 | 0 | 180 | 0 | 0 | 0 | 25 | 0 | 0 | 0 | 0 | 0 |
| 2A-13 | 5.3 | 0 | 0 | 0 | 30 | 0 | 0 | 60 | 0 | 75 | 0 | 0 | 0 | 0 | 0 | 0 | 0 |
| 2A-14 | 5.3 | 0 | 0 | 0 | 30 | 0 | 25 | 0 | 120 | 0 | 0 | 0 | 0 | 0 | 0 | 0 | 0 |
| 2A-15 | 5.3 | 0 | 0 | 0 | 30 | 160 | 25 | 0 | 0 | 0 | 0 | 0 | 0 | 0 | 0 | 0 | 0 |
| 2A-16 | 5.3 | 0 | 0 | 0 | 30 | 0 | 0 | 240 | 0 | 0 | 0 | 0 | 0 | 0 | 0 | 0 | 0 |
| 2A-17 | 5.3 | 0 | 0 | 0 | 30 | 0 | 25 | 180 | 0 | 0 | 0 | 0 | 0 | 0 | 0 | 0 | 0 |
| 2A-18 | 5.3 | 0 | 0 | 0 | 30 | 0 | 0 | 0 | 0 | 100 | 0 | 0 | 0 | 0 | 0 | 0 | 0 |
| 2A-19 | 5.3 | 0 | 0 | 0 | 50 | 0 | 0 | 0 | 140 | 0 | 0 | 0 | 0 | 0 | 0 | 0 | 0 |
| 2A-20 | 5.2 | 10 | 0 | 0 | 0 | 0 | 0 | 0 | 150 | 0 | 0 | 0 | 0 | 0 | 0.1 | 0 | 0 |
| 2A-21 | 5.2 | 0 | 10 | 0 | 0 | 0 | 0 | 0 | 150 | 0 | 0 | 0 | 0 | 0 | 0.1 | 0 | 0 |
| 2A-22 | 3.5 | 0 | 0 | 0 | 0 | 0 | 130 | 0 | 0 | 0 | 0 | 0 | 0 | 0 | 0.1 | 0 | 0 |
| 2A-23 | 5.2 | 0 | 0 | 0 | 10 | 0 | 120 | 120 | 0 | 0 | 0 | 0 | 0 | 0 | 0.1 | 0 | 0 |
| 2A-24 | 5.2 | 0 | 0 | 0 | 10 | 0 | 120 | 120 | 0 | 0 | 0 | 0 | 0 | 0 | 0.05 | 0 | 0 |
| 2A-25 | 5.2 | 0 | 0 | 0 | 10 | 0 | 120 | 120 | 0 | 0 | 0 | 0 | 0 | 0 | 0.01 | 0 | 0 |
| 2A-26 | 5.2 | 0 | 0 | 0 | 10 | 0 | 120 | 120 | 0 | 0 | 0 | 0 | 0 | 0 | 0 | 0.05 | 0.05 |
| 2A-27 | 5.2 | 0 | 0 | 0 | 10 | 0 | 120 | 120 | 0 | 0 | 0 | 0 | 0 | 0 | 0 | 0 | 0.1 |
| 2A-28 | 5.2 | 0 | 0 | 10 | 0 | 0 | 120 | 120 | 0 | 0 | 0 | 0 | 0 | 0 | 0.05 | 0 | 0 |
| 2A-29 | 5.2 | 0 | 0 | 20 | 0 | 0 | 100 | 150 | 0 | 0 | 0 | 0 | 0 | 0 | 0 | 0.05 | 0 |
| 2A-30 | 5.2 | 0 | 0 | 0 | 20 | 0 | 100 | 150 | 0 | 0 | 0 | 0 | 0 | 0 | 0.01 | 0 | 0 |
| 2A-31 | 5.2 | 0 | 0 | 0 | 20 | 0 | 120 | 120 | 0 | 0 | 0 | 0 | 0 | 0 | 0 | 0.01 | 0 |
| 2A-32 | 5.2 | 0 | 0 | 0 | 0 | 0 | 120 | 120 | 0 | 0 | 0 | 0 | 0 | 0 | 0.1 | 0 | 0 |
| 2A-33 | 5.2 | 0 | 0 | 10 | 10 | 0 | 100 | 120 | 0 | 0 | 0 | 0 | 0 | 0 | 0.1 | 0 | 0 |
| 2A-34 | 5.2 | 0 | 0 | 0 | 30 | 0 | 0 | 240 | 0 | 0 | 0 | 0 | 0 | 0 | 0.1 | 0 | 0 |
| 2A-35 | 5.2 | 8 | 18 | 0 | 0 | 65 | 0 | 0 | 100 | 0 | 0 | 0 | 0 | 0 | 0 | 0 | 0 |
| 2A-36 | 5.2 | 20 | 0 | 0 | 0 | 65 | 0 | 0 | 100 | 0 | 0 | 0 | 0 | 0 | 0 | 0 | 0 |
| 2A-37 | 5.2 | 0 | 20 | 0 | 0 | 65 | 0 | 0 | 100 | 0 | 0 | 0 | 0 | 0 | 0 | 0 | 0 |
| 2A-38 | 3.5 | 0 | 0 | 0 | 0 | 0 | 130 | 0 | 0 | 0 | 0 | 0 | 0 | 0 | 0 | 0 | 0 |
| 2A-39 | 3.5 | 0 | 0 | 0 | 0 | 0 | 0 | 240 | 0 | 0 | 0 | 0 | 0 | 0 | 0 | 0 | 0 |
| 2A-40 | 5.2 | 0 | 0 | 0 | 0 | 0 | 0 | 240 | 0 | 0 | 0 | 0 | 0 | 0 | 0 | 0 | 0 |
| 2A-41 | 3.5 | 0 | 0 | 0 | 0 | 0 | 100 | 100 | 0 | 0 | 0 | 0 | 0 | 0 | 0 | 0 | 0 |
| 2A-42 | 5.2 | 0 | 0 | 0 | 0 | 0 | 100 | 100 | 0 | 0 | 0 | 0 | 0 | 0 | 0 | 0 | 0 |
| 2A-43 | 3.5 | 0 | 0 | 0 | 0 | 0 | 150 | 50 | 0 | 0 | 0 | 0 | 0 | 0 | 0 | 0 | 0 |
| 2A-44 | 5.2 | 0 | 0 | 0 | 10 | 0 | 150 | 0 | 0 | 0 | 0 | 0 | 0 | 0 | 0.1 | 0 | 0 |
| 2A-45 | 5.2 | 0 | 0 | 0 | 10 | 240 | 0 | 0 | 0 | 0 | 0 | 0 | 0 | 0 | 0 | 0 | 0 |
| 2A-46 | 5.2 | 0 | 0 | 0 | 10 | 240 | 0 | 0 | 0 | 0 | 0 | 10 | 0 | 0 | 0 | 0 | 0 |
| 2A-47 | 5.2 | 0 | 0 | 0 | 10 | 240 | 0 | 0 | 0 | 0 | 0 | 50 | 0 | 0 | 0 | 0 | 0 |
| 2A-48 | 5.2 | 0 | 0 | 0 | 20 | 240 | 0 | 0 | 0 | 0 | 0 | 0 | 0 | 0 | 0 | 0 | 0 |
| 2A-49 | 5.2 | 0 | 0 | 0 | 0 | 0 | 0 | 240 | 0 | 0 | 0 | 0 | 0 | 0 | 0 | 0 | 0 |
| 2A-50 | 5.2 | 0 | 0 | 0 | 0 | 0 | 100 | 100 | 0 | 0 | 0 | 0 | 0 | 0 | 0 | 0 | 0 |
| 2A-51 | 5.3 | 0 | 0 | 0 | 20 | 240 | 0 | 0 | 20 | 0 | 0 | 0 | 0 | 0 | 0 | 0 | 0 |
| 2A-52 | 5.3 | 0 | 0 | 0 | 20 | 200 | 0 | 0 | 40 | 0 | 0 | 0 | 0 | 0 | 0 | 0 | 0 |
| 2A-53 | 5.3 | 0 | 0 | 0 | 20 | 0 | 25 | 220 | 0 | 0 | 0 | 0 | 0 | 0 | 0 | 0 | 0 |
| 2A-54 | 5.3 | 0 | 0 | 0 | 20 | 0 | 25 | 180 | 20 | 0 | 0 | 0 | 0 | 0 | 0 | 0 | 0 |
| 2A-55 | 5.3 | 0 | 0 | 0 | 0 | 240 | 0 | 0 | 20 | 0 | 0 | 0 | 0 | 0 | 0 | 0 | 0 |
| 2A-56 | 5.3 | 0 | 0 | 0 | 0 | 0 | 30 | 220 | 0 | 0 | 0 | 0 | 0 | 0 | 0.1 | 0 | 0 |
| 2A-57 | 5.3 | 0 | 0 | 0 | 0 | 0 | 30 | 220 | 0 | 0 | 0 | 0 | 0 | 0 | 0 | 0 | 0 |
| 2A-58 | 5.3 | 0 | 0 | 0 | 20 | 0 | 0 | 240 | 20 | 0 | 0 | 0 | 0 | 0 | 0 | 0 | 0 |
| 2A-59 | 5.3 | 0 | 0 | 0 | 20 | 0 | 0 | 200 | 40 | 0 | 0 | 0 | 0 | 0 | 0 | 0 | 0 |
| 2A-60 | 5.3 | 0 | 0 | 0 | 20 | 220 | 25 | 0 | 0 | 0 | 0 | 0 | 0 | 0 | 0 | 0 | 0 |
| 2A-61 | 5.3 | 0 | 0 | 0 | 20 | 180 | 25 | 0 | 0 | 20 | 75 | 0 | 0 | 0 | 0 | 0 | 0 |
| 2A-62 | 5.3 | 0 | 0 | 0 | 0 | 0 | 0 | 240 | 20 | 0 | 0 | 0 | 0 | 0 | 0 | 0 | 0 |
| 2A-63 | 5.3 | 0 | 0 | 0 | 20 | 240 | 0 | 0 | 20 | 0 | 0 | 0 | 0 | 0 | 0 | 0 | 0 |

Block 2B Table

| Form. No. | pH | Citrate (mM) | Na Phos (mM) | Succinate (mM) | His (mM) | Mannitol (mM) | Arg (mM) | Gly (mM) | NaCl (mM) | Na2SO4 (mM) | K Phos (mM) | MgCl2 (mM) | Met (mM) | EDTA (% w/v) | PS 80 (% w/v) | PS 20 (% w/v) | F68 (% w/v) |
|---|---|---|---|---|---|---|---|---|---|---|---|---|---|---|---|---|---|
| 2B-1 | 5.2 | 0 | 0 | 0 | 30 | 0 | 0 | 180 | 40 | 0 | 0 | 0 | 0 | 0 | 0 | 0 | 0 |
| 2B-2 | 5.2 | 0 | 0 | 0 | 30 | 0 | 25 | 200 | 0 | 0 | 0 | 0 | 0 | 0 | 0 | 0 | 0 |
| 2B-3 | 5.2 | 0 | 0 | 0 | 30 | 0 | 25 | 180 | 20 | 0 | 0 | 0 | 0 | 0 | 0 | 0 | 0 |
| 2B-4 | 5.2 | 0 | 0 | 0 | 30 | 0 | 25 | 180 | 0 | 15 | 0 | 0 | 0 | 0 | 0 | 0 | 0 |
| 2B-5 | 5.2 | 0 | 0 | 0 | 30 | 0 | 0 | 180 | 0 | 0 | 30 | 0 | 0 | 0 | 0 | 0 | 0 |

-continued

Block 2B Table

| Form. No. | pH | Citrate (mM) | Na Phos (mM) | Succinate (mM) | His (mM) | Mannitol (mM) | Arg (mM) | Gly (mM) | NaCl (mM) | Na2SO4 (mM) | K Phos (mM) | MgCl2 (mM) | Met (mM) | EDTA (% w/v) | PS 80 (% w/v) | PS 20 (% w/v) | F68 (% w/v) |
|---|---|---|---|---|---|---|---|---|---|---|---|---|---|---|---|---|---|
| 2B-6 | 5.2 | 0 | 0 | 0 | 30 | 0 | 0 | 180 | 15 | 0 | 15 | 0 | 0 | 0 | 0 | 0 | 0 |
| 2B-7 | 5.2 | 0 | 0 | 0 | 30 | 0 | 0 | 180 | 0 | 15 | 15 | 0 | 0 | 0 | 0 | 0 | 0 |
| 2B-8 | 5.2 | 0 | 0 | 0 | 30 | 0 | 25 | 0 | 15 | 0 | 75 | 0 | 0 | 0 | 0 | 0 | 0 |
| 2B-9 | 5.2 | 0 | 0 | 0 | 30 | 0 | 25 | 140 | 0 | 0 | 30 | 0 | 0 | 0 | 0 | 0 | 0 |
| 2B-10 | 5.2 | 0 | 0 | 0 | 0 | 0 | 0 | 240 | 20 | 0 | 0 | 0 | 0 | 0 | 0 | 0 | 0 |
| 2B-11 | 5.3 | 0 | 0 | 0 | 30 | 0 | 0 | 180 | 0 | 30 | 0 | 0 | 0 | 0 | 0 | 0 | 0 |
| 2B-12 | 5.3 | 0 | 0 | 0 | 30 | 0 | 0 | 180 | 0 | 0 | 0 | 25 | 0 | 0 | 0 | 0 | 0 |
| 2B-13 | 5.3 | 0 | 0 | 0 | 30 | 0 | 0 | 60 | 0 | 75 | 0 | 0 | 0 | 0 | 0 | 0 | 0 |
| 2B-14 | 5.3 | 0 | 0 | 0 | 30 | 0 | 25 | 0 | 120 | 0 | 0 | 0 | 0 | 0 | 0 | 0 | 0 |
| 2B-15 | 5.3 | 0 | 0 | 0 | 30 | 160 | 25 | 0 | 0 | 0 | 0 | 0 | 0 | 0 | 0 | 0 | 0 |
| 2B-16 | 5.3 | 0 | 0 | 0 | 30 | 0 | 0 | 240 | 0 | 0 | 0 | 0 | 0 | 0 | 0 | 0 | 0 |
| 2B-17 | 5.3 | 0 | 0 | 0 | 30 | 0 | 25 | 180 | 0 | 0 | 0 | 0 | 0 | 0 | 0 | 0 | 0 |
| 2B-18 | 5.3 | 0 | 0 | 0 | 30 | 0 | 0 | 0 | 0 | 100 | 0 | 0 | 0 | 0 | 0 | 0 | 0 |
| 2B-19 | 5.3 | 0 | 0 | 0 | 50 | 0 | 0 | 0 | 140 | 0 | 0 | 0 | 0 | 0 | 0 | 0 | 0 |
| 2B-20 | 5.2 | 10 | 0 | 0 | 0 | 0 | 0 | 0 | 150 | 0 | 0 | 0 | 0 | 0 | 0.1 | 0 | 0 |
| 2B-21 | 5.2 | 0 | 10 | 0 | 0 | 0 | 0 | 0 | 150 | 0 | 0 | 0 | 0 | 0 | 0.1 | 0 | 0 |
| 2B-22 | 3.5 | 0 | 0 | 0 | 0 | 0 | 130 | 0 | 0 | 0 | 0 | 0 | 0 | 0 | 0.1 | 0 | 0 |
| 2B-23 | 5.2 | 0 | 0 | 0 | 10 | 0 | 120 | 120 | 0 | 0 | 0 | 0 | 0 | 0 | 0.1 | 0 | 0 |
| 2B-24 | 5.2 | 0 | 0 | 0 | 10 | 0 | 120 | 120 | 0 | 0 | 0 | 0 | 0 | 0 | 0.05 | 0 | 0 |
| 2B-25 | 5.2 | 0 | 0 | 0 | 10 | 0 | 120 | 120 | 0 | 0 | 0 | 0 | 0 | 0 | 0.01 | 0 | 0 |
| 2B-26 | 5.2 | 0 | 0 | 0 | 10 | 0 | 120 | 120 | 0 | 0 | 0 | 0 | 0 | 0 | 0 | 0.05 | 0.05 |
| 2B-27 | 5.2 | 0 | 0 | 0 | 10 | 0 | 120 | 120 | 0 | 0 | 0 | 0 | 0 | 0 | 0 | 0 | 0.1 |
| 2B-28 | 5.2 | 0 | 0 | 10 | 0 | 0 | 120 | 120 | 0 | 0 | 0 | 0 | 0 | 0 | 0.05 | 0 | 0 |
| 2B-29 | 5.2 | 0 | 0 | 20 | 0 | 0 | 100 | 150 | 0 | 0 | 0 | 0 | 0 | 0 | 0 | 0.05 | 0 |
| 2B-30 | 5.2 | 0 | 0 | 0 | 20 | 0 | 100 | 150 | 0 | 0 | 0 | 0 | 0 | 0 | 0.01 | 0 | 0 |
| 2B-31 | 5.2 | 0 | 0 | 0 | 20 | 0 | 120 | 120 | 0 | 0 | 0 | 0 | 0 | 0 | 0 | 0.01 | 0 |
| 2B-32 | 5.2 | 0 | 0 | 0 | 0 | 0 | 120 | 120 | 0 | 0 | 0 | 0 | 0 | 0 | 0.1 | 0 | 0 |
| 2B-33 | 5.2 | 0 | 0 | 10 | 10 | 0 | 100 | 120 | 0 | 0 | 0 | 0 | 0 | 0 | 0.1 | 0 | 0 |
| 2B-34 | 5.2 | 0 | 0 | 0 | 30 | 0 | 0 | 240 | 0 | 0 | 0 | 0 | 0 | 0 | 0.1 | 0 | 0 |
| 2B-35 | 5.2 | 8 | 18 | 0 | 0 | 65 | 0 | 0 | 100 | 0 | 0 | 0 | 0 | 0 | 0 | 0 | 0 |
| 2B-36 | 5.2 | 20 | 0 | 0 | 0 | 65 | 0 | 0 | 100 | 0 | 0 | 0 | 0 | 0 | 0 | 0 | 0 |
| 2B-37 | 5.2 | 0 | 20 | 0 | 0 | 65 | 0 | 0 | 100 | 0 | 0 | 0 | 0 | 0 | 0 | 0 | 0 |
| 2B-38 | 3.5 | 0 | 0 | 0 | 0 | 0 | 130 | 0 | 0 | 0 | 0 | 0 | 0 | 0 | 0 | 0 | 0 |
| 2B-39 | 3.5 | 0 | 0 | 0 | 0 | 0 | 0 | 240 | 0 | 0 | 0 | 0 | 0 | 0 | 0 | 0 | 0 |
| 2B-40 | 5.2 | 0 | 0 | 0 | 0 | 0 | 0 | 240 | 0 | 0 | 0 | 0 | 0 | 0 | 0 | 0 | 0 |
| 2B-41 | 3.5 | 0 | 0 | 0 | 0 | 0 | 100 | 100 | 0 | 0 | 0 | 0 | 0 | 0 | 0 | 0 | 0 |
| 2B-42 | 5.2 | 0 | 0 | 0 | 0 | 0 | 100 | 100 | 0 | 0 | 0 | 0 | 0 | 0 | 0 | 0 | 0 |
| 2B-43 | 3.5 | 0 | 0 | 0 | 0 | 0 | 150 | 50 | 0 | 0 | 0 | 0 | 0 | 0 | 0 | 0 | 0 |
| 2B-44 | 5.2 | 0 | 0 | 0 | 10 | 0 | 150 | 0 | 0 | 0 | 0 | 0 | 0 | 0 | 0.1 | 0 | 0 |
| 2B-45 | 5.2 | 0 | 0 | 0 | 10 | 240 | 0 | 0 | 0 | 0 | 0 | 0 | 0 | 0 | 0 | 0 | 0 |
| 2B-46 | 5.2 | 0 | 0 | 0 | 10 | 240 | 0 | 0 | 0 | 0 | 0 | 10 | 0 | 0 | 0 | 0 | 0 |
| 2B-47 | 5.2 | 0 | 0 | 0 | 10 | 240 | 0 | 0 | 0 | 0 | 0 | 50 | 0 | 0 | 0 | 0 | 0 |
| 2B-48 | 5.2 | 0 | 0 | 0 | 20 | 240 | 0 | 0 | 0 | 0 | 0 | 0 | 0 | 0 | 0 | 0 | 0 |
| 2B-49 | 5.2 | 0 | 0 | 0 | 0 | 0 | 0 | 240 | 0 | 0 | 0 | 0 | 0 | 0 | 0 | 0 | 0 |
| 2B-50 | 5.2 | 0 | 0 | 0 | 0 | 0 | 100 | 100 | 0 | 0 | 0 | 0 | 0 | 0 | 0 | 0 | 0 |
| 2B-51 | 5.3 | 0 | 0 | 0 | 20 | 240 | 0 | 0 | 20 | 0 | 0 | 0 | 0 | 0 | 0 | 0 | 0 |
| 2B-52 | 5.3 | 0 | 0 | 0 | 20 | 200 | 0 | 0 | 40 | 0 | 0 | 0 | 0 | 0 | 0 | 0 | 0 |
| 2B-53 | 5.3 | 0 | 0 | 0 | 20 | 0 | 25 | 220 | 0 | 0 | 0 | 0 | 0 | 0 | 0 | 0 | 0 |
| 2B-54 | 5.3 | 0 | 0 | 0 | 20 | 0 | 25 | 180 | 20 | 0 | 0 | 0 | 0 | 0 | 0 | 0 | 0 |
| 2B-55 | 5.3 | 0 | 0 | 0 | 0 | 240 | 0 | 0 | 20 | 0 | 0 | 0 | 0 | 0 | 0 | 0 | 0 |
| 2B-56 | 5.3 | 0 | 0 | 0 | 0 | 0 | 30 | 220 | 0 | 0 | 0 | 0 | 0 | 0 | 0.1 | 0 | 0 |
| 2B-57 | 5.3 | 0 | 0 | 0 | 0 | 0 | 30 | 220 | 0 | 0 | 0 | 0 | 0 | 0 | 0 | 0 | 0 |
| 2B-58 | 5.3 | 0 | 0 | 0 | 20 | 0 | 0 | 240 | 20 | 0 | 0 | 0 | 0 | 0 | 0 | 0 | 0 |
| 2B-59 | 5.3 | 0 | 0 | 0 | 20 | 0 | 0 | 200 | 40 | 0 | 0 | 0 | 0 | 0 | 0 | 0 | 0 |
| 2B-60 | 5.3 | 0 | 0 | 0 | 20 | 220 | 25 | 0 | 0 | 0 | 0 | 0 | 0 | 0 | 0 | 0 | 0 |
| 2B-61 | 5.3 | 0 | 0 | 0 | 20 | 180 | 25 | 0 | 20 | 0 | 0 | 0 | 0 | 0 | 0 | 0 | 0 |
| 2B-62 | 5.3 | 0 | 0 | 0 | 0 | 0 | 0 | 240 | 20 | 0 | 0 | 0 | 0 | 0 | 0 | 0 | 0 |
| 2B-63 | 5.3 | 0 | 0 | 0 | 20 | 240 | 0 | 0 | 20 | 0 | 0 | 0 | 0 | 0 | 0 | 0 | 0 | it is expected that high concentration adalimumab formulations in Block 2A (100 mg/mL) and 2B (150 mg/mL) exhibit stability and viscosity comparable to, or better than, other formulations at 50 mg/mL or 100 mg/mL (e.g. commercial adalimumab formulations). However, if desired, further improvements in stability or viscosity may be achieved by adding additional stabilizers or viscosity modifiers.

Characterization and Stability Studies

Block 2 formulations were examined in a 4 week stability study. Samples were stored for 2 weeks at 40° C. and for 4 weeks at 25' C. Various measurements were taken at t0, t2 (2 weeks at 40° C.), and t4 (4 weeks at 25° C.). Measurements included MFI, viscosity, conductivity, pH, A280, RP, SEC, and CEX.

| Block 2 Viscosity and Conductivity at t0 | | | |
|---|---|---|---|
| Form No | Viscosity (mPa·s) | Conductivity (mS/cm) | Tonicity (mOsM) |
| 2A-51 | 2.52 | 3.55 | 296 |
| 2A-52 | 2.69 | 5.04 | 292 |
| 2A-53 | 2.31 | 3.73 | 285 |
| 2A-54 | 2.44 | 5.50 | 281 |
| 2A-55 | 2.70 | 2.71 | 276 |
| 2A-56 | 2.55 | 3.20 | 274 |
| 2A-57 | 2.48 | 2.66 | 274 |
| 2A-58 | 2.42 | 3.91 | 296 |
| 2A-59 | 2.47 | 5.60 | 292 |
| 2A-60 | 2.54 | 2.94 | 285 |
| 2A-61 | 2.69 | 5.91 | 297 |
| 2B-62 | 5.71 | 2.90 | 276 |
| 2B-56 | 5.80 | 3.03 | 274 |
| 2B-57 | 5.69 | 3.03 | 274 |
| 2B-63 | 5.76 | 3.38 | 296 |

Viscosities were evaluated at shear rates for 500 l/s at 25'C. At t0, all high concentration adalimumab formulations had low viscosities. Tonicity values are calculated and demonstrate that the formulations are within the range of 250 to 350 milliosmolar, i.e. isotonic. As a result of the formulations containing ionic excipients (e.g. buffer, salt), all high concentration adalimumab formulations had a conductivity of 2.66 mS/cm or greater.

| Block 2 pH stability | | | |
|---|---|---|---|
| Form No | t0 pH | t2 pH | t4 pH |
| 2A-51 | 5.37 | 5.39 | 5.35 |
| 2A-52 | 5.40 | 5.40 | 5.38 |
| 2A-53 | 5.39 | 5.41 | 5.38 |
| 2A-54 | 5.36 | 5.37 | 5.36 |
| 2A-55 | 5.27 | 5.32 | 5.30 |
| 2A-56 | 5.24 | 5.31 | 5.26 |
| 2A-57 | 5.23 | 5.30 | 5.26 |
| 2A-58 | 5.36 | 5.41 | 5.37 |
| 2A-59 | 5.39 | 5.43 | 5.39 |
| 2A-60 | 5.32 | 5.37 | 5.32 |
| 2A-61 | 5.41 | 5.46 | 5.43 |
| 2B-62 | 5.34 | 5.38 | 5.36 |
| 2B-56 | 5.36 | 5.39 | 5.39 |
| 2B-57 | 5.33 | 5.37 | 5.35 |
| 2B-63 | 5.32 | 5.36 | 5.34 |

The pH of all high concentration adalimumab formulations was stable.

Concentration Stability Studies

Concentration of adalimumab was measured by A280. The experimental procedure included correcting for scattering by subtracting (directly) A320. Samples diluted to 0.3 mg/mL in water for A280 measurement.

| Block 2 concentrations t0, t2, and t4 | | | |
|---|---|---|---|
| Form No | Conc t0 (mg/mL) | Conc t2 (mg/mL) | Conc t4 (mg/mL) |
| 2A-51 | 96.4 | 92.0 | 95.7 |
| 2A-52 | 95.3 | 95.1 | 95.7 |
| 2A-53 | 96.2 | 952 | 96.0 |
| 2A-54 | 961 | 95.7 | 96.8 |
| 2A-55 | 102.6 | 98.9 | 99.6 |
| 2A-56 | 98.5 | 98.1 | 100.2 |
| 2A-57 | 100.4 | 100.2 | 100.9 |
| 2A-58 | 94.3 | 96.3 | 96.9 |
| 2A-59 | 96.8 | 95.7 | 96.4 |
| 2A-60 | 98.2 | 95.8 | 95.8 |
| 2A-61 | 95.2 | 100.0 | 96.3 |
| 2B-62 | 149.9 | 154.5 | 152.7 |
| 2B-56 | 150.6 | 150.4 | 147.8 |
| 2B-57 | 150.5 | 148.4 | 147.3 |
| 2B-63 | 141.9 | 142.2 | 141.5 |

The concentration of adalimumab in all high concentration adalimumab formulations was stable.

CEX Stability Studies

Stability of adalimumab in high concentration formulations was evaluated by CEX. The tables below list the relative peak areas for the main peak (MP), the acidic region (pre-MP), and the basic region (post-MP). The delta (Δ) is the difference in relative peak area between t0 and t2 or t4.

| Block 2 CEX t0 and t2 | | | | | | | | | |
|---|---|---|---|---|---|---|---|---|---|
| Form No | t0 MP | t2 MP | Δ MP | t0 Acidic | t2 Acidic | Δ Acidic | t0 Basic | t2 Basic | Δ Basic |
| 2A-51 | 75.06 | 64.02 | 11.04 | 17.88 | 25.47 | 7.58 | 7.06 | 10.51 | 3.46 |
| 2A-52 | 74.79 | 63.95 | 10.83 | 17.84 | 25.48 | 7.64 | 7.37 | 10.57 | 3.20 |
| 2A-53 | 74.89 | 63.04 | 11.85 | 17.96 | 26.70 | 8.74 | 7.14 | 10.26 | 3.12 |
| 2A-54 | 74.72 | 63.18 | 11.54 | 18.11 | 26.25 | 8.14 | 7.17 | 10.57 | 3.40 |
| 2A-55 | 75.06 | 64.23 | 10.83 | 17.84 | 25.28 | 7.44 | 7.10 | 10.50 | 3.39 |
| 2A-56 | 75.09 | 62.57 | 12.52 | 17.76 | 27.02 | 9.26 | 7.15 | 10.41 | 3.26 |
| 2A-57 | 75.08 | 63.08 | 11.99 | 17.88 | 26.51 | 8.63 | 7.04 | 10.40 | 3.36 |
| 2A-58 | 75.00 | 62.71 | 12.30 | 18.01 | 27.00 | 9.00 | 6.99 | 10.29 | 3.30 |
| 2A-59 | 74.90 | 62.88 | 12.03 | 18.01 | 26.75 | 8.73 | 7.08 | 10.38 | 3.29 |
| 2A-60 | 75.24 | 63.47 | 11.78 | 17.74 | 25.74 | 8.00 | 7.02 | 10.80 | 3.78 |
| 2A-61 | 75.09 | 64.20 | 10.90 | 17.79 | 25.22 | 7.43 | 7.11 | 10.58 | 3.47 |
| 2B-62 | 74.67 | 62.46 | 12.21 | 18.09 | 27.28 | 9.19 | 7.24 | 10.26 | 3.02 |
| 2B-56 | 74.87 | 62.49 | 12.37 | 17.88 | 27.23 | 9.35 | 7.25 | 10.26 | 3.02 |
| 2B-57 | 75.02 | 62.78 | 12.24 | 17.80 | 26.81 | 9.01 | 7.18 | 10.42 | 3.24 |
| 2B-63 | 75.15 | 63.15 | 12.00 | 17.87 | 26.11 | 8.24 | 6.98 | 10.74 | 3.76 |

| Block 2 CEX t0 and t4 | | | | | | | | | |
|---|---|---|---|---|---|---|---|---|---|
| Form No | t0 MP | t4 MP | Δ MP | t0 Acidic | t4 Acidic | Δ Acidic | t0 Basic | t4 Basic | Δ Basic |
| 2A-51 | 75.06 | 72.24 | 2.82 | 17.88 | 19.38 | 1.49 | 7.06 | 8.38 | 1.33 |
| 2A-52 | 74.79 | 72.34 | 2.44 | 17.84 | 19.34 | 1.49 | 7.37 | 8.32 | 0.95 |
| 2A-53 | 74.89 | 72.12 | 2.77 | 17.96 | 19.79 | 1.83 | 7.14 | 8.09 | 0.94 |
| 2A-54 | 74.72 | 71.91 | 2.81 | 18.11 | 19.75 | 1.64 | 7.17 | 8.34 | 1.16 |
| 2A-55 | 75.06 | 72.00 | 3.06 | 17.84 | 19.59 | 1.76 | 7.10 | 8.40 | 1.30 |
| 2A-56 | 75.09 | 71.39 | 3.69 | 17.76 | 20.33 | 2.57 | 7.15 | 8.27 | 1.12 |
| 2A-57 | 75.08 | 71.67 | 3.41 | 17.88 | 20.01 | 2.13 | 7.04 | 8.32 | 1.28 |
| 2A-58 | 75.00 | 71.62 | 3.38 | 18.01 | 20.08 | 2.07 | 6.99 | 8.30 | 1.31 |
| 2A-59 | 74.90 | 71.78 | 3.12 | 18.01 | 19.90 | 1.89 | 7.08 | 8.32 | 1.24 |
| 2A-60 | 75.24 | 72.17 | 3.07 | 17.74 | 19.52 | 1.78 | 7.02 | 8.31 | 1.29 |
| 2A-61 | 75.09 | 72.43 | 2.66 | 17.79 | 19.38 | 1.59 | 7.11 | 8.19 | 1.07 |
| 2B-62 | 74.67 | 71.70 | 2.97 | 18.09 | 20.10 | 2.01 | 7.24 | 8.20 | 0.96 |
| 2B-56 | 74.87 | 71.44 | 3.42 | 17.88 | 20.25 | 2.37 | 7.25 | 8.31 | 1.05 |
| 2B-57 | 75.02 | 71.71 | 3.31 | 17.80 | 20.02 | 2.22 | 7.18 | 8.27 | 1.09 |
| 2B-63 | 75.15 | 72.03 | 3.12 | 17.87 | 19.57 | 1.70 | 6.98 | 8.40 | 1.42 |

Surprisingly, the CEX results show that high concentration adalimumab formulations without a buffer are not less stable than formulations with a buffer. Formulations 2A-51 and 2A-55 are identical except 2A-55 lacks a buffer. At t2, t4 the Δ MP, Δ Acidic, and Δ Basic values for these formulations were not significantly different demonstrating that high concentration adalimumab formulations are stable with or with buffer.

It was also surprising to discover that high concentration adalimaumb formulations without a surfactant are not less stable than formulations with a surfactant. Formulations 2A-56 and 2A-57 are identical except 2A-57 lacks a surfactant. At t2, t4 the Δ MP, Δ Acidic, and A Basic values for these formulations were not significantly different demonstrating that high concentration adalimumab formulations without a surfactant are stable.

Formulations with amino acid stabilizers appeared to have slightly more loss of main peak at t2 versus mannitol/NaCl formulations. Despite these small changes, all that high concentration adalimaumb formulations demonstrated suitable stabilities SEC Stability Studies Stability of adalimumab in high concentration forulations was evaluated by SEC. The tables below list the relative peak areas for the main peak (MP), high molecular weight species (HMW), and low molecular weight species (LMW). The delta (Δ) is the difference in relative peak area between t0 and t2 or t4.

| Block 2 SEC t0 and t2 | | | | | | | | | |
|---|---|---|---|---|---|---|---|---|---|
| Form No | t0 MP | t2 MP | Δ MP | HMW t0 | HMW t2 | Δ HMW | LMW t0 | LMW t2 | Δ LMW |
| 2A-51 | 99.60 | 98.71 | 0.89 | 0.15 | 0.27 | 0.12 | 0.25 | 1.02 | 0.77 |
| 2A-52 | 99.58 | 98.65 | 0.94 | 0.17 | 0.34 | 0.17 | 0.24 | 1.01 | 0.77 |
| 2A-53 | 99.62 | 98.72 | 0.90 | 0.13 | 0.31 | 0.18 | 0.25 | 0.98 | 0.72 |
| 2A-54 | 99.59 | 98.64 | 0.95 | 0.13 | 0.29 | 0.16 | 0.28 | 1.07 | 0.79 |
| 2A-55 | 99.42 | 98.49 | 0.93 | 0.28 | 0.51 | 0.23 | 0.31 | 1.00 | 0.69 |
| 2A-56 | 99.50 | 98.54 | 0.96 | 0.20 | 0.46 | 0.25 | 0.29 | 1.00 | 0.71 |
| 2A-57 | 99.57 | 98.52 | 1.05 | 0.21 | 0.50 | 0.29 | 0.22 | 0.98 | 0.76 |
| 2A-58 | 99.61 | 98.62 | 1.00 | 0.13 | 0.33 | 0.20 | 0.25 | 1.06 | 0.80 |
| 2A-59 | 99.55 | 98.66 | 0.89 | 0.14 | 0.33 | 0.19 | 0.31 | 1.01 | 0.70 |
| 2A-60 | 99.57 | 98.72 | 0.86 | 0.14 | 0.26 | 0.12 | 0.29 | 1.02 | 0.73 |
| 2A-61 | 99.59 | 98.73 | 0.86 | 0.15 | 0.27 | 0.13 | 0.26 | 1.00 | 0.73 |
| 2B-62 | 99.51 | 98.29 | 1.22 | 0.20 | 0.69 | 0.49 | 0.29 | 1.02 | 0.73 |
| 2B-56 | 99.53 | 98.34 | 1.20 | 0.21 | 0.65 | 0.44 | 0.26 | 1.02 | 0.76 |
| 2B-57 | 99.59 | 98.38 | 1.20 | 0.18 | 0.61 | 0.43 | 0.24 | 1.01 | 0.77 |
| 2B-63 | 99.53 | 98.57 | 0.96 | 0.19 | 0.40 | 0.21 | 0.29 | 1.03 | 0.75 |

| Block 2 SEC t0 and t2 | | | | | | | | | |
|---|---|---|---|---|---|---|---|---|---|
| Form No | t0 MP | t4 MP | Δ MP | HMW t0 | HMW t4 | Δ HMW | LMW t0 | LMW t4 | Δ LMW |
| 2A-51 | 99.60 | 99.18 | 0.42 | 0.15 | 0.19 | 0.04 | 0.25 | 0.63 | 0.38 |
| 2A-52 | 99.58 | 99.23 | 0.35 | 0.17 | 0.24 | 0.06 | 0.24 | 0.54 | 0.29 |
| 2A-53 | 99.62 | 99.25 | 0.37 | 0.13 | 0.18 | 0.05 | 0.25 | 0.57 | 0.32 |
| 2A-54 | 99.59 | 99.24 | 0.35 | 0.13 | 0.19 | 0.06 | 0.28 | 0.57 | 0.29 |
| 2A-55 | 99.42 | 99.00 | 0.41 | 0.28 | 0.44 | 0.17 | 0.31 | 0.55 | 0.25 |
| 2A-56 | 99.50 | 98.95 | 0.56 | 0.20 | 0.44 | 0.24 | 0.29 | 0.61 | 0.32 |
| 2A-57 | 99.57 | 99.09 | 0.48 | 0.21 | 0.30 | 0.09 | 0.22 | 0.62 | 0.40 |
| 2A-58 | 99.61 | 99.29 | 0.32 | 0.13 | 0.20 | 0.07 | 0.25 | 0.50 | 0.25 |
| 2A-59 | 99.55 | 99.23 | 0.33 | 0.14 | 0.23 | 0.09 | 0.31 | 0.55 | 0.24 |
| 2A-60 | 99.57 | 99.26 | 0.31 | 0.14 | 0.17 | 0.03 | 0.29 | 0.57 | 0.28 |

-continued

| Block 2 SEC t0 and t2 | | | | | | | | | |
|---|---|---|---|---|---|---|---|---|---|
| Form No | t0 MP | t4 MP | Δ MP | HMW t0 | HMW t4 | Δ HMW | LMW t0 | LMW t4 | Δ LMW |
| 2A-61 | 99.59 | 99.22 | 0.37 | 0.15 | 0.19 | 0.05 | 0.26 | 0.59 | 0.33 |
| 2B-62 | 99.51 | 99.04 | 0.47 | 0.20 | 0.38 | 0.18 | 0.29 | 0.58 | 0.29 |
| 2B-56 | 99.53 | 99.00 | 0.53 | 0.21 | 0.37 | 0.16 | 0.26 | 0.63 | 0.37 |
| 2B-57 | 99.59 | 99.09 | 0.50 | 0.18 | 0.33 | 0.15 | 0.24 | 0.58 | 0.35 |
| 2B-63 | 99.53 | 99.13 | 0.39 | 0.19 | 0.32 | 0.14 | 0.29 | 0.54 | 0.26 |

The SEC results show buffer free high concentration adalimaumb formulations tend to have more HMW at both 100 and 150 mg/mL. It was also observed that 150 mg/mL formulations degraded faster than 100 mg/mL formulations, generally through formation of HMW species. Overall, only small changes were observed in these formulations demonstrating that the high concentration adalimaumb formulations are stable.

Particle Stability Studies

Stability of adalimumab in high concentration formulations was evaluated by measuring the size and number of particles by MFI. Sample were evaluated by MFI analysis.

The difference between total particles and non-silicone oil particles are the number of silicone oil particles.

Particle counts for particles ≥10 μm and ≥25 μm were generally low in all high concentration adalimaumb formulations. Despite the fact that many of these formulations did not have a buffer or a surfactant, all were within USP 788 guidelines. These results demonstrate that the high concentration adalimaumb formulations are stable.

In conclusion, high concentration adalimaumb formulations have suitable viscosity for administration via a needle (e.g. subcutaneous administration) and are stable as demonstrated by pH, CEX, SEC, and MFI analyses.

| Block 2 MFi t0 | | | | | | | | |
|---|---|---|---|---|---|---|---|---|
| | Total (particles/mL) | | | | Non-silicone Oil (particles/mL) | | | |
| Form No | ≥2 μm | ≥5 μm | ≥10 μm | ≥25 μm | ≥2 μm | ≥5 μm | ≥10 μm | ≥25 μm |
| 2A-51 | 579 | 199 | 78 | 19 | 533 | 176 | 65 | 12 |
| 2A-52 | 1092 | 187 | 57 | 10 | 908 | 175 | 55 | 10 |
| 2A-53 | 575 | 118 | 33 | 2 | 500 | 116 | 33 | 2 |
| 2A-54 | 1129 | 429 | 212 | 40 | 1036 | 395 | 192 | 34 |
| 2A-55 | 3529 | 793 | 223 | 32 | 3056 | 731 | 210 | 29 |
| 2A-56 | 712 | 134 | 48 | 2 | 466 | 117 | 48 | 2 |
| 2A-57 | 4762 | 1231 | 242 | 6 | 4012 | 1126 | 229 | 6 |
| 2A-58 | 1268 | 426 | 118 | 15 | 1192 | 401 | 105 | 11 |
| 2A-59 | 624 | 139 | 64 | 4 | 504 | 124 | 60 | 4 |
| 2A-60 | 978 | 258 | 78 | 8 | 798 | 227 | 69 | 6 |
| 2A-61 | 3655 | 1010 | 258 | 19 | 3161 | 921 | 235 | 19 |
| 2B-62 | 648 | 175 | 39 | 11 | 579 | 168 | 37 | 9 |
| 2B-56 | 306 | 65 | 10 | 2 | 218 | 53 | 8 | 0 |
| 2B-57 | 1202 | 242 | 71 | 8 | 1052 | 214 | 63 | 8 |
| 2B-63 | 2933 | 606 | 156 | 6 | 2514 | 541 | 139 | 4 |

| Block 2 MFi t4 | | | | | | | | |
|---|---|---|---|---|---|---|---|---|
| | Total (particles/mL) | | | | Non-silicone Oil (particles/mL) | | | |
| Form No | ≥2 μm | ≥5 μm | ≥10 μm | ≥25 μm | ≥2 μm | ≥5 μm | ≥10 μm | ≥25 μm |
| 2A-51 | 3459 | 795 | 241 | 39 | 3025 | 715 | 220 | 34 |
| 2A-52 | 3385 | 961 | 374 | 51 | 3031 | 898 | 339 | 51 |
| 2A-53 | 1171 | 212 | 75 | 6 | 1014 | 187 | 62 | 6 |
| 2A-54 | 2206 | 714 | 247 | 36 | 2025 | 650 | 228 | 31 |
| 2A-55 | 1778 | 510 | 155 | 33 | 1615 | 478 | 141 | 29 |
| 2A-56 | 772 | 136 | 34 | 11 | 615 | 103 | 32 | 11 |
| 2A-57 | 1100 | 304 | 90 | 17 | 879 | 256 | 84 | 17 |
| 2A-58 | 2641 | 651 | 124 | 6 | 2177 | 592 | 115 | 6 |
| 2A-59 | 1853 | 518 | 143 | 17 | 1614 | 487 | 136 | 15 |
| 2A-60 | 1032 | 266 | 61 | 8 | 858 | 235 | 55 | 8 |
| 2A-61 | 1144 | 361 | 117 | 21 | 1085 | 332 | 103 | 21 |
| 2B-62 | 573 | 155 | 46 | 2 | 514 | 139 | 42 | 2 |
| 2B-56 | 170 | 42 | 8 | 0 | 109 | 29 | 4 | 0 |
| 2B-57 | 831 | 248 | 86 | 11 | 768 | 208 | 63 | 0 |
| 2B-63 | 867 | 183 | 53 | 6 | 747 | 155 | 44 | 6 |

Example 4. Stable High Concentration Adalimumab Formulations—Block 3

Block 3 Study Design

All Block 3 formulations comprise a high concentration of adalimumab and a surfactant. The majority of Block 3 formulations contain a buffer, either succinate or histidine.

Examples of Block 3 formulations are set forth in the tables below. Block 3A formulations comprise adalimumab at about 100 mg/mL and Block 3B formulations comprise adalimumab at about 150 mg/mL.

| Block 3A Table | | | | | | | | | | | | | | | | |
|---|---|---|---|---|---|---|---|---|---|---|---|---|---|---|---|---|
| Form. No. | pH | His (mM) | Na Pyrohos (mM) | Na Phos (mM) | Citric Acid (mM) | Citrate (mM) | Na acetate (mM) | Acetate (mM) | Succinate (mM) | Gly (mM) | NaCl (mM) | mannitol (mM) | trehalose (mM) | sorbitol (mg/mL) | Arg (mM) | Adipate (mM) | PS 80 |
| 3A-1 | 5.2 | 0 | 0 | 14.5 | 0 | 7.0 | 0.0 | 0 | 0 | 0 | 105 | 66 | 0 | 0 | 0 | 0 | 0.1 |
| 3A-2 | 5.2 | 0 | 0 | 0 | 0 | 0 | 0 | 0 | 0 | 0 | 105 | 66 | 0 | 0 | 0 | 23 | 0.1 |
| 3A-3 | 5.2 | 0 | 0 | 0 | 0 | 2.4 | 0 | 20 | 0 | 0 | 105 | 66 | 0 | 0 | 0 | 0 | 0.1 |
| 3A-4 | 5.2 | 0 | 0 | 0 | 0 | 0 | 0 | 0 | 10 | 0 | 100 | 0 | 0 | 10 | 24 | 0 | 0.1 |
| 3A-5 | 6.5 | 0 | 0 | 0 | 0 | 0 | 0 | 15 | 0 | 0 | 0 | 0 | 240 | 0 | 10 | 0 | 0.1 |
| 3A-6 | 6.25 | 0 | 0 | 0 | 0 | 0 | 0 | 0 | 25 | 0 | 0 | 0 | 215 | 0 | 0 | 0 | 0.1 |
| 3A-7 | 6.25 | 25 | 0 | 0 | 0 | 0 | 0 | 0 | 0 | 0 | 0 | 240 | 0 | 0 | 0 | 0 | 0.1 |
| 3A-8 | 5.3 | 0 | 0 | 0 | 0 | 0 | 0 | 0 | 0 | 0 | 0 | 231 | 0 | 0 | 0 | 0 | 0.1 |
| 3A-9 | 5.3 | 0 | 0 | 10 | 0 | 0 | 0 | 0 | 0 | 0 | 88 | 0 | 107 | 0 | 0 | 0 | 0.1 |
| 3A-10 | 5.3 | 0 | 0 | 6 | 0 | 0 | 0 | 0 | 4 | 0 | 88 | 0 | 107 | 0 | 0 | 0 | 0.1 |
| 3A-11 | 5.3 | 0 | 0 | 0 | 0 | 0 | 0 | 0 | 0 | 0 | 0 | 0 | 0 | 0 | 0 | 0 | 0.1 |
| 3A-12 | 5.2 | 0 | 0 | 0 | 0 | 0 | 0 | 17 | 0 | 0 | 103 | 66 | 0 | 0 | 0 | 0 | 0.1 |
| 3A-13 | 5.2 | 0 | 14.1 | 0 | 1 | 6.8 | 0 | 0 | 0 | 0 | 105 | 66 | 0 | 0 | 0 | 0 | 0.1 |
| 3A-14 | 5.2 | 0 | 0 | 0 | 0 | 0 | 1 | 19 | 0 | 0 | 26.35 | 203 | 0 | 0 | 0 | 0 | 0.1 |

| Block 3B Table | | | | | | | | | | | | | | | | |
|---|---|---|---|---|---|---|---|---|---|---|---|---|---|---|---|---|
| Form. No. | pH | His (mM) | Na Pyrohos (mM) | Na Phos (mM) | Citric Acid (mM) | Citrate (mM) | Na acetate (mM) | Acetate (mM) | Succinate (mM) | Gly (mM) | NaCl (mM) | mannitol (mM) | trehalose (mM) | sorbitol (mg/mL) | Arg (mM) | Adipate (mM) | PS 80 |
| 3B-1 | 5.2 | 0 | 0 | 14.5 | 0 | 7.0 | 0.0 | 0 | 0 | 0 | 105 | 66 | 0 | 0 | 0 | 0 | 0.1 |
| 3B-2 | 5.2 | 0 | 0 | 0 | 0 | 0 | 0 | 0 | 0 | 0 | 105 | 66 | 0 | 0 | 0 | 23 | 0.1 |
| 3B-3 | 5.2 | 0 | 0 | 0 | 0 | 2.4 | 0 | 20 | 0 | 0 | 105 | 66 | 0 | 0 | 0 | 0 | 0.1 |
| 3B-4 | 5.2 | 0 | 0 | 0 | 0 | 0 | 0 | 0 | 10 | 0 | 100 | 0 | 0 | 10 | 24 | 0 | 0.1 |
| 3B-5 | 6.5 | 0 | 0 | 0 | 0 | 0 | 0 | 15 | 0 | 0 | 0 | 0 | 240 | 0 | 10 | 0 | 0.1 |
| 3B-6 | 6.25 | 0 | 0 | 0 | 0 | 0 | 0 | 0 | 25 | 0 | 0 | 0 | 215 | 0 | 0 | 0 | 0.1 |
| 3B-7 | 6.25 | 25 | 0 | 0 | 0 | 0 | 0 | 0 | 0 | 0 | 0 | 240 | 0 | 0 | 0 | 0 | 0.1 |
| 3B-8 | 5.3 | 0 | 0 | 0 | 0 | 0 | 0 | 0 | 0 | 0 | 0 | 231 | 0 | 0 | 0 | 0 | 0.1 |
| 3B-9 | 5.3 | 0 | 0 | 10 | 0 | 0 | 0 | 0 | 0 | 0 | 88 | 0 | 107 | 0 | 0 | 0 | 0.1 |
| 3B-10 | 5.3 | 0 | 0 | 6 | 0 | 0 | 0 | 0 | 4 | 0 | 88 | 0 | 107 | 0 | 0 | 0 | 0.1 |
| 3B-11 | 5.3 | 0 | 0 | 0 | 0 | 0 | 0 | 0 | 0 | 0 | 0 | 0 | 0 | 0 | 0 | 0 | 0.1 |
| 3B-12 | 5.2 | 0 | 0 | 0 | 0 | 0 | 0 | 17 | 0 | 0 | 103 | 66 | 0 | 0 | 0 | 0 | 0.1 |
| 3B-13 | 5.2 | 0 | 14.1 | 0 | 1 | 6.8 | 0 | 0 | 0 | 0 | 105 | 66 | 0 | 0 | 0 | 0 | 0.1 |
| 3B-14 | 5.2 | 0 | 0 | 0 | 0 | 0 | 1 | 19 | 0 | 0 | 26.35 | 203 | 0 | 0 | 0 | 0 | 0.1 |

It is expected that high concentration adalimumab formulations in Block 3A (100 mg/mL) and 3B (150 mg/mL) exhibit stability and viscosity comparable to, or better, than other formulations at 50 mg/mL or 100 mg/mL (e.g. commercial adalimumab formulations). However, if desired, further improvements in stability or viscosity may be achieved by adding additional stabilizers or viscosity modifiers.

Example 5. Stable High Concentration Adalimumab Formulations—Block 4

Block 4 Study Design

Block 4 formulations evaluate high concentration adalimumab formulations with or without an acetate buffer. Many Block 4 formulations comprise a high concentration of adalimumab, an acetate buffer, optionally a tonicity agent, and optionally a surfactant. Other Block 4 formulations comprise a high concentration of adalimumab, a tonicity agent and optionally a surfactant, wherein the composition is free, or substantially free, of acetate.

Examples of Block 4 formulations are set forth in the tables below. Block 4A formulations comprise adalimumab at about 100 mg/mL and Block 4B formulations comprise adalimumab at about 150 mg/mL. Blocks 4A and 4B also include formulations without acetate for evaluation as controls and alternate formulations (4A-3, 4A-4, 4A-13, 4B-3, 4B-4, and 4B-13).

| Block 4A Table | | | | | | | | |
|---|---|---|---|---|---|---|---|---|
| Form. No. | pH | acetate (mM) | trehalose (mM) | mannitol (mM) | sorbitol (mM) | xylitol (mM) | NaCl (mM) | Ps 80 (% w/v) | benzyl alcohol (% w/v) |
| 4A-1 | 4.5 | 30 | 0 | 0 | 0 | 0 | 140 | 0 | 0 |
| 4A-2 | 5.5 | 30 | 0 | 270 | 0 | 0 | 0 | 0 | 0 |
| 4A-3 | 5.5 | 0 | 0 | 0 | 0 | 0 | 140 | 0 | 0 |
| 4A-4 | 5.5 | 0 | 0 | 0 | 0 | 270 | 0 | 0 | 0 |
| 4A-5 | 5.0 | 20 | 0 | 0 | 270 | 0 | 0 | 0.05 | 0 |
| 4A-6 | 5.5 | 20 | 0 | 0 | 0 | 270 | 0 | 0.05 | 0 |
| 4A-7 | 5.2 | 20 | 0 | 0 | 270 | 0 | 0 | 0 | 0.9 |
| 4A-8 | 5.2 | 20 | 230 | 0 | 0 | 0 | 0 | 0 | 0 |
| 4A-9 | 4.5 | 10 | 65 | 0 | 0 | 0 | 100 | 0 | 0 |
| 4A-10 | 5.2 | 10 | 0 | 0 | 270 | 0 | 0 | 0 | 0.9 |
| 4A-11 | 6.0 | 30 | 0 | 0 | 0 | 0 | 140 | 0 | 0.9 |
| 4A-12 | 5.2 | 10 | 0 | 270 | 0 | 0 | 0 | 0.1 | 0 |
| 4A-13 | 5.2 | 0 | 0 | 65 | 0 | 0 | 100 | 0.1 | 0 |
| 4A-14 | 5.0 | 10 | 0 | 0 | 0 | 0 | 140 | 0.1 | 0.9 |
| 4A-15 | 5.0 | 10 | 230 | 0 | 0 | 0 | 0 | 0.1 | 0.9 |

| Block 4B Table | | | | | | | | |
|---|---|---|---|---|---|---|---|---|
| Form. No. | pH | acetate (mM) | trehalose (mM) | mannitol (mM) | sorbitol (mM) | xylitol (mM) | NaCl (mM) | Ps 80 (% w/v) | benzyl alcohol (% w/v) |
| 4B-1 | 4.5 | 30 | 0 | 0 | 0 | 0 | 140 | 0 | 0 |
| 4B-2 | 5.5 | 30 | 0 | 270 | 0 | 0 | 0 | 0 | 0 |
| 4B-3 | 5.5 | 0 | 0 | 0 | 0 | 0 | 140 | 0 | 0 |
| 4B-4 | 5.5 | 0 | 0 | 0 | 0 | 270 | 0 | 0 | 0 |
| 4B-5 | 5.0 | 20 | 0 | 0 | 270 | 0 | 0 | 0.05 | 0 |
| 4B-6 | 5.5 | 20 | 0 | 0 | 0 | 270 | 0 | 0.05 | 0 |
| 4B-7 | 5.2 | 20 | 0 | 0 | 270 | 0 | 0 | 0 | 0.9 |
| 4B-8 | 5.2 | 20 | 230 | 0 | 0 | 0 | 0 | 0 | 0 |
| 4B-9 | 4.5 | 10 | 65 | 0 | 0 | 0 | 100 | 0 | 0 |
| 4B-10 | 5.2 | 10 | 0 | 0 | 270 | 0 | 0 | 0 | 0.9 |
| 4B-11 | 6.0 | 30 | 0 | 0 | 0 | 0 | 140 | 0 | 0.9 |
| 4B-12 | 5.2 | 10 | 0 | 270 | 0 | 0 | 0 | 0.1 | 0 |
| 4B-13 | 5.2 | 0 | 0 | 65 | 0 | 0 | 100 | 0.1 | 0 |
| 4B-14 | 5.0 | 10 | 0 | 0 | 0 | 0 | 140 | 0.1 | 0.9 |
| 4B-15 | 5.0 | 10 | 230 | 0 | 0 | 0 | 0 | 0.1 | 0.9 |

It is expected that high concentration adalimumab formulations in Block 4A (100 mg/ml) and 4B (150 mg/mL) exhibit stability and viscosity comparable to, or better, than other formulations at 50 mg/mL or 100 mg/mL (e.g. commercial adalimumab formulations). However, if desired, further improvements in stability or viscosity may be achieved by adding additional stabilizers or viscosity modifiers.

Example 6. Sub-Visible Particles in Adalimumab Formulations

This example describes the methods used to quantify sub-visible particles (SVPs), which are one indication of quality of the formulation (fewer particles=higher quality). Assessment of the relevant manufacturing and storage conditions that may lead to increased amounts of SVPs is done to determine the probability of occurrence of the SVPs, and to characterize the types and amounts of SVPs (2-10 μm and >10 μm).

Analytical methods useful for assessing SVPs include flow imaging (flow microscopy), e.g., the FlowCAM® system (Fluid Imaging Technologies, Inc., Scarborough, Me.), and Micro-Flow Imaging ("MFI"; ProteinSimple, San Jose, Calif.), dynamic light scattering, and asymmetrical flow field flow fractionation (AF4). Methods for using these systems are known in the art and available from the respective manufacturers.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A stable aqueous pharmaceutical composition comprising:
   a concentration of adalimumab greater than about 50 mg/mL and less than or equal to about 200 mg/mL; and
   ionic excipients, wherein the ionic excipients comprise about 10 mM to 50 mM of histidine, about 13 mM to 140 mM of NaCl, and about 90 mM to 240 mM of glycine, wherein the ionic excipients contribute to the composition having conductivity greater than 2.5 mS/cm;

wherein the composition has: an osmolarity of about 140 to about 400 mOsm/L; a pH of about 5 to about 6; and a viscosity equal to or less than about 20 cP, and
the composition is stable for two weeks at 40° C., and for four weeks at 25° C.

2. The composition of claim 1, wherein the composition is suitable for administration to a subject.

3. The composition of claim 1, wherein the composition is isotonic, has a concentration of adalimumab of about 100 to about 200 mg/mL, and is free, or substantially free, of citrate buffer.

4. The composition of claim 1, wherein the composition has a viscosity equal to or less than about 15 cP.

5. The composition of claim 1, wherein the composition comprises mannitol, sorbitol, trehalose, or a combination thereof.

6. The composition of claim 1, wherein the composition comprises sucrose, lactose, glucose, maltose, or a combination thereof.

7. The composition of claim 1, wherein the composition comprises a surfactant selected from polysorbate 20, polysorbate 80, SDS, poloxamer 188 (Pluronic® F68), or a combination thereof, wherein the surfactant has a concentration of about 0.01% w/v to about 5% w/v.

8. The composition of claim 1, wherein the composition is free, or substantially free, of polyol.

9. The composition of claim 1, wherein the composition is free, or substantially free, of surfactant.

10. The composition of claim 1, wherein the composition is free, or substantially free, of buffer.

11. The composition of claim 1, wherein the composition is free, or substantially free, of both polyol and surfactant.

12. The composition of claim 1, wherein the ionic excipient is a physiologically acceptable salt, and the composition is free, or substantially free, of (i) buffer; (ii) polyol; (iii) surfactant; (iv) both polyol and surfactant; or (v) polyol, surfactant, and buffer.

13. The composition of claim 1, wherein the composition has a viscosity less than 2 cP.

14. The composition of claim 1, wherein the composition is stable at 2° C. to 8° C. (i) for at least three months; (ii) for at least six months; or (iii) for at least one year.

15. The composition of claim 1 prepared by modifying a pre-existing adalimumab formulation having a pH of about 5 to about 6 and no more than about 50 mg/mL of adalimumab, wherein the modification consists solely of increasing the concentration of adalimumab in the pre-existing formulation to a concentration of at least 100 mg/mL, without altering the identity or concentration of any excipients present in the pre-existing formulation.

\* \* \* \* \*